(12) United States Patent
Cui et al.

(10) Patent No.: US 11,008,337 B2
(45) Date of Patent: *May 18, 2021

(54) CHIRAL DIARYL MACROCYCLES AS MODULATORS OF PROTEIN KINASES

(71) Applicant: Turning Point Therapeutics, Inc., San Diego, CA (US)

(72) Inventors: Jingrong J. Cui, San Diego, CA (US); Yishan Li, San Diego, CA (US); Evan W. Rogers, San Diego, CA (US); Dayong Zhai, San Diego, CA (US); Wei Deng, San Diego, CA (US); Jane Ung, San Diego, CA (US)

(73) Assignee: Turning Point Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/425,407

(22) Filed: May 29, 2019

(65) Prior Publication Data
US 2019/0284209 A1 Sep. 19, 2019

Related U.S. Application Data

(62) Division of application No. 15/740,462, filed as application No. PCT/US2016/040329 on Jun. 30, 2016, now Pat. No. 10,316,044.

(60) Provisional application No. 62/353,728, filed on Jun. 23, 2016, provisional application No. 62/188,043, filed on Jul. 2, 2015.

(51) Int. Cl.
| | |
|---|---|
| *A61K 31/407* | (2006.01) |
| *A61K 31/4353* | (2006.01) |
| *C07D 209/56* | (2006.01) |
| *C07D 221/22* | (2006.01) |
| *C07D 498/22* | (2006.01) |
| *C07D 498/14* | (2006.01) |

(52) U.S. Cl.
CPC ......... *C07D 498/22* (2013.01); *C07D 498/14* (2013.01)

(58) Field of Classification Search
CPC .............. A61K 31/407; A61K 31/4353; C07D 209/56; C07D 221/22
USPC ..................... 514/286, 410; 546/74; 548/425
See application file for complete search history.

(56) References Cited

U.S. PATENT DOCUMENTS

| | | | |
|---|---|---|---|
| 4,838,925 A | 6/1989 | Tseng | |
| 4,847,382 A | 7/1989 | Hallenbach | |
| 5,639,778 A | 6/1997 | Andersson | |
| 5,698,578 A | 12/1997 | Heath, Jr. | |
| 8,497,270 B2 | 7/2013 | Thuring | |
| 8,680,111 B2 | 3/2014 | Bailey | |
| 8,815,872 B2 | 8/2014 | Yu | |
| 8,933,084 B2 | 1/2015 | Andrews | |
| 9,714,258 B2 | 7/2017 | Cui | |
| 10,246,466 B2 | 4/2019 | Cui | |
| 10,294,242 B2 | 5/2019 | Cui | |
| 10,316,044 B2 | 6/2019 | Cui | |
| 10,689,400 B2 | 6/2020 | Cui | |
| 2011/0294801 A1 | 12/2011 | Yu | |
| 2013/0143895 A1 | 6/2013 | McAllister | |
| 2013/0203776 A1 | 8/2013 | Andrews | |
| 2013/0245021 A1 | 9/2013 | Bi | |
| 2013/0252961 A1 | 9/2013 | Bailey | |
| 2014/0107099 A1 | 4/2014 | Blaney | |
| 2014/0206605 A1 | 7/2014 | Beutner | |
| 2016/0159808 A1 | 6/2016 | Kawasaki | |
| 2016/0339027 A1 | 11/2016 | Carter | |
| 2017/0002023 A1 | 1/2017 | Cui | |
| 2017/0334929 A1 | 11/2017 | Cui | |
| 2018/0186813 A1 | 7/2018 | Cui | |
| 2018/0194777 A1 | 7/2018 | Cui | |
| 2018/0325901 A1 | 11/2018 | Cui | |

FOREIGN PATENT DOCUMENTS

| | | |
|---|---|---|
| CL | 2012003227 | 2/2013 |
| CN | 102143750 | 8/2011 |
| CN | 102971322 | 3/2013 |
| JP | 2012502043 | 1/2012 |
| WO | 2002046197 A | 6/2002 |

(Continued)

OTHER PUBLICATIONS

Maulik, G., et al. Role of the hepatocyte growth factor receptor, MET, in oncogenesis and potential for therapeutic inhibition. Cytokine Growth Factor Rev. 2002, 13, 41-59.

(Continued)

*Primary Examiner* — Douglas M Willis
(74) *Attorney, Agent, or Firm* — Mintz Levin Cohn Ferris Glovsky and Popeo P.C.

(57) ABSTRACT

The present disclosure relates to certain chiral diaryl macrocyclic derivatives, of the formula I:

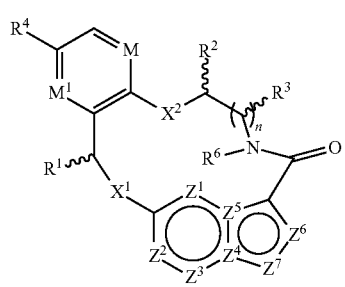

pharmaceutical compositions containing them, and methods of using them to treat cancer, pain, neurological diseases, autoimmune diseases, and inflammation.

22 Claims, No Drawings

(56) References Cited

FOREIGN PATENT DOCUMENTS

| | | |
|---|---|---|
| WO | 2010028116 | 3/2010 |
| WO | 2010033941 | 3/2010 |
| WO | 2010048314 | 4/2010 |
| WO | 2010051549 | 5/2010 |
| WO | 2011146336 | 11/2011 |
| WO | 2012034091 | 3/2012 |
| WO | 2012136859 | 10/2012 |
| WO | 2013001310 | 1/2013 |
| WO | 2013028465 | 2/2013 |
| WO | 2013045653 | 4/2013 |
| WO | 2013132376 | 9/2013 |
| WO | 2013134219 | 9/2013 |
| WO | 2013134228 | 9/2013 |
| WO | 2013147711 | 10/2013 |
| WO | 2015112806 | 7/2015 |
| WO | 2017004342 | 1/2017 |
| WO | 2017007759 | 1/2017 |
| WO | 2017015367 | 1/2017 |
| WO | 2018022911 | 2/2018 |
| WO | 2018140554 | 8/2018 |
| WO | 2019023417 | 1/2019 |

OTHER PUBLICATIONS

Smolen, G. A., et al. Amplification of MET may identify a subset of cancers with extreme sensitivity to the selective tyrosine kinase inhibitor PHA-665752. Proc. Natl. Acad. Sci. U.S. A. 2006, 103, 2316-2321.
Ghiso, E.; Giordano, S. Targeting MET: why, where and how? Curr. Opin. Pharmacol. 2013, 13, 511-518.
Otsuka, T., et al. MET autocrine activation induces development of malignant melanoma and acquisition of the metastatic phenotype. Cancer Res. 1998, 58, 5157-5167.
Xie, Q., et al. Hepatocyte growth factor (HGF) autocrine activation predicts sensitivity to MET inhibition in alioblastoma. Proc. Natl. Acad. Sci. U.S. A. 2012, 109, 570-575.
Kentsis, A., et al. Autocrine activation of the MET receptor tyrosine kinase in acute myeloid leukemia. Nat. Medd. 2012, 18, 1118-1122.
Yu, Helena A., et al. Analysis of tumor specimens at the time of acquired resistance to EGFR-TKI therapy in 155 patients with EGFR-mutant lung cancers. Clin. Cancer Res. 2013, 19, 2240-2247.
Yano, S., et al. Hepatocyte growth factor induces gefitinib resistance of lung adenocarcinoma with epidermal growth factor receptor-activating mutations. Cancer Res. 2008, 68, 9479-9487.
Bardelli, A., et al. Amplification of the Mli'T Receptor Drives Resistance to Anti-EGFR Therapies in Colorectal Cancer. Cancer Discov. 2013, 3, 658-673.
Straussman, R., et al. Tumour micro-environment elicits innate resistance to RAF inhibitors through HGF secretion. Nature 2012, 487, 500-504.
Harbinski, F., et al. Rescue screens with secreted proteins reveal compensatory potential of receptor tyrosine kinases in driving cancer growth. Cancer Discov. 2012, 2, 948-959.
Parsons, S. J., et al. Src family kinases, key regulators of signal transduction. Oncogene, 2004, 23, 7906-7909.
Wojcik, E. J., et al. A novel activating function of SRC and STAT3 on HGF transcription in mammary carcinoma cells. Oncogene. 2006, 25, 2773-84.
Dulak AM et al. HGF-independent potentiation of EGFR action by Mli'1'. Oncogene. 2011, 30, 3625-3635.
Stabile, L. P., et al. c-SRC activation mediates erlotinib resistance in head and neck cancer by stimulating MET. Clin Cancer Res. 2012, 19, 1-13.
Sen, B., et al. Distinct interactions between SRC and MET in mediating resistance to SRC inhibition in head and neck cancer. Clin Cancer Res. 2010, 17, 1-11.
Bertotti, A., et al. Inhibition of SRC impairs the growth of MET-addicted gastric tumors. Clin Cancer Res. 2010, 16,3933-3943.

Wrobel CN, et al. Autocrine CSFIR activation promotes SRC-dependent disruption of mammary epithelial architecture. J Cell Biol. 2004, 165, 263-273.
Ravi V, et al. Treatment of tenosynovial giant cell tumor and pigmented villonodular synovitis. Curr Opin Oncol. 2011, 23, 361-366.
Gridelli, C. et al., Cancer Treat Rev. 2014, 40, 300-306.
Toso, A. et al., Cell Reports 2014, 9, 75-89.
Shaw, A. T. et al., N Engl J Med. 2014, 371(21):1963-1971.
Politi K, Clin Cancer Res. 2014, 20, 5576.
Crystal AS, Science. 2014, 346, 1480.
Vaishnavi A, et al Cancer Discov. 2015, 5, 25.
Park, K-S, et al. J Clin Invest. 2014, 124(7)3003-3015.
Shi L, et al. Br J Cancer. 2014, 111(12):2316-27.
Stransky N, et al. Nature Communications 2014, 5, 4846.
Schwarz LJ, et al. J Clin Invest. 2014, 124, 5490-5502.
Rudd ML, et al. BMC Cancer 2014, 14, 884.
Furman RR, et al. New England Journal of Medicine, 2014, 370, 2352-2354.
Uguen A, et al Future Oncol. Jun. 3, 2016, Epub ahead of print.
Gao SP, et al. Sci Signal. 206, 9 (421):ra33: published online Mar. 29, 2016.
Balko JM, et al. Sci Transl Med. 2016, 8 (334):ra53, published Apr. 13, 2016.
Serrels A, et al, Cells 2015, 163, 160-173.
Xu T, et al. Cancer Lett. 2016, 377(2): 140-8, published online Apr. 25, 2016.
Elias D., et al Pharmacological Research 2015, 100, 250-254.
Ambrogio C, et al, Nature Medicine, 2016, 22, 270-277, published Feb. 8, 2016.
Pubchem, Compound Summary for SID 252159180, available date; Aug. 10, 2015, retrieved Aug. 31, 2017, retrieved from: https://pubchem.ncbi.nlm.nih.gov/substance/252159180.
Rahal, "The development of Potent and Selective RET inhibitors", Presentation at Annual AACR Meeting, Apr. 18, 2016.
Gunderson AJ, et al. Cancer Discov. 2016, 6, 270-285, published online Dec. 29, 2015.
Buchert M, et al. Oncogene, 2016, 25, 939-951; published May 18, 2015.
Wiesner T, et al Nature 2015, 526, 453-457.
Voena C, et al. Oncotarget, Apr. 23, 2016, 8955.
Morgillo F, Della Corte CM, Fasano M. et al. Mechanisms of resistance to EGFR-targeted drugs: lunch cancer. ESMO Open 2016;1: e000060, published online May 11, 2016.
International Search Report and Written Opinion prepared for PCT/US2017/044214, dated Dec. 1, 2017, 11 pages.
Liu Z, et al. J. Clin. Endocrinol. Metab. 2004, 89, 3503-3509.
Manning, G. et al., Science 2002, 298, 1912-1934.
International Search Report and Written Opinion prepared for PCT/US2015/012597, dated Aug. 28, 2015, 11 pages.
International Search Report and Written Opinion prepared for PCT/US2016/043132, dated Sep. 28, 2016, 8 pages.
PubChem-CID-98009788, Create Date: Dec. 11, 2015 (Dec. 11, 2015).
Miller et al., "Solvent Systems for Crystallization and Polymorph Selection" Chapter 3 in Solvent Systems and Their Selection in Pharmaceutics and Biopharmaceutics Series Biotechnology: Pharmaceutical Aspects vol. VI Augustijns, Patrick; Brewster, Marcus (Eds.) 2007.
Peterson et al., "Expanding the Scope of Crystal Form Evaluation in Parmaceutical Science" Journal of Pharmacy & Pharmaceutical Science 2006 9(3):317-326.
European Search Report issued in EP 16828471, completed Mar. 15, 2019.
European Search Report issued in EP 16818768, completed Jan. 22, 2019.
Johnson et al., "Discovery of (10R)-7-Amino-12-fluoro-2,10,16-trimethyl-15-oxo-10,15,16,17-tetrahydro-2H-8,4-(methano)pyrazolo[4,3-h][2,5,11]-benzoxadiazacyclotetradecine-3-carbonitrile (PF-06463922), a Macrocyclic Inhibitor of Anaplastic Lymphoma Kinase (ALK) and c-ros Oncogene 1 (ROS1) with

(56) References Cited

OTHER PUBLICATIONS

Preclinical Brain Exposure and Broad-Spectrum Potency against ALK-Resistant Mutations", J. Med. Chem., Jun. 12, 2014, 57, 4720-4744.
Zou et al., "PF-06463922 is a potent and selective next-generation ROS1/ALK inhibitor capable of blocking crizotinib-resistant ROS1 mutations", PNAS, Mar. 17, 2015, vol. 112, No. 11, 3493-3498.
Jordan, "Tamoxifen: A Most Unlikely Pioneering Medicine", Nature Reviews, vol. 2, Mar. 2003, pp. 205-213.
Hackam et al., "Translation of Research evidence From Animals to Humans", JAMA, 2006; 296(14): 1731-1732.
Liu L, et al. Nature, 2012, 483, 608-612.
Zardan A., et al. Oncogenesis 2014, 3, e 115.
Mulligan, LM. Nat Rev Cancer. 2014, 14(3):173-86.
Fujita-Sato, S., et al. Enhanced MET Translation and Signaling Sustains K-Ras-Driven Proliferation under Anchorage-Independent Growth Conditions. Cancer Res. 2015, 75, 2851-2862.
Song N, et al. Cetuximab-induced MET activation acts as a novel resistance mechanism in colon cancer cells. Int J Mol Sci. 2014, 15, 5838-5851.
Ries CH, et al. Targeting tumor-associated macrophages with anti-CSF1R antibody reveals a strategy for cancer therapy. Cancer Cell. 2014, 25, 846-859.
Baldanzi et al., "Physiological Signaling and Structure of the HGF Receptor MET", Biomedicines 2015, 3, 1-31. First published Dec. 31, 2014.
Okamoto et al., "Identification of c-Src as a Potential Activation as a Cause of Resistance to c-Src Published online Apr. 20, 2010 Inhibition", Therapeutic Target for Gastric Cancer and of MET Mol Cancer Ther., May 2010; 9(5): 1188-97.
Heynen et al., "Resistance to targeted cancer drugs through hepatocyte growth factor signaling", Cell Cycle, 2014, 13:24, 3808-3817. Accepted Nov. 11, 2014.
Vergani et al., "Identification of MET and SRC Activation in Melanoma Cell Lines Showing Primary Resistance to PLX4032", Neoplasia. Dec. 2011; 13(12): 1132-42.
Pennacchietti et al., "Microenvironment-Derived HGF Overcomes Genetically Determined Sensitivity Anti-MET Drugs", Cancer Res. Nov. 15, 2014; 74(22): 6598-609. Published online Sep. 12, 2014.
Lim et al.,"Discovery of 5-Amino-N-(IH-pyrazol-4-yl)pyrazolo[I,5-a]pyrimidine-3-carboxamide Inhibitors of IRAK4," ACS Medicinal Chemistry Letters (2015), 6(6), 683-688.
Pachter et al., "The Chemistry of Hortiamine and 6-Methoxyrhetsinine," J. Am. Chem. Soc., 1961, 83, 635-642.
Wang et al., "Discovery of novel pyrazolo[1,5-a]pyrimidines as potent pan-Pim inhibitors by structure- and property-based drug design," Bioorganic & Medicinal Chemistry Letters (2013), 23(11), 3149-3153.
Gavrin et al., "Synthesis of Pyrazolo[1,5-alpha]pyrimidinone Regioisomers," Journal of Organic Chemistry (2007), 72(3), 1043-1046.
Rover et al., "Identification of 4-methyl-1,2,3,4, 10, 1 Oa-hexahydropyrazino[I,2-a]indoles as 5-HT2C receptor agonists," Bioorganic & Medicinal Chemistry Letters (2005), 15(15), 3604-3608.
Halland et al. "Small Macrocycles as Highly Active Integrin 0131 Antagonists," ACS Medicinal Chemistry Letters, Jan. 10, 2014, 5, 193-198.
Kiselyov, Alexander S., "Solid support synthesis of 15-membered macrocycles containing a serotonin unit," Tetrahedron Letters 46 (2005) 3007-3010.
Sawyers, C., Nature 2004, 432, 294-297.
Park, M. et al., Cell 1986, 45, 895-904.
Bottaro, D. P. etal., Science 1991, 251, 802-804.
Trusolino, L. et al., Nature Rev. Mol. Cell Biol. 2010, 11, 834-848.
Gherardi, E. et al., Nature Rev. Cancer 2012, 12, 89-103.
Engelman, J. A. et al., Science 2007, 316, 1039-1043.
Wilson, T.R. et al., Nature 2012, 487, 505-509.
Pulford, K. et al., Cell Mol. Life Sci. 2004, 61, 2939.
Morris, S.W. et al., Science 1994, 263, 1281.
Bischof, D. et al., Mol. Cell Biol., 1997, 17, 2312-2325.
Soda, M. et al., Nature 2007, 448, 561-566.
Mosse, Y. P. et al., Nature 2008, 455, 930-935.
Thiele, C. J. et al., Clin. Cancer Res. 2009, 15, 5962-5967.
Pierotti, M.A. et al., Cancer Lett. 2006, 232, 90-98.
Vaishnavi, A. et al., Nat. Med. 2013, 19, 1469-1472.
Verma, A. etal., Mol. CancerTher. 2011, JO, 1763-1773.
Zhang, Z. et al., Nat. Genet. 2012, 44, 852-860.
Cui, J. J. et al., J. Med. Chem. 2011, 54, 6342-6363.
Katayama, R. et al., Sci. Transl. Med. 2012, 4, 120ra17.
Quintas-Cardama, A. et al., Nat. Rev. Drug Discov. 2011, 10(2), 127-40.
Pesu, M. et al., Immunol. Rev. 2008, 223, 132-142.
Murray, P.J., J. Immunol. 2007, 178(5), 2623-2329.
Muller, M. et al., Nature 1993, 366(6451), 129-135.
International Search Report and Written Opinion prepared for PCT /US2016/040329, dated Sep. 7, 2016, 13 pages.
International Search Report and Written Opinion prepared for PCT /US2016/040972, dated Sep. 13, 2016, 8 pages.
Bender AT, et al. Clinical Immunology 2016, 164, 65-77, available online Jan. 25, 2016.
Gargalionis et al., "The molecular rationale of Src inhibition in colorectal carcinomas", Int. J. Cancer: 134, 2019-2029 (2014). Published online Jun. 21, 2013.
Neubauer, H. et al., Cell 1998 93(3), 397-409.
Nosaka, T. et al., Science 1995, 270(5237), 800-802.
Vainchenker, W. et al., Semin. Cell. Dev. Biol. 2008, 19(4), 385-393.
Levine, R.L. etal., Cancer Cell 2005, 7(4), 387-397.
Kralovics, R. et al., N. Engl. J. Med. 2005, 253(17), 1779-1790.
James, C. et al., Nature 2005, 434(7037), 1144-1148.
Baxter, E.J. et al. Lancet 2005, 365(9464), 1054-1061.
Sonbol, M.B. et al., Ther. Adv. Hematol. 2013, 4(1), 15-35.
LaFave, L.M. et al., Trends Pharmacol. Sci. 2012, 33(11), 574-582.
Verstovsek, S. et al., N. Engl. J. Med. 2012, 366(9), 799-807.
Quintas-Cardama, A. et al., Blood 2010, 115(15), 3109-3117.
Nefedova, Y. et al., Cancer Res 2005; 65(20): 9525-35.
Davies, K. D. et al., Clin Cancer Res 2013, 19 (15): 4040-4045.
Awad, M. M. et al., N Engl J Med. 2013, 368(25):2396-2401.
Charest A, et al Genes Chromosomes Cancer 2003, 37, 58.
Takeuchi K, et al Nat. Med. 2012, 18, 378.
Gu TL, et al PLoS One. 2011, 6, e15640.
Lacronique V, et al. Science 1997, 278, 5341, 1309-12.
Reiter A, et al. Cancer Res. 2005, 65, 7, 2662-7.
Zhang S, et al Trends Pharmacol Sci. 2012, 33, 122.
Bromann PA, Oncogene 2004, 23, 7957-7968.
Golubovskaya VM, Front Biosci (Landmark Ed). ; 19: 687-706.
Summy JM, et al. Cancer Metastasis Rev. 2003, 22, 337-358.
Scancier F. et al. PLoS One. 2011, 6(2): el 7237.
Ongusaha PP, et al. EMBO J. 2003, 22, 1289-1301.
Chiron D, et al. Cancer Discovery, 2014, 4, 1022-1035.
Woyach JA, el al. New England Journal of Medicine, 2014, 370, 2286-2294.
Hammerman PS, et al. Cancer Discov. 2011, 1, 78-89.
Tomasson MH, et al. Blood 2008, 111:4797-4808.
Yu J. et al., Cancer Cell, 2010, 17, 5, 443-54.
Advani, A.S. et al. Leukemia Research, 2002, 26, 8, 713-720.
Gottesman, M.M., Annu. Rev. Med., 2002, 53, 615-627.
Anastassiadis T, et al Nat Biotechnol. 2011, 29, 1039.
Vetrie D. et al. Nature 1993, 361, 226-233.
Mohamed AJ et al, immunological Reviews, 2009, 228, 58-73.
Grande, E. et al., Mol. Cancer Ther. 2011, 10, 569-579.
Monti, E 2007. Molecular Determinants of Intrinsic Multidrug Resistance in Cancer Cells and Tumors in B. Teicher (Ed.), Cancer Drug Resistance (pp. 241-260).
McCarthy et al. "Tropomyosin receptor kinase inhibitors: a patent update 2009-2013," Expert Opinions 2014, pp. 731-744.
Couronne L, et al. Blood 2013, 122, 811.
Di Paolo JA, et al. Nature Chemical Bioloav 2011, 7, 41-50.
Schiller J H et al., N Engl J Med, 346: 92-98, 2002.
Takahashi, M. et al. Cell. 1985, 42:581-588.
Pachnis, V., et al. Development 1993, 119, 1005-1017.
Schuchardt, A. et al. Nature 1994, 367:380-383.

(56) References Cited

OTHER PUBLICATIONS

Grieco, M. et al. Cell. 1990, 23; 60 (4):557-63.
Gainor JF, Shaw AT. Oncologist. 2013, 18(7):865-75.
Liu W, et al. Oncotarget. 2015, 6: 35522-35541.
Cooper, C. S., et al Molecular cloning of a new transforming gene from a chemically transformed human cell line. Nature 1984, 311, 29-33.
Boccaccio, C.; Comoglio, P. M. Invasive growth: a MET-driven generic programme for cancer and stem cells. Nat. Rev. Cancer 2006, 6, 637-645.
Ma, PC et al. Expression and mutational analysis of MET in human solid cancers. Genes Chromosomes Cancer 2008, 47, 1025-1037.
Zou et al., "An orally available small-molecule inhibitor of c-Met, PF-2341066, exhibits cytoreductive antitumor efficacy through anti proliferative and antiangiogenic mechanisms," Cancer Res., 2007, 67, 4408-17.
Sato, Kentaro, "Wide Use of Deuterium" Wakgo Organic Square, 2010, 33, pp. 1-3.
Buteau, Kristein, "Deuterated Drugs: Unexpectedly Nonobvious?" J. High Tech. Law, 2009, pp. 22-74.

CHIRAL DIARYL MACROCYCLES AS MODULATORS OF PROTEIN KINASES

CROSS REFERENCE TO RELATED APPLICATIONS

This application claims the benefit of U.S. patent application Ser. No. 15/740,462, filed on Dec. 28, 2017, which is a National Stage Entry of PCT/US2016/040329, filed on Jun. 30, 2016, which claims priority from U.S. Provisional Patent Application Ser. No. 62/188,043, filed on Jul. 2, 2015, and U.S. Provisional Patent Application Ser. No. 62/353,728, filed on Jun. 23, 2016, the entire disclosures of which are incorporated herein by reference.

TECHNICAL FIELD

The present disclosure relates to certain chiral diaryl macrocyclic derivatives, pharmaceutical compositions containing them, and methods of using them to treat cancer, pain, neurological diseases, autoimmune diseases, and inflammation.

BACKGROUND

Protein kinases are key regulators for cell growth, proliferation and survival. Genetic and epigenetic alterations accumulate in cancer cells leading to abnormal activation of signal transduction pathways which drive malignant processes. Manning, G. et al., *Science* 2002, 298, 1912-1934. Pharmacological inhibition of these signaling pathways presents promising intervention opportunities for targeted cancer therapies. Sawyers, C., *Nature* 2004, 432, 294-297.

ALK, along with leukocyte tyrosine kinase (LTK), is grouped within the insulin receptor (IR) superfamily of receptor tyrosine kinases. ALK is mainly expressed in the central and peripheral nervous systems suggesting a potential role in normal development and function of the nervous system. Pulford, K. et al., *Cell Mol. Life Sci.* 2004, 61, 2939. ALK was first discovered as a fusion protein, NPM (nucleophosmin)-ALK, encoded by a fusion gene arising from the t(2; 5)(p23; q35) chromosomal translocation in anaplastic large cell lymphoma (ALCL) cell lines. Morris, S. W. et al., *Science* 1994, 263, 1281. More than twenty distinct ALK translocation partners have been discovered in many cancers, including ALCL (60-90% incidence), inflammatory myofibroblastic tumors (IMT, 50-60%), non-small cell lung carcinomas (NSCLC, 3-7%), colorectal cancers (CRC, 0-2.4%), breast cancers (0-2.4%), and other carcinomas. Grande, E. et al., *Mol. Cancer Ther.* 2011, 10, 569-579. The ALK-fusion proteins are located in the cytoplasm, and the fusion partners with ALK play a role in dimerization or oligomerization of the fusion proteins through a coil-coil interaction to generate constitutive activation of ALK kinase function. Bischof, D. et al., *Mol. Cell Biol.*, 1997, 17, 2312-2325. EML4-ALK, which comprises portions of the echinoderm microtubule associated protein-like 4 (EML4) gene and the ALK gene, was first discovered in NSCLC, is highly oncogenic, and was shown to cause lung adenocarcinoma in transgenic mice. Soda, M. et al., *Nature* 2007, 448, 561-566. Oncogenic point mutations of ALK in both familial and sporadic cases of neuroblastoma. Mossé, Y. P. et al., *Nature* 2008, 455, 930-935. ALK is an attractive molecular target for cancer therapeutic intervention because of the important roles in haematopoietic, solid, and mesenchymal tumors. Grande, supra.

The tropomyosin-related receptor tyrosine kinases (Trks) are the high-affinity receptor for neurotrophins (NTs), a nerve growth factor (NGF) family of proteins. Members of the Trk family are highly expressed in cells of neural origin. Activation of Trks (TrkA, TrkB, and TrkC) by their preferred neurotrophins (NGF to TrkA, brain-derived neurotrophic factor [BDNF] and NT4/5 to TrkB, and NT3 to TrkC) mediates the survival and differentiation of neurons during development. The NT/Trk signaling pathway functions as an endogenous system that protects neurons after biochemical insults, transient ischemia, or physical injury. Thiele, C. J. et al., *Clin. Cancer Res.* 2009, 15, 5962-5967. However, Trk was originally cloned as an oncogene fused with the tropomyosin gene in the extracellular domain. The activating mutations caused by chromosomal rearrangements or mutations in NTRK1 (TrkA) has been identified in papillary and medullary thyroid carcinoma, and recently in non-small cell lung cancer. Pierotti, M. A. et al., *Cancer Lett.* 2006, 232, 90-98; Vaishnavi, A. et al., *Nat. Med.* 2013, 19, 1469-1472. Because Trks play important roles in pain sensation as well as tumor cell growth and survival signaling, inhibitors of Trk receptor kinases may provide benefits as treatments for pain and cancer.

The Janus family of kinases (JAKs) includes JAK1, JAK2, JAK3 and TYK2, and are cytoplastic tyrosine kinases required for the physiologic signaling of cytokines and growth factors. Quintas-Cardama, A. et al., *Nat. Rev. Drug Discov.* 2011, 10(2), 127-40; Pesu, M. et al., *Immunol. Rev.* 2008, 223, 132-142; Murray, P. J., *J. Immunol.* 2007, 178(5), 2623-2329. JAKs activate by ligand-induced oligomerization, resulting in the activation of downstream transcriptional signaling pathway called STAT (signal transducers and activators of transcription). The phosphorylated STATs dimerize and translocate into nucleus to drive the expression of specific genes involved in proliferation, apoptosis, differentiation, which are essential for hematopoiesis, inflammation and immune response. Murray, supra.

Mouse knockout studies have implicated the primary roles of JAK-STAT signaling with some overlap between them. JAK1 plays a critical role in the signaling of various proinflammatory cytokines such as IL-1, IL-4, IL-6, and tumor necrosis factor alpha (TNFα). Muller, M. et al., *Nature* 1993, 366(6451), 129-135. JAK2 functions for hematopoietic growth factors signaling such as Epo, IL-3, IL-5, GM-CSF, thrombopoietin growth hormone, and prolactin-mediated signaling. Neubauer, H. et al., *Cell* 1998 93(3), 397-409. JAK3 plays a role in mediating immune responses, and TYK2 associates with JAK2 or JAK3 to transduce signaling of cytokines, such as IL-12. Nosaka, T. et al., *Science* 1995, 270(5237), 800-802; Vainchenker, W. et al., *Semin. Cell. Dev. Biol.* 2008, 19(4), 385-393.

Aberrant regulation of JAK/STAT pathways has been implicated in multiple human pathological diseases, including cancer (JAK2) and rheumatoid arthritis (JAK1, JAK3). A gain-of-function mutation of JAK2 (JAK2V617F) has been discovered with high frequency in MPN patients. Levine, R. L. et al., *Cancer Cell* 2005, 7(4), 387-397; Kralovics, R. et al., *N. Engl. J. Med.* 2005, 253(17), 1779-1790; James, C. et al., *Nature* 2005, 434(7037), 1144-1148; Baxter, E. J. et al. *Lancet* 2005, 365(9464), 1054-1061. The mutation in the JH2 pseudokinase domain of JAK2 leads to constitutively kinase activity. Cells containing JAK2V617F mutantation acquire cytokine-independent growth ability and often become tumor, providing strong rational for the development of JAK inhibitors as target therapy.

Multiple JAK inhibitors in clinical trial showed significant benefit in splenomegaly and disease related constitutional symptoms for the myelofibrosis patients, including the first FDA-approved JAK2 inhibitor ruxolitinib in 2011. Quintas-Cardama, supra; Sonbol, M. B. et al., *Ther. Adv. Hematol.* 2013, 4(1), 15-35; LaFave, L. M. et al., *Trends Pharmacol. Sci.* 2012, 33(11), 574-582. The recently collected clinical data related to ruxolitinib treatment indicated that JAK inhibitors work on both JAK2 wild-type and JAK2 mutated cases. Verstovsek, S. et al., *N. Engl. J. Med.* 2012, 366(9), 799-807; Quintas-Cardama, A. et al., *Blood* 2010, 115(15), 3109-3117. The discovery of selective inhibitors of JAK2 vs JAK1/3 remains an unsolved challenge. In addition, hyperactivation of the JAK2/signal transducers and activators of transcription 3 (JAK2/STAT3) is responsible for abnormal dendritic cell differentiation leading to abnormal dendritic cell differentiation and accumulation of immunosuppressive myeloid cells in cancer (Nefedova, Y. et al., *Cancer Res* 2005; 65(20): 9525-35). In Pten-null senescent tumors, activation of the Jak2/Stat3 pathway establishes an immunosuppressive tumor microenvironment that contributes to tumor growth and chemoresistance (Toso, A. et al., *Cell Reports* 2014, 9, 75-89). Therefore, pharmacologic inhibition of the JAK2/STAT3 pathway can be an important new therapeutic strategy to enhance antitumor activity via the regulation of antitumor immunity.

ROS1 kinase is a receptor tyrosine kinase with an unknown ligand. The normal functions of human ROS1 kinase have not been fully understood. However, it has been reported that ROS1 kinase undergoes genetic rearrangements to create constitutively active fusion proteins in a variety of human cancers including glioblastoma, non-small cell lung cancer (NSCLC), cholangiocarcinoma, ovarian cancer, gastric adenocarcinoma, colorectal cancer, inflammatory myofibroblastic tumor, angiosarcoma, and epithelioid hemangioendothelioma (Davies, K. D. et al., *Clin Cancer Res* 2013, 19 (15): 4040-4045). Targeting ROS1 fusion proteins with crizotinib has demonstrated promising clinical efficacy in NSCLC patients whose tumors are positive for ROS1 genetic abnormalities (Shaw, A. T. et al., *N Engl J Med.* 2014, 371(21):1963-1971). Acquired resistant mutations have been observed in crizotinib treatment patients (Awad, M. M. et al., *N Engl J Med.* 2013, 368(25): 2396-2401). It is urgent to develop the second generation of ROS1 inhibitors for overcoming crizotinib ROS1 resistance.

Crizotinib (PF-02341066) is a tyrosine kinase drug targeting MET/ALK/ROS1/RON with moderate activity against TRKs and AXL. Cui, J. J. et al., *J. Med. Chem.* 2011, 54, 6342-6363. It was approved to treat certain patients with late-stage (locally advanced or metastatic) NSCLC that expresses the abnormal ALK fusion gene identified by a companion diagnostic test (Vysis ALK Break Apart FISH Probe Kit). Similar to imatinib and other kinase inhibitor drugs, resistance invariably develops after a certain time of treatment with crizotinib. The resistance mechanisms include ALK gene amplification, secondary ALK mutations, and aberrant activation of other kinases including KIT and EGFR. Katayama, R. et al., *Sci. Transl. Med.* 2012, 4, 120ra17. Based on the clinical success of second generation ABL inhibitors for the treatment of imatinib resistance in CML patients, a second generation of ALK inhibitors is emerging. These drugs target the treatment of crizotinib-refractory or resistant NSCLC patient with more potent inhibition against both wild and mutant ALK proteins. Gridelli, C. et al., *Cancer Treat Rev.* 2014, 40, 300-306.

There remains a need for small molecule inhibitors of these multiple protein or tyrosine kinase targets with desirable pharmaceutical properties. Certain chiral diaryl macrocyclic compounds have been found in the context of this disclosure to have this advantageous activity profile.

SUMMARY

In one aspect, the disclosure relates to a compound of the formula I

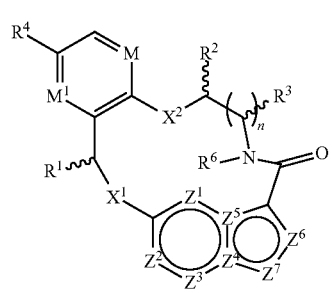

wherein
M is $CR^{4a}$ or N;
$M^1$ is $CR^5$ or N;
$X^1$ and $X^2$ are independently S, S(O), S(O)$_2$, O or N(R$^9$);
$R^1$ is H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^7$ or —C(O)NR$^7$R$^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^7$ or —C(O)NR$^7$R$^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl; or R$^2$ and R$^3$ taken together with the carbon atoms to which they are attached optionally form a C$_5$-C$_7$ cycloalkyl or a 5- to 7-membered heterocycloalkyl; or R$^2$ and R$^6$ taken together with the atoms to which they are attached optionally form a 5- to 7-membered heterocycloalkyl;

R$^4$, R$^{4a}$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, C$_3$-C$_6$ cycloalkyl, or monocyclic 5- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or heteroaryl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —OC$_1$-C$_6$ alkyl, —OH, —NH$_2$, —NH(C$_1$-C$_6$ alkyl), —NH(phenyl), —NH(heteroaryl), —CN, or —CF$_3$, n is 1 or 2; and provided that at least one of Z$^1$, Z$^2$, Z$^3$, Z$^4$, Z$^5$, Z$^6$ or Z$^7$ is N or NH; and provided that at least one R$^1$, R$^2$ or R$^3$ is not H;

or a pharmaceutically acceptable salt thereof.

In one aspect, the disclosure relates to a compound of the formula I-1

I-1 wherein

M is CR$^{4a}$ or N;

X$^1$ and X$^2$ are independently S, S(O), S(O)$_2$, O or N(R$^9$);

R$^1$ is C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each of R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$, R$^{4a}$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, C$_3$-C$_6$ cycloalkyl, or monocyclic 5- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or heteroaryl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —OC$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof.

In another aspect, the disclosure relates to a compound of the formula Ia

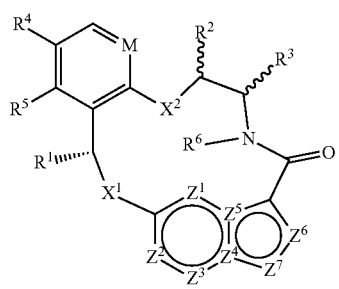

Ia wherein

M is CR$^{4a}$ or N;

X$^1$ and X$^2$ are independently S, S(O), S(O)$_2$, O or N(R$^9$);

R$^1$ is C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each of R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$, R$^{4a}$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, C$_3$-C$_6$ cycloalkyl, or monocyclic 5- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or heteroaryl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —OC$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof.

In another aspect, the disclosure relates to a compound of the formula Ib

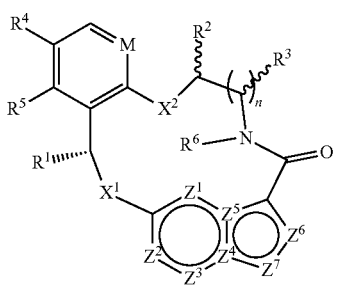

wherein

M is $CR^{4a}$ or N;

$X^1$ and $X^2$ are independently S, S(O), S(O)$_2$, O or N(R$^9$);

$R^1$ is $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^7$ or —C(O)NR$^7$R$^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^7$ or —C(O)NR$^7$R$^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, $C_3$-$C_6$ cycloalkyl, or 3- to 7-membered heterocycloalkyl; or $R^2$ and $R^3$ taken together with the carbon atoms to which they are attached optionally form a $C_5$-$C_7$ cycloalkyl or a 5- to 7-membered heterocycloalkyl; or $R^2$ and $R^6$ taken together with the atoms to which they are attached optionally form a 5- to 7-membered heterocycloalkyl;

$R^4$, $R^{4a}$ and $R^5$ are each independently H, fluoro, chloro, bromo, $C_1$-$C_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, $C_3$-$C_6$ cycloalkyl, or monocyclic 5- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or heteroaryl;

each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —OR$^7$;

each $Z^1$, $Z^2$, $Z^3$, $Z^4$, $Z^5$, $Z^6$ or $Z^7$ is independently N, NH, or C(R$^{10}$), wherein each $R^{10}$ is independently H, deuterium, halogen, $C_1$-$C_6$ alkyl, —OC$_1$-C$_6$ alkyl, —OH, —NH$_2$, —NH(C$_1$-C$_6$ alkyl), —NH(phenyl), —NH(heteroaryl), —CN, or —CF$_3$, n is 1 or 2; and provided that at least one of $Z^1$, $Z^2$, $Z^3$, $Z^4$, $Z^5$, $Z^6$ or $Z^7$ is N or NH;

or a pharmaceutically acceptable salt thereof.

In another aspect, the disclosure relates to a compound of the formula Ic

Ic wherein

M is $CR^{4a}$ or N;

$X^1$ and $X^2$ are independently S, S(O), S(O)$_2$, O or N(R$^9$);

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^7$ or —C(O)NR$^7$R$^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl; or R$^2$ and R$^3$ taken together with the carbon atoms to which they are attached optionally form a C$_5$-C$_7$ cycloalkyl or a 5- to 7-membered heterocycloalkyl; or R$^2$ and R$^6$ taken together with the atoms to which they are attached optionally form a 5- to 7-membered heterocycloalkyl;

R$^4$, R$^{4a}$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, C$_3$-C$_6$ cycloalkyl, or monocyclic 5- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or heteroaryl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —O—C$_1$-C$_6$ alkyl, —OH, —NH$_2$, —NH(C$_1$-C$_6$ alkyl), —NH(phenyl), —NH(heteroaryl), —CN, or —CF$_3$, n is 1 or 2; and provided that at least one of Z$^1$, Z$^2$, Z$^3$, Z$^4$, Z$^5$, Z$^6$ or Z$^7$ is N or NH;

or a pharmaceutically acceptable salt thereof.

In another aspect, the disclosure relates to a compound of the formula II

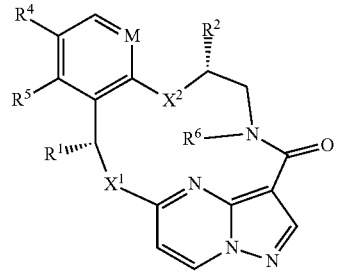

wherein

M is CH or N;

X$^1$ and X$^2$ are independently S, S(O), S(O)$_2$, O or N(R$^9$);

each of R$^1$ and R$^2$ is independently C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, —C$_3$-C$_6$ cycloalkyl, or 3- to 7-membered heterocycloalkyl;

R$^4$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, C$_3$-C$_6$ cycloalkyl, or monocyclic 5- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or heteroaryl; and each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, $C_1$-$C_6$ alkyl, $C_1$-$C_6$ haloalkyl or —$OR^7$;

or a pharmaceutically acceptable salt thereof.

In another aspect, the disclosure relates to a compound of the formula III

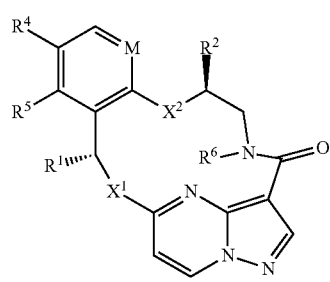

III wherein

M is CH or N;

$X^1$ and $X^2$ are independently S, S(O), S(O)$_2$, O or N($R^9$);

each of $R^1$ and $R^2$ is independently $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)$OR^7$ or —C(O)$NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)$NH_2$, —NHC(O)NH$C_1$-$C_6$ alkyl, N($C_1$-$C_6$ alkyl)C(O)$NH_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)$OC_1$-$C_6$ alkyl, —N($C_1$-$C_6$ alkyl)C(O)$OC_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)$NH_2$, —NHS(O)$_2NH_2$, —N($C_1$-$C_6$ alkyl)S(O)$NH_2$, —N($C_1$-$C_6$ alkyl)S(O)$_2NH_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —$CO_2H$, —C(O)$OC_1$-$C_6$ alkyl, —C(O)$NH_2$, —C(O)NH($C_1$-$C_6$ alkyl), —C(O)N($C_1$-$C_6$ alkyl)$_2$, —$SC_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^4$ and $R^5$ are each independently H, fluoro, chloro, bromo, $C_1$-$C_6$ alkyl, —OH, —CN, —$OC_1$-$C_6$ alkyl, —$NHC_1$-$C_6$ alkyl, —N($C_1$-$C_6$ alkyl)$_2$ or —$CF_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —$OC_1$-$C_6$ alkyl, —$NH_2$, —NH($C_1$-$C_6$ alkyl), —N($C_1$-$C_6$ alkyl)$_2$, —$CO_2H$, —C(O)$OC_1$-$C_6$ alkyl, —C(O)$NH_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^7$;

or a pharmaceutically acceptable salt thereof.

In another aspect, the disclosure relates to a compound of the formula IV

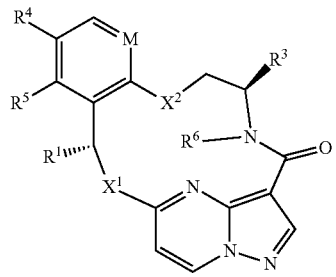

IV wherein

M is CH or N;

$X^1$ and $X^2$ are independently S, S(O), S(O)$_2$, O or N($R^9$);

each of $R^1$ and $R^3$ is independently $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)$OR^7$ or —C(O)$NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)$NH_2$, —NHC(O)NH$C_1$-$C_6$ alkyl, —N($C_1$-$C_6$ alkyl)C(O)$NH_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)$OC_1$-$C_6$ alkyl, —N($C_1$-$C_6$ alkyl)C(O)$OC_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)$NH_2$, —NHS(O)$_2NH_2$, —N($C_1$-$C_6$ alkyl)S(O)$NH_2$, —N($C_1$-$C_6$ alkyl)S(O)$_2NH_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —$CO_2H$, —C(O)$OC_1$-$C_6$ alkyl, —C(O)$NH_2$, —C(O)NH($C_1$-$C_6$ alkyl), —C(O)N($C_1$-$C_6$ alkyl)$_2$, —$SC_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^4$ and $R^5$ are each independently H, fluoro, chloro, bromo, $C_1$-$C_6$ alkyl, —OH, —CN, —$OC_1$-$C_6$ alkyl, —$NHC_1$-$C_6$ alkyl, —N($C_1$-$C_6$ alkyl)$_2$ or —$CF_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —$OC_1$-$C_6$ alkyl, —$NH_2$, —NH($C_1$-$C_6$ alkyl), —N($C_1$-$C_6$ alkyl)$_2$, —$CO_2H$, —C(O)$OC_1$-$C_6$ alkyl, —C(O)$NH_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^7$;

or a pharmaceutically acceptable salt thereof.

In another aspect, the disclosure relates to a compound of the formula V

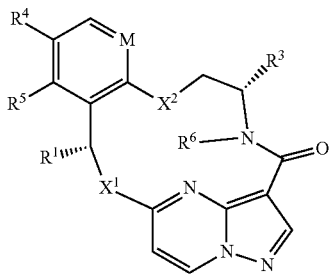

V wherein

M is CH or N;

$X^1$ and $X^2$ are independently S, S(O), S(O)$_2$, O or N($R^9$);

each of $R^1$ and $R^3$ is independently $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)$OR^7$ or —C(O)$NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O) $C_1$-$C_6$ alkyl, —N($C_1$-$C_6$ alkyl)C(O)$C_1$-$C_6$ alkyl, —NHC(O) NH$_2$, —NHC(O)NH$C_1$-$C_6$ alkyl, —N($C_1$-$C_6$ alkyl)C(O) NH$_2$, —N($C_1$-$C_6$ alkyl)C(O)NH$C_1$-$C_6$ alkyl, —NHC(O)N ($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl) S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S (O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH ($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^4$ and $R^5$ are each independently H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^7$;

or a pharmaceutically acceptable salt thereof.

In another aspect, the disclosure relates to a compound of the formula VI

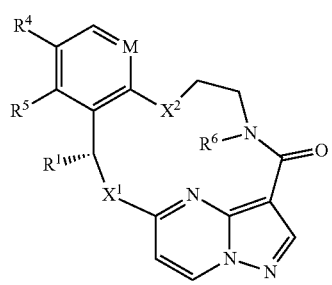

VI wherein

M is CH or N;

$X^1$ and $X^2$ are independently S, S(O), S(O)$_2$, O or N($R^9$);

$R^1$ is $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)$OR^7$ or —C(O)$NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C (O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O) NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS (O)$_2$NH($C_1$-$C_6$ alkyl), —NHS(O)N($C_1$-$C_6$ alkyl)$_2$, —NHS (O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O) NH($C_1$-$C_6$ alkyl), —S(O)$_2$NH($C_1$-$C_6$ alkyl), —S(O)N($C_1$-

C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, C$_3$-C$_6$ cycloalkyl, or monocyclic 5- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or heteroaryl; and each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^7$;

or a pharmaceutically acceptable salt thereof.

In another aspect, the disclosure relates to a compound selected from the group consisting of

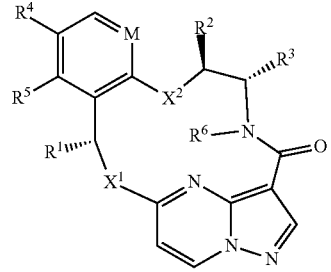
X

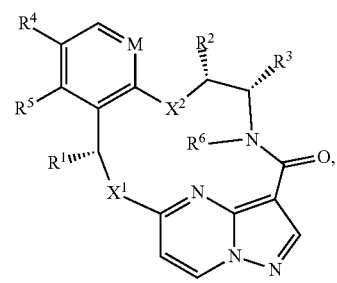
VII

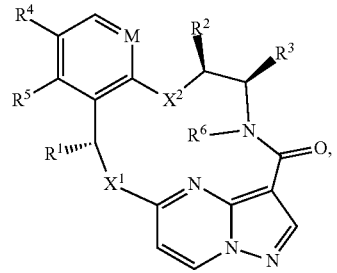
VIII

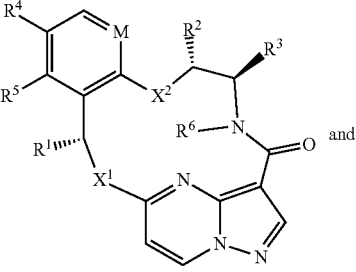
IX and wherein
M is CH or N;
X$^1$ and X$^2$ are independently S, S(O), S(O)$_2$, O or N(R$^9$);
R$^1$ is C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$;
wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^2$ and R$^3$ taken together with the carbon atoms to which they are attached optionally form a C$_5$-C$_7$ cycloalkyl or a 5- to 7-membered heterocycloalkyl;

R$^4$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, C$_3$-C$_6$ cycloalkyl, or monocyclic 5- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or heteroaryl; and each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^7$;

or a pharmaceutically acceptable salt thereof.

In another aspect, the disclosure relates to a compound selected from the group consisting of

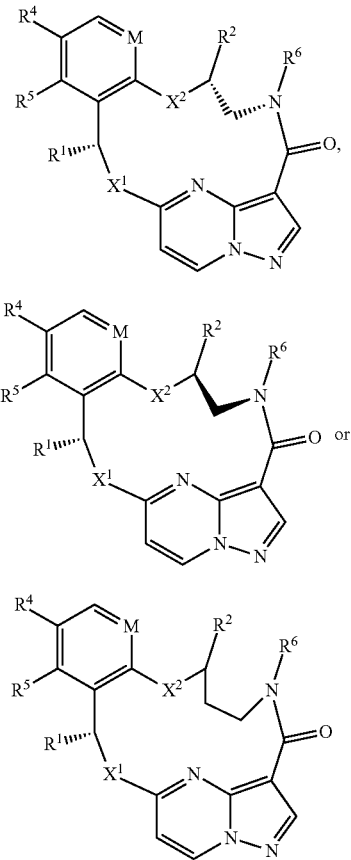

wherein

M is CH or N;

$X^1$ and $X^2$ are independently S, S(O), S(O)$_2$, O or N($R^9$);

$R^1$ is $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)$OR^7$ or —C(O)$NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —$NH_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)$NH_2$, —NHC(O)NH$C_1$-$C_6$ alkyl, —N($C_1$-$C_6$ alkyl)C(O)$NH_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)$NH_2$, —NHS(O)$_2NH_2$, —N($C_1$-$C_6$ alkyl)S(O)$NH_2$, —N($C_1$-$C_6$ alkyl)S(O)$_2NH_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —$CO_2H$, —C(O)O$C_1$-$C_6$ alkyl, —C(O)$NH_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^2$ and $R^6$ taken together with the atoms to which they are attached optionally form a 5- to 7-membered heterocycloalkyl;

$R^4$ and $R^5$ are each independently H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$ or —$CF_3$;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^7$;

or a pharmaceutically acceptable salt thereof.

In another aspect, the disclosure relates to a pharmaceutical composition comprising a compound of the Formula I, I-1, Ia, Ib, Ic, II, III, IV, V, VI, VII, VIII, IX, X, XI, XII or XIII, or a pharmaceutically acceptable salt thereof, and optionally at least one diluent, carrier or excipient.

In another aspect, the disclosure is directed to a method of treating cancer, pain, neurological diseases, autoimmune diseases, or inflammation comprising administering to a subject in need of such treatment an effective amount of at least one compound of Formula I, I-1, Ia, Ib, Ic, II, III, IV, V, VI, VII, VIII, IX, X, XI, XII or XIII, or a pharmaceutically acceptable salt thereof.

In another aspect, the disclosure is directed to use of a compound of Formula I, I-1, Ia, Ib, Ic, II, III, IV, V, VI, VII, VIII, IX, X, XI, XII or XIII, or a pharmaceutically acceptable salt thereof, in the preparation of a medicament for the treatment of cancer, pain, neurological diseases, autoimmune diseases, or inflammation.

In another aspect, the disclosure is directed to use of a compound of Formula I, I-1, Ia, Ib, Ic, II, III, IV, V, VI, VII, VIII, IX, X, XI, XII or XIII, or a pharmaceutically acceptable salt thereof, for treating cancer, pain, neurological diseases, autoimmune diseases, or inflammation In another aspect, the disclosure is directed to use of a compound of Formula I, I-1, Ia, Ib, Ic, II, III, IV, V, VI, VII, VIII, IX, X, XI, XII or XIII, or a pharmaceutically acceptable salt thereof, in the preparation of a medicament for the treatment of such diseases and medical conditions, and the use of such compounds and salts for treatment of such diseases and medical conditions.

In yet another aspect, the disclosure relates to a method of inhibiting protein or tyrosine kinases, including one or more of MET, ALK, ROS1, AXL, TRKs, and JAKs, comprising contacting a cell comprising one or more of such kinases with an effective amount of at least one compound of Formula I, I-1, Ia, Ib, Ic, II, III, IV, V, VI, VII, VIII, IX, X, XI, XII or XIII, or a pharmaceutically acceptable salt thereof, and/or with at least one pharmaceutical composition of the disclosure, wherein the contacting is in vitro, ex vivo, or in vivo.

Additional embodiments, features, and advantages of the disclosure will be apparent from the following detailed description and through practice of the disclosure. The compounds of the present disclosure can be described as embodiments in any of the following enumerated clauses.

It will be understood that any of the embodiments described herein can be used in connection with any other embodiments described herein to the extent that the embodiments do not contradict one another.

1. A compound of the formula I

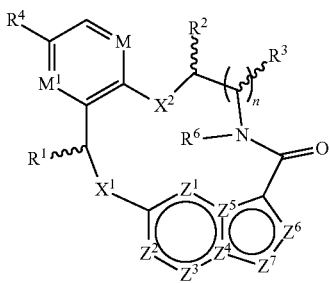

I wherein
M is $CR^{4a}$ or N;
$M^1$ is $CR^5$ or N;
$X^1$ and $X^2$ are independently S, S(O), S(O)$_2$, O or N($R^9$);
$R^1$ is H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl; or $R^2$ and $R^3$ taken together with the carbon atoms to which they are attached optionally form a $C_5$-$C_7$ cycloalkyl or a 5- to 7-membered heterocycloalkyl; or $R^2$ and $R^6$ taken together with the atoms to which they are attached optionally form a 5- to 7-membered heterocycloalkyl;

$R^4$, $R^{4a}$ and $R^5$ are each independently H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or heteroaryl;

each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —O$R^7$;

each $Z^1$, $Z^2$, $Z^3$, $Z^4$, $Z^5$, $Z^6$ or $Z^7$ is independently N, NH, or C($R^{10}$), wherein each $R^{10}$ is independently H, deuterium, halogen, $C_1$-$C_6$ alkyl, —O$C_1$-$C_6$ alkyl, —OH, —NH$_2$, —NH($C_1$-$C_6$ alkyl), —NH(phenyl), —NH(heteroaryl), —CN, or —CF$_3$;

n is 1 or 2; and provided that at least one of $Z^1$, $Z^2$, $Z^3$, $Z^4$, $Z^5$, $Z^6$ or $Z^7$ is N or NH; and provided that at least one $R^1$, $R^2$ or $R^3$ is not H;

or a pharmaceutically acceptable salt thereof.

1a. A compound of the formula I-1

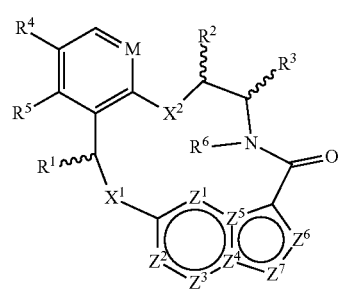

I-1 wherein

M is CR$^{4a}$ or N;

X$^1$ and X$^2$ are independently S, S(O), S(O)$_2$, O or N(R$^9$);

R$^1$ is C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each of R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$, R$^{4a}$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, C$_3$-C$_6$ cycloalkyl, or monocyclic 5- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or heteroaryl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —OC$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof.

2. The compound of clause 1 or 1a, having the formula Ia

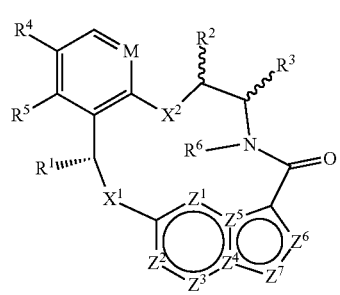

Ia wherein

M is CR$^{4a}$ or N;

X$^1$ and X$^2$ are independently S, S(O), S(O)$_2$, O or N(R$^9$);

R$^1$ is C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-

$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each of $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^7$ or —C(O)NR$^7$R$^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^4$, $R^{4a}$ and $R^5$ are each independently H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or heteroaryl;

each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —OR$^7$;

each $Z^1$, $Z^2$, $Z^3$, $Z^4$, $Z^5$, $Z^6$ or $Z^7$ is independently N, NH, or C(R$^{10}$), wherein each $R^{10}$ is independently H, deuterium, halogen, $C_1$-$C_6$ alkyl, —O$C_1$-$C_6$ alkyl, —OH, —NH$_2$, —NH($C_1$-$C_6$ alkyl), —NH(phenyl), —NH(heteroaryl), —CN, or —CF$_3$, and provided that at least one of $Z^1$, $Z^2$, $Z^3$, $Z^4$, $Z^5$, $Z^6$ or $Z^7$ is N or NH;

or a pharmaceutically acceptable salt thereof.

2a. The compound of clause 1 or 1a, having the formula Ib

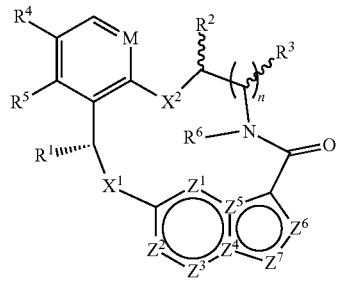

wherein

M is CR$^{4a}$ or N;

$X^1$ and $X^2$ are independently S, S(O), S(O)$_2$, O or N(R$^9$);

$R^1$ is $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^7$ or —C(O)NR$^7$R$^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NHC$_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^7$ or —C(O)NR$^7$R$^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-

$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl; or $R^2$ and $R^3$ taken together with the carbon atoms to which they are attached optionally form a $C_5$-$C_7$ cycloalkyl or a 5- to 7-membered heterocycloalkyl; or $R^2$ and $R^6$ taken together with the atoms to which they are attached optionally form a 5- to 7-membered heterocycloalkyl;

$R^4$, $R^{4a}$ and $R^5$ are each independently H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or heteroaryl;

each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —O$R^7$;

each $Z^1$, $Z^2$, $Z^3$, $Z^4$, $Z^5$, $Z^6$ or $Z^7$ is independently N, NH, or C($R^{10}$), wherein each $R^{10}$ is independently H, deuterium, halogen, $C_1$-$C_6$ alkyl, —O$C_1$-$C_6$ alkyl, —OH, —NH$_2$, —NH($C_1$-$C_6$ alkyl), —NH(phenyl), —NH(heteroaryl), —CN, or —CF$_3$, n is 1 or 2; and provided that at least one of $Z^1$, $Z^2$, $Z^3$, $Z^4$, $Z^5$, $Z^6$ or $Z^7$ is N or NH;

or a pharmaceutically acceptable salt thereof.

2b. The compound of clause 1 or 1a, having the formula Ic wherein

M is C$R^{4a}$ or N;

$X^1$ and $X^2$ are independently S, S(O), S(O)$_2$, O or N($R^9$);

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl; or $R^2$ and $R^3$ taken together with the carbon atoms to which they are attached optionally form a $C_5$-$C_7$ cycloalkyl or a 5- to 7-membered heterocycloalkyl; or $R^2$ and $R^6$ taken together with the atoms to which they are attached optionally form a 5- to 7-membered heterocycloalkyl;

$R^4$, $R^{4a}$ and $R^5$ are each independently H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or heteroaryl;

each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —O$R^7$;

each $Z^1$, $Z^2$, $Z^3$, $Z^4$, $Z^5$, $Z^6$ or $Z^7$ is independently N, NH, or C($R^{10}$), wherein each $R^{10}$ is independently H, deuterium, halogen, $C_1$-$C_6$ alkyl, —O—$C_1$-$C_6$ alkyl, —OH, —NH$_2$, —NH($C_1$-$C_6$ alkyl), —NH(phenyl), —NH(heteroaryl), —CN, or —CF$_3$, n is 1 or 2; and provided that at least one of $Z^1$, $Z^2$, $Z^3$, $Z^4$, $Z^5$, $Z^6$ or $Z^7$ is N or NH;

or a pharmaceutically acceptable salt thereof.

3. The compound of clause 1, 1a, 2, 2a or 2b, or a pharmaceutically acceptable salt thereof, wherein $Z^1$, $Z^4$ and $Z^7$ are N and $Z^2$, $Z^3$, $Z^5$ and $Z^6$ are CH.

4. The compound of any one of the preceding clauses, or a pharmaceutically acceptable salt thereof, wherein $X^1$ is N($R^9$).

5. The compound of any one of the preceding clauses, or a pharmaceutically acceptable salt thereof, wherein $R^9$ is H.

6. The compound of any one of the preceding clauses, or a pharmaceutically acceptable salt thereof, wherein $X^2$ is O.

7. The compound of any one of the preceding clauses, or a pharmaceutically acceptable salt thereof, wherein $R^2$ is $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl, and $R^3$ is H.

8. The compound of any one of clauses 1 to 6, or a pharmaceutically acceptable salt thereof, wherein $R^2$ is H, and $R^3$ is $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl.

9. The compound of any one of clauses 1 to 6, or a pharmaceutically acceptable salt thereof, wherein $R^2$ and $R^3$ are H.

10. The compound of any one of clauses 1 to 7, having the formula II

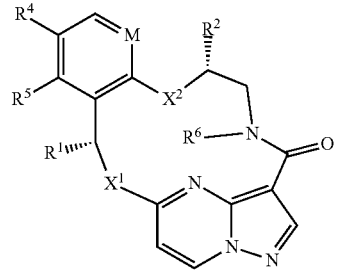

wherein

M is CH or N;

$X^1$ and $X^2$ are independently S, S(O), S(O)$_2$, O or N($R^9$);

each of $R^1$ and $R^2$ is independently $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, —$C_3$-$C_6$ cycloalkyl, or 3- to 7-membered heterocycloalkyl;

$R^4$ and $R^5$ are each independently H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^7$;

or a pharmaceutically acceptable salt thereof.

11. The compound of any one of clauses 1 to 7, having the formula III

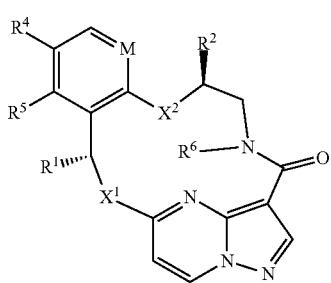

wherein

M is CH or N;

$X^1$ and $X^2$ are independently S, S(O), S(O)$_2$, O or N($R^9$);

each of $R^1$ and $R^2$ is independently $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)$OR^7$ or —C(O)$NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)$NH_2$, —NHC(O)NH$C_1$-$C_6$ alkyl, —N($C_1$-$C_6$ alkyl)C(O)$NH_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)$OC_1$-$C_6$ alkyl, —N($C_1$-$C_6$ alkyl)C(O)$OC_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)$NH_2$, —NHS(O)$_2NH_2$, —N($C_1$-$C_6$ alkyl)S(O)$NH_2$, —N($C_1$-$C_6$ alkyl)S(O)$_2NH_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —$CO_2H$, —C(O)$OC_1$-$C_6$ alkyl, —C(O)$NH_2$, —C(O)NH($C_1$-$C_6$ alkyl), —C(O)N($C_1$-$C_6$ alkyl)$_2$, —$SC_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^4$ and $R^5$ are each independently H, fluoro, chloro, bromo, $C_1$-$C_6$ alkyl, —OH, —CN, —$OC_1$-$C_6$ alkyl, —NH$C_1$-$C_6$ alkyl, —N($C_1$-$C_6$ alkyl)$_2$ or —$CF_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —$OC_1$-$C_6$ alkyl, —$NH_2$, —NH($C_1$-$C_6$ alkyl), —N($C_1$-$C_6$ alkyl)$_2$, —$CO_2H$, —C(O)$OC_1$-$C_6$ alkyl, —C(O)$NH_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^7$;

or a pharmaceutically acceptable salt thereof.

12. The compound of any one of clauses 1 to 6 or 8, having the formula IV

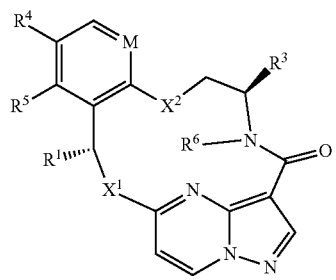

wherein

M is CH or N;

$X^1$ and $X^2$ are independently S, S(O), S(O)$_2$, O or N($R^9$);

each of $R^1$ and $R^3$ is independently $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)$OR^7$ or —C(O)$NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)$NH_2$, —NHC(O)NH$C_1$-$C_6$ alkyl, N($C_1$-$C_6$ alkyl)C(O)$NH_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)$OC_1$-$C_6$ alkyl, —N($C_1$-$C_6$ alkyl)C(O)$OC_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)$NH_2$, —NHS(O)$_2NH_2$, —N($C_1$-$C_6$ alkyl)S(O)$NH_2$, —N($C_1$-$C_6$ alkyl)S(O)$_2NH_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —$CO_2H$, —C(O)$OC_1$-$C_6$ alkyl, —C(O)$NH_2$, —C(O)NH($C_1$-$C_6$ alkyl), —C(O)N($C_1$-$C_6$ alkyl)$_2$, —$SC_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^4$ and $R^5$ are each independently H, fluoro, chloro, bromo, $C_1$-$C_6$ alkyl, —OH, —CN, —$OC_1$-$C_6$ alkyl, —NH$C_1$-$C_6$ alkyl, —N($C_1$-$C_6$ alkyl)$_2$ or —$CF_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —$OC_1$-$C_6$ alkyl, —$NH_2$, —NH($C_1$-$C_6$ alkyl), —N($C_1$-$C_6$ alkyl)$_2$, —$CO_2H$, —C(O)$OC_1$-$C_6$ alkyl, —C(O)$NH_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^7$;

or a pharmaceutically acceptable salt thereof.

13. The compound of any one of clauses 1 to 6 or 8, having the formula V

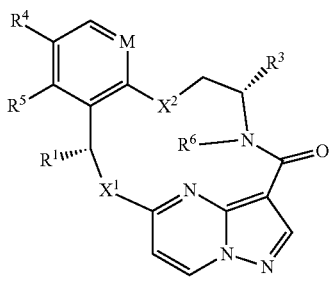

V wherein

M is CH or N;

$X^1$ and $X^2$ are independently S, S(O), S(O)$_2$, O or N($R^9$);

each of $R^1$ and $R^3$ is independently $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)$OR^7$ or —C(O)$NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^4$ and $R^5$ are each independently H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^7$;

or a pharmaceutically acceptable salt thereof.

14. The compound of any one of clauses 1 to 6 or 9, having the formula VI

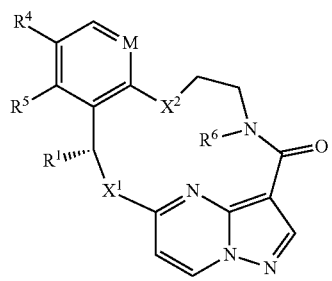

VI wherein

M is CH or N;

$X^1$ and $X^2$ are independently S, S(O), S(O)$_2$, O or N($R^9$);

$R^1$ is $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)$OR^7$ or —C(O)$NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-

$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^4$ and $R^5$ are each independently H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —OR$^7$;

or a pharmaceutically acceptable salt thereof.

14a. The compound of any one of clauses 1, 1a, 2 or 2a having a formula selected from the group consisting of

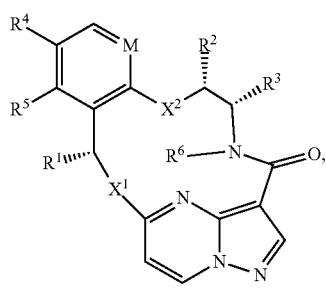

VII

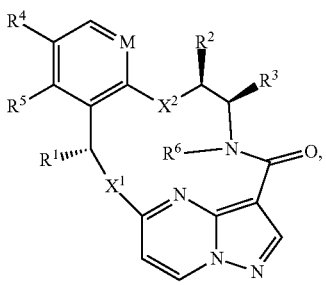

VIII

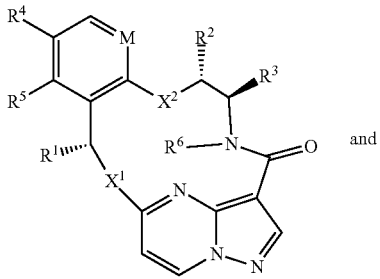

IX and

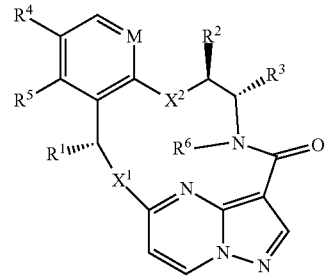

X wherein

M is CH or N;

$X^1$ and $X^2$ are independently S, S(O), S(O)$_2$, O or N($R^9$);

$R^1$ is $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^7$ or —C(O)NR$^7$R$^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^2$ and $R^3$ taken together with the carbon atoms to which they are attached optionally form a $C_5$-$C_7$ cycloalkyl or a 5- to 7-membered heterocycloalkyl;

$R^4$ and $R^5$ are each independently H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^7$;

or a pharmaceutically acceptable salt thereof.

14b. The compound of any one of clauses 1, 1a, 2 or 2a having a formula selected from the group consisting of

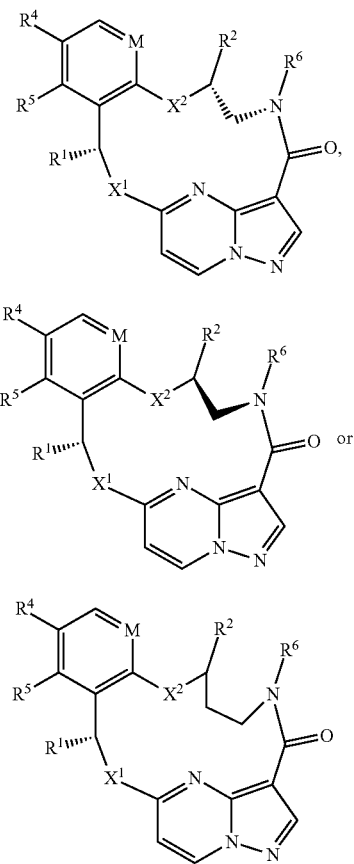

wherein
M is CH or N;
$X^1$ and $X^2$ are independently S, S(O), S(O)$_2$, or N($R^9$);
$R^1$ is $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)$OR^7$ or —C(O)$NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^2$ and $R^6$ taken together with the atoms to which they are attached optionally form a 5- to 7-membered heterocycloalkyl;

$R^4$ and $R^5$ are each independently H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$ or —$CF_3$;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^7$;

or a pharmaceutically acceptable salt thereof.

15. The compound of any one of the preceding clauses, or a pharmaceutically acceptable salt thereof, wherein $R^5$ is —H.

16. The compound of any one of the preceding clauses, or a pharmaceutically acceptable salt thereof, wherein $R^4$ is —F.

17. The compound of any one of clauses 1-7, 10, 11, 15 or 16, or a pharmaceutically acceptable salt thereof, wherein $R^2$, when present, is $C_1$-$C_6$ alkyl and each hydrogen atom in $C_1$-$C_6$ alkyl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl or 3- to 7-membered heterocycloalkyl.

18. The compound of any one of clauses 1-7, 10, 11 or 15 to 17, or a pharmaceutically acceptable salt thereof, wherein $R^2$, when present, is $C_1$-$C_6$ alkyl substituted with one or more moieties selected from group consisting of —F, —OH, —O$C_1$-$C_6$ alkyl, —NH$_2$, —NH($C_1$-$C_6$ alkyl), and —N($C_1$-$C_6$ alkyl)$_2$.

19. The compound of any one of clauses 1-7, 10, 11 or 15 to 18, or a pharmaceutically acceptable salt thereof, wherein $R^2$, when present, is methyl.

20. The compound of any one of clauses 1-7, 10, 11 or 15 to 18, or a pharmaceutically acceptable salt thereof, wherein $R^2$, when present, is ethyl.

21. The compound of any one of clauses 1-7, 10, 11 or 15 to 18, or a pharmaceutically acceptable salt thereof, wherein $R^2$, when present, is hydroxymethyl.

22. The compound of any one of clauses 1-7, 10, 11 or 15 to 18, or a pharmaceutically acceptable salt thereof, wherein $R^2$, when present, is fluoromethyl.

23. The compound of any one of clauses 1-7, 10, 11 or 15 to 18, or a pharmaceutically acceptable salt thereof, wherein $R^2$, when present, is methoxymethyl.

24. The compound of any one of clauses 1-7, 10, 11 or 15 to 18, or a pharmaceutically acceptable salt thereof, wherein $R^2$, when present, is difluoromethyl.

25. The compound of any one of clauses 1-7, 10, 11 or 15 to 18, or a pharmaceutically acceptable salt thereof, wherein $R^2$, when present, is trifluoromethyl.

26. The compound of any one of clauses 1-7, 10, 11 or 15 to 18, or a pharmaceutically acceptable salt thereof, wherein $R^2$, when present, is $C_1$-$C_6$ alkyl substituted with —$NH_2$, —$NH(C_1$-$C_6$ alkyl), or —$N(C_1$-$C_6$ alkyl$)_2$.

27. The compound of any one of clauses 1-7, 10, 11 or 15 to 18, or a pharmaceutically acceptable salt thereof, wherein $R^2$, when present, is methyl substituted with —$NH_2$, —$NH(C_1$-$C_6$ alkyl), or —$N(C_1$-$C_6$ alkyl$)_2$.

28. The compound of any one of clauses 1-7, 10, 11 or 15 to 18, or a pharmaceutically acceptable salt thereof, wherein $R^2$, when present, is methyl substituted with —$N(CH_3)_2$.

29. The compound of any one of clauses 1-7, 10, 11, 15 or 16, or a pharmaceutically acceptable salt thereof, wherein $R^2$, when present, is —$C(O)NR^7R^8$.

30. The compound of clause 29, or a pharmaceutically acceptable salt thereof, wherein $R^7$ and $R^8$ are H.

31. The compound of any one of clauses 1-6, 8, 12, 13, 15 or 16, or a pharmaceutically acceptable salt thereof, wherein $R^3$, when present, is $C_1$-$C_6$ alkyl and each hydrogen atom in $C_1$-$C_6$ alkyl is independently optionally substituted by deuterium, halogen, —OH, —CN, —$OC_1$-$C_6$ alkyl, —$NH_2$, —$NH(C_1$-$C_6$ alkyl), —$N(C_1$-$C_6$ alkyl$)_2$, $NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$-$C_6$ alkyl, $N(C_1$-$C_6$ alkyl)$C(O)NH_2$, —$N(C_1$-$C_6$ alkyl)$C(O)NHC_1$-$C_6$ alkyl, —$NHC(O)N(C_1$-$C_6$ alkyl$)_2$, —$N(C_1$-$C_6$ alkyl)$C(O)N(C_1$-$C_6$ alkyl$)_2$, —$NHC(O)OC_1$-$C_6$ alkyl, —$N(C_1$-$C_6$ alkyl)$C(O)OC_1$-$C_6$ alkyl, —$NHS(O)(C_1$-$C_6$ alkyl), —$NHS(O)_2(C_1$-$C_6$ alkyl), —$N(C_1$-$C_6$ alkyl)$S(O)(C_1$-$C_6$ alkyl), —$N(C_1$-$C_6$ alkyl)$S(O)_2(C_1$-$C_6$ alkyl), —$NHS(O)NH_2$, —$NHS(O)_2NH_2$, —$N(C_1$-$C_6$ alkyl)$S(O)NH_2$, —$N(C_1$-$C_6$ alkyl)$S(O)_2NH_2$, —$NHS(O)NH(C_1$-$C_6$ alkyl), —$NHS(O)_2NH(C_1$-$C_6$ alkyl), —$NHS(O)N(C_1$-$C_6$ alkyl$)_2$, —$NHS(O)_2N(C_1$-$C_6$ alkyl$)_2$, —$N(C_1$-$C_6$ alkyl)$S(O)NH(C_1$-$C_6$ alkyl), —$N(C_1$-$C_6$ alkyl)$S(O)_2NH(C_1$-$C_6$ alkyl), —$N(C_1$-$C_6$ alkyl)$S(O)N(C_1$-$C_6$ alkyl$)_2$, —$N(C_1$-$C_6$ alkyl)$S(O)_2N(C_1$-$C_6$ alkyl$)_2$, —$CO_2H$, —$C(O)OC_1$-$C_6$ alkyl, —$C(O)NH_2$, —$C(O)NH(C_1$-$C_6$ alkyl), —$C(O)N(C_1$-$C_6$ alkyl$)_2$, —$SC_1$-$C_6$ alkyl, —$S(O)C_1$-$C_6$ alkyl, —$S(O)_2C_1$-$C_6$ alkyl, —$S(O)NH(C_1$-$C_6$ alkyl), —$S(O)_2NH(C_1$-$C_6$ alkyl), —$S(O)N(C_1$-$C_6$ alkyl$)_2$, —$S(O)_2N(C_1$-$C_6$ alkyl$)_2$, —$P(C_1$-$C_6$ alkyl$)_2$, —$P(O)(C_1$-$C_6$ alkyl$)_2$, $C_3$-$C_6$ cycloalkyl or 3- to 7-membered heterocycloalkyl.

32. The compound of any one of clauses 1-6, 8, 12, 13, 15, 16 or 31, or a pharmaceutically acceptable salt thereof, wherein $R^3$, when present, is $C_1$-$C_6$ alkyl substituted with one or more moieties selected from group consisting of —F, —OH, —$OC_1$-$C_6$ alkyl, —$NH_2$, —$NH(C_1$-$C_6$ alkyl), and —$N(C_1$-$C_6$ alkyl$)_2$.

33. The compound of any one of clauses 1-6, 8, 12, 13, 15, 16, 31 or 32, or a pharmaceutically acceptable salt thereof, wherein $R^3$, when present, is methyl.

34. The compound of any one of clauses 1-6, 8, 12, 13, 15, 16, 31 or 32, or a pharmaceutically acceptable salt thereof, wherein $R^3$, when present, is ethyl.

35. The compound of any one of clauses 1-6, 8, 12, 13, 15, 16, 31 or 32, or a pharmaceutically acceptable salt thereof, wherein $R^3$, when present, is hydroxymethyl.

36. The compound of any one of clauses 1-6, 8, 12, 13, 15, 16, 31 or 32, or a pharmaceutically acceptable salt thereof, wherein $R^3$, when present, is fluoromethyl.

37. The compound of any one of clauses 1-6, 8, 12, 13, 15, 16, 31 or 32, or a pharmaceutically acceptable salt thereof, wherein $R^3$, when present, is methoxymethyl.

38. The compound of any one of clauses 1-6, 8, 12, 13, 15, 16, 31 or 32, or a pharmaceutically acceptable salt thereof, wherein $R^3$, when present, is difluoromethyl.

39. The compound of any one of clauses 1-6, 8, 12, 13, 15, 16, 31 or 32, or a pharmaceutically acceptable salt thereof, wherein $R^3$, when present, is trifluoromethyl.

40. The compound of any one of clauses 1-6, 8, 12, 13, 15, 16, 31 or 32, or a pharmaceutically acceptable salt thereof, wherein $R^3$, when present, is $C_1$-$C_6$ alkyl substituted with —$NH_2$, —$NH(C_1$-$C_6$ alkyl) or —$N(C_1$-$C_6$ alkyl$)_2$.

41. The compound of any one of clauses 1-6, 8, 12, 13, 15, 16, 31 or 32, or a pharmaceutically acceptable salt thereof, wherein $R^3$, when present, is methyl substituted with —$NH_2$, —$NH(C_1$-$C_6$ alkyl) or —$N(C_1$-$C_6$ alkyl$)_2$.

42. The compound of any one of clauses 1-6, 8, 12, 13, 15, 16, 31 or 32, or a pharmaceutically acceptable salt thereof, wherein $R^3$, when present, is methyl substituted with —$N(CH_3)_2$.

43. The compound of any one of clauses 1-6, 8, 12, 13, 15 or 16, or a pharmaceutically acceptable salt thereof, wherein $R^3$, when present, is —$C(O)NR^7R^8$.

44. The compound of clause 43, or a pharmaceutically acceptable salt thereof, wherein $R^7$ and $R^8$ are H.

45. The compound of any one of the preceding clauses, or a pharmaceutically acceptable salt thereof, wherein $R^1$, when present, is $C_1$-$C_6$ alkyl and each hydrogen atom in $C_1$-$C_6$ alkyl is independently optionally substituted by deuterium, halogen, —OH, —CN, —$OC_1$-$C_6$ alkyl, —$NH_2$, —$NH(C_1$-$C_6$ alkyl), —$N(C_1$-$C_6$ alkyl$)_2$, —$NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$-$C_6$ alkyl, $N(C_1$-$C_6$ alkyl)$C(O)NH_2$, —$N(C_1$-$C_6$ alkyl)$C(O)NHC_1$-$C_6$ alkyl, —$NHC(O)N(C_1$-$C_6$ alkyl$)_2$, —$N(C_1$-$C_6$ alkyl)$C(O)N(C_1$-$C_6$ alkyl$)_2$, —$NHC(O)OC_1$-$C_6$ alkyl, —$N(C_1$-$C_6$ alkyl)$C(O)OC_1$-$C_6$ alkyl, —$NHS(O)(C_1$-$C_6$ alkyl), —$NHS(O)_2(C_1$-$C_6$ alkyl), —$N(C_1$-$C_6$ alkyl)$S(O)(C_1$-$C_6$ alkyl), —$N(C_1$-$C_6$ alkyl)$S(O)_2(C_1$-$C_6$ alkyl), —$NHS(O)NH_2$, —$NHS(O)_2NH_2$, —$N(C_1$-$C_6$ alkyl)$S(O)NH_2$, —$N(C_1$-$C_6$ alkyl)$S(O)_2NH_2$, —$NHS(O)NH(C_1$-$C_6$ alkyl), —$NHS(O)_2NH(C_1$-$C_6$ alkyl), —$NHS(O)N(C_1$-$C_6$ alkyl$)_2$, —$NHS(O)_2N(C_1$-$C_6$ alkyl$)_2$, —$N(C_1$-$C_6$ alkyl)$S(O)NH(C_1$-$C_6$ alkyl), —$N(C_1$-$C_6$ alkyl)$S(O)_2NH(C_1$-$C_6$ alkyl), —$N(C_1$-$C_6$ alkyl)$S(O)N(C_1$-$C_6$ alkyl$)_2$, —$N(C_1$-$C_6$ alkyl)$S(O)_2N(C_1$-$C_6$ alkyl$)_2$, —$CO_2H$, —$C(O)OC_1$-$C_6$ alkyl, —$C(O)NH_2$, —$C(O)NH(C_1$-$C_6$ alkyl), —$C(O)N(C_1$-$C_6$ alkyl$)_2$, —$SC_1$-$C_6$ alkyl, —$S(O)C_1$-$C_6$ alkyl, —$S(O)_2C_1$-$C_6$ alkyl, —$S(O)NH(C_1$-$C_6$ alkyl), —$S(O)_2NH(C_1$-$C_6$ alkyl), —$S(O)N(C_1$-$C_6$ alkyl$)_2$, —$S(O)_2N(C_1$-$C_6$ alkyl$)_2$, —$P(C_1$-$C_6$ alkyl$)_2$, —$P(O)(C_1$-$C_6$ alkyl$)_2$, $C_3$-$C_6$ cycloalkyl or 3- to 7-membered heterocycloalkyl.

46. The compound of any one of the preceding clauses, or a pharmaceutically acceptable salt thereof, wherein R¹, when present, is $C_1$-$C_6$ alkyl substituted with one or more —F or —OH.

47. The compound of any one of clauses 1 to 46, or a pharmaceutically acceptable salt thereof, wherein R¹, when present, is $C_1$-$C_6$ alkyl.

48. The compound of any one of clauses 1 to 46, or a pharmaceutically acceptable salt thereof, wherein R¹, when present, is methyl.

49. The compound of any one of clauses 1 to 46, or a pharmaceutically acceptable salt thereof, wherein R¹, when present, is ethyl.

50. The compound of any one of clauses 1 to 46, or a pharmaceutically acceptable salt thereof, wherein R¹, when present, is 2-hydroxy-ethyl.

51. The compound of any one of clauses 1 to 46, or a pharmaceutically acceptable salt thereof, wherein R¹, when present, is 2-fluoro-ethyl.

52. The compound of any one of clauses 1 to 46, or a pharmaceutically acceptable salt thereof, wherein R¹, when present, is 2-hydroxy-2-propyl.

53. The compound of any one of the preceding clauses, or a pharmaceutically acceptable salt thereof, wherein M is $CR^{4a}$ 54. The compound of any one of the preceding clauses, or a pharmaceutically acceptable salt thereof, wherein M is $CR^{4a}$, and $R^{4a}$ is H.

55. The compound of clause 1, of the formula selected from the group consisting of

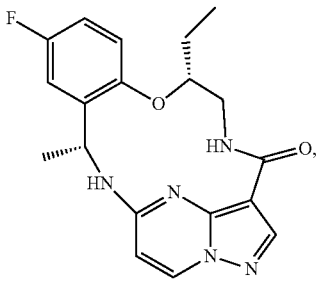

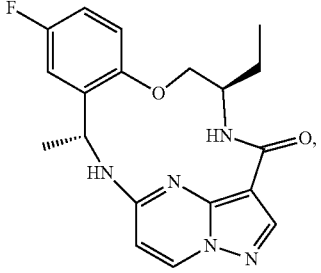

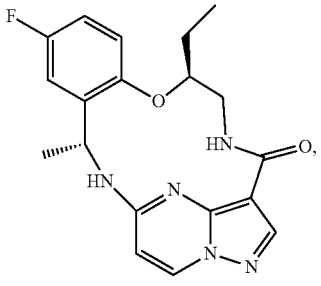

-continued

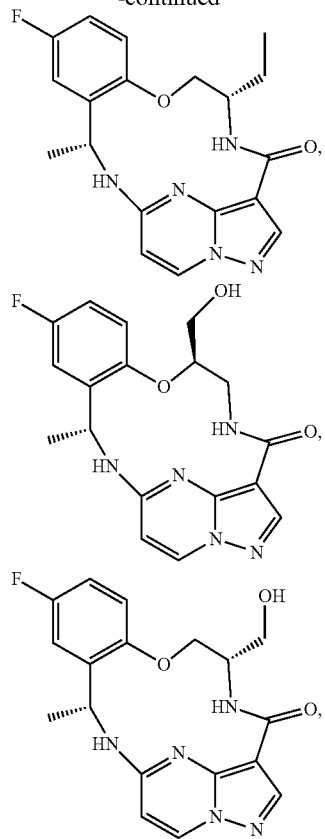

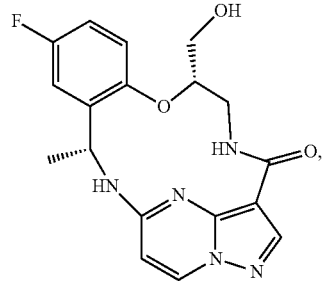

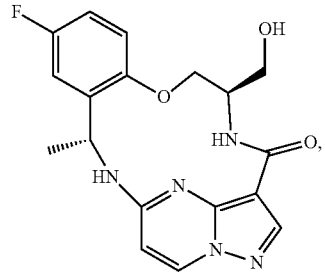

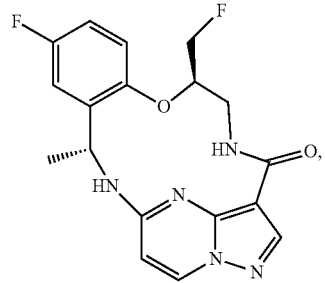

-continued
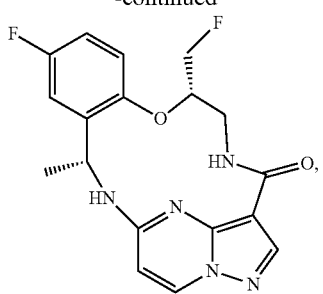
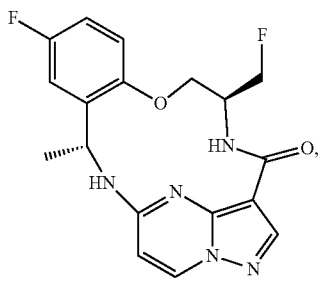
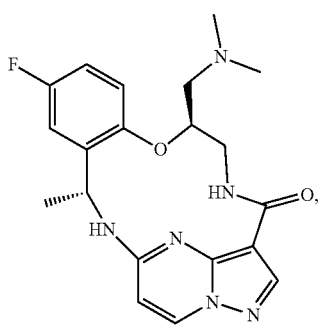
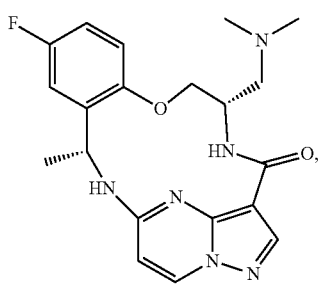
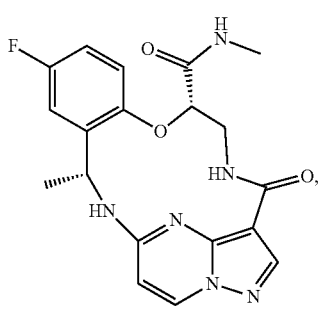
-continued
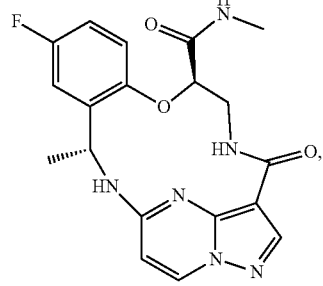
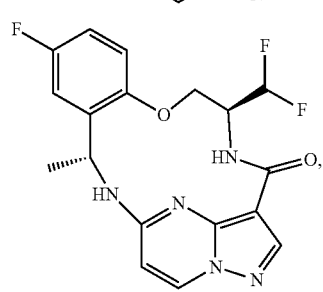
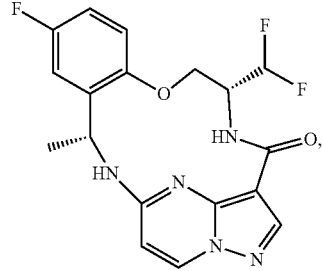
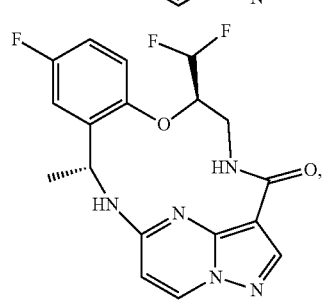
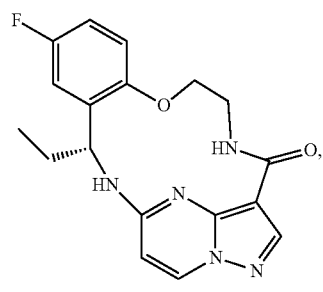
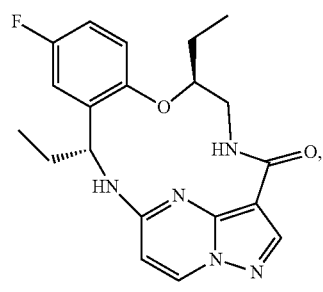

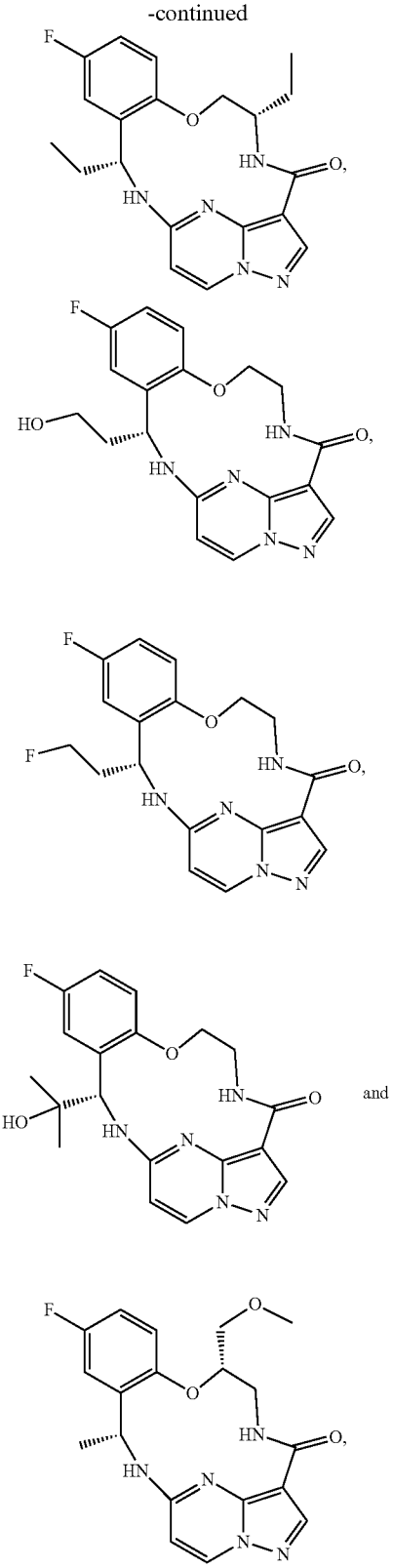
or a pharmaceutically acceptable salt thereof.
56. The compound of clause 1, of the formula selected from the group consisting of
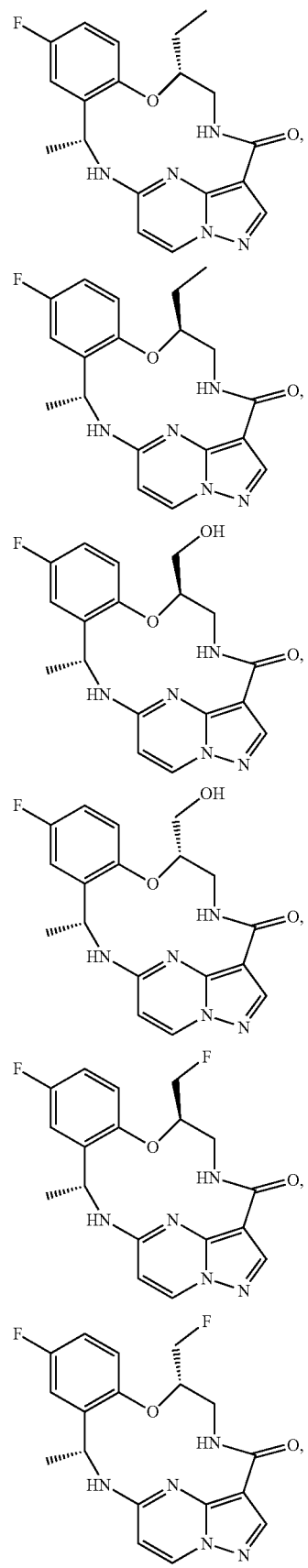

-continued
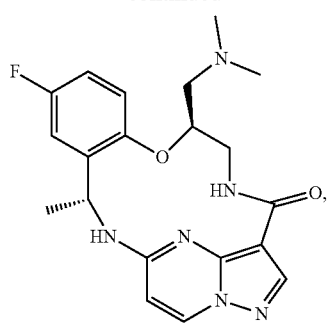
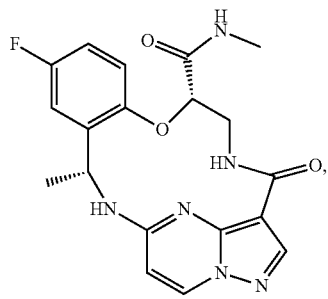
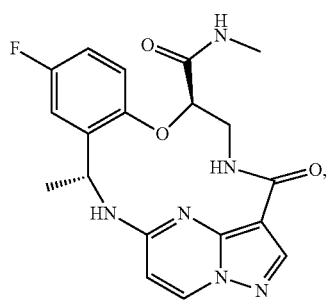
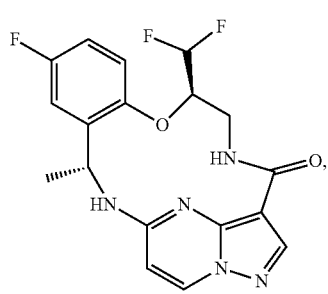
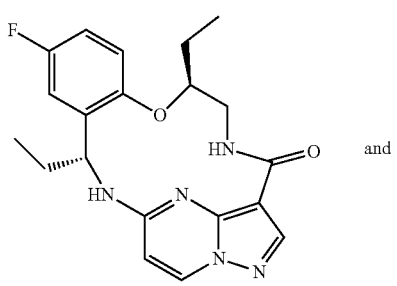 and
-continued
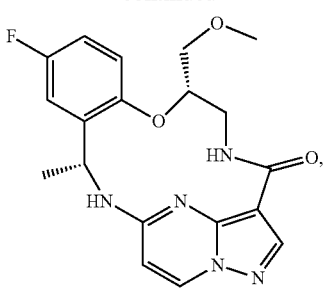
or a pharmaceutically acceptable salt thereof.
57. The compound of clause 1, of the formula selected from the group consisting of
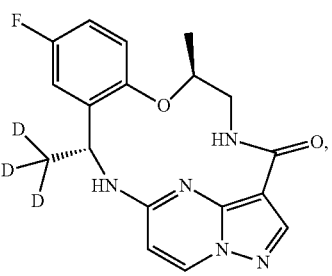
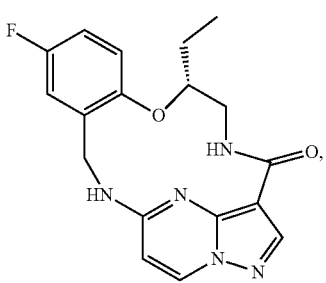
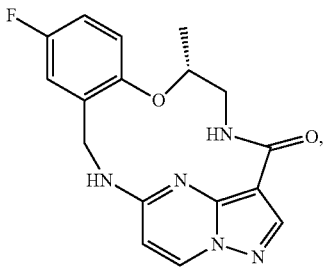
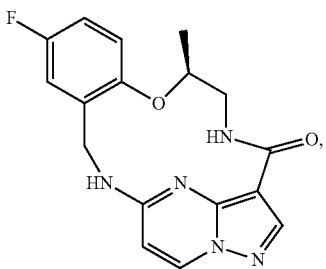

49
-continued
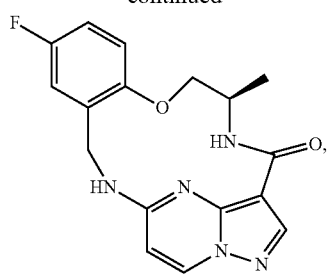
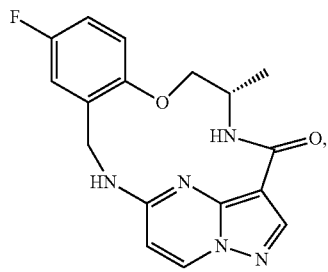
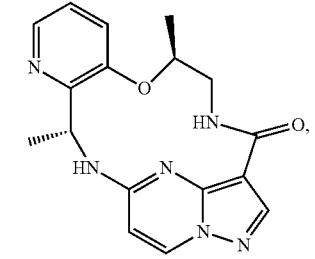
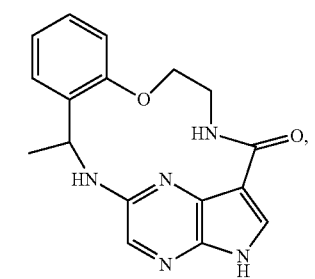
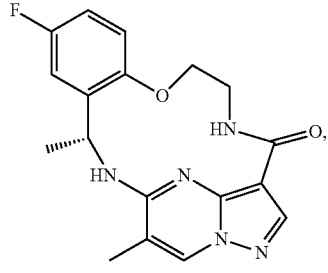
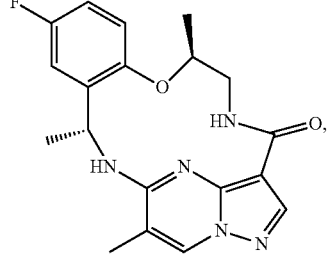
50
-continued
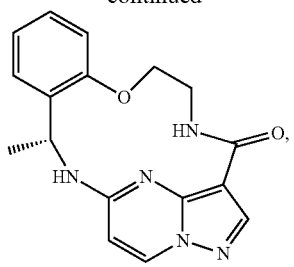
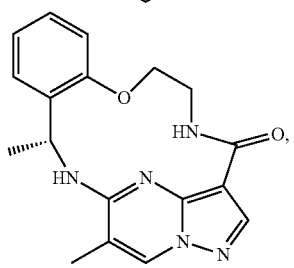
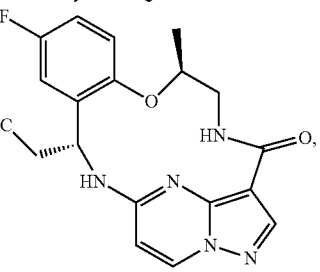
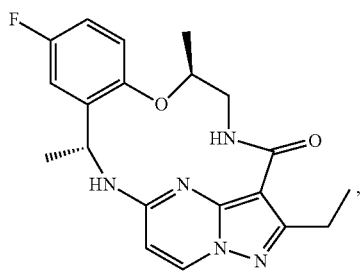
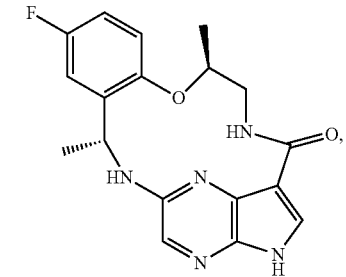
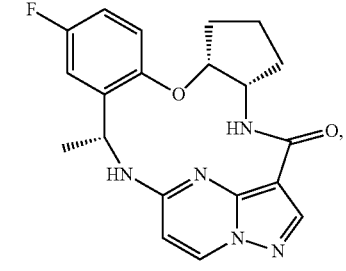

51
-continued
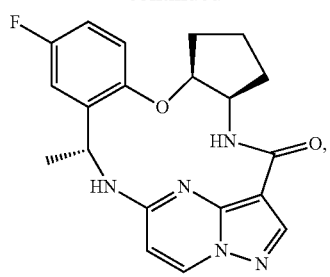
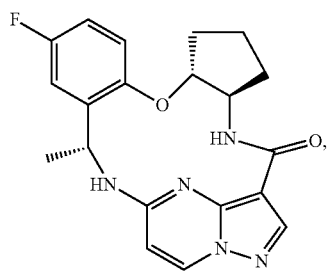
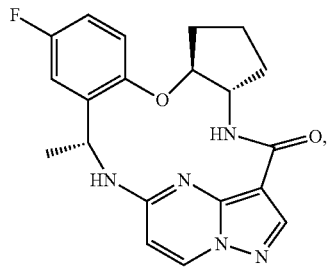
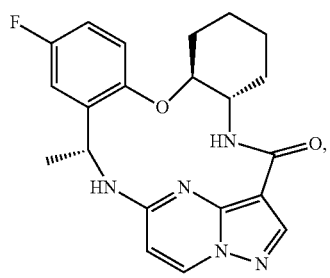
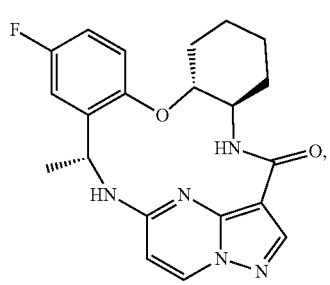
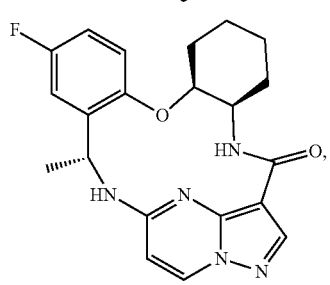
52
-continued
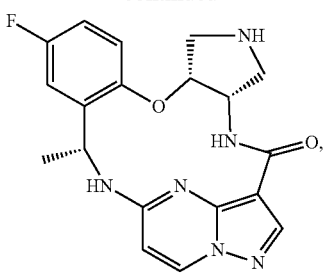
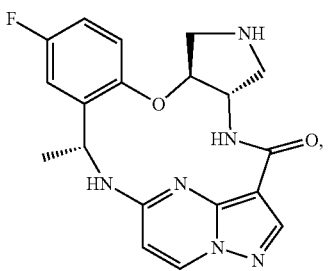
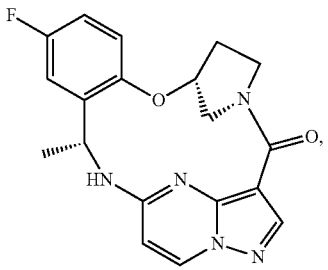
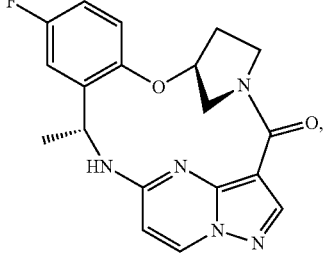
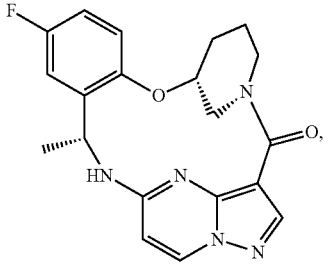
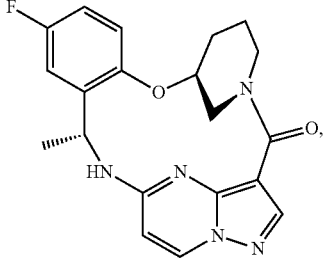

-continued
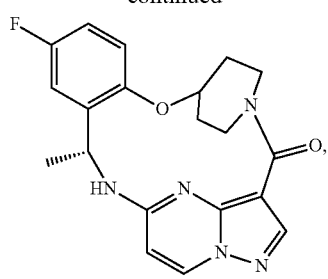
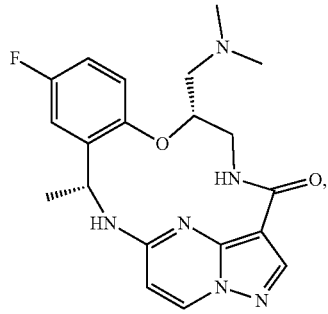
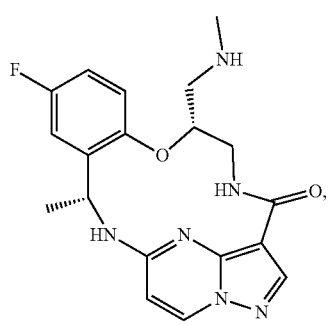
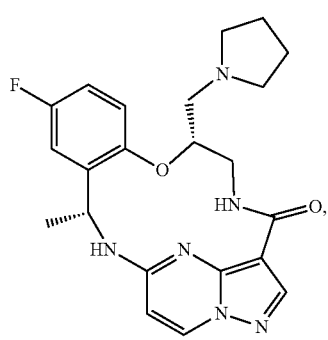
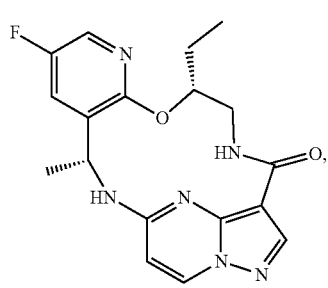
-continued
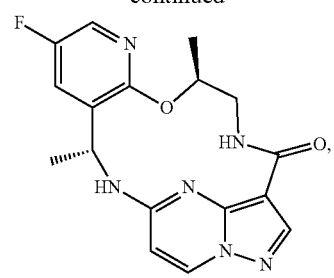
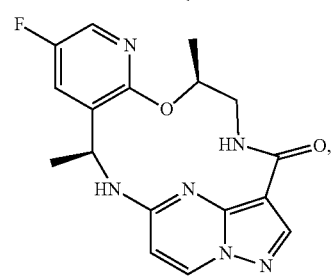
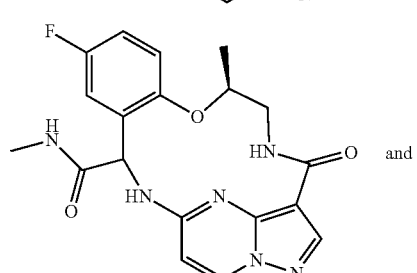
and
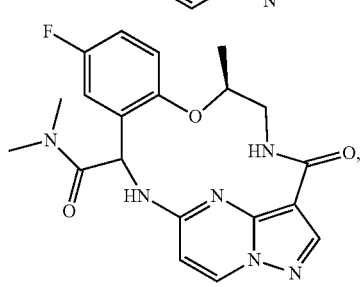
or a pharmaceutically acceptable salt thereof.
58. The compound of clause 1, of the formula selected from the group consisting of
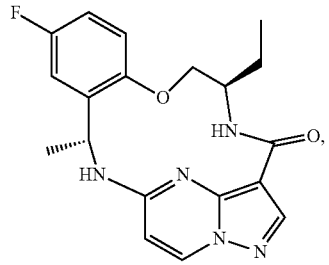

-continued
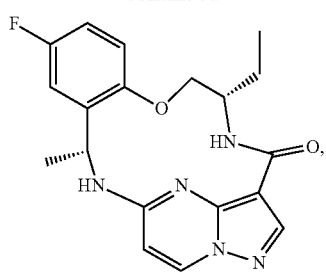
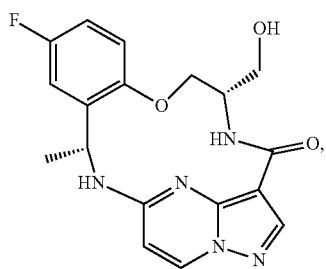
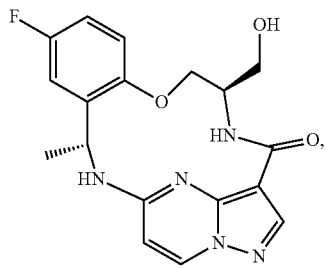
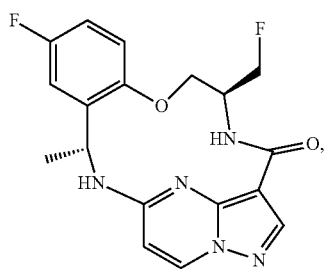
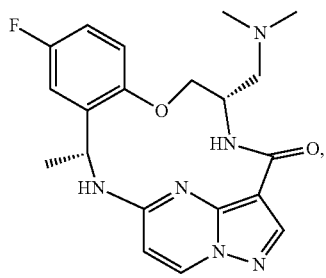
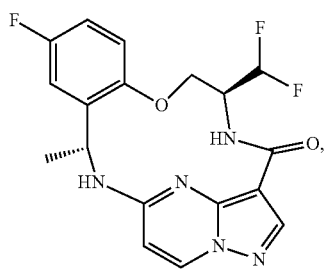
-continued
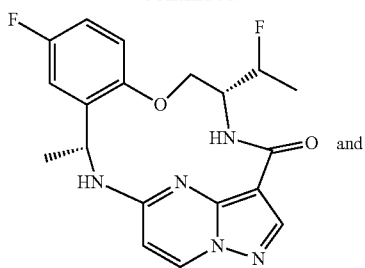
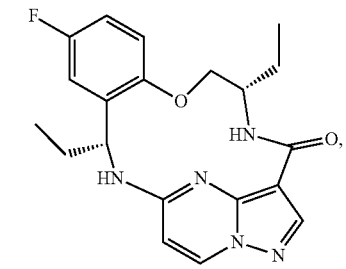
or a pharmaceutically acceptable salt thereof.
59. The compound of clause 1, of the formula selected from the group consisting of
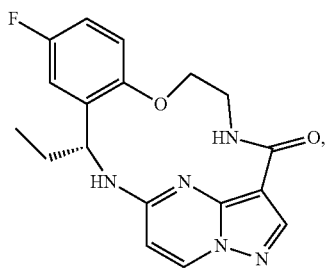
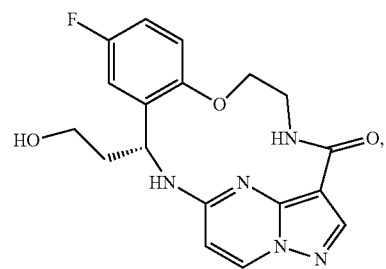
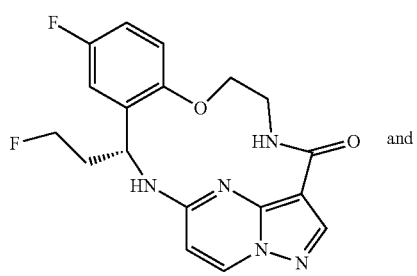

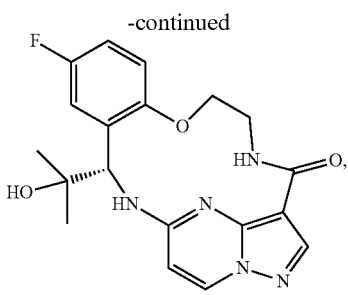

or a pharmaceutically acceptable salt thereof.

60. The compound of clause 1, of the formula selected from the group consisting of

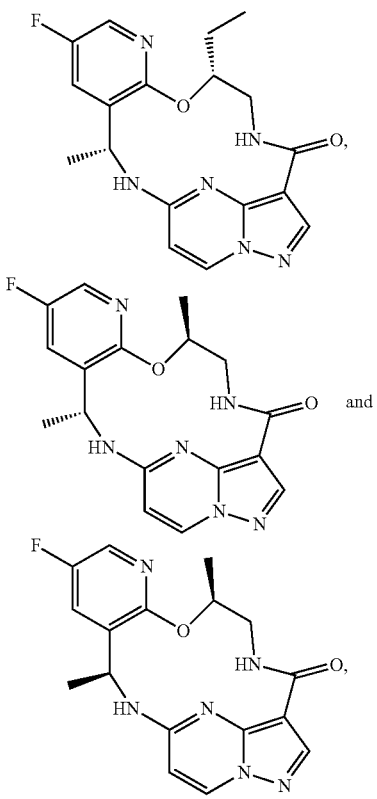

or a pharmaceutically acceptable salt thereof.

61. A pharmaceutical composition comprising a compound of any one of the preceding clauses, or a pharmaceutically acceptable salt thereof, and optionally at least one diluent, carrier or excipient.

62. A method of treating cancer, pain, neurological diseases, autoimmune diseases, or inflammation comprising administering to a subject in need of such treatment an effective amount of at least one compound of any one of clauses 1 to 60, or a pharmaceutically acceptable salt thereof.

63. Use of a compound of any one of clauses 1 to 60, or a pharmaceutically acceptable salt thereof, in the preparation of a medicament for the treatment of cancer, pain, neurological diseases, autoimmune diseases, or inflammation.

64. Use of a compound of any one of clauses 1 to 60, or a pharmaceutically acceptable salt thereof, for treating cancer, pain, neurological diseases, autoimmune diseases, or inflammation.

65. A method of inhibiting protein or tyrosine kinases, including one or more of MET, ALK, ROS1, AXL, TRKs, and JAKs, comprising contacting a cell comprising one or more of such kinases with an effective amount of at least one compound of any one of clauses 1 to 60, or a pharmaceutically acceptable salt thereof, and/or with at least one pharmaceutical composition of the disclosure, wherein the contacting is in vitro, ex vivo, or in vivo.

66. A compound of any one of clauses 1 to 60 for use in treating cancer in a patient.

67. A compound of any one of clauses 1 to 60 for use in treating inflammation in a patient.

DETAILED DESCRIPTION

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Chemical nomenclature for compounds described herein has generally been derived using the commercially-available ACD/Name 2014 (ACD/Labs) or ChemBioDraw Ultra 13.0 (Perkin Elmer).

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

Definitions

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$. Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkenyl" includes a chain of carbon atoms, which is optionally branched, and contains from 2 to 20 carbon atoms, and also includes at least one carbon-carbon double bond (i.e. C=C). It will be understood that in certain embodiments, alkenyl may be advantageously of limited length, including $C_2$-$C_{12}$, $C_2$-$C_9$, $C_2$-$C_5$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. C≡C). It will be understood that in certain embodiments, alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthylenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, including an all-carbon 5-member/6-member or 6-member/6-member fused bicyclic ring, or a multicyclic fused ring (a "fused" ring system means that each ring in the system shares an adjacent pair of carbon atoms with each other ring in the system) group, where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_9$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like. Illustrative examples of cycloalkyl groups shown in graphical representations include the following entities, in the form of properly bonded moieties:

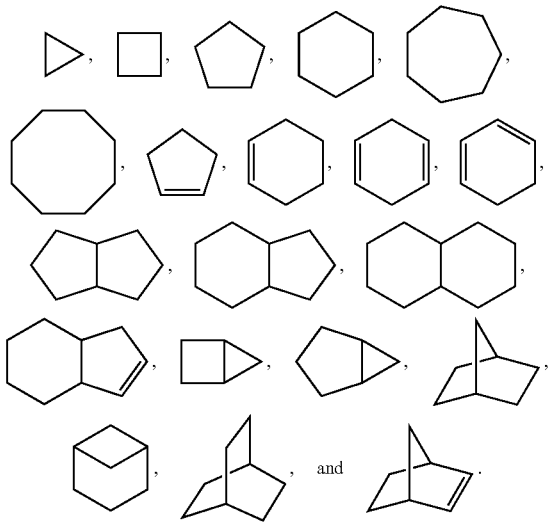

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one of more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1,2,3,4-tetrahydropyridinyl, and the like. Illustrative examples of heterocycloalkyl groups shown in graphical representations include the following entities, in the form of properly bonded moieties:

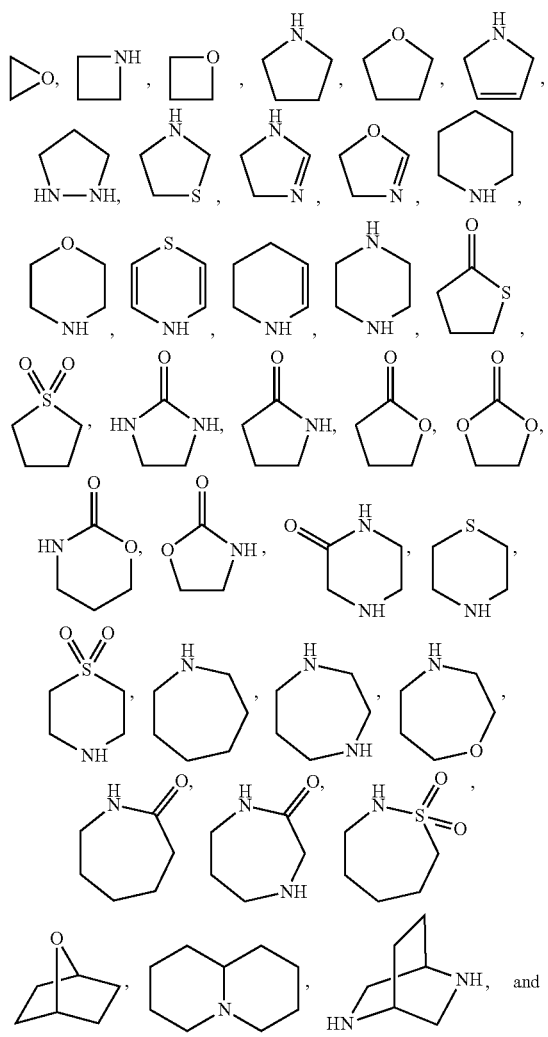

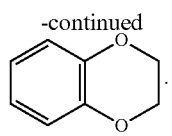

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like. Illustrative examples of heteroaryl groups shown in graphical representations, include the following entities, in the form of properly bonded moieties:

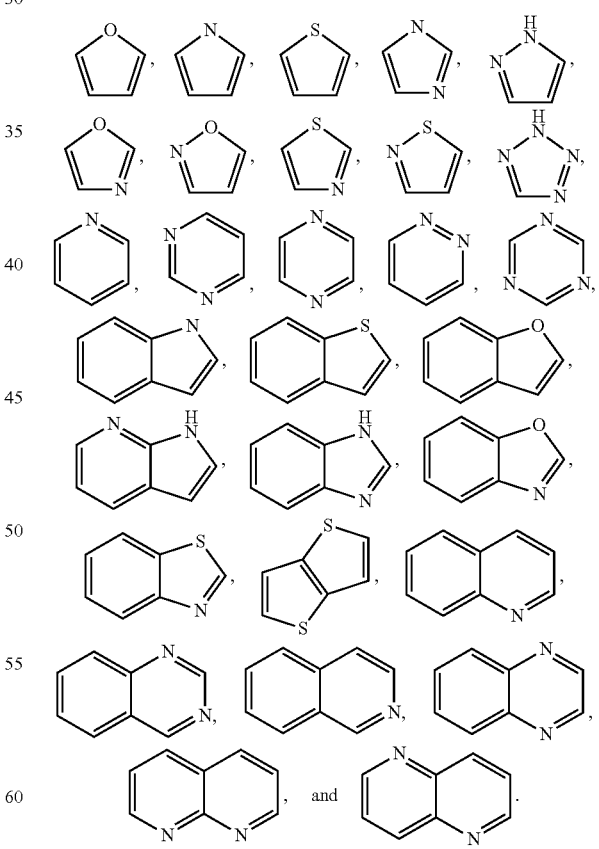

As used herein, "hydroxy" or ""hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "cyano" refers to a —CN group.

The term "oxo" represents a carbonyl oxygen. For example, a cyclopentyl substituted with oxo is cyclopentanone.

As used herein, "bond" refers to a covalent bond.

The term "substituted" means that the specified group or moiety bears one or more substituents. The term "unsubstituted" means that the specified group bears no substituents.

Where the term "substituted" is used to describe a structural system, the substitution is meant to occur at any valency-allowed position on the system. In some embodiments, "substituted" means that the specified group or moiety bears one, two, or three substituents. In other embodiments, "substituted" means that the specified group or moiety bears one or two substituents. In still other embodiments, "substituted" means the specified group or moiety bears one substituent.

As used herein, "optional" or "optionally" means that the subsequently described event or circumstance may but need not occur, and that the description includes instances where the event or circumstance occurs and instances in which it does not. For example, "wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by $C_1$-$C_6$ alkyl" means that an alkyl may be but need not be present on any of the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl by replacement of a hydrogen atom for each alkyl group, and the description includes situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is substituted with an alkyl group and situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, the term "pharmaceutically acceptable salt" refers to those salts which counter ions which may be used in pharmaceuticals. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

Pharmaceutically acceptable salts are well known to those skilled in the art, and any such pharmaceutically acceptable salt may be contemplated in connection with the embodiments described herein. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of Formula I, I-1, Ia, Ib, Ic, II, III, IV, V, VI, VII, VIII, IX, X, XI, XII or XIII that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethane-sulfonic acid, or any compatible mixture of acids such as those given as examples herein, and any other acid and mixture thereof that are regarded as equivalents or acceptable substitutes in light of the ordinary level of skill in this technology.

The disclosure also relates to pharmaceutically acceptable prodrugs of the compounds of Formula I, I-1, Ia, Ib, Ic, II, III, IV, V, VI, VII, VIII, IX, X, XI, XII or XIII, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula I, I-1, Ia, Ib, Ic, II, III, IV, V, VI, VII, VIII, IX, X, XI, XII or XIII). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The present disclosure also relates to pharmaceutically active metabolites of compounds of Formula I, I-1, Ia, Ib, Ic, II, III, IV, V, VI, VII, VIII, IX, X, XI, XII or XIII, and uses of such metabolites in the methods of the disclosure. A "pharmaceutically active metabolite" means a pharmacologically active product of metabolism in the body of a compound of Formula I, I-1, Ia, Ib, Ic, II, III, IV, V, VI, VII, VIII, IX, X, XI, XII or XIII or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof. For example, it will be appreciated that compounds depicted by a structural formula containing the symbol " ∿∿ " include both stereoisomers for the carbon atom to which the symbol " ∿∿ " is attached, specifically both the bonds " ▬■ " and " ⦀⦀⦀⦀ " are encompassed by the meaning of " ∿∿ ". For example, in some exemplary embodiments, certain compounds provided herein can be described by the formula

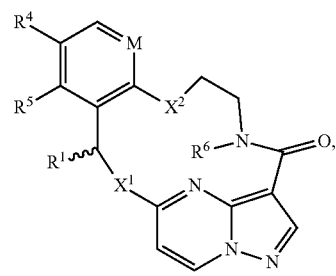

which formula will be understood to encompass compounds having both stereochemical configurations at the relevant carbon atom, specifically in this example

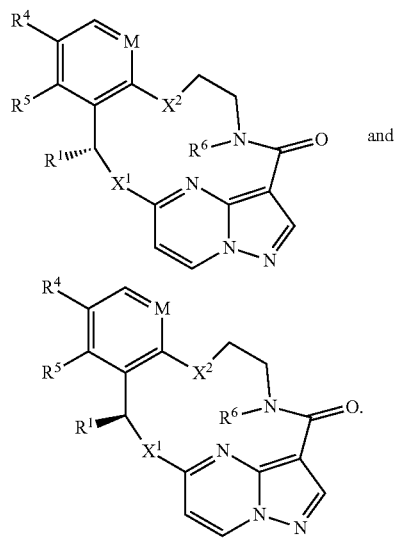

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{125}$I, respectively. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

Representative Embodiments

In some embodiments, compounds described herein comprise a moiety of the formula

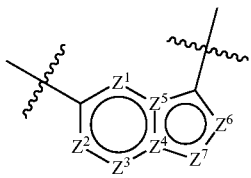

wherein $Z^1$-$Z^7$ are defined as described herein. In other embodiments, compounds described herein comprise a moiety of the formula

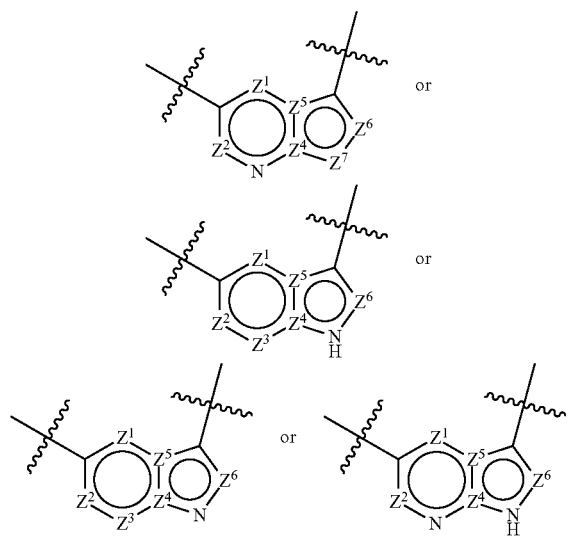

wherein $Z^1$-$Z^7$ are otherwise defined as described herein. In still other embodiments, compounds described herein comprise a moiety of the formula

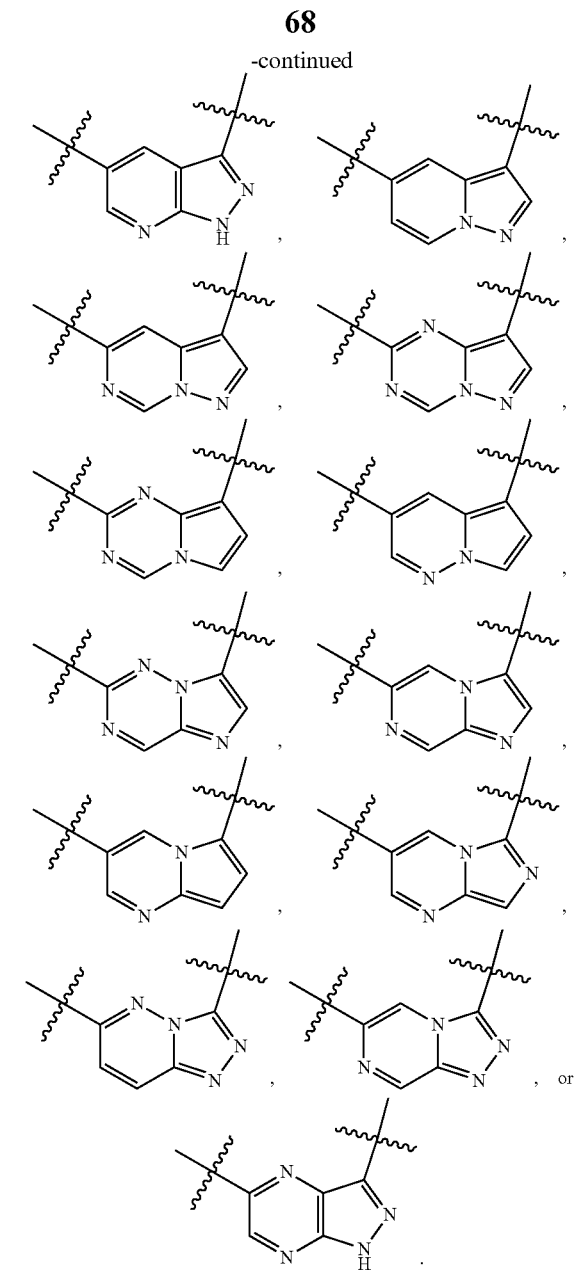

In still other embodiments, compounds described herein comprise a moiety of the formula

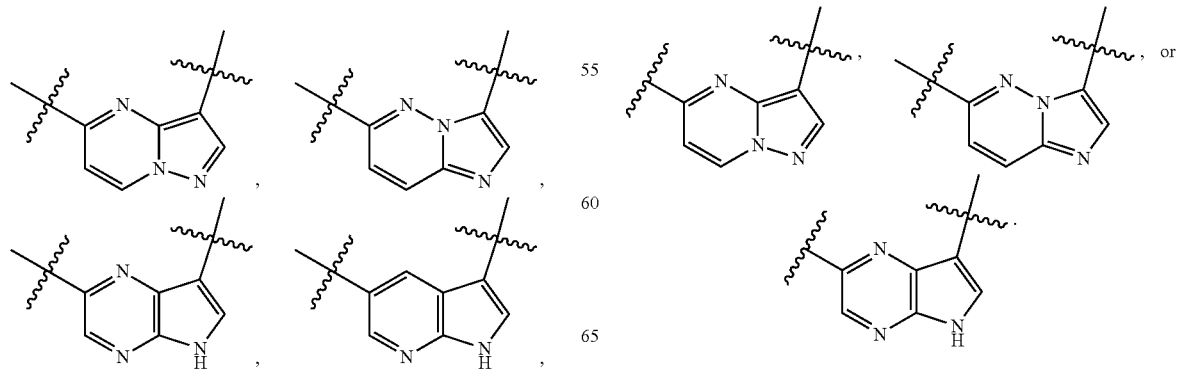

In still other embodiments, compounds described herein comprise a moiety of the formula

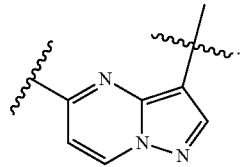 [SMILES: *c1ccn2ncc(*)c2n1]

In some embodiments, $Z^1$, $Z^4$ and $Z^7$ are N, and $Z^2$, $Z^3$, $Z^5$ and $Z^6$ are $C(R^1)$. In some embodiments, $Z^1$, $Z^4$ and $Z^7$ are N, and $Z^2$, $Z^3$, $Z^5$ and $Z^6$ are $C(R^{10})$, wherein each $R^{10}$ is H. In some embodiments, $Z^1$ and $Z^3$ are N, $Z^7$ is NH and $Z^2$, $Z^4$, $Z^5$, and $Z^6$ are $C(R^{10})$. In some embodiments, $Z^1$ and $Z^3$ are N, $Z^7$ is NH and $Z^2$, $Z^4$, $Z^5$, and $Z^6$ are $C(R^{10})$, wherein each $R^{10}$ is H. In some embodiments, $Z^1$, $Z^3$ and $Z^6$ are N, $Z^7$ is NH and $Z^2$, $Z^4$ and $Z^5$ are $C(R^{10})$. In some embodiments, $Z^1$, $Z^3$ and $Z^6$ are N, $Z^7$ is NH and $Z^2$, $Z^4$ and $Z^5$ are $C(R^1)$, wherein each $R^{10}$ is H. In some embodiments, $Z^3$ is N, $Z^7$ is NH and $Z^1$, $Z^2$, $Z^4$, $Z^5$, and $Z^6$ are $C(R^{10})$. In some embodiments, $Z^3$ is N, $Z^7$ is NH and $Z^1$, $Z^2$, $Z^4$, $Z^5$, and $Z^6$ are $C(R^{10})$, wherein each $R^{10}$ is H. In some embodiments, $Z^3$ and $Z^6$ are N, $Z^7$ is NH and $Z^1$, $Z^2$, $Z^4$ and $Z^5$ are $C(R^{10})$. In some embodiments, $Z^3$ and $Z^6$ are N, $Z^7$ is NH and $Z^1$, $Z^2$, $Z^4$ and $Z^5$ are $C(R^1)$, wherein each $R^{10}$ is H. In some embodiments, $Z^2$, $Z^4$ and $Z^7$ are N and $Z^1$, $Z^3$, $Z^5$ and $Z^6$ are $C(R^1)$. In some embodiments, $Z^2$, $Z^4$ and $Z^7$ are N and $Z^1$, $Z^3$, $Z^5$ and $Z^6$ are $C(R^{10})$, wherein each $R^{11}$ is H. In some embodiments, $Z^1$, $Z^5$ and $Z^7$ are N and $Z^2$, $Z^3$, $Z^4$ and $Z^6$ are $C(R^{11})$. In some embodiments, $Z^1$, $Z^5$ and $Z^7$ are N and $Z^2$, $Z^3$, $Z^4$ and $Z^6$ are $C(R^{10})$, wherein each $R^{10}$ is H. In some embodiments, $Z^1$, $Z^2$, $Z^4$ and $Z^7$ are N and $Z^3$, $Z^5$ and $Z^6$ are $C(R^{10})$. In some embodiments, $Z^1$, $Z^2$, $Z^4$ and $Z^7$ are N and $Z^3$, $Z^5$ and $Z^6$ are $C(R^{10})$, wherein each $R^{10}$ is H. In some embodiments, $Z^1$, $Z^2$, $Z^5$ and $Z^7$ are N and $Z^3$, $Z^4$ and $Z^6$ are $C(R^{10})$. In some embodiments, $Z^1$, $Z^2$, $Z^5$ and $Z^7$ are N and $Z^3$, $Z^4$ and $Z^6$ are $C(R^{10})$, wherein each $R^{10}$ is H. In some embodiments, $Z^3$, $Z^5$ and $Z^6$ are N and $Z^1$, $Z^2$, $Z^4$ and $Z^7$ are $C(R^{10})$. In some embodiments, $Z^3$, $Z^5$ and $Z^6$ are N and $Z^1$, $Z^2$, $Z^4$ and $Z^7$ are $C(R^{10})$, wherein each $R^{10}$ is H. In some embodiments, $Z^1$, $Z^5$, $Z^6$ and $Z^7$ are N and $Z^2$, $Z^3$ and $Z^4$ are $C(R^{10})$. In some embodiments, $Z^1$, $Z^5$, $Z^6$ and $Z^7$ are N and $Z^2$, $Z^3$ and $Z^4$ are $C(R^{10})$ wherein each $R^{10}$ is H. In some embodiments, $Z^1$, $Z^2$ and $Z^4$ are N and $Z^3$, $Z^5$, $Z^6$ and $Z^7$ are $C(R^{10})$. In some embodiments, $Z^1$, $Z^2$ and $Z^4$ are N and $Z^3$, $Z^5$, $Z^6$ and $Z^7$ are $C(R^{10})$, wherein each $R^{10}$ is H. In some embodiments, $Z^1$, $Z^3$ and $Z^4$ are N and $Z^2$, $Z^5$, $Z^6$ and $Z^7$ are $C(R^{10})$. In some embodiments, $Z^1$, $Z^3$ and $Z^4$ are N and $Z^2$, $Z^5$, $Z^6$ and $Z^7$ are $C(R^{10})$, wherein each $R^{10}$ is H. In some embodiments, $Z^3$ and $Z^4$ are N and $Z^1$, $Z^2$, $Z^5$, $Z^6$ and $Z^7$ are $C(R^{10})$. In some embodiments, $Z^3$ and $Z^4$ are N and $Z^1$, $Z^2$, $Z^5$, $Z^6$ and $Z^7$ are $C(R^{10})$, wherein each $R^{10}$ is H. In some embodiments, $Z^2$, $Z^5$ and $Z^7$ are N and $Z^1$, $Z^3$, $Z^4$ and $Z^6$ are $C(R^{10})$. In some embodiments, $Z^2$, $Z^5$ and $Z^7$ are N and $Z^1$, $Z^3$, $Z^4$ and $Z^6$ are $C(R^{10})$, wherein each $R^{10}$ is H. In some embodiments, $Z^3$ and $Z^5$ are N and $Z^1$, $Z^2$, $Z^4$, $Z^6$ and $Z^7$ are $C(R^{10})$. In some embodiments, $Z^3$ and $Z^5$ are N and $Z^1$, $Z^2$, $Z^4$, $Z^6$ and $Z^7$ are $C(R^{10})$, wherein each $R^{10}$ is H. In some embodiments, $Z^2$, $Z^5$, $Z^6$ and $Z^7$ are N and $Z^1$, $Z^3$ and $Z^4$ are $C(R^{10})$. In some embodiments, $Z^2$, $Z^5$, $Z^6$ and $Z^7$ are N and $Z^1$, $Z^3$ and $Z^4$ are $C(R^{10})$, wherein each $R^{10}$ is H.

In some embodiments, $X^1$ is —$N(R^9)$—. In some embodiments, $X^2$ is —O—. In some embodiments, $X^1$ is —$N(R^9)$—, and $X^2$ is —O—. In some embodiments, M is CH or N. In some embodiments, M is N. In some embodiments, M is CH. In some embodiments, $M^1$ is CH or N. In some embodiments, $M^1$ is N. In some embodiments, $M^1$ is CH.

In some embodiments, $R^1$ is $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)$OR^7$ or —C(O)$NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)$NH_2$, —NHC(O)NH$C_1$-$C_6$ alkyl, —N($C_1$-$C_6$ alkyl)C(O)$NH_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)$OC_1$-$C_6$ alkyl, —N($C_1$-$C_6$ alkyl)C(O)$OC_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)$NH_2$, NHS(O)$_2NH_2$, —N($C_1$-$C_6$ alkyl)S(O)$NH_2$, —N($C_1$-$C_6$ alkyl)S(O)$_2NH_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —$CO_2$H, —C(O)$OC_1$-$C_6$ alkyl, —C(O)$NH_2$, —C(O)NH($C_1$-$C_6$ alkyl), —C(O)N($C_1$-$C_6$ alkyl)$_2$, —$SC_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl or 3- to 7-membered heterocycloalkyl.

In some embodiments, $R^1$ is $C_1$-$C_6$ alkyl, wherein each hydrogen atom is independently optionally substituted by deuterium, halogen, —OH, —CN, —$OC_1$-$C_6$ alkyl, —$NH_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)$NH_2$, —NHC(O)NH$C_1$-$C_6$ alkyl, —N($C_1$-$C_6$ alkyl)C(O)$NH_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)$OC_1$-$C_6$ alkyl, —N($C_1$-$C_6$ alkyl)C(O)$OC_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)$NH_2$, —NHS(O)$_2NH_2$, —N($C_1$-$C_6$ alkyl)S(O)$NH_2$, —N($C_1$-$C_6$ alkyl)S(O)$_2NH_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —$CO_2$H, —C(O)$OC_1$-$C_6$ alkyl, —C(O)$NH_2$, —C(O)NH($C_1$-$C_6$ alkyl), —C(O)N($C_1$-$C_6$ alkyl)$_2$, —$SC_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl.

In some embodiments, $R^1$ is methyl, ethyl, isopropyl, 2-hydroxy-2-propryl, 2-hydroxyethyl or 2-fluoroethyl. In some embodiments, $R^1$ is methyl. In some embodiments, $R^1$ is ethyl. In some embodiments, $R^1$ is isopropyl. In some embodiments, $R^1$ is 2-hydroxy-2-propryl. In some embodiments, $R^1$ is 2-hydroxyethyl. In some embodiments, $R^1$ is 2-fluoroethyl. In some embodiments, $R^1$ is $D_3C$—. In some embodiments, $R^1$ is —C(O)$NH_2$, —C(O)NH($C_1$-$C_6$ alkyl) or —C(O)N($C_1$-$C_6$ alkyl). In some embodiments, $R^1$ is —C(O)$NHCH_3$. In some embodiments, $R^1$ is —C(O)N($CH_3$)$_2$. In some embodiments, $R^1$ is cyanomethyl.

In some embodiments, $R^2$ is $C_1$-$C_6$ alkyl or —C(O)NR$^7$R$^8$, wherein each hydrogen atom in $C_1$-$C_6$ alkyl is independently optionally substituted with one or more moieties selected from group consisting of —F, —OH, —OC$_1$-C$_6$ alkyl, —NH$_2$, —NH(C$_1$-C$_6$ alkyl), and —N(C$_1$-C$_6$ alkyl)$_2$. In some embodiments, $R^2$ is $C_1$-$C_6$ alkyl or —C(O)NR$^7$R$^8$, wherein each hydrogen atom in $C_1$-$C_6$ alkyl is independently optionally substituted with one or more moieties selected from group consisting of —F, —OH, —OC$_1$-C$_6$ alkyl, —NH$_2$, —NH(C$_1$-C$_6$ alkyl), and —N(C$_1$-C$_6$ alkyl)$_2$, and $R^3$ is H.

In some embodiments, $R^3$ is $C_1$-$C_6$ alkyl or —C(O)NR$^7$R$^8$, wherein each hydrogen atom in $C_1$-$C_6$ alkyl is independently optionally substituted with one or more moieties selected from group consisting of —F, —OH, —OC$_1$-C$_6$ alkyl, —NH$_2$, —NH(C$_1$-C$_6$ alkyl), and —N(C$_1$-C$_6$ alkyl)$_2$. In some embodiments, $R^3$ is $C_1$-$C_6$ alkyl or —C(O)NR$^7$R$^8$, wherein each hydrogen atom in $C_1$-$C_6$ alkyl is independently optionally substituted with one or more moieties selected from group consisting of —F, —OH, —OC$_1$-C$_6$ alkyl, —NH$_2$, —NH(C$_1$-C$_6$ alkyl), and —N(C$_1$-C$_6$ alkyl)$_2$, and $R^2$ is H.

In some embodiments, $R^2$ and $R^3$ combine to form a $C_3$-$C_6$ cycloalkyl. In some embodiments, $R^2$ and $R^3$ combine to form a cyclopentyl ring. In some embodiments, $R^2$ and $R^3$ combine to form a cyclohexyl ring. In some embodiments, $R^2$ and $R^3$ combine to form a 3- to 7-membered heterocycloalkyl. In some embodiments, $R^2$ and $R^3$ combine to form a pyrrolidinyl ring. In some embodiments, $R^2$ and $R^3$ combine to form a piperidinyl ring. In some embodiments, $R^2$ and $R^6$ combine to form a pyrrolidine ring. In some embodiments, $R^2$ and $R^6$ combine to form a piperidinyl ring.

In some embodiments, $R^4$ and $R^5$ are each independently H, fluoro, chloro, bromo, methyl, ethyl, propyl, isopropyl, —OH, methoxy, ethoxy, isopropoxy, —CN, or —CF$_3$. In some embodiments, $R^4$ is H, fluoro, chloro, bromo, methyl, ethyl, propyl, isopropyl, —OH, methoxy, ethoxy, isopropoxy, —CN, or —CF$_3$, and $R^5$ is H. In some embodiments, $R^4$ is fluoro, and $R^5$ is H.

In other embodiments, the compound of Formula I, I-1, Ia, Ib, Ic, II, III, IV, V, VI, VII, VIII, IX, X, XI, XII or XIII is selected from the group consisting of (7R,13R)-7-ethyl-11-fluoro-13-methyl-6,7,13,14-tetrahydro-1,15-ethenopyrazolo[4,3-f][1,4,8,10]benzoxatriazacyclotridecin-4(5H)-one, (6R,13R)-6-ethyl-11-fluoro-13-methyl-6,7,13,14-tetrahydro-1,15-etheno-pyrazolo[4,3-f][1,4,8,10]benzoxatriazacyclotridecin-4(5H)-one, (7S,13R)-7-ethyl-11-fluoro-13-methyl-6,7,13,14-tetrahydro-1,15-ethenopyrazolo[4,3-f][1,4,8,10]benzoxatriaza-cyclotridecin-4(5H)-one, (6S,13R)-6-ethyl-11-fluoro-13-methyl-6,7,13,14-tetrahydro-1,15-ethenopyrazolo[4,3-f][1,4,8,10]benzoxatriazacyclotridecin-4(5H)-one, (7R,13R)-11-fluoro-7-(hydroxymethyl)-13-methyl-6,7,13,14-tetrahydro-1,15-ethenopyrazolo[4,3-f][1,4,8,10]benzoxatriazacyclotridecin-4(5H)-one, (6S,13R)-11-fluoro-6-(hydroxymethyl)-13-methyl-6,7,13,14-tetrahydro-1,15-ethenopyrazolo[4,3-f][1,4,8,10]benzoxatriazacyclotridecin-4(5H)-one, (7S,13R)-11-fluoro-7-(hydroxymethyl)-13-methyl-6,7,13,14-tetrahydro-1,15-ethenopyrazolo[4,3-f][1,4,8,10]-benzoxatriazacyclotridecin-4(5H)-one, (6R,13R)-11-fluoro-6-(hydroxymethyl)-13-methyl-6,7,13,14-tetrahydro-1,15-ethenopyrazolo[4,3-f][1,4,8,10]benzoxatriazacyclotridecin-4(5H)-one, (7R,13R)-11-fluoro-7-(fluoromethyl)-13-methyl-6,7,13,14-tetrahydro-1,15-ethenopyrazolo[4,3-f][1,4,8,10]benzoxatriazacyclotridecin-4(5H)-one, (7S,13R)-11-fluoro-7-(fluoromethyl)-13-methyl-6,7,13,14-tetrahydro-1,15-ethenopyrazolo[4,3-f][1,4,8,10]benzoxatriazacyclotridecin-4(5H)-one, (6S,13R)-11-fluoro-6-(fluoromethyl)-13-methyl-6,7,13,14-tetrahydro-1,15-ethenopyrazolo[4,3-f][1,4,8,10]benzoxatriazacyclotridecin-4(5H)-one, (7R,13R)-7-[(dimethylamino)methyl]-11-fluoro-13-methyl-6,7,13,14-tetrahydro-1,15-ethenopyrazolo[4,3-f][1,4,8,10]benzoxatriazacyclotridecin-4(5H)-one, (6S,13R)-6-[(dimethylamino)methyl]-11-fluoro-13-methyl-6,7,13,14-tetrahydro-1,15-ethenopyrazolo[4,3-f][1,4,8,10]benzoxatriaza-cyclotridecin-4(5H)-one, (7S,13R)-7-(N-methylcarboxamide)-11-fluoro-13-methyl-6,7,13,14-tetrahydro-1,15-ethenopyrazolo[4,3-f][1,4,8,10]benzoxatriazacyclotridecin-4(5H)-one, (7R,13R)-7-(N-methylcarboxamide)-11-fluoro-13-methyl-6,7,13,14-tetrahydro-1,15-ethenopyrazolo[4,3-f][1,4,8,10]benzoxatriazacyclotridecin-4(5H)-one, (6R,13R)-6-(difluoromethyl)-11-fluoro-13-methyl-6,7,13,14-tetrahydro-1,15-ethenopyrazolo[4,3-f][1,4,8,10]benzoxatriazacyclotridecin-4(5H)-one, (6S,13R)-6-(difluoromethyl)-11-fluoro-13-methyl-6,7,13,14-tetrahydro-1,15-ethenopyrazolo[4,3-f][1,4,8,10]benzoxatriazacyclotridecin-4(5H)-one, (7R,13R)-7-(difluoromethyl)-11-fluoro-13-methyl-6,7,13,14-tetrahydro-1,15-ethenopyrazolo[4,3-f][1,4,8,10]benzoxatriazacyclotridecin-4(5H)-one, (13R)-13-ethyl-11-fluoro-6,7,13,14-tetrahydro-1,15-ethenopyrazolo[4,3-f][1,4,8,10]benzoxatriazacyclotridecin-4(5H)-one, (7S,13R)-7,13-diethyl-11-fluoro-6,7,13,14-tetrahydro-1,15-ethenopyrazolo[4,3-f][1,4,8,10]benzoxatriaza-cyclotridecin-4(5H)-one, (6S,13R)-6,13-diethyl-11-fluoro-6,7,13,14-tetrahydro-1,15-ethenopyrazolo[4,3-f][1,4,8,10]benzoxatriazacyclotridecin-4(5H)-one, (13R)-11-fluoro-13-(2-hydroxyethyl)-6,7,13,14-tetrahydro-1,15-ethenopyrazolo[4,3-f][1,4,8,10]benzoxatriaza-cyclotridecin-4(5H)-one, (13R)-11-fluoro-13-(2-fluoroethyl)-6,7,13,14-tetrahydro-1,15-ethenopyrazolo[4,3-f][1,4,8,10]benzoxatriazacyclotridecin-4(5H)-one, (13S)-11-fluoro-13-(2-hydroxypropan-2-yl)-6,7,13,14-tetrahydro-1,15-ethenopyrazolo[4,3-f][1,4,8,10]benzoxatriaza-cyclotridecin-4(5H)-one, (7S,13R)-11-fluoro-7-(methoxymethyl)-13-methyl-6,7,13,14-tetrahydro-1,15-ethenopyrazolo[4,3-f][1,4,8,10]benzoxatriazacyclotridecin-4(5H)-one, (7S,13R)-11-fluoro-7-methyl-13-($^2$H$_3$)methyl-6,7,13,14-tetrahydro-1,15-ethenopyrazolo[4,3-f][1,4,8,10]benzoxatriazacyclotridecin-4(5H)-one, (7R)-7-ethyl-11-fluoro-6,7,13,14-tetrahydro-1,15-ethenopyrazolo[4,3-f][1,4,8,10]benzoxatriazacyclotridecin-4(5H)-one, (7R)-11-fluoro-7-methyl-6,7,13,14-tetrahydro-1,15-ethenopyrazolo[4,3-f][1,4,8,10]benzoxatriazacyclotridecin-4(5H)-one, (7S)-11-fluoro-7-methyl-6,7,13,14-tetrahydro-1,15-ethenopyrazolo[4,3-f][1,4,8,1]benzoxatriazacyclotridecin-4(5H)-one, (6R)-11-fluoro-6-methyl-6,7,13,14-tetrahydro-1,15-ethenopyrazolo[4,3-f][1,4,8,10]benzoxatriazacyclotridecin-4(5H)-one, (6S)-11-fluoro-6-methyl-6,7,13,14-tetrahydro-1,15-ethenopyrazolo[4,3-f][1,4,8,10]benzoxatriazacyclotridecin-4(5H)-one, (7S,13R)-7,13-dimethyl-6,7,13,14-tetrahydro-1,15-ethenopyrazolo[4,3-f]pyrido[2,3-l][1,4,8,10]oxatriazacyclotridecin-4(5H)-one, 7-methyl-6,7,14,15-tetrahydro-2H-3,5-(azenometheno)pyrrolo[3,4-f][1,4,8,10]benzoxatriazacyclotridecin-16(13H)-one, (13R)-11-fluoro-13,17-dimethyl-6,7,13,14-tetrahydro-1,15-ethenopyrazolo[4,3-f][1,4,8,10]benzoxatriaza-cyclotridecin-4(5H)-one, (7S,13R)-11-fluoro-7,13,17-trimethyl-6,7,13,14-tetrahydro-1,15-ethenopyrazolo[4,3-f][1,4,8,10]benzoxatriazacyclotridecin-4(5H)-one, (13R)-13-methyl-6,7,13,14-tetrahydro-1,15-ethenopyrazolo[4,3-f][1,4,8,10]benzoxatriaza-cyclotridecin-4(5H)-one, (13R)-13,17-dimethyl-6,7,13,14-tetrahydro-1,15-ethenopyrazolo[4,3- f][1,4,8,10]benzoxatriazacyclotridecin-4(5H)-one, [(7S,13R)-11-fluoro-7-methyl-4-oxo-4,5,6,7,13,14-hexahydro-1,15-ethenopyrazolo[4,3-f][1,4,8,10]benzoxatriazacyclotridecin-13-yl]acetonitrile, (7S,13R)-3-ethyl-11-fluoro-7,13-dimethyl-6,7,13,14-tetrahydro-1,15-ethenopyrazolo[4,3-f][1,4,8,10]benzoxatriazacyclotridecin-4(5H)-one, (7R,13S)-9-fluoro-7,13-dimethyl-6,7,14,15-tetrahydro-2H-3,5-(azenometheno)pyrrolo[3,4-f][1,4,8,10]benzoxatriaza-cyclotridecin-16(13H)-one, (3aR,9R,17aS)-7-fluoro-9-methyl-1,2,3,3a,9,10,17,17a-octahydro-16H-11,13-ethenocyclopenta[b]pyrazolo[4,3-f][1,4,8,10]benzoxatriazacyclotridecin-16-one, (3aS,9R,17aR)-7-fluoro-9-methyl-1,2,3,3a,9,10,17,17a-octahydro-16H-11,13-ethenocyclopenta[b]pyrazolo[4,3-f][1,4,8,10]benzoxatriazacyclotridecin-16-one, (3aR,9R,17aR)-7-fluoro-9-methyl-1,2,3,3a,9,10,17,17a-octahydro-16H-11,13-ethenocyclopenta[b]pyrazolo[4,3-f][1,4,8,10]benzoxatriazacyclotridecin-16-one, (4aS,10R,18aS)-8-fluoro-10-methyl-2,3,4,4a,10,11,18,18a-octahydro-12,14-ethenodibenzo[b,l]pyrazolo[4,3-f][1,4,8,10]oxatriaza-cyclotridecin-17(1H)-one, (4aR,1bR,18aR)-8-fluoro-10-methyl-2,3,4,4a,10,11,18,18a-octahydro-12,14-ethenodibenzo[b,l]pyrazolo[4,3-f][1,4,8,10]oxatriazacyclotridecin-17(1H)-one, (3aS,9R,17aS)-7-fluoro-9-methyl-1,2,3,3a,9,10,17,17a-octahydro-16H-11,13-ethenocyclopenta[b]pyrazolo[4,3-f][1,4,8,10]benzoxatriazacyclotridecin-16-one, (4aS,10R,18aR)-8-fluoro-10-methyl-2,3,4,4a,10,11,18,18a-octahydro-12,14-ethenodibenzo[b,l]pyrazolo[4,3-f][1,4,8,10]oxatriazacyclotridecin-17(1H)-one, (3aR,9R,17aS)-7-fluoro-9-methyl-1,2,3,3a,9,10,17,17a-octahydro-16H-11,13-ethenopyrazolo[4,3-J]pyrrolo[3,4-b][1,4,8,10]benzoxatriazacyclotridecin-16-one, (3aS,9R,17aS)-7-fluoro-9-methyl-1,2,3,3a,9,10,17,17a-octahydro-16H-11,13-ethenopyrazolo[4,3-f]pyrrolo[3,4-b][1,4,8,10]benzoxatriazacyclotridecin-16-one, (8R,14R)-12-fluoro-14-methyl-7,8,14,15-tetrahydro-4H,6H-1,16-etheno-5,8-methanopyrazolo[4,3-g][1,5,9,11]benzoxatriazacyclotetradecin-4-one, (8S,14R)-12-fluoro-14-methyl-7,8,14,15-tetrahydro-4H,6H-1,16-etheno-5,8-methanopyrazolo[4,3-g][1,5,9,11]benzoxatriazacyclotetradecin-4-one, (9R,15R)-13-fluoro-15-methyl-6,7,8,9,15,16-hexahydro-4H-1,17-etheno-5,9-methanopyrazolo[4,3-h][1,6,10,12]benzoxatriazacyclopentadecin-4-one, (9S,15R)-13-fluoro-15-methyl-6,7,8,9,15,16-hexahydro-4H-1,17-etheno-5,9-methanopyrazolo[4,3-h][1,6,10,12]benzoxatriazacyclopentadecin-4-one, (14R)-12-fluoro-14-methyl-7,8,14,15-tetrahydro-4H,6H-5,8-ethano-1,16-ethenopyrazolo[4,3-g][1,5,9,11]benzoxatriazacyclotetradecin-4-one, (7S,13R)-7-[(dimethylamino)methyl]-11-fluoro-13-methyl-6,7,13,14-tetrahydro-1,15-ethenopyrazolo[4,3-f][1,4,8,10]benzoxatriazacyclotridecin-4(5H)-one, (7R,13R)-11-fluoro-13-methyl-7-[(methylamino)methyl]-6,7,13,14-tetrahydro-1,15-ethenopyrazolo[4,3-f][1,4,8,10]benzoxatriazacyclotridecin-4(5H)-one, (7S,13R)-11-fluoro-13-methyl-7-[(pyrrolidin-1-yl)methyl]-6,7,13,14-tetrahydro-1,15-ethenopyrazolo[4,3-f][1,4,8,10]benzoxatriazacyclotridecin-4(5H)-one, (7R,13R)-7-ethyl-11-fluoro-13-methyl-6,7,13,14-tetrahydro-1,15-ethenopyrazolo[4,3-f]pyrido[3,2-l][1,4,8,10]oxatriazacyclotridecin-4(5H)-one, (7S,13S)-11-fluoro-7,13-dimethyl-6,7,13,14-tetrahydro-1,15-ethenopyrazolo[4,3-f]pyrido[3,2-l][1,4,8,10]oxatriazacyclotridecin-4(5H)-one, (7S,13R)-11-fluoro-7,13-dimethyl-6,7,13,14-tetrahydro-1,15-ethenopyrazolo[4,3-f]pyrido[3,2-l][1,4,8,10]oxatriazacyclotridecin-4(5H)-one, (7S)-11-fluoro-N,7-dimethyl-4-oxo-4,5,6,7,13,14-hexahydro-1,15-ethenopyrazolo[4,3-f][1,4,8,10]benzoxatriazacyclotridecine-13-carboxamide and (7S)-11-fluoro-N,N,7-trimethyl-4-oxo-4,5,6,7,13,14-hexahydro-1,15-ethenopyrazolo[4,3-f][1,4,8,10]benzoxatriazacyclotridecine-13-carboxamide or a pharmaceutically acceptable salt thereof.

The following represent illustrative embodiments of compounds of the formula I, I-1, Ia, Ib, Ic, II, III, IV, V, VI, VII, VIII, IX, X, XI, XII and XIII:

| Compound | Structure | Name |
|---|---|---|
| 1 | 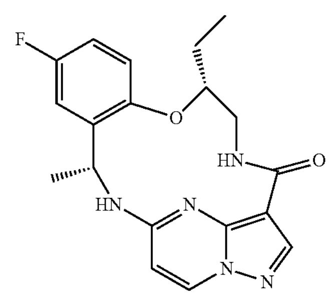 [SMILES: CC[C@@H]1CNC(=O)c2cnn3ccc(nc23)N[C@H](C)c2cc(F)ccc2O1] | (7R,13R)-7-ethyl-11-fluoro-13-methyl-6,7,13,14-tetrahydro-1,15-ethenopyrazolo[4,3-f][1,4,8,10]benzoxatriaza-cyclotridecin-4(5H)-one |
| 2 | 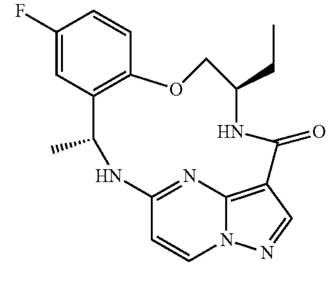 [SMILES: CC[C@@H]1COc2ccc(F)cc2[C@@H](C)Nc2ccn3ncc(c3n2)C(=O)N1] | (6R,13R)-6-ethyl-11-fluoro-13-methyl-6,7,13,14-tetrahydro-1,15-ethenopyrazolo[4,3-f][1,4,8,10]benzoxatriaza-cyclotridecin-4(5H)-one |

-continued

| Compound | Structure | Name |
|---|---|---|
| 3 | 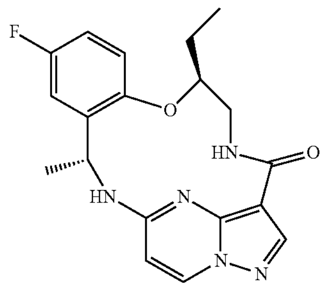 [SMILES: CC[C@H]1CNC(=O)c2cnn3ccc(nc23)N[C@H](C)c2cc(F)ccc2O1] | (7S,13R)-7-ethyl-11-fluoro-13-methyl-6,7,13,14-tetrahydro-1,15-ethenopyrazolo[4,3-f][1,4,8,10]benzoxatriaza-cyclotridecin-4(5H)-one |
| 4 | 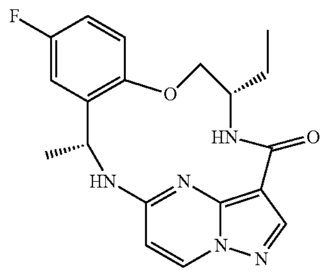 [SMILES: CC[C@H]1COc2ccc(F)cc2[C@@H](C)Nc2ccn3ncc(c3n2)C(=O)N1] | (6S,13R)-6-ethyl-11-fluoro-13-methyl-6,7,13,14-tetrahydro-1,15-ethenopyrazolo[4,3-f][1,4,8,10]benzoxatriaza-cyclotridecin-4(5H)-one |
| 5 | 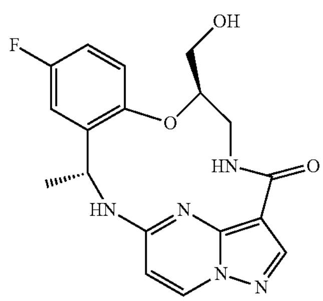 [SMILES: C[C@H]1Nc2ccn3ncc(c3n2)C(=O)NC[C@H](CO)Oc2ccc(F)cc21] | (7R,13R)-11-fluoro-7-(hydroxymethyl)-13-methyl-6,7,13,14-tetrahydro-1,15-ethenopyrazolo[4,3-f][1,4,8,10]benzoxatriaza-cyclotridecin-4(5H)-one |
| 6 | 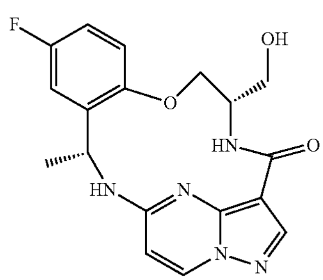 [SMILES: C[C@H]1Nc2ccn3ncc(c3n2)C(=O)N[C@@H](CO)COc2ccc(F)cc21] | (6S,13R)-11-fluoro-6-(hydroxymethyl)-13-methyl-6,7,13,14-tetrahydro-1,15-ethenopyrazolo[4,3-f][1,4,8,10]benzoxatriaza-cyclotridecin-4(5H)-one |
| 7 | 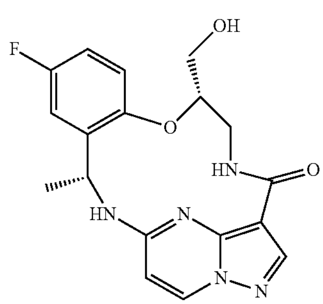 [SMILES: C[C@H]1Nc2ccn3ncc(c3n2)C(=O)NC[C@@H](CO)Oc2ccc(F)cc21] | (7S,13R)-11-fluoro-7-(hydroxymethyl)-13-methyl-6,7,13,14-tetrahydro-1,15-ethenopyrazolo[4,3-f][1,4,8,10]benzoxatriaza-cyclotridecin-4(5H)-one |

| Compound | Structure | Name |
|---|---|---|
| 8 | 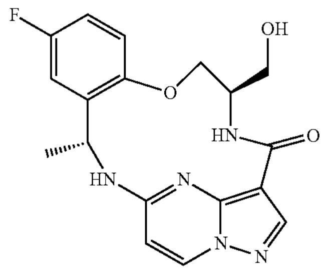 [SMILES: C[C@H]1Nc2ccn3ncc(c3n2)C(=O)N[C@H](CO)COc2ccc(F)cc21] | (6R,13R)-11-fluoro-6-(hydroxymethyl)-13-methyl-6,7,13,14-tetrahydro-1,15-ethenopyrazolo[4,3-f][1,4,8,10]benzoxatriaza-cyclotridecin-4(5H)-one |
| 9 | 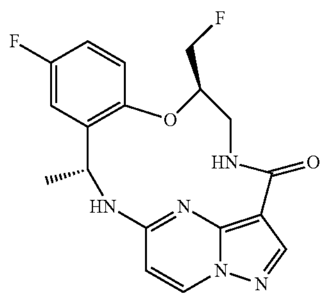 [SMILES: C[C@H]1Nc2ccn3ncc(c3n2)C(=O)NC[C@H](CF)Oc2ccc(F)cc21] | (7R,13R)-11-fluoro-7-(fluoromethyl)-13-methyl-6,7,13,14-tetrahydro-1,15-ethenopyrazolo[4,3-f][1,4,8,10]benzoxatriaza-cyclotridecin-4(5H)-one |
| 10 | 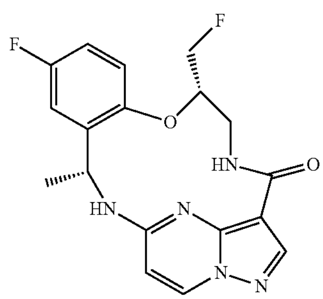 [SMILES: C[C@H]1Nc2ccn3ncc(c3n2)C(=O)NC[C@@H](CF)Oc2ccc(F)cc21] | (7S,13R)-11-fluoro-7-(fluoromethyl)-13-methyl-6,7,13,14-tetrahydro-1,15-ethenopyrazolo[4,3-f][1,4,8,10]benzoxatriaza-cyclotridecin-4(5H)-one |
| 11 | 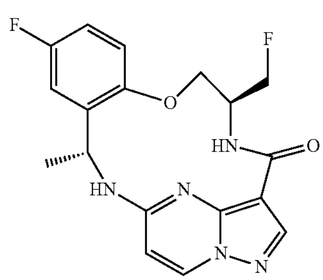 [SMILES: C[C@H]1Nc2ccn3ncc(c3n2)C(=O)N[C@H](CF)COc2ccc(F)cc21] | (6S,13R)-11-fluoro-6-(fluoromethyl)-13-methyl-6,7,13,14-tetrahydro-1,15-ethenopyrazolo[4,3-f][1,4,8,10]benzoxatriaza-cyclotridecin-4(5H)-one |
| 12 | 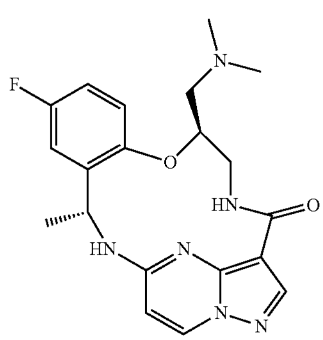 [SMILES: C[C@H]1Nc2ccn3ncc(c3n2)C(=O)NC[C@H](CN(C)C)Oc2ccc(F)cc21] | (7R,13R)-7-[(dimethylamino)methyl]-11-fluoro-13-methyl-6,7,13,14-tetrahydro-1,15-ethenopyrazolo[4,3-f][1,4,8,10]benzoxatriaza-cyclotridecin-4(5H)-one |

-continued

| Compound | Structure | Name |
|---|---|---|
| 13 | 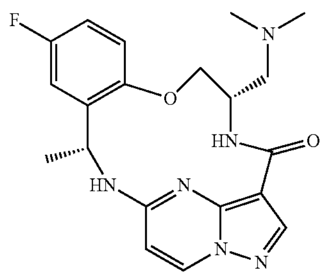 [SMILES: C[C@H]1Nc2ccn3ncc(c3n2)C(=O)N[C@@H](CN(C)C)COc2ccc(F)cc21] | (6S,13R)-6-[(dimethylamino)methyl]-11-fluoro-13-methyl-6,7,13,14-tetrahydro-1,15-ethenopyrazolo[4,3-f][1,4,8,10]benzoxatriaza-cyclotridecin-4(5H)-one |
| 14 | 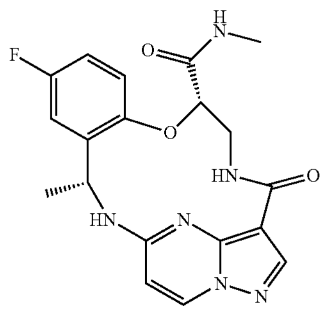 [SMILES: CNC(=O)[C@@H]1CNC(=O)c2cnn3ccc(nc23)N[C@H](C)c2cc(F)ccc2O1] | (7S,13R)-7-(N-methylcarboxamide)-11-fluoro-13-methyl-6,7,13,14-tetrahydro-1,15-ethenopyrazolo[4,3-f][1,4,8,10]benzoxatriaza-cyclotridecin-4(5H)-one |
| 15 | 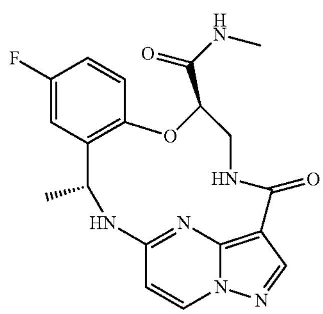 [SMILES: CNC(=O)[C@H]1CNC(=O)c2cnn3ccc(nc23)N[C@H](C)c2cc(F)ccc2O1] | (7R,13R)-7-(N-methylcarboxamide)-11-fluoro-13-methyl-6,7,13,14-tetrahydro-1,15-ethenopyrazolo[4,3-f][1,4,8,10]benzoxatriaza-cyclotridecin-4(5H)-one |
| 16 | 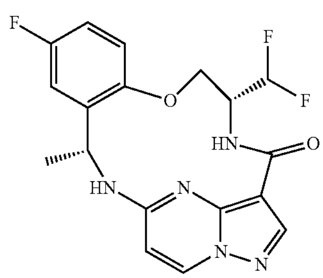 [SMILES: C[C@H]1Nc2ccn3ncc(c3n2)C(=O)N[C@@H](C(F)F)COc2ccc(F)cc21] | (6R,13R)-6-(difluoromethyl)-11-fluoro-13-methyl-6,7,13,14-tetrahydro-1,15-ethenopyrazolo[4,3-f][1,4,8,10]benzoxatriaza-cyclotridecin-4(5H)-one |
| 17 | 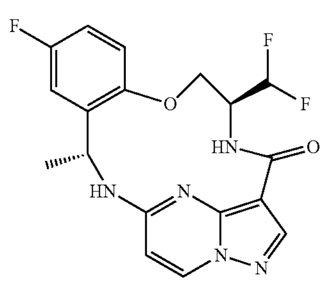 [SMILES: C[C@H]1Nc2ccn3ncc(c3n2)C(=O)N[C@H](C(F)F)COc2ccc(F)cc21] | (6S,13R)-6-(difluoromethyl)-11-fluoro-13-methyl-6,7,13,14-tetrahydro-1,15-ethenopyrazolo[4,3-f][1,4,8,10]benzoxatriaza-cyclotridecin-4(5H)-one |

| Compound | Structure | Name |
| --- | --- | --- |
| 18 | 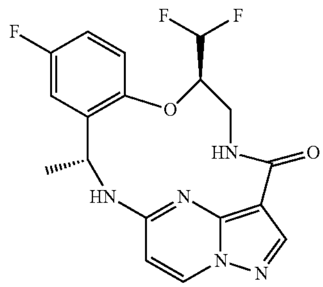 [SMILES: C[C@H]1Nc2ccn3ncc(c3n2)C(=O)NC[C@H](C(F)F)Oc2ccc(F)cc21] | (7R,13R)-7-(difluoromethyl)-11-fluoro-13-methyl-6,7,13,14-tetrahydro-1,15-ethenopyrazolo[4,3-f][1,4,8,10]benzoxatriaza-cyclotridecin-4(5H)-one |
| 19 | 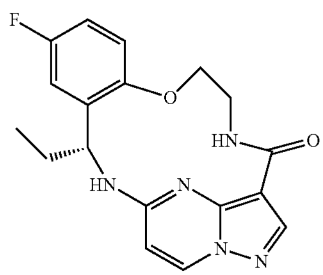 [SMILES: CC[C@H]1Nc2ccn3ncc(c3n2)C(=O)NCCOc2ccc(F)cc21] | (13R)-13-ethyl-11-fluoro-6,7,13,14-tetrahydro-1,15-ethenopyrazolo[4,3-f][1,4,8,10]benzoxatriaza-cyclotridecin-4(5H)-one |
| 20 | 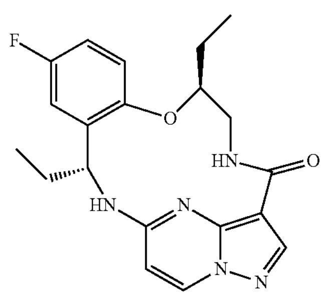 [SMILES: CC[C@H]1CNC(=O)c2cnn3ccc(nc23)N[C@H](CC)c2cc(F)ccc2O1] | (7S,13R)-7,13-diethyl-11-fluoro-6,7,13,14-tetrahydro-1,15-ethenopyrazolo[4,3-f][1,4,8,10]benzoxatriaza-cyclotridecin-4(5H)-one |
| 21 | 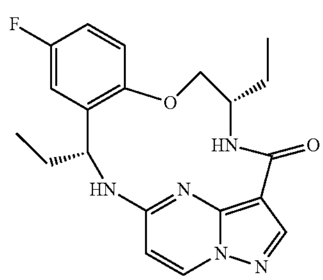 [SMILES: CC[C@H]1COc2ccc(F)cc2[C@@H](CC)Nc2ccn3ncc(c3n2)C(=O)N1] | (6S,13R)-6,13-diethyl-11-fluoro-6,7,13,14-tetrahydro-1,15-ethenopyrazolo[4,3-f][1,4,8,10]benzoxatriaza-cyclotridecin-4(5H)-one |
| 22 | 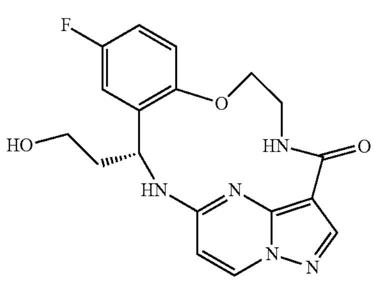 [SMILES: O=C1NCCOc2ccc(F)cc2[C@@H](CCO)Nc2ccn3ncc1c3n2] | (13R)-11-fluoro-13-(2-hydroxyethyl)-6,7,13,14-tetrahydro-1,15-ethenopyrazolo[4,3-f][1,4,8,10]benzoxatriaza-cyclotridecin-4(5H)-one |

| Compound | Structure | Name |
|---|---|---|
| 23 | 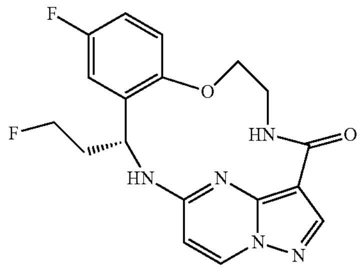 [SMILES: O=C1NCCOc2ccc(F)cc2[C@@H](CCF)Nc2ccn3ncc1c3n2] | (13R)-11-fluoro-13-(2-fluoroethyl)-6,7,13,14-tetrahydro-1,15-ethenopyrazolo[4,3-f][1,4,8,10]benzoxatriaza-cyclotridecin-4(5H)-one |
| 24 | 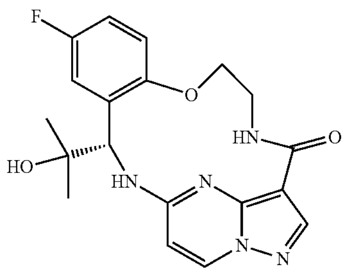 [SMILES: CC(C)(O)[C@H]1Nc2ccn3ncc(c3n2)C(=O)NCCOc2ccc(F)cc21] | (13S)-11-fluoro-13-(2-hydroxypropan-2-yl)-6,7,13,14-tetrahydro-1,15-ethenopyrazolo[4,3-f][1,4,8,10]benzoxatriaza-cyclotridecin-4(5H)-one |
| 25 | 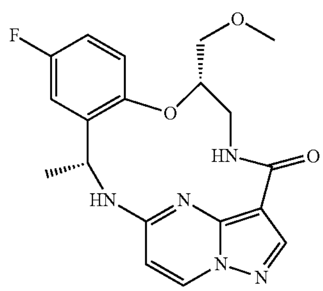 [SMILES: COC[C@@H]1CNC(=O)c2cnn3ccc(nc23)N[C@H](C)c2cc(F)ccc2O1] | (7S,13R)-11-fluoro-7-(methoxymethyl)-13-methyl-6,7,13,14-tetrahydro-1,15-ethenopyrazolo[4,3-f][1,4,8,10]benzoxatriaza-cyclotridecin-4(5H)-one |
| 26 | 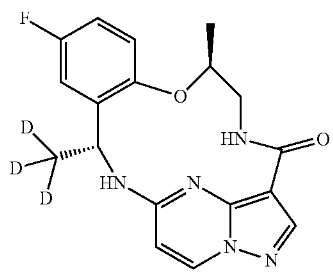 [SMILES: [2H]C([2H])([2H])[C@H]1Nc2ccn3ncc(c3n2)C(=O)NC[C@H](C)Oc2ccc(F)cc21] | (7S,13R)-11-fluoro-7-methyl-13-($^2$H$_3$)methyl-6,7,13,14-tetrahydro-1,15-ethenopyrazolo[4,3-f][1,4,8,10]benzoxatriaza-cyclotridecin-4(5H)-one |
| 27 | 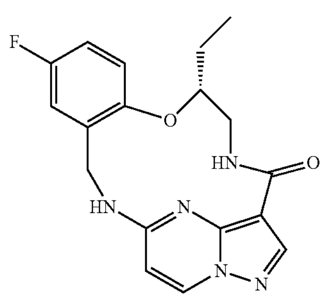 [SMILES: CC[C@@H]1CNC(=O)c2cnn3ccc(nc23)NCc2cc(F)ccc2O1] | (7R)-7-ethyl-11-fluoro-6,7,13,14-tetrahydro-1,15-ethenopyrazolo[4,3-f][1,4,8,10]benzoxatriaza-cyclotridecin-4(5H)-one |

| Compound | Structure | Name |
|---|---|---|
| 28 | 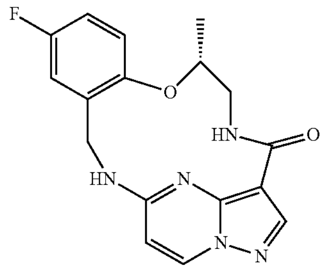 [SMILES: C[C@@H]1CNC(=O)c2cnn3ccc(nc23)NCc2cc(F)ccc2O1] | (7R)-11-fluoro-7-methyl-6,7,13,14-tetrahydro-1,15-ethenopyrazolo[4,3-f][1,4,8,10]benzoxatriaza-cyclotridecin-4(5H)-one |
| 29 | 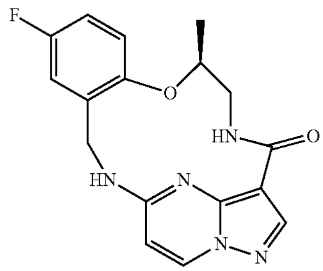 [SMILES: C[C@H]1CNC(=O)c2cnn3ccc(nc23)NCc2cc(F)ccc2O1] | (7S)-11-fluoro-7-methyl-6,7,13,14-tetrahydro-1,15-ethenopyrazolo[4,3-f][1,4,8,10]benzoxatriaza-cyclotridecin-4(5H)-one |
| 30 | 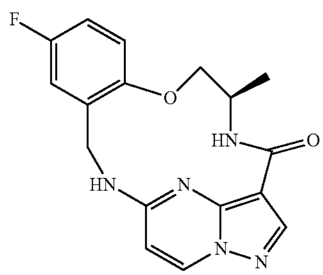 [SMILES: C[C@@H]1COc2ccc(F)cc2CNc2ccn3ncc(c3n2)C(=O)N1] | (6R)-11-fluoro-6-methyl-6,7,13,14-tetrahydro-1,15-ethenopyrazolo[4,3-f][1,4,8,10]benzoxatriaza-cyclotridecin-4(5H)-one |
| 31 | 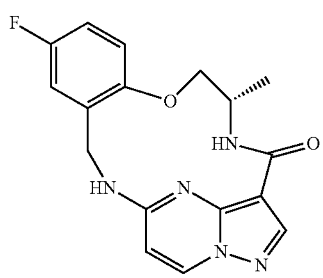 [SMILES: C[C@H]1COc2ccc(F)cc2CNc2ccn3ncc(c3n2)C(=O)N1] | (6S)-11-fluoro-6-methyl-6,7,13,14-tetrahydro-1,15-ethenopyrazolo[4,3-f][1,4,8,10]benzoxatriaza-cyclotridecin-4(5H)-one |
| 32 | 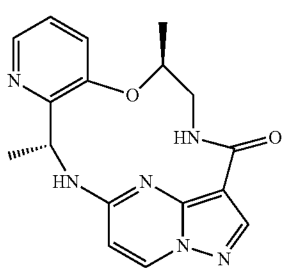 [SMILES: C[C@H]1CNC(=O)c2cnn3ccc(nc23)N[C@H](C)c2ncccc2O1] | (7S,13R)-7,13-dimethyl-6,7,13,14-tetrahydro-1,15-ethenopyrazolo[4,3-f]pyrido[2,3-l][1,4,8,10]oxatriaza-cyclotridecin-4(5H)-one |

-continued

| Compound | Structure | Name |
|---|---|---|
| 33 | 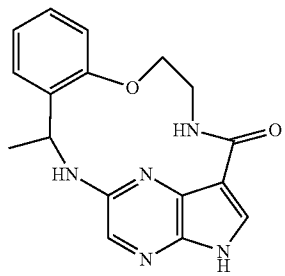 [SMILES: CC1Nc2cnc3[nH]cc(c3n2)C(=O)NCCOc2ccccc21] | 7-methyl-6,7,14,15-tetrahydro-2H-3,5-(azenometheno)pyrrolo[3,4-f][1,4,8,10]benzoxatriaza-cyclotridecin-16(13H)-one |
| 34 | 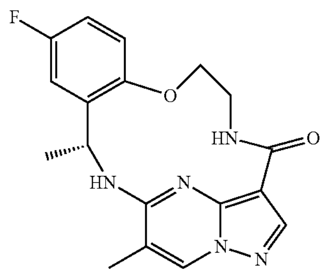 [SMILES: Cc1cn2ncc3c2nc1N[C@H](C)c1cc(F)ccc1OCCNC3=O] | (13R)-11-fluoro-13,17-dimethyl-6,7,13,14-tetrahydro-1,15-ethenopyrazolo[4,3-f][1,4,8,10]benzoxatriaza-cyclotridecin-4(5H)-one |
| 35 | 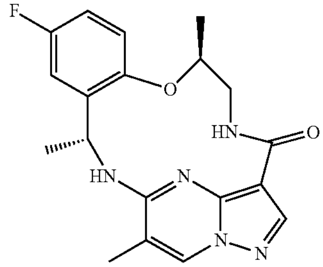 [SMILES: Cc1cn2ncc3c2nc1N[C@H](C)c1cc(F)ccc1O[C@@H](C)CNC3=O] | (7S,13R)-11-fluoro-7,13,17-trimethyl-6,7,13,14-tetrahydro-1,15-ethenopyrazolo[4,3-f][1,4,8,10]benzoxatriaza-cyclotridecin-4(5H)-one |
| 36 | 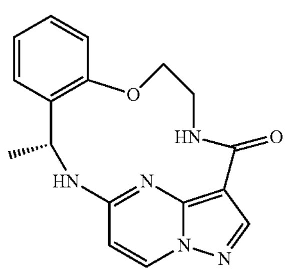 [SMILES: C[C@H]1Nc2ccn3ncc(c3n2)C(=O)NCCOc2ccccc21] | (13R)-13-methyl-6,7,13,14-tetrahydro-1,15-ethenopyrazolo[4,3-f][1,4,8,10]benzoxatriaza-cyclotridecin-4(5H)-one |
| 37 | 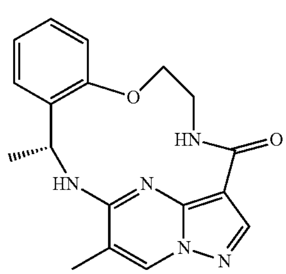 [SMILES: Cc1cn2ncc3c2nc1N[C@H](C)c1ccccc1OCCNC3=O] | (13R)-13,17-dimethyl-6,7,13,14-tetrahydro-1,15-ethenopyrazolo[4,3-f][1,4,8,10]benzoxatriaza-cyclotridecin-4(5H)-one |

| Compound | Structure | Name |
|---|---|---|
| 38 | 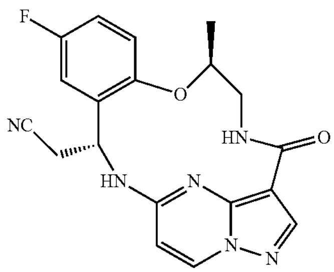 [SMILES: C[C@H]1CNC(=O)c2cnn3ccc(nc23)N[C@H](CC#N)c2cc(F)ccc2O1] | [(7S,13R)-11-fluoro-7-methyl-4-oxo-4,5,6,7,13,14-hexahydro-1,15-ethenopyrazolo[4,3-f][1,4,8,10]benzoxatriaza-cyclotridecin-13-yl]acetonitrile |
| 39 | 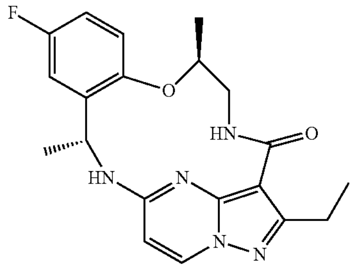 [SMILES: CCc1nn2ccc3nc2c1C(=O)NC[C@H](C)Oc1ccc(F)cc1[C@@H](C)N3] | (7S,13R)-3-ethyl-11-fluoro-7,13-dimethyl-6,7,13,14-tetrahydro-1,15-ethenopyrazolo[4,3-f][1,4,8,10]benzoxatriaza-cyclotridecin-4(5H)-one |
| 40 | 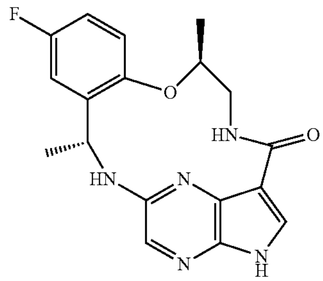 [SMILES: C[C@H]1CNC(=O)c2c[nH]c3ncc(nc23)N[C@H](C)c2cc(F)ccc2O1] | (7R,13S)-9-fluoro-7,13-dimethyl-6,7,14,15-tetrahydro-2H-3,5-(azenometheno)pyrrolo[3,4-f][1,4,8,10]benzoxatriaza-cyclotridecin-16(13H)-one |
| 41 | 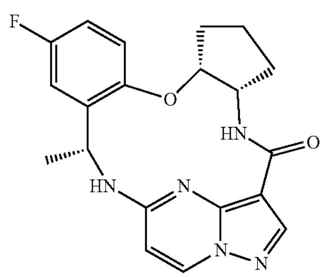 [SMILES: C[C@H]1Nc2ccn3ncc(c3n2)C(=O)N[C@H]2CCC[C@H]2Oc2ccc(F)cc21] | (3αR,9R,17αS)-7-fluoro-9-methyl-1,2,3,3α,9,10,17,17α-octahydro-16H-11,13-ethenocyclopenta[b]pyrazolo[4,3-f][1,4,8,10]benzoxatriaza-cyclotridecin-16-one |
| 42 | 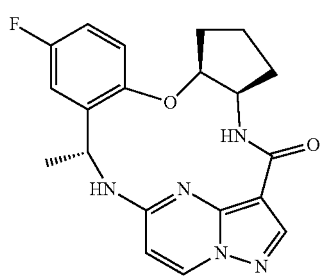 [SMILES: C[C@H]1Nc2ccn3ncc(c3n2)C(=O)N[C@@H]2CCC[C@@H]2Oc2ccc(F)cc21] | (3αS,9R,17αR)-7-fluoro-9-methyl-1,2,3,3α,9,10,17,17α-octahydro-16H-11,13-ethenocyclopenta[b]pyrazolo[4,3-f][1,4,8,10]benzoxatriaza-cyclotridecin-16-one |

| Compound | Structure | Name |
|---|---|---|
| 43 | 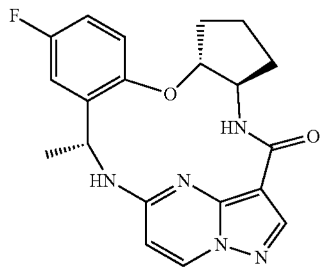 [SMILES: C[C@H]1Nc2ccn3ncc(c3n2)C(=O)N[C@@H]2CCC[C@H]2Oc2ccc(F)cc21] | (3αR,9R,17αR)-7-fluoro-9-methyl-1,2,3,3α,9,10,17,17α-octahydro-16H-11,13-ethenocyclopenta[b]pyrazolo[4,3-f][1,4,8,10]benzoxatriazacyclotridecin-16-one |
| 44 | 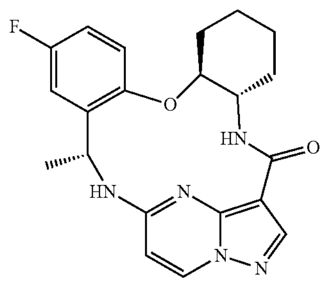 [SMILES: C[C@H]1Nc2ccn3ncc(c3n2)C(=O)N[C@H]2CCCC[C@@H]2Oc2ccc(F)cc21] | (4αS,10R,18αS)-8-fluoro-10-methyl-2,3,4,4α,10,11,18,18α-octahydro-12,14-ethenodibenzo[b,l]pyrazolo[4,3-f][1,4,8,10]oxatriazacyclotridecin-17(1H)-one |
| 45 | 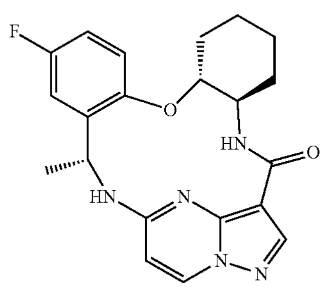 [SMILES: C[C@H]1Nc2ccn3ncc(c3n2)C(=O)N[C@@H]2CCCC[C@H]2Oc2ccc(F)cc21] | (4αR,10R,18αR)-8-fluoro-10-methyl-2,3,4,4α,10,11,18,18α-octahydro-12,14-ethenodibenzo[b,l]pyrazolo[4,3-f][1,4,8,10]oxatriazacyclotridecin-17(1H)-one |
| 46 | 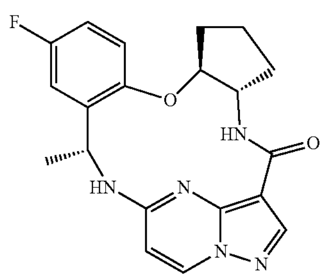 [SMILES: C[C@H]1Nc2ccn3ncc(c3n2)C(=O)N[C@H]2CCC[C@@H]2Oc2ccc(F)cc21] | (3αS,9R,17αS)-7-fluoro-9-methyl-1,2,3,3α,9,10,17,17α-octahydro-16H-11,13-ethenocyclopenta[b]pyrazolo[4,3-f][1,4,8,10]benzoxatriazacyclotridecin-16-one |
| 47 | 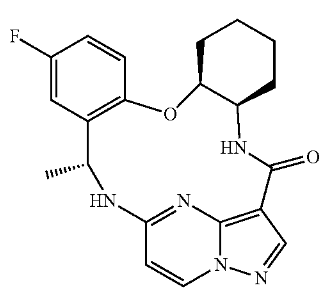 [SMILES: C[C@H]1Nc2ccn3ncc(c3n2)C(=O)N[C@@H]2CCCC[C@@H]2Oc2ccc(F)cc21] | (4αS,10R,18αR)-8-fluoro-10-methyl-2,3,4,4α,10,11,18,18α-octahydro-12,14-ethenodibenzo[b,l]pyrazolo[4,3-f][1,4,8,10]oxatriazacyclotridecin-17(1H)-one |

-continued

| Compound | Structure | Name |
|---|---|---|
| 48 | 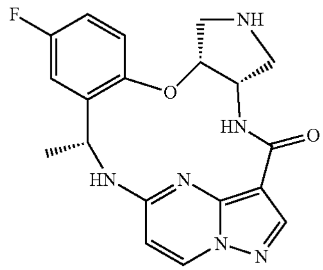 [SMILES: C[C@H]1Nc2ccn3ncc(c3n2)C(=O)N[C@H]2CNC[C@H]2Oc2ccc(F)cc21] | (3αR,9R,17αS)-7-fluoro-9-methyl-1,2,3,3α,9,10,17,17α-octahydro-16H-11,13-ethenopyrazolo[4,3-f]pyrrolo[3,4-b][1,4,8,10]benzoxatriaza-cyclotridecin-16-one |
| 49 | 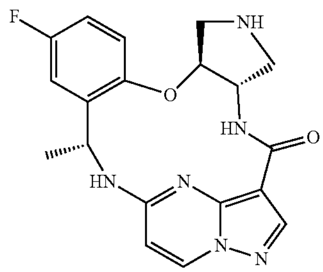 [SMILES: C[C@H]1Nc2ccn3ncc(c3n2)C(=O)N[C@H]2CNC[C@@H]2Oc2ccc(F)cc21] | (3αS,9R,17αS)-7-fluoro-9-methyl-1,2,3,3α,9,10,17,17α-octahydro-16H-11,13-ethenopyrazolo[4,3-f]pyrrolo[3,4-b][1,4,8,10]benzoxatriaza-cyclotridecin-16-one |
| 50 | 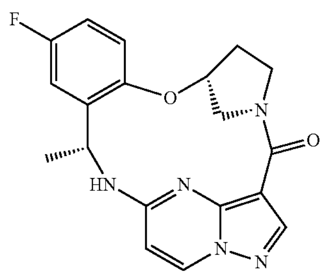 | (8R,14R)-12-fluoro-14-methyl-7,8,14,15-tetrahydro-4H,6H-1,16-etheno-5,8-methanopyrazolo[4,3-g][1,5,9,11]benzoxatriaza-cyclotetradecin-4-one |
| 51 | 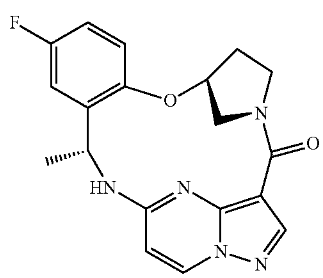 | (8S,14R)-12-fluoro-14-methyl-7,8,14,15-tetrahydro-4H,6H-1,16-etheno-5,8-methanopyrazolo[4,3-g][1,5,9,11]benzoxatriaza-cyclotetradecin-4-one |
| 52 | 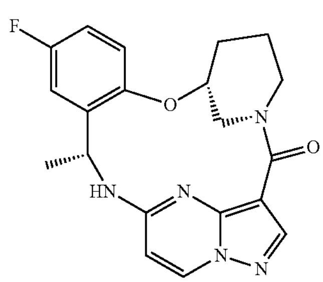 | (9R,15R)-13-fluoro-15-methyl-6,7,8,9,15,16-hexahydro-4H-1,17-etheno-5,9-methanopyrazolo[4,3-h][1,6,10,12]benzoxatriaza-cyclopentadecin-4-one |

| Compound | Structure | Name |
|---|---|---|
| 53 | 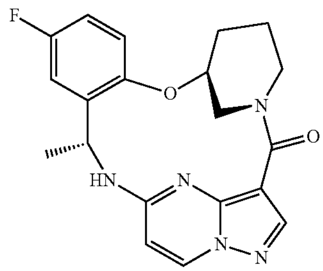 | (9S,15R)-13-fluoro-15-methyl-6,7,8,9,15,16-hexahydro-4H-1,17-etheno-5,9-methanopyrazolo[4,3-h][1,6,10,12]benzoxatriaza-cyclopentadecin-4-one |
| 54 | 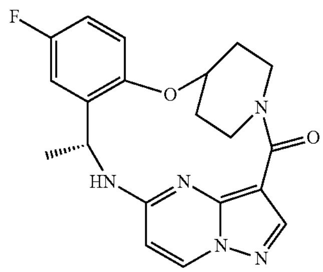 [SMILES: C[C@H]1Nc2ccn3ncc(c3n2)C(=O)N2CCC(CC2)Oc2ccc(F)cc21] | (14R)-12-fluoro-14-methyl-7,8,14,15-tetrahydro-4H,6H-5,8-etheno-1,16-ethenopyrazolo[4,3-g][1,5,9,11]benzoxatriaza-cyclotetradecin-4-one |
| 55 | 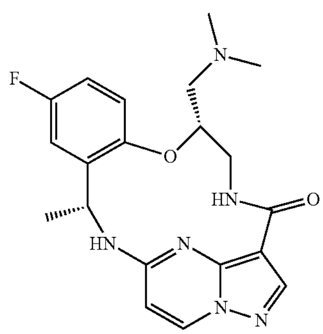 [SMILES: C[C@H]1Nc2ccn3ncc(c3n2)C(=O)NC[C@@H](CN(C)C)Oc2ccc(F)cc21] | (7S,13R)-7-[(dimethylamino)methyl]-11-fluoro-13-methyl-6,7,13,14-tetrahydro-1,15-ethenopyrazolo[4,3-f][1,4,8,10]benzoxatriaza-cyclotridecin-4(5H)-one |
| 56 | 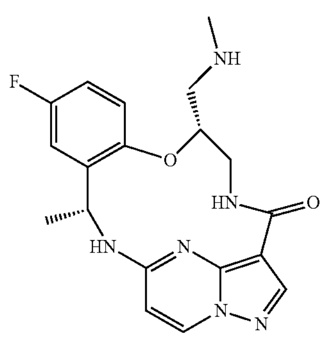 [SMILES: CNC[C@@H]1CNC(=O)c2cnn3ccc(nc23)N[C@H](C)c2cc(F)ccc2O1] | (7R,13R)-11-fluoro-13-methyl-7-[(methylamino)methyl]-6,7,13,14-tetrahydro-1,15-ethenopyrazolo[4,3-f][1,4,8,10]benzoxatriaza-cyclotridecin-4(5H)-one |
| 57 | 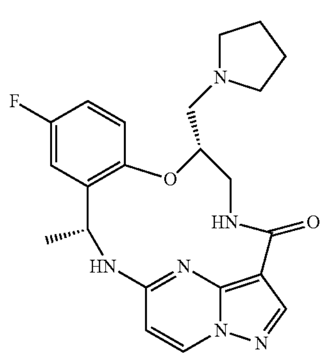 [SMILES: C[C@H]1Nc2ccn3ncc(c3n2)C(=O)NC[C@@H](CN2CCCC2)Oc2ccc(F)cc21] | (7S,13R)-11-fluoro-13-methyl-7-[(pyrrolidin-1-yl)methyl]-6,7,13,14-tetrahydro-1,15-ethenopyrazolo[4,3-f][1,4,8,10]benzoxatriaza-cyclotridecin-4(5H)-one |

| Compound | Structure | Name |
|---|---|---|
| 58 | 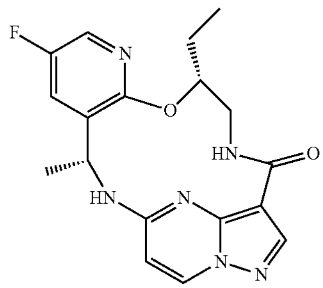 [SMILES: CC[C@@H]1CNC(=O)c2cnn3ccc(nc23)N[C@H](C)c2cc(F)cnc2O1] | (7R,13R)-7-ethyl-11-fluoro-13-methyl-6,7,13,14-tetrahydro-1,15-ethenopyrazolo[4,3-f]pyrido[3,2-l][1,4,8,10]oxatriaza-cyclotridecin-4(5H)-one |
| 59 | 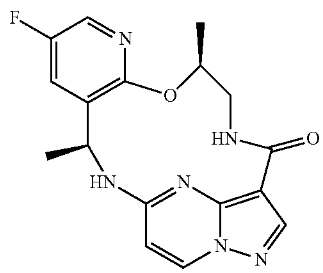 [SMILES: C[C@@H]1Nc2ccn3ncc(c3n2)C(=O)NC[C@H](C)Oc2ncc(F)cc21] | (7S,13S)-11-fluoro-7,13-dimethyl-6,7,13,14-tetrahydro-1,15-ethenopyrazolo[4,3-f]pyrido[3,2-l][1,4,8,10]oxatriaza-cyclotridecin-4(5H)-one |
| 60 | 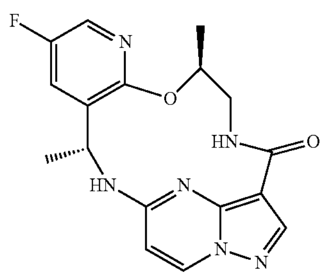 [SMILES: C[C@H]1CNC(=O)c2cnn3ccc(nc23)N[C@H](C)c2cc(F)cnc2O1] | (7S,13R)-11-fluoro-7,13-dimethyl-6,7,13,14-tetrahydro-1,15-ethenopyrazolo[4,3-f]pyrido[3,2-l][1,4,8,10]oxatriaza-cyclotridecin-4(5H)-one |
| 61 | 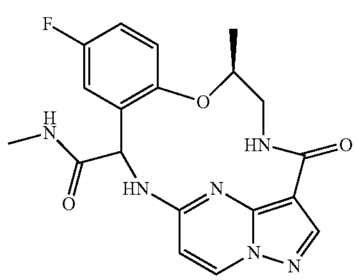 [SMILES: CNC(=O)C1Nc2ccn3ncc(c3n2)C(=O)NC[C@H](C)Oc2ccc(F)cc21] | (7S)-11-fluoro-N,7-dimethyl-4-oxo-4,5,6,7,13,14-hexahydro-1,15-ethenopyrazolo[4,3-f][1,4,8,10]benzoxatriaza-cyclotridecine-13-carboxamide |
| 62 | 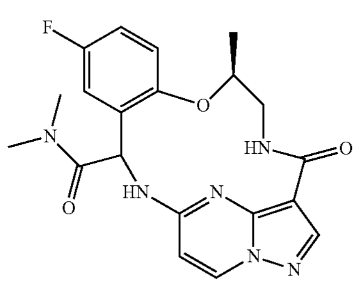 [SMILES: C[C@H]1CNC(=O)c2cnn3ccc(nc23)NC(C(=O)N(C)C)c2cc(F)ccc2O1] | (7S)-11-fluoro-N,N,7-trimethyl-4-oxo-4,5,6,7,13,14-hexahydro-1,15-ethenopyrazolo[4,3-f][1,4,8,10]benzoxatriaza-cyclotridecine-13-carboxamide |

Those skilled in the art will recognize that the species listed or illustrated herein are not exhaustive, and that additional species within the scope of these defined terms may also be selected.

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, rectal, nasal, topical, or ocular routes, or by inhalation. Preferably, the compositions are formulated for intravenous or oral administration.

For oral administration, the compounds the invention may be provided in a solid form, such as a tablet or capsule, or as a solution, emulsion, or suspension. To prepare the oral compositions, the compounds of the invention may be formulated to yield a dosage of, e.g., from about 0.1 mg to 1 g daily, or about 1 mg to 50 mg daily, or about 50 to 250 mg daily, or about 250 mg to 1 g daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier. The inventive compositions may be formulated for rectal administration as a suppository.

For topical applications, the compounds of the present invention are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the invention may utilize a patch formulation to effect transdermal delivery.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

The term "subject" refers to a mammalian patient in need of such treatment, such as a human.

Exemplary diseases include cancer, pain, neurological diseases, autoimmune diseases, and inflammation. Cancer includes, for example, lung cancer, colon cancer, breast cancer, prostate cancer, hepatocellular carcinoma, renal cell carcinoma, gastric and esophago-gastric cancers, glioblastoma, head and neck cancers, inflammatory myofibroblastic tumors, and anaplastic large cell lymphoma. Pain includes, for example, pain from any source or etiology, including cancer pain, pain from chemotherapeutic treatment, nerve pain, pain from injury, or other sources. Autoimmune diseases include, for example, rheumatoid arthritis, Sjogren syndrome, Type I diabetes, and lupus. Exemplary neurological diseases include Alzheimer's Disease, Parkinson's Disease, Amyotrophic lateral sclerosis, and Huntington's disease. Exemplary inflammatory diseases include atherosclerosis, allergy, and inflammation from infection or injury.

In one aspect, the compounds and pharmaceutical compositions of the invention specifically target tyrosine receptor kinases, in particular MET, ALK, AXL, TRKs, and JAKs. Thus, these compounds and pharmaceutical compositions can be used to prevent, reverse, slow, or inhibit the activity of one or more of these kinases. In preferred embodiments, methods of treatment target cancer. In other embodiments, methods are for treating lung cancer or non-small cell lung cancer.

In the inhibitory methods of the invention, an "effective amount" means an amount sufficient to inhibit the target protein. Measuring such target modulation may be performed by routine analytical methods such as those described below. Such modulation is useful in a variety of settings, including in vitro assays. In such methods, the cell is preferably a cancer cell with abnormal signaling due to upregulation of MET, ALK, AXL, TRKs, and/or JAKs.

In treatment methods according to the invention, an "effective amount" means an amount or dose sufficient to generally bring about the desired therapeutic benefit in subjects needing such treatment. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about from about 0.1 mg to 1 g daily, or about 1 mg to 50 mg daily, or about 50 to 250 mg daily, or about 250 mg to 1 g daily. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Drug Combinations

The inventive compounds described herein may be used in pharmaceutical compositions or methods in combination with one or more additional active ingredients in the treatment of the diseases and disorders described herein. Further additional active ingredients include other therapeutics or agents that mitigate adverse effects of therapies for the intended disease targets. Such combinations may serve to increase efficacy, ameliorate other disease symptoms, decrease one or more side effects, or decrease the required dose of an inventive compound. The additional active ingredients may be administered in a separate pharmaceutical composition from a compound of the present invention or may be included with a compound of the present invention in a single pharmaceutical composition. The additional active ingredients may be administered simultaneously with, prior to, or after administration of a compound of the present invention.

Combination agents include additional active ingredients are those that are known or discovered to be effective in treating the diseases and disorders described herein, including those active against another target associated with the disease. For example, compositions and formulations of the invention, as well as methods of treatment, can further comprise other drugs or pharmaceuticals, e.g., other active agents useful for treating or palliative for the target diseases or related symptoms or conditions. For cancer indications, additional such agents include, but are not limited to, kinase inhibitors, such as EGFR inhibitors (e.g., erlotinib, gefitinib), Raf inhibitors (e.g., vemurafenib), VEGFR inhibitors (e.g., sunitinib), ALK inhibitors (e.g., crizotinib) standard chemotherapy agents such as alkylating agents, antimetabolites, anti-tumor antibiotics, topoisomerase inhibitors, platinum drugs, mitotic inhibitors, antibodies, hormone therapies, or corticosteroids. For pain indications, suitable combination agents include anti-inflammatories such as NSAIDs. The pharmaceutical compositions of the invention may additional comprise one or more of such active agents, and methods of treatment may additionally comprise administering an effective amount of one or more of such active agents.

Chemical Synthesis

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

Abbreviations

The examples described herein use materials, including but not limited to, those described by the following abbreviations known to those skilled in the art:

| | |
|---|---|
| g | grams |
| eq | equivalents |
| mmol | millimoles |
| mL | milliliters |
| EtOAc | ethyl acetate |
| MHz | megahertz |
| ppm | parts per million |
| δ | chemical shift |
| s | singlet |
| d | doublet |
| t | triplet |
| q | quartet |

| | |
|---|---|
| quin | quintet |
| br | broad |
| m | multiplet |
| Hz | hertz |
| THF | tetrahydrofuran |
| °C. | degrees Celsius |
| PE | petroleum ether |
| EA | ethyl acetate |
| $R_f$ | retardation factor |
| N | normal |
| J | coupling constant |
| DMSO-$d_6$ | deuterated dimethyl sulfoxide |
| n-BuOH | n-butanol |
| DIEA | n,n-diisopropylethylamine |
| TMSCl | trimethylsilyl chloride |
| min | minutes |
| hr | hours |
| Me | methyl |
| Et | ethyl |
| i-Pr | isopropyl |
| TLC | thin layer chromatography |
| M | molar |
| Compd# | compound number |
| MS | mass spectrum |
| m/z | mass-to-charge ratio |
| Ms | methanesulfonyl |
| FDDP | pentafluorophenyl diphenylphosphinate |
| Boc | tert-butyloxycarbonyl |
| TFA | trifluoroacetic acid |
| Tos | toluenesulfonyl |
| DMAP | 4-(dimethylamino)pyridine |
| μM | micromolar |
| ATP | adenosine triphosphate |
| $IC_{50}$ | half maximal inhibitory concentration |
| U/mL | units of activity per milliliter |
| HOBt | hydroxybenzotriazol |
| MOM | methoxymethy |
| DIPEA | diisopropylethylamine |
| Deoxo-Fluor | bis(2-methoxyethyl)aminosulfur trifluoride |
| Hunig's base | diisopropylethylamine |
| DIAD | diisopropyl azodicarboxylate |
| TFAA | Trifluoroacetic acid |
| SEM | trimethylsilylethyoxymethyl |
| DMF | dimethylformamide |
| DCM | dichloromethane |
| DEAD | diethyl azodicarboxylate |
| MeTHF | 2-methyltetrahydrofuran |

General Method A.

Preparation of ethyl (R)-5-((1-(5-fluoro-2-hydroxyphenyl)ethyl)amino)pyrazolo[1,5-a]pyrimidine-3-carboxylate (A-1)

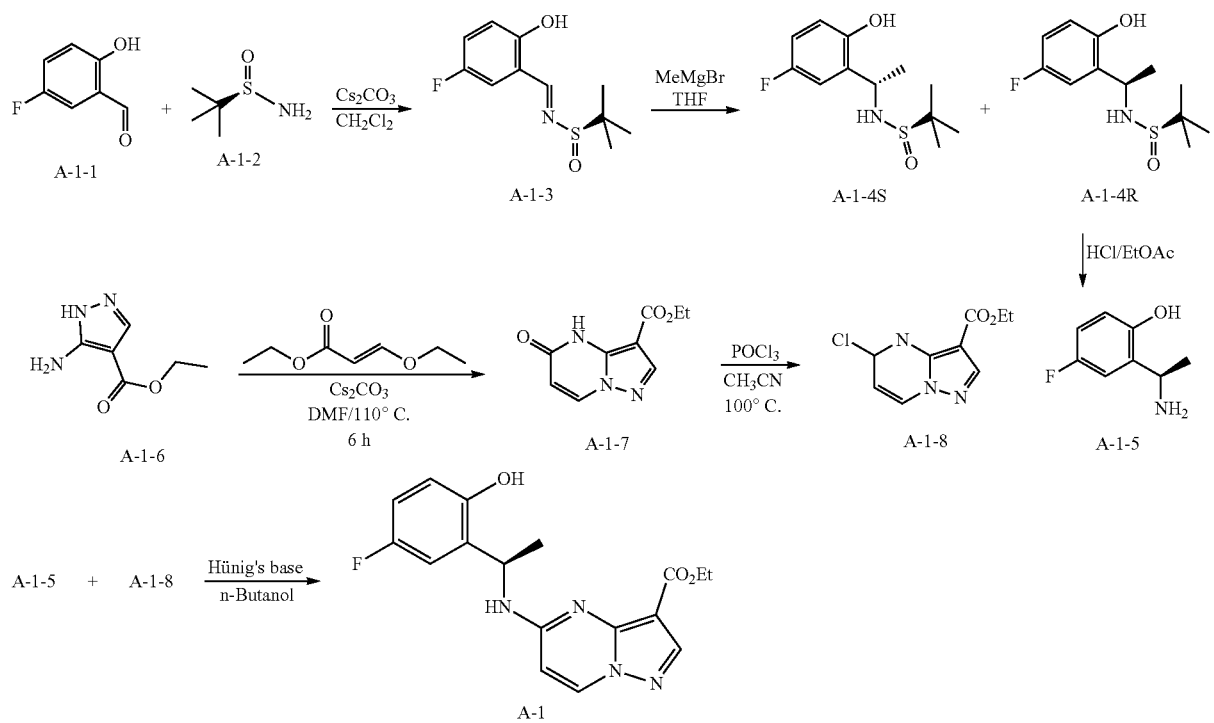

Step 1. Preparation of (R)—N-(5-fluoro-2-hydroxybenzylidene)-2-methylpropane-2-sulfinamide (A-1-3)

To a solution of (R)-2-methylpropane-2-sulfinamide (Sigma-Aldrich, 20.00 g, 165.02 mmol, 1.00 eq.) and 5-fluoro-2-hydroxybenzaldehyde (Sigma-Aldrich, 23.12 g, 165.02 mmol, 1.00 eq.) in dichloromethane (200.00 mL)

was added Cs₂CO₃ (161.30 g, 495.06 mmol, 3.00 eq.). The mixture was stirred at ambient temperature for 16 hours. The reaction mixture was quenched by addition of water (200 mL) at 0° C. and then extracted with EtOAc (200 mL×4). The combined organic layers were washed with brine (500 mL), dried over Na₂SO₄, filtered and concentrated. The residue was purified by a silica gel column eluting with petroleum ether/ethyl acetate from 20:1 to 1:1 to provide A-1-3 (18.00 g, 73.98 mmol, 44.83% yield) as a white solid. ¹H NMR (CDCl₃, 400 MHz) δ ppm 8.66 (s, 1H), 7.19 (dt, J=2.4, 5.2 Hz, 2H), 7.03-6.96 (m, 1H), 1.29 (s, 9H).

Step 2. Preparation of (R)—N—((R)-1-(5-fluoro-2-hydroxyphenyl)ethyl)-2-methylpropane-2-sulfinamide (A-1-4R)

To a solution of A-1-3 (6.00 g, 24.66 mmol, 1.00 eq.) in THF (50.00 mL) was added a solution of MeMgBr in THF (2M, 61.7 mL, 123.30 mmol, 5.00 eq.) drop-wise at −65° C. under N₂. Then the mixture was warmed to ambient temperature and stirred for 18 hours. The reaction mixture was quenched by addition of water (20 mL) at 0° C., and the mixture was extracted with EtOAc (20 mL×3). The combined organic layers were washed with brine (50 mL), dried over Na₂SO₄, filtered and concentrated under reduced pressure. The residue was purified by a silica gel eluting with petroleum ether/ethyl acetate from 50/1 to 1:1) to give A-1-4R (Rf: 0.5, PE:EA=1:1) (1.8 g, 28% yield) and A-1-4S (Rf: 0.4, PE:EA=1:1). ¹HNMR of A-1-4R (CDCl₃, 400 MHz) δ 9.34 (s, 1H), 6.76 (dd, J=2.8, 8.8 Hz, 1H), 6.54 (dt, J=2.9, 8.5 Hz, 1H), 6.38 (dd, J=4.8, 8.8 Hz, 1H), 5.27 (d, J=8.0 Hz, 1H), 4.36 (quin, J=7.2 Hz, 1H), 1.52 (d, J=7.0 Hz, 3H), 1.29 (s, 9H). ¹HNMR of A-1-4S (CDCl₃, 400 MHz) 8.81 (s, 1H), 6.88 (dd, J=2.6, 9.2 Hz, 1H), 6.84-6.76 (m, 1H), 6.76-6.70 (m, 1H), 4.75-4.63 (m, 1H), 4.26 (d, J=4.5 Hz, 1H), 1.58 (d, J=6.8 Hz, 3H), 1.27 (s, 9H).

Step 3. Preparation of (R)-2-(1-aminoethyl)-4-fluorophenol (A-1-5)

A solution of A-1-4R (1.80 g, 6.94 mmol, 1.00 eq.) in HCl/EtOAc (20.00 mL, 4N) was stirred at ambient temperature for 2 hours, and then the mixture was concentrated to provide A-1-5 as a white solid HCl salt (1.10 g, 5.74 mmol, 82.70% yield). ¹HNMR (DMSO-d₆, 400 MHz) δ 10.24 (s, 1H), 8.48 (br. s., 3H), 7.31 (dd, J=2.9, 9.7 Hz, 1H), 7.05-6.99 (m, 1H), 6.98-6.93 (m, 1H), 4.59-4.45 (m, 1H), 1.46 (d, J=6.8 Hz, 3H).

Step 4. Preparation of ethyl 5-oxo-4H-pyrazolo[1,5-a]pyrimidine-3-carboxylate (A-1-7)

To a mixture of ethyl 5-amino-1H-pyrazole-4-carboxylate (150.00 g, 1.08 mmol) and ethyl (E)-3-ethoxyprop-2-enoate (292.16 g, 2.03 mol) in DMF (3.2 L) was added Cs₂CO₃ (656.77 g, 2.02 mol) in one portion at 20° C. under N₂. The mixture was stirred at 110° C. for 6 h. TLC (PE:EtOAc=1:1) showed the reaction was completed. The mixture was cooled to 20° C. and filtered through a celite pad. The filter cake was washed with ethyl acetate (3×30 mL). The filtrate was added to H₂O (2 L) and acidified with HOAc to pH=4. The resultant precipitate was filtered to afford A-1-7 (173.00 g, 834.98 mmol, 86.36% yield) as a white solid: ¹H NMR (400 MHz, DMSO-d₆) δ 8.54 (d, J=7.91 Hz, 1H), 8.12 (s, 1H), 6.13 (d, J=7.91 Hz, 1H), 4.27 (q, J=7.11 Hz, 2H), 1.28 (t, J=7.09 Hz, 3H).

Step 5: Preparation of 5-chloropyrazolo[1,5-a]pyrimidine-3-carboxylate (A-1-8)

To a mixture of A-1-7 (158.00 g, 762.59 mmol) in MeCN (1.6 L) was added POCl₃ (584.64 g, 3.81 mol) at 20° C. under N₂. The mixture was stirred at 100° C. for 2 h. TLC (PE:EA=1:1) showed the reaction was completed. The mixture was cooled to 20° C. and poured into ice-water (5000 mL) in portions at 0° C. and stirred for 20 min. The precipitate was filtered and dried to afford A-1-8 (110.00 g, 487.52 mmol, 63.93% yield) as a white solid: ¹H NMR (400 MHz, DMSO-d₆) δ 9.33 (d, J=7.28 Hz, 1H), 8.66 (s, 1H), 7.41 (d, J=7.15 Hz, 1H), 4.31 (q, J=7.15 Hz, 2H), 1.32 (t, J=7.09 Hz, 3H).

Step 6. Preparation of ethyl (R)-5-((1-(5-fluoro-2-hydroxyphenyl)ethyl)amino)pyrazolo[1,5-a]pyrimidine-3-carboxylate (A-1)

To a solution of A-1-5 (1.10 g, 7.09 mmol, 1.00 eq.) and A-1-8 (1.60 g, 7.09 mmol, 1.00 eq.) in n-BuOH (30.00 mL) was added DIEA (5.50 g, 42.53 mmol, 6.00 eq.). The mixture was stirred at 120° C. for 2 hrs. The reaction mixture was quenched by addition of water (20 mL) at ambient temperature, and extracted with EtOAc (20 mL×3). The combined organic layers were washed with brine (50 mL), dried over Na₂SO₄, filtered and concentrated. The residue was purified by column chromatography (SiO₂, Petroleum ether/Ethyl acetate=10/1 to 1:3) to provide A-1 (1.15 g, 3.31 mmol, 46.69% yield, ee>97% purity) as a white solid.

Preparation of ethyl (R)-5-((1-(5-fluoro-2-hydroxyphenyl)propyl)amino)pyrazolo[1,5-a]pyrimidine-3-carboxylate (A-2)

General method A was followed for the preparation of A-2 using EtMgBr in step 2.

Preparation of (R)—N—((R)-1-(5-fluoro-2-hydroxyphenyl)-3-hydroxypropyl)-2-methylpropane-2-sulfinamide (A-3-5)

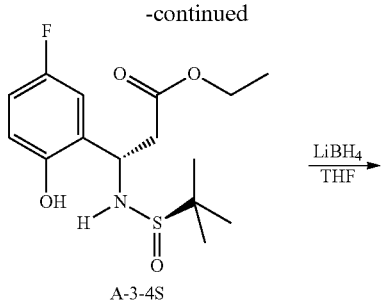

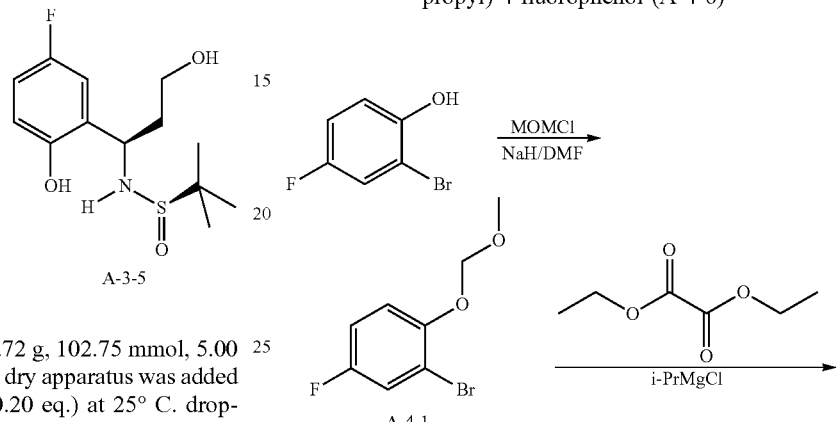

Step 1. To a suspension of Zn (6.72 g, 102.75 mmol, 5.00 eq.) in anhydrous THF (50 mL) in a dry apparatus was added TMSCl (446.51 mg, 4.11 mmol, 0.20 eq.) at 25° C. dropwise. The mixture was stirred for 10 min followed by heating under nitrogen to 40-50° C. To the mixture was added ethyl 2-bromoacetate (10.30 g, 61.65 mmol, 3.00 eq.) in anhydrous THF (500 mL) drop-wise over 20 min, and then the reaction was stirred at 40-50° C. for 30 min. The black mixture was cooled to 0° C. and a solution of A-1-3 (5.00 g, 20.55 mmol, 1.00 eq.) in THF (500 mL) was added. The reaction was stirred at 25° C. for 2 hr, quenched with saturated NH$_4$Cl (100 mL), and extracted with EtOAc (300 mL×3). The combined organic layers were washed with water (300 mL×2) and brine (300 mL×2), dried over anhydrous Na$_2$SO$_4$, filtered and concentrated. The residue was purified with a silica gel column (100-200 mesh) eluting with petroleum ether/ethyl acetate from 50/1, 10/1 to afford A-3-4S (4.35 g, 13.13 mmol, 63.87% yield) and A-3-4R (0.52 g, 16.35% yield) as white solids. $^1$HNMR of A-3-4S: (400 MHz, CHLOROFORM-d) δ 8.77 (s, 1H), 6.90 (dd, J=3.0, 9.0 Hz, 1H), 6.86-6.80 (m, 1H), 6.78-6.72 (m, 1H), 5.33 (d, J=5.0 Hz, 1H), 4.97-4.90 (m, 1H), 4.21-4.14 (m, 2H), 3.03-2.94 (m, 1H), 2.93-2.84 (m, 1H), 1.29-1.24 (m, 12H); $^1$HNMR of A-3-4R: (400 MHz, CHLOROFORM-d) δ 9.43 (s, 1H), 6.79 (dd, J=2.9, 8.7 Hz, 1H), 6.45 (dt, J=3.0, 8.5 Hz, 1H), 6.16 (dd, J=4.6, 8.9 Hz, 1H), 5.53 (d, J=9.8 Hz, 1H), 4.65 (dt, J=5.3, 9.8 Hz, 1H), 4.13-4.07 (m, 2H), 3.01 (dd, J=9.7, 15.4 Hz, 1H), 2.63 (dd, J=5.1, 15.4 Hz, 1H), 1.29-1.24 (m, 12H).

Step 2. To a solution of A-3-4R (500.00 mg, 1.51 mmol, 1.00 eq.) in anhydrous THF (5.00 mL) was added LiBH$_4$ (131.44 mg, 6.04 mmol, 4.00 eq.) at 0° C. portion-wise. The mixture was stirred at ambient temperature for 2 hrs. The reaction mixture was quenched with saturated NH$_4$Cl (50 mL), and then diluted by EtOAc (100 mL) and extracted with EtOAc (100 mL×3). The combined organic layers were washed with brine (50 mL), dry over Na$_2$SO$_4$, filtered and concentrated to provide A-3-5 (360.00 mg, 1.24 mmol, 82.39% yield) as a white solid. $^1$HNMR (400 MHz, CHLOROFORM-d) δ 9.13 (br. s., 1H), 6.79 (dd, J=2.8, 8.7 Hz, 1H), 6.53 (dt, J=3.0, 8.5 Hz, 1H), 6.27 (dd, J=4.7, 8.7 Hz, 1H), 5.19 (d, J=9.2 Hz, 1H), 4.42 (q, J=7.7 Hz, 1H), 3.71 (td, J=5.7, 10.8 Hz, 1H), 3.61-3.46 (m, 1H), 2.27-2.09 (m, 1H), 1.97 (dt, J=6.5, 13.0 Hz, 1H), 1.28 (s, 9H).

Preparation of ethyl (R)-5-((1-(5-fluoro-2-hydroxyphenyl)-3-hydroxypropyl)amino)pyrazolo[1,5-a]pyrimidine-3-carboxylate (A-3)

General method A was followed for the preparation of A-3 using A-3-5 in step 3.

Preparation of (S)-2-(1-amino-2-hydroxy-2-methylpropyl)-4-fluorophenol (A-4-6)

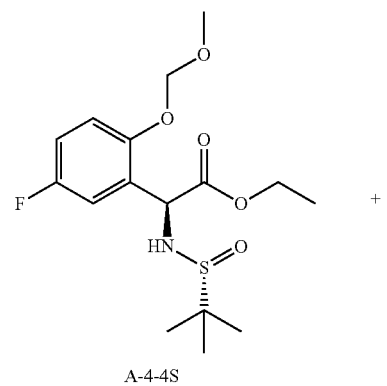

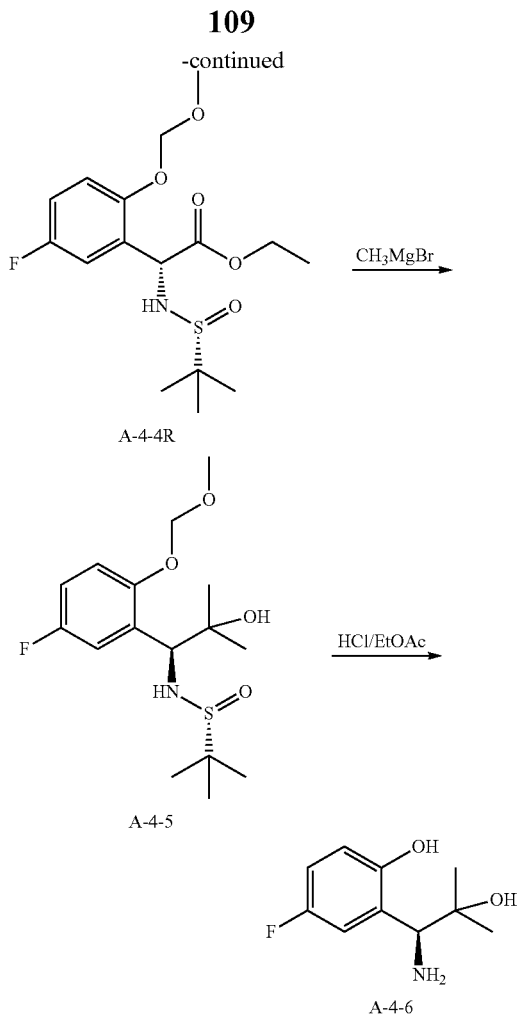

CHLOROFORM-d) δ 7.56 (dd, J=3.2, 8.2 Hz, 1H), 7.30-7.24 (m, 1H), 7.23-7.18 (m, 1H), 5.15 (s, 2H), 4.48-4.34 (m, 2H), 3.48 (s, 3H), 1.40 (t, J=7.2 Hz, 3H).

Step 3. To a mixture of A-4-2 (5.70 g, 22.25 mmol, 1.00 eq.) and (R)-2-methylpropane-2-sulfinamide (4.05 g, 33.38 mmol, 1.50 eq.) in THF (50.00 mL) was added Ti(OEt)$_4$ (7.61 g, 33.38 mmol, 1.50 eq.) in one portion at ambient temperature under N$_2$. The mixture was heated to 70° C. and stirred for 12 hours. TLC showed the starting material was consumed completely. The mixture was cooled to ambient temperature and concentrated in vacuum at 45° C. The residue was poured into water (100 mL). The aqueous phase was extracted with ethyl acetate (300 mL×3). The combined organic phase was washed with brine (300 mL), dried with anhydrous Na$_2$SO$_4$, filtered and concentrated in vacuum. The residue was purified by silica gel chromatography (column height: 250 mm, diameter: 100 mm, 100-200 mesh silica gel, Petroleum ether/Ethyl acetate=20/1, 5/1) to afford A-4-3 (3.20 g, 8.90 mmol, 40.02% yield) as a yellow oil. $^1$HNMR (400 MHz, CHLOROFORM-d) δ 7.56 (dd, J=3.2, 8.2 Hz, 1H), 7.30-7.24 (m, 1H), 7.23-7.18 (m, 1H), 5.15 (s, 2H), 4.48-4.34 (m, 2H), 3.48 (s, 3H), 1.40 (t, J=7.2 Hz, 3H).

Step 4. To a solution of A-4-3 (3.00 g, 8.69 mmol, 1.00 eq.) in MeOH (30.00 mL) was added NaBH$_4$ (361.44 mg, 9.56 mmol, 1.10 eq.) portion-wise at 0° C. under N$_2$. The reaction mixture was warmed to ambient temperature for 2 hours. The reaction was quenched with ice-water (50 mL) slowly and then extracted with DCM (100 mL×3). The combined organic phase was washed with brine (100 mL), dried over anhydrous Na$_2$SO$_4$, filtered and concentrated in vacuum. The residue was purified by column chromatography (SiO$_2$, Petroleum ether/Ethyl acetate=10/1 to 3:1) to afford A-4-4S (1.20 g, 4.98 mmol, 38% yield, first fraction) and A-4-4R (600 mg, 19%, second fraction) were obtained as an oil. $^1$HNMR of A-4-4S (400 MHz, CHLOROFORM-d) δ 7.11 (dd, J=4.4, 9.0 Hz, 1H), 7.04 (dd, J=3.2, 8.8 Hz, 1H), 7.00-6.93 (m, 1H), 5.33 (d, J=8.0 Hz, 1H), 5.18 (s, 2H), 4.41 (d, J=8.0 Hz, 1H), 4.23-4.12 (m, 2H), 3.49 (s, 3H), 1.23-1.17 (m, 12H). $^1$HNMR of A-4-4R (400 MHz, CHLOROFORM-d) δ 7.12 (dd, J=4.4, 8.8 Hz, 1H), 7.02-6.94 (m, 2H), 5.41 (d, J=4.0 Hz, 1H), 5.16 (s, 2H), 4.61 (d, J=4.0 Hz, 1H), 4.29-4.13 (m, 2H), 3.50 (s, 3H), 1.24-1.17 (m, 12H).

Step 5. To a solution of A-4-4S (600.00 mg, 1.66 mmol, 1.00 eq.) in THF (10.00 mL) was added MeMgBr (3 M in Et$_2$O, 4.43 mL, 8.00 eq.) drop-wise at −78° C. under N$_2$. The mixture was stirred at ambient temperature for 12 hr. The mixture was poured into saturated NH$_4$Cl (20 mL) and stirred for 10 min. The aqueous phase was extracted with ethyl acetate (50 mL×3) and, the combined organic phase was washed with brine (50 mL), dried with anhydrous Na$_2$SO$_4$, filtered and concentrated in vacuum to afford A-4-5 (542.00 mg, 1.56 mmol, 93.97% yield) as yellow solid. $^1$HNMR (400 MHz, CHLOROFORM-d) δ 7.13 (dd, J=4.4, 9.0 Hz, 1H), 7.08-7.02 (m, 1H), 6.96-6.89 (m, 1H), 5.24-5.15 (m, 2H), 4.67-4.35 (m, 2H), 3.50 (s, 3H), 1.35 (s, 3H), 1.21 (s, 9H), 1.10 (s, 3H).

Step 6. Compound A-4-5 (540.00 mg, 1.55 mmol, 1.00 eq.) was dissolved in HCl/dioxane (4N, 5.00 mL) was stirred at ambient temperature under N$_2$ for 2 hr. TLC showed the reaction complete. Methanol (20 mL) was added to the mixture and stirred at ambient temperature for 10 min. Then the solvent was removed under reduced pressure to give A-4-6 which was used for the next step without further purification.

Step 1. To a solution of 2-bromo-4-fluorophenol (Sigma-Aldrich, 13.00 g, 68.06 mmol, 1.00 eq.) in THF (100.00 mL) was added NaH (2.72 g, 60% in oil, 68.06 mmol, 1.00 eq.) at 0° C. under N$_2$ for 5 hours, followed by addition of MOMCl (3.02 g, 37.51 mmol, 0.55 eq.). The mixture was stirred at 16° C. for 10 hours, quenched by water (200 ml), and extracted with EtOAc (100 ml×3). The combined organic layers were washed with brine (200 ml), dried over Na$_2$SO$_4$, and concentrated to give A-4-1 (9.00 g, 38.29 mmol, 56.26% yield) as an oil.

Step 2. To a solution of A-4-1 (14.00 g, 59.56 mmol, 1.00 eq.) in anhydrous THF (140.00 mL) was added i-PrMgCl—LiCl in THF (1.3 M, 45.82 mL, 1.00 eq.) drop-wise at −78° C. in 30 min under N$_2$. The mixture was warmed to 25° C. for 1.5 h, and the resulting mixture was added drop-wise to diethyl oxalate (43.39 g, 296.90 mmol, 5.00 eq.) in THF (140 ml) at −30° C. in 20 min under N$_2$. The mixture was warmed to 25° C. for 1.5 hr. TLC showed the starting material was consumed completely. The reaction was quenched with the addition of water (200 mL) slowly, and stirred for 10 min. The organic layer was separated and the aqueous phase was extracted with ethyl acetate (500 mL×3). The combined organic layers were washed with saturated brine (500 mL), dried with anhydrous Na$_2$SO$_4$, filtered and concentrated in vacuum. The residue was purified by silica gel chromatography eluting with petroleum ether/ethyl acetate from 50/1 to 10/1) to afford A-4-2 (5.70 g, 23.53 mmol, 39.6% yield) as a yellow oil. $^1$HNMR (400 MHz, Preparation of ethyl (S)-5-((1-(5-fluoro-2-hydroxy-phenyl)-2-hydroxy-2-methylpropyl)amino)pyrazolo[1,5-a]pyrimidine-3-carboxylate (A-4)

A-4 was prepared with the general method A using A-4-6 in step 3.

Preparation of 2-(1-aminoeth-1-yl)-3-hydroxypyridine (A-6-3)

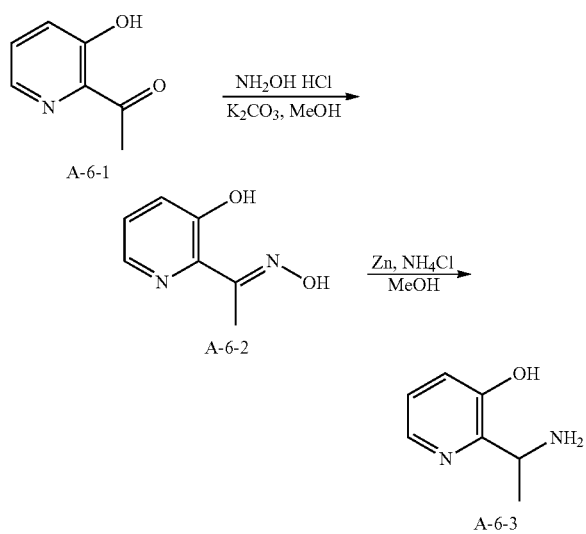

Step 1. To a solution of Compound A-6-1 (8.00 g, 58.33 mmol, 1.00 eq.) and potassium carbonate (24.19 g, 175.00 mmol, 3.00 eq.) in Methanol (50.00 mL) was added hydroxylamine hydrochloride (5.31 g, 75.83 mmol, 1.30 eq.). The mixture was stirred at 25° C. for 12 hours. TLC (Petroleum ether/Ethyl acetate=1/1) showed the starting material was consumed completely and one new spot was found. The mixture was pour into H$_2$O (100 mL) and extracted by ethyl acetate (100 mL*3). The organic layer washed by brine (100 mL), dry over anhydrous sodium sulfate and concentrated to give Compound A-6-2 (5.50 g, 36.15 mmol, 61.97% yield) as a yellow solid.

Step 2. To a solution of Compound A-6-2 (5.50 g, 36.15 mmol, 1.00 eq.) and zinc power (9.46 g, 144.59 mmol, 4.00 eq.) in ethanol (10.00 mL) was added ammonium chloride (11.15 g, 144.59 mmol, 4.00 eq.). The mixture was stirred at 0-25° C. for 18 hours. TLC (Petroleum ether/Ethyl acetate=1/1) showed the starting material was consumed completely and one new major spot was found. The mixture was filtered and the filtrate was concentrated to give Compound A-6-3 (4.00 g, 28.95 mmol, 80.08% yield) as a yellow solid. $^1$HNMR: (400 MHz, DMSO-d6) δ: 7.75 (d, J=4.4 Hz, 1H), 7.27 (d, J=8.0 Hz, 1H), 7.17 (dd, J=4.4, 8.0 Hz, 1H), 4.51 (q, J=6.4 Hz, 1H), 1.28 (d, J=6.4 Hz, 3H)

A-5 was prepared following the procedure for A-1 using 2-(aminomethyl)-4-fluorophenol and ethyl 5-chloropyrazolo[1,5-a]pyrimidine-3-carboxylate as starting material.

A-6 was prepared following the procedure for A-1 using A-6-3 and ethyl 5-chloropyrazolo[1,5-a]pyrimidine-3-carboxylate as starting material.

| Compd # | Structure | MS m/z | $^1$H NMR (400 MHz, CDCl$_3$) δ ppm |
|---|---|---|---|
| A-1 | 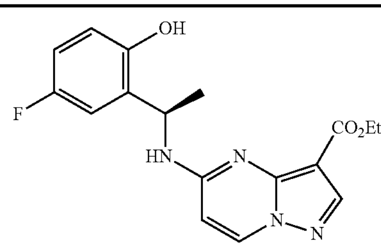 | 345.2 | 9.10 (br. s., 1H), 8.18 (s, 1H), 8.08 (d, J = 7.5 Hz, 1H), 6.88-6.83 (m, 2H), 6.81-6.73 (m, 1H), 6.05 (d, J = 7.5 Hz, 1H), 5.63-5.52 (m, 2H), 4.44-4.28 (m, 2H), 1.54 (d, J = 6.4 Hz, 3H), 1.34 (t, J = 7.1 Hz, 3H) |
| A-2 | 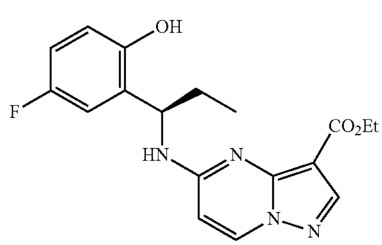 [SMILES: CCOC(=O)c1cnn2ccc(N[C@H](CC)c3cc(F)ccc3O)nc12] | 359.0 | 9.11 (br. s., 1H), 8.26 (s, 1H), 8.16 (d, J = 7.5 Hz, 1H), 6.96 (dd, J = 5.1, 8.7 Hz, 1H), 6.91-6.81 (m, 2H), 6.18 (d, J = 7.5 Hz, 1H), 5.73 (d, J = 8.5 Hz, 1H), 5.36 (q, J = 7.8 Hz, 1H), 4.51-4.38 (m, 2H), 2.08-1.88 (m, 2H), 1.43 (t, J = 7.2 Hz, 3H), 0.97 (t, J = 7.3 Hz, 3H) |
| A-3 | 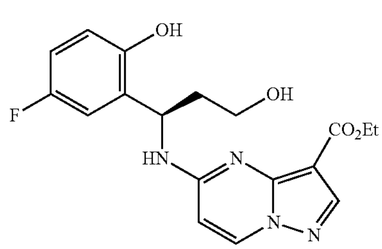 [SMILES: CCOC(=O)c1cnn2ccc(N[C@H](CCO)c3cc(F)ccc3O)nc12] | 375.1 | 8.23 (s, 1H), 8.16 (d, J = 7.5 Hz, 1H), 6.97-6.88 (m, 2H), 6.87-6.81 (m, 1H), 6.28 (d, J = 7.8 Hz, 1H), 6.16 (d, J = 7.5 Hz, 1H), 5.66 (br. s., 1H), 4.45-4.34 (m, 2H), 3.86-3.65 (m, 2H), 3.47 (br. s., 1H), 2.29-2.19 (m, 1H), 2.15-2.07 (m, 1H), 1.39 (t, J = 7.0 Hz, 3H) |

| Compd # | Structure | MS m/z | $^1$H NMR (400 MHz, CDCl$_3$) δ ppm |
|---|---|---|---|
| A-4 | 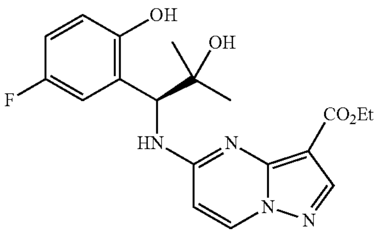 [SMILES: CCOC(=O)c1cnn2ccc(N[C@@H](c3cc(F)ccc3O)C(C)(C)O)nc12] | 389.2 | 8.30 (br. s., 1H), 8.22 (s, 1H), 8.18 (d, J = 7.8 Hz, 1H), 7.38 (d, J = 7.2 Hz, 1H), 6.99 (dd, J = 5.2, 8.8 Hz, 1H), 6.86 (dt, J = 3.0, 8.4 Hz, 1H), 6.40 (d, J = 8.4 Hz, 1H), 6.20 (d, J = 7.6 Hz, 1H), 5.40 (d, J = 7.8 Hz, 1H), 4.47-4.36 (m, 2H), 1.51 (s, 3H), 1.41 (t, J = 7.0 Hz, 3H), 1.23 (s, 3H) |
| A-5 | 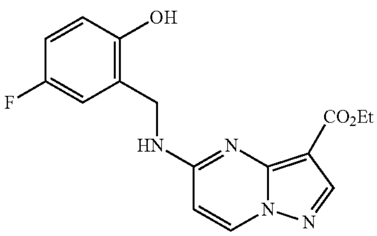 [SMILES: CCOC(=O)c1cnn2ccc(NCc3cc(F)ccc3O)nc12] | 331.2 | (300 MHz, DMSO-d6) δ ppm 9.61 (br. s., 1H), 8.52 (d, J = 7.2 Hz, 1H), 8.28 (t, J = 5.4 Hz, 1H), 8.13 (s, 1H), 7.24 (d, J = 7.2 Hz, 1H), 6.93-6.89 (m, 1H), 6.87-6.77 (m, 1H), 6.44 (d, J = 7.5 Hz, 1H), 4.51 (d, J = 5.4 Hz, 2H), 4.20 (q, J = 7.2 Hz, 2H), 1.27 (t, J = 7.2 Hz, 3H) |
| A-6 | 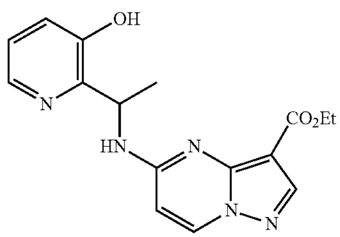 [SMILES: CCOC(=O)c1cnn2ccc(NC(C)c3ncccc3O)nc12] | 328.2 | (400 MHz, DMSO-d6) δ ppm 10.10 (br. s., 1H), 8.52 (d, J = 8.0 Hz, 1H), 8.27 (d, J = 8.0 Hz, 1H), 8.14 (s, 1H), 8.05 (d, J = 3.6 Hz, 1H), 7.27-7.13 (m, 2H), 6.64 (d, J = 8.0 Hz, 1H), 5.75 (t, J = 7.2 Hz, 1H), 4.20 (q, J = 6.8 Hz, 2H), 1.45 (d, J = 6.4 Hz, 3H), 1.31 (d, J = 14.4 Hz, 3H) |

General Method B.

Preparation of (7S,13R)-7-ethyl-11-fluoro-13-methyl-6,7,13,14-tetrahydro-1,15-ethenopyrazolo[4,3-f][1,4,8,10]benzoxatriazacyclotridecin-4(5H)-one (1) and (6S,13R)-6-ethyl-11-fluoro-13-methyl-6,7,13,14-tetrahydro-1,15-ethenopyrazolo[4,3-f][1,4,8,10]benzoxatriazacyclotridecin-4(5H)-one (2)

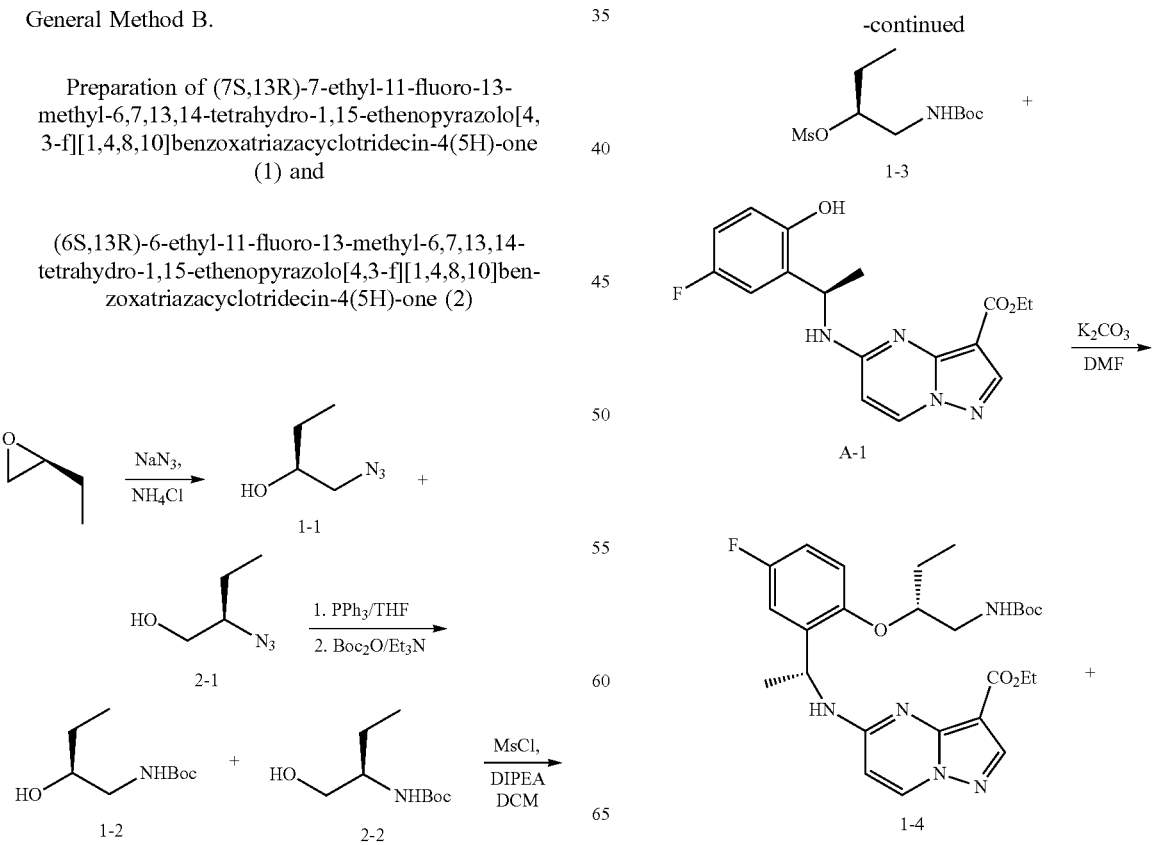

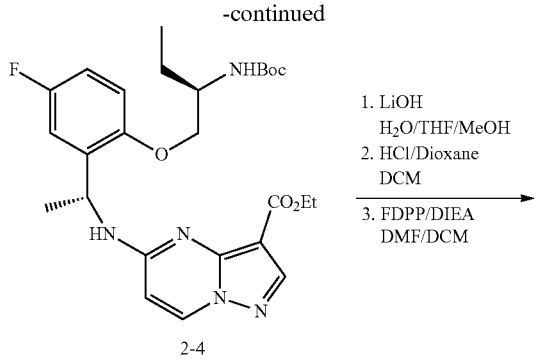

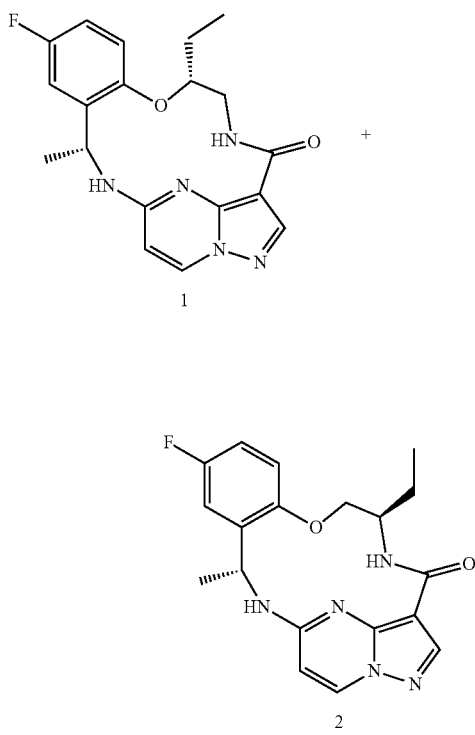

hours, quenched by addition to water (50 mL), extracted with DCM (3×50 mL), dried with Na$_2$SO$_4$, and concentrated under reduced pressure. Flash chromatography (ISCO system, silica (40 g), 0-35% ethyl acetate in hexane) provided the first fraction of 1-2 (1.379 g, 61.86% yield). LC-MS m/z 212.2 (M+Na)$^+$; $^1$H NMR (500 MHz, DMSO-d6) δ ppm 6.62 (br t, J=5.73 Hz, 1H) 4.50 (d, J=5.16 Hz, 1H) 3.34 (br s, 1H) 2.87-2.96 (m, 1H) 2.78-2.86 (m, 1H), 1.38-1.44 (m, 1H) 1.37 (s, 9H) 1.15-1.26 (m, 1H) 0.84 (t, J=7.45 Hz, 3H). The second fraction was a mixture of 1-2 and 2-2 (0.625 g, 28.03% yield).

Step 3. To a solution of 1-2 (467.00 mg, 2.47 mmol) and CH$_3$SO$_2$Cl (325.38 mg, 2.84 mmol) in DCM (12.35 mL) at −20° C. was added Hunig's base (957.67 mg, 7.41 mmol). The reaction was warmed to ambient temperature, stirred for 22 hours, and then quenched by addition to water (50 mL). The mixture was extracted with DCM (3×50 mL), dried with Na$_2$SO$_4$ and concentrated under reduced pressure. Flash chromatography (ISCO system, silica (24 g), 0-35% ethyl acetate in hexane) provided 1-3 (623.90 mg, 2.33 mmol, 94.48% yield). LC-MS m/z 290.1 (M+Na)$^+$.

Step 4. To a solution of 1-3 (116.46 mg, 0.436 mmol) and A-1 (120.00 mg, 0.348 mmol) in DMF (1.74 mL) was added K$_2$CO$_3$ (240.82 mg, 1.74 mmol). The mixture was heated at 80° C. with stirring for 24 hours, cooled to ambient temperature, diluted with DCM (3 mL), filtered through a syringe filter, and concentrated under reduced pressure. Flash chromatography (ISCO system, silica (12 g), 0-40% ethyl acetate in hexane) provided a mixture of 1-4 and 2-4 (59.40 mg, 0.115 mmol, 33.06% yield). LC-MS m/z 516.3 (M+H)$^+$.

Step 5: To a solution of the mixture of 1-4 and 2-4 (59.40 mg, 0.115 mmol) in MeOH (3.03 mL) and THF (1.49 mL) was added a solution of LiOH in H$_2$O (2M, 1.00 mL). The mixture was heated at 70° C. for 3 hours, cooled to ambient temperature, diluted with water and methanol, and then quenched with aqueous HCl solution (2M, 1.00 mL) to acidic. The mixture was extracted with DCM (3×5 mL), dried with Na$_2$SO$_4$ and concentrated under reduced pressure. The residue was dried under high vacuum overnight, and then dissolved in DCM (4.0 mL) followed by addition of HCl in 1,4-dioxane (4M, 2.0 mL) and stirring at ambient temperature for 2 hours. The mixture was concentrated under reduced pressure, and dried under high vacuum. The solid was dissolved in DMF (2 mL) and DCM (10 mL) and to the solution was added FDPP (50.76 mg, 0.132 mmol) and Hunig's base (74.23 mg, 0.574 mmol). The mixture was stirred for 2 hours, and then quenched with aqueous Na$_2$CO$_3$ solution (2M, 12 mL). The mixture was stirred for 5 min, and then extracted with DCM (4×10 mL). The combined extracts were dried with Na$_2$SO$_4$ and concentrated under reduced pressure. Flash chromatography (ISCO system, silica (12 g), 0-10% methanol in dichloromethane) followed by provided pure 1 (3.56 mg), 2 (3.83 mg), and a mixture of 1 and 2 (23.94 mg) with a total yield of 73.85%.

Compounds 3-8 were prepared using General Method B. In step 1, (R)-2-ethyloxirane was used for 3 and 4, (S)-2-((methoxymethoxy)methyl)oxirane for 5 and 6 followed by acid deprotection of the acetal, and (R)-2-((methoxymethoxy)methyl)oxirane for 7 and 8 followed by acid deprotection of the acetal.

Step 1: To a solution of (S)-2-ethyloxirane (1.00 g, 13.87 mmol) in H$_2$O (3.08 mL), MeOH (21.58 mL) and THF (3.08 mL) were added NaN$_3$ (4.51 g, 69.35 mmol) and NH$_4$Cl (1.71 g, 31.90 mmol). The reaction mixture was heated at 75° C. for 4 hours, and then cooled to ambient temperature followed by addition of water (100 mL). The mixture was extracted with ethyl acetate (3×50 mL), and the combined extracts were washed with brine (50 mL), dried over Na$_2$SO$_4$, and concentrated under reduced pressure. The crude product mixture of 1-1 and 2-1 was used in the next step without further purification.

Step 2. To a solution of 1-1 and 2-1 (1.35 g, 11.73 mmol) in THF (30.00 mL) was added PPh$_3$ (4.61 g, 17.60 mmol), and the reaction solution was stirred at ambient temperature for 65 hours. TLC demonstrated the completion of the conversion. To the reaction solution was added H$_2$O (3.00 g, 166.48 mmol), and the mixture was stirred for 7 hours followed by addition of a solution of Boc$_2$O (3.21 g, 14.72 mmol) and triethylamine (2.38 g, 23.56 mmol) in THF (30 mL). The reaction was stirred at ambient temperature for 19

General Method C.

Preparation of (7R,13R)-11-fluoro-7-(fluoromethyl)-13-methyl-6,7,13,14-tetrahydro-1,15-ethenopyrazolo[4,3-f][1,4,8,10]benzoxatriazacyclotridecin-4(5H)-one (9)

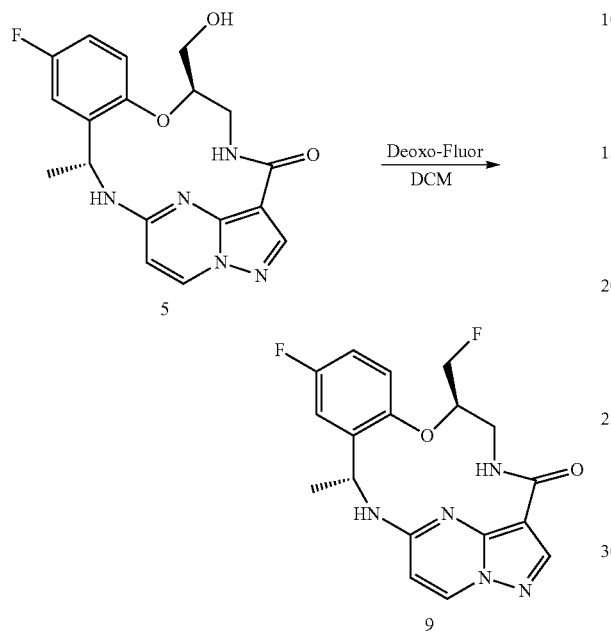

To a solution of 5 (3.00 mg, 0.0081 mmol) in DCM (0.161 mL) was added Deoxo-Fluor (3.58 mg, 0.0162 mmol). The mixture was stirred for 30 min, quenched with saturated NaHCO₃ solution (3 mL), extracted with DCM (3×3 mL), dried with Na₂SO₄, and concentrated under reduced pressure. Flash chromatography (ISCO system, silica (12 g), 0-17.5% methanol in dichloromethane) provided 9 (1.30 mg, 43.1% yield).

Compounds 10 and 11 were prepared using General Method C starting from compounds 7 and 8, respectively.

General Method D.

Preparation of (7R,13R)-7-[(dimethylamino)methyl]-11-fluoro-13-methyl-6,7,13,14-tetrahydro-1,15-ethenopyrazolo[4,3-f][1,4,8,10]benzoxatriazacyclotridecin-4(5H)-one (12)

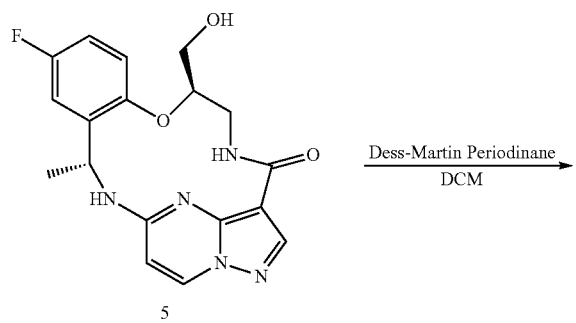

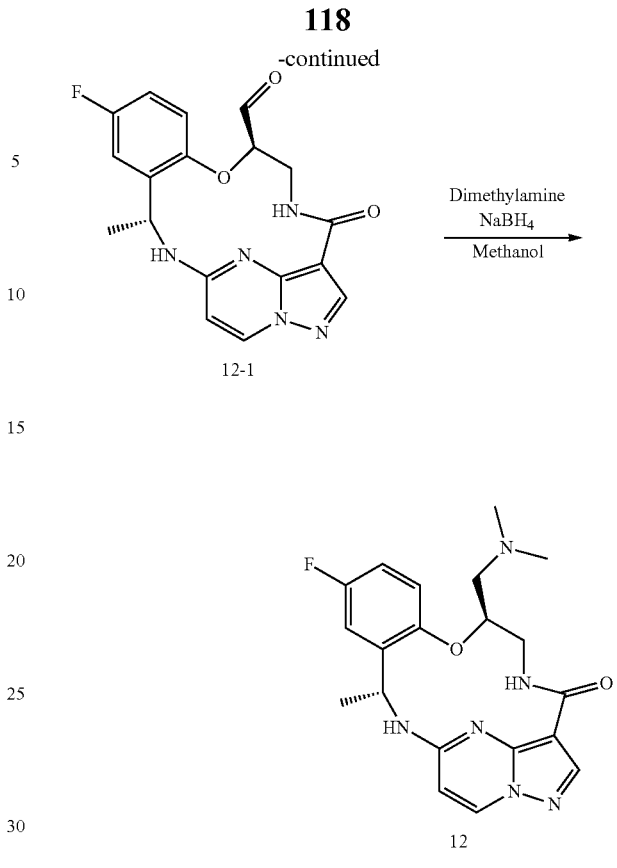

Step 1. To a solution of 5 (11.00 mg, 0.0296 mmol) in DCM (0.60 mL) was added Dess-Martin Periodinane (25.13 mg, 0.0592 mmol). The mixture was stirred at ambient temperature for 30 min, quenched with saturated NaHCO₃ solution (3 mL), extracted with DCM:MeOH (5×3 mL, 1:1), dried with Na₂SO₄, and concentrated under reduced pressure. Flash chromatography (ISCO system, silica (12 g), 0-22.5% methanol in dichloromethane) of the residue provided the aldehyde 12-1 (8.10 mg, 0.0219 mmol, 74.04% yield). LC-MS m/z 370.2 (M+H)⁺.

Step 2. To a solution of 12-1 (5.00 mg, 0.0135 mmol) in MeOH was added dimethylamine (2 M, 0.034 mL). The mixture was heated at 60° C. for 2 hrs, and cooled to ambient temperature followed by addition of sodium borohydride (1.54 mg, 0.0406 mmol) and stirred for 1 h. Additional portion of dimethylamine in THF (2M, 1 mL) and excess amount of NaBH4 were added to drive the reaction to completion. The mixture was heated at 45° C. overnight, and concentrated to dryness. The residue was dissolved in MeOH and aqueous HCl (2M, 0.40 mL) was added. The mixture was stirred for 30 min followed by addition of aqueous NaOH solution (2M, 0.45 mL), extracted with DCM (4×3 mL). The combined extracts were dried with Na₂SO₄ and concentrated under reduced pressure. Flash chromatography (0.060 mL TEA was added during compound loading] (ISCO system, silica (12 g), 0-25% methanol in dichloromethane) provided 12 (1.89 mg, 0.0474 mmol, 35.03% yield) as a white solid.

General Method E.

Preparation of (6S,13R)-6-[(dimethylamino)methyl]-11-fluoro-13-methyl-6,7,13,14-tetrahydro-1,15-ethenopyrazolo[4,3-f][1,4,8,10]benzoxatriazacyclotridecin-4(5H)-one (13)

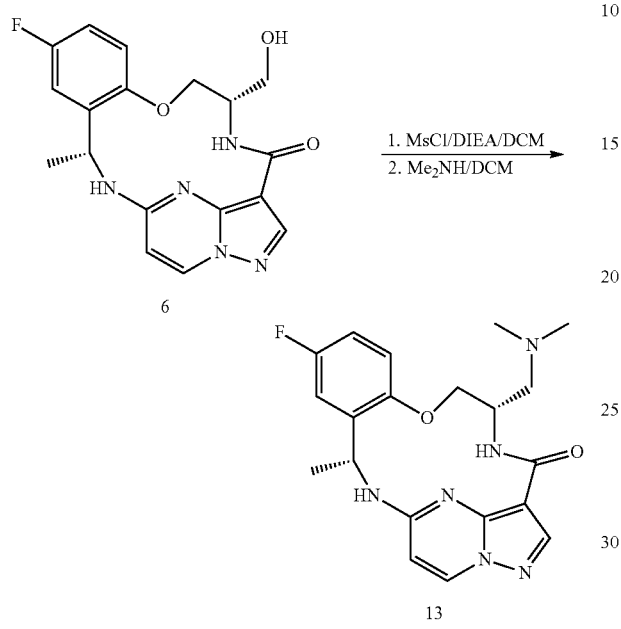

To a solution of 6 (7.20 mg, 0.0194 mmol) and CH₃SO₂Cl (8.88 mg, 0.0776 mmol) in DCM (0.50 mL) at −20° C. was added Hunig's base (37.59 mg, 0.291 mmol). The reaction was warmed to ambient temperature, stirred for 1 hour, and then quenched by addition of saturated bicarbonate solution (2 mL). The mixture was extracted with DCM (3×3 mL), dried with Na₂SO₄, and concentrated under reduced pressure to dryness. A solution of dimethylamine in THF (2 M, 1.98 mL) was added to the residue flask. The mixture was heated at 70° C. for 6 hours, and concentrated under reduced pressure. Flash chromatography (ISCO system, C18 (30 g gold col), 0-100% acetonitrile in water w/0.035% TFA) provided 13 as a TFA salt (2.93 mg).

General Method F.

Preparation of (7S,13R)-11-fluoro-N,13-dimethyl-4-oxo-4,5,6,7,13,14-hexahydro-1,15-ethenopyrazolo[4,3-f][1,4,8,10]benzoxatriazacyclotridecine-7-carboxamide (14) and (7R,13R)-11-fluoro-N,13-dimethyl-4-oxo-4,5,6,7,13,14-hexahydro-1,15-ethenopyrazolo[4,3-f][1,4,8,10]benzoxatriazacyclotridecine-7-carboxamide (15)

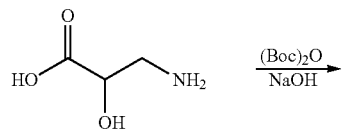

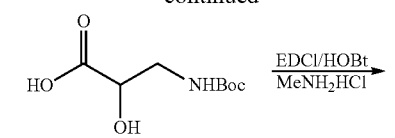

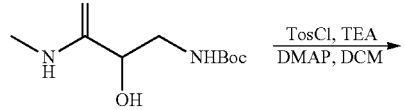

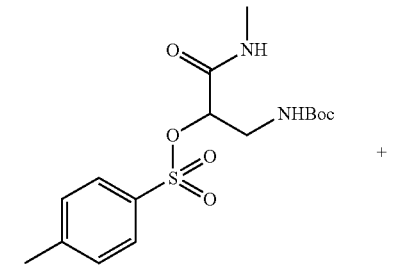

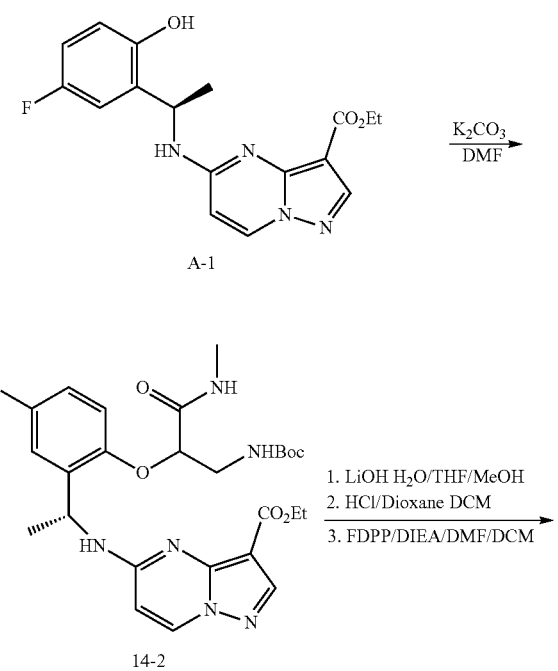

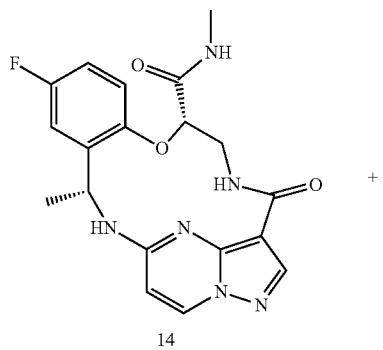

-continued

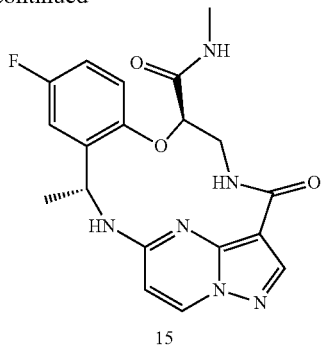
15

To a solution of 3-amino-2-hydroxypropanoic acid (3.50 g, 33.30 mmol, 1.00 eq.) in 1,4-dioxane (30.00 mL) was added NaOH (1.33 g, 33.30 mmol, 1.00 eq.) in H₂O (30.00 ml) drop-wise at 0° C. The mixture was stirred at 0° C. for 1 hr followed by addition of (Boc)₂O (8.29 g, 37.97 mmol, 1.14 eq.). The mixture was warmed to ambient temperature and stirred for 11 hours, quenched with addition of aqueous HCl solution (1M, 5 mL) at 0° C. to adjust pH-6, and then extracted with EtOAc (20 mL×3). The combined organic layers were washed with brine (50 mL), dried over Na₂SO₄, filtered, and concentrated under reduced pressure to 3-((tert-butoxycarbonyl)amino)-2-hydroxypropanoic acid (3.50 g) which was used directly without further purification. ¹H NMR (400 MHz, CDCl₃) δ 7.93 (br. s., 1H), 5.41 (br. s., 1H), 4.32 (br. s., 1H), 3.65-3.40 (m, 2H), 1.42 (s, 9H).

Step 2. To a solution of 3-((tert-butoxycarbonyl)amino)-2-hydroxypropanoic acid (1.00 g, 4.87 mmol, 1.00 eq.) in DCM (24.00 mL) and DMF (24.00 mL) was added methanamine (1.32 g, 19.49 mmol, 4.00 eq., HCl salt), EDCI (1.40 g, 7.31 mmol, 1.50 eq.), HOBt (987 mg, 7.31 mmol, 1.50 eq.) and 4-methylmorpholine (2.96 g, 29.24 mmol, 6.00 eq.). The mixture was stirred at ambient temperature for 16 h, and then concentrated. The residue was diluted with citric acid (100 mL) and extracted with EtOAc(200 mL×2). The combined organic layers were washed with aqueous saturated NaHCO₃ (100 mL), dried over MgSO₄, filtered and concentrated in vacuo to provide tert-butyl (2-hydroxy-3-(methylamino)-3-oxopropyl)carbamate (980.00 mg, 4.49 mmol, 92.20% yield) as a white solid. ¹H NMR (CDCl₃, 400 MHz) δ 7.03 (br. s., 1H), 5.41-5.14 (m, 2H), 4.19 (d, J=2.8 Hz, 1H), 3.65-3.55 (m, 1H), 3.54-3.44 (m, 1H), 2.85 (d, J=5.2 Hz, 3H), 1.45 (s, 9H).

Step 3. To a stirred solution of tert-butyl (2-hydroxy-3-(methylamino)-3-oxopropyl)carbamate (980.00 mg, 4.49 mmol, 1.00 eq.) in DCM (60.00 mL) was added TEA (2.27 g, 22.45 mmol, 5.00 eq.), 4-methylbenzenesulfonyl chloride (1.71 g, 8.98 mmol, 2.00 eq.) and catalytic amount DMAP (54.86 mg, 449.03 μmol, 0.10 eq.) at 0° C. for 15 min. The reaction was stirred at ambient temperature for 12 h, quenched by addition of citric acid (100 mL), then diluted with EtOAc (100 mL), and extracted with EtOAc(100 mL×3). The combined organic layers were washed with saturated NaHCO₃ (100 mL), dried over anhydrous sodium sulfate, filtered and concentrated under reduced pressure. The residue was purified by column chromatography (SiO2, Petroleum ether/Ethyl acetate=10/1 to 1:1) to provide 14-1 (1.05 g, 2.82 mmol, 62.80% yield) as a white solid. ¹H NMR (CDCl₃, 400 MHz) 7.84 (d, J=8.0 Hz, 1H), 7.39 (d, J=8.0 Hz, 1H), 6.38 (br. s., 1H), 4.87 (t, J=4.8 Hz, 1H), 4.77 (br. s., 1H), 3.62-3.40 (m, 2H), 2.80 (d, J=4.8 Hz, 3H), 2.47 (s, 3H), 1.41 (s, 9H).

Step 4. To a solution of A-1 (75.00 mg, 0.218 mmol) and 14-1 (89.23 mg, 0.240 mmol) in DMF (1.1 mL) was added K₂CO₃ (150.52 mg, 1.09 mmol). The mixture was heated to 70° C. with stirring for 75 hour with the addition of more K₂CO₃ and 14-1 each day to drive the reaction to completion. The reaction was cooled to ambient temperature, diluted with DCM (3 mL), filtered through a syringe filter, and concentrated under reduced pressure. Flash chromatography (ISCO system, silica (12 g), 0-100% ethyl acetate in hexane) provided 14-2 (65.00 mg, 0.119 mmol, 54.8% yield). LC-MS m/z 545.3 (M+H)⁺.

Step 5. To a solution of 14-2 (65.00 mg, 0.119 mmol) in MeOH (2.98 mL) and THF (2.01 mL) at ambient temperature was added aqueous LiOH solution (2.0 M, 2.01 mL). The mixture was heated at 70° C. for 2 hours, cooled to ambient temperature, diluted with water and methanol, and then quenched with aqueous HCl solution (2.0 M2.01 mL) to acidic. The mixture was extracted with DCM (3×5 mL), dried with Na₂SO₄, concentrated under reduced pressure, and dried under high vacuum overnight. To the residue was added DCM (3.00 mL) followed by addition of HCl in 1,4-dioxane (4 M, 2.00 mL). The mixture was stirred ambient temperature for 1.5 hour, concentrated under reduced pressure, and dried under high vacuum. To the residue was added DMF (4.00 mL) and FDPP (50.34 mg, 0.131 mmol) followed by the addition of Hunig's base (76.97 mg, 0.596 mmol). The mixture was stirred at ambient temperature for 1.5 hour, quenched with aqueous Na₂CO₃ solution (2M, 4.0 mL), and stirred for 5 min. The mixture was extracted with DCM (4×10 mL), and the combined extracts were dried with Na₂SO₄ and concentrated under reduced pressure. Flash chromatography (ISCO system, silica (12 g), 0-17.5% methanol in dichloromethane) provided pure 14 (2.29 mg) as the first fraction and 15 (3.63 mg) as the last fraction. The middle fraction (12.8 mg) was a mixture of 14 and 15.

General Method G.

Preparation of (6R,13R)-6-(difluoromethyl)-11-fluoro-13-methyl-6,7,13,14-tetrahydro-1,15-ethenopyrazolo[4,3-f][1,4,8,10]benzoxatriazacyclotridecin-4(5H)-one (16), (6S,13R)-6-(difluoromethyl)-11-fluoro-13-methyl-6,7,13,14-tetrahydro-1,15-ethenopyrazolo[4,3-f][1,4,8,10] benzoxatriazacyclotridecin-4(5H)-one (17), and (7R,13R)-7-(difluoromethyl)-11-fluoro-13-methyl-6,7,13,14-tetrahydro-1,15-ethenopyrazolo[4,3-f][1,4,8,10]benzoxatriazacyclotridecin-4(5H)-one (18)

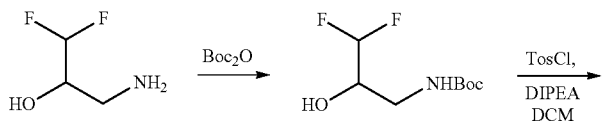

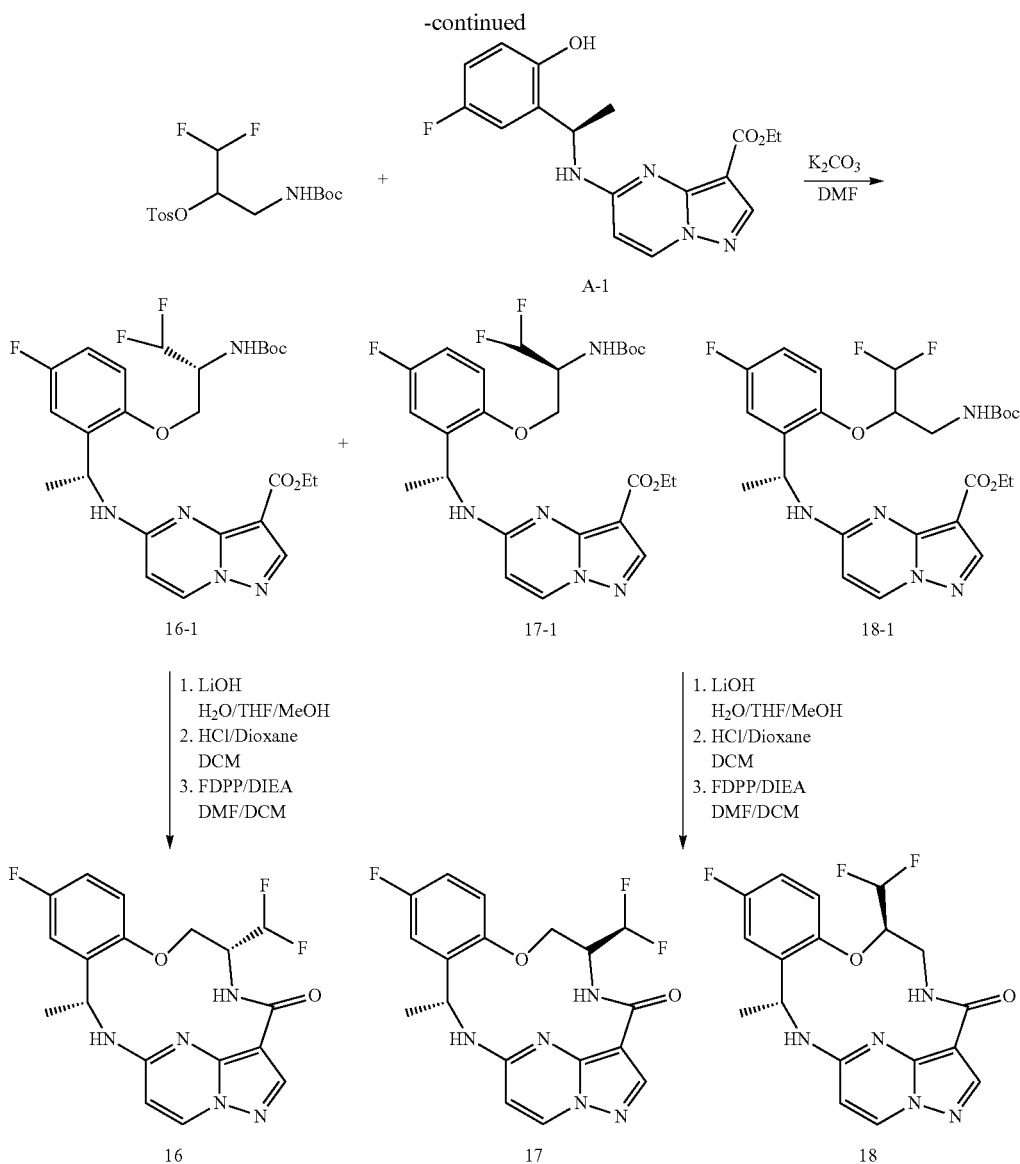

Step 1. To a solution of 3-amino-1,1-difluoropropan-2-ol hydrochloride salt (150.29 mg, 1.16 mmol) and Boc-anhydride (316.46 mg, 1.45 mmol) in THF (5.8 mL) was added Hunig's base (449.76 mg, 3.48 mmol). The mixture was stirred for 18 hours, and concentrated under reduced pressure. Flash chromatography (ISCO system, silica (12 g), 0-40% ethyl acetate in hexane) provided tert-butyl (3,3-difluoro-2-hydroxypropyl)carbamate (195.20 mg, 0.924 mmol, 79.8% yield).

Step 2. To a solution of tert-butyl (3,3-difluoro-2-hydroxypropyl)carbamate (195.20 mg, 0.924 mmol), TosCl (211.44 mg, 1.11 mmol), and DMAP (5.65 mg, 0.462 mmol) in DCM (4.6 mL) at −78° C. was added Hunig's base (358.33 mg, 2.77 mmol). The reaction was warmed to ambient temperature, stirred for 15 hours, and then quenched by addition to water (15 mL). The mixture was extracted with DCM (3×10 mL), dried with $Na_2SO_4$ and concentrated under reduced pressure. Flash chromatography (ISCO system, silica (12 g), 0-25% ethyl acetate in hexane) provided 3-[(tert-butoxycarbonyl)amino]-1,1-difluoropropan-2-yl 4-methylbenzenesulfonate (240.60 mg, 0.658 mmol, 71.25% yield).

Step 3. To a solution of A-1 (75.00 mg, 0.218 mmol) and 3-[(tert-butoxycarbonyl)amino]-1,1-difluoropropan-2-yl 4-methylbenzenesulfonate (95.50 mg, 0.261 mmol) in DMF (1.09 mL) was added $K_2CO_3$ (150.52 mg, 1.09 mmol). The mixture was heated at 80° C. with stirring for 18 hours, cooled to ambient temperature, diluted with DCM (3 mL), filtered through a syringe filter, and concentrated under reduced pressure. Flash chromatography (ISCO system, silica (12 g), 0-50% ethyl acetate in hexane) provided the first fraction which was identified as 16-1 (26.00 mg, 0.0484 mmol, 22.21% yield), and the second fraction as a mixture of 17-1 and 18-1 (26.7 mg).

Step 4. 16-1 was converted to 16 using the method of Step 5 in General Method B. The mixture of 17-1 and 18-1 were converted to a mixture of macrocyclic compounds which was separated with flash chromatography (ISCO system, silica (12 g), 0-7.5% methanol in dichloromethane) to provide 17 and 18.

Compounds 19 and 22-24 were prepared according to General Method F using t-butyl (2-chloroethyl)carbamate in the place of 14-1 and A-2-A-4 in Step 1.

Compounds 20 and 21 were prepared according to General Method B using A-2 in the place of A-1 in Step 4.

Compound 25 were prepared according to General Method B using (2R)-2-(methoxymethyl)oxirane in the place of 2-ethyloxirane in Step 1.

General Method H.

Preparation of (7S,13R)-11-fluoro-7-methyl-13-($^2$H$_3$)methyl-6,7,13,14-tetrahydro-1,15-ethenopyrazolo[4,3-f][1,4,8,10]benzoxatriazacyclotridecin-4(5H)-one (26)

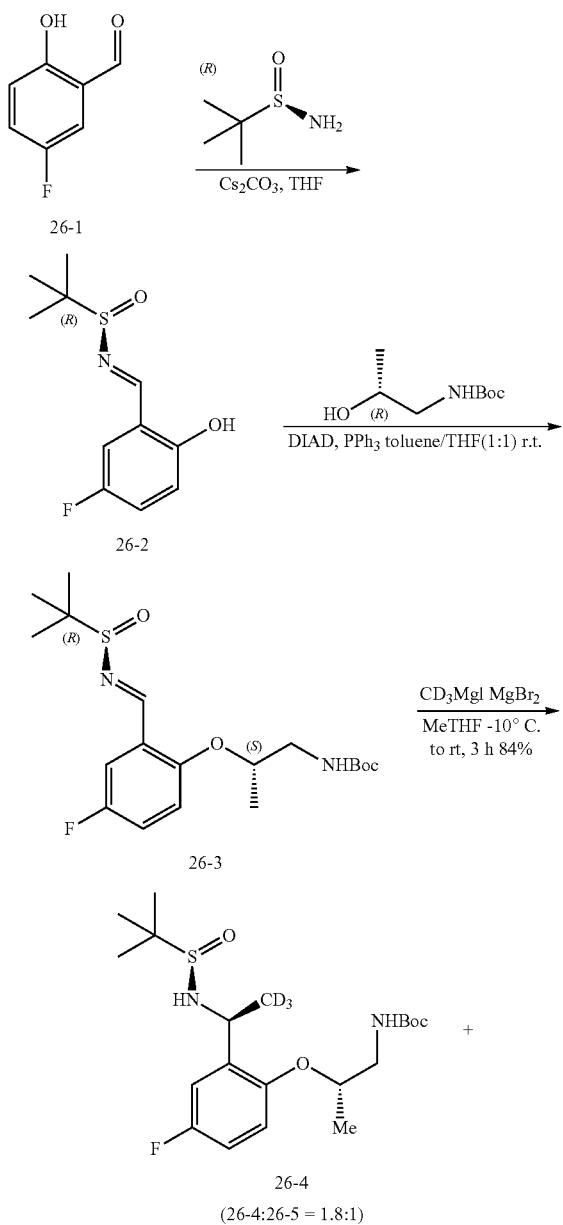

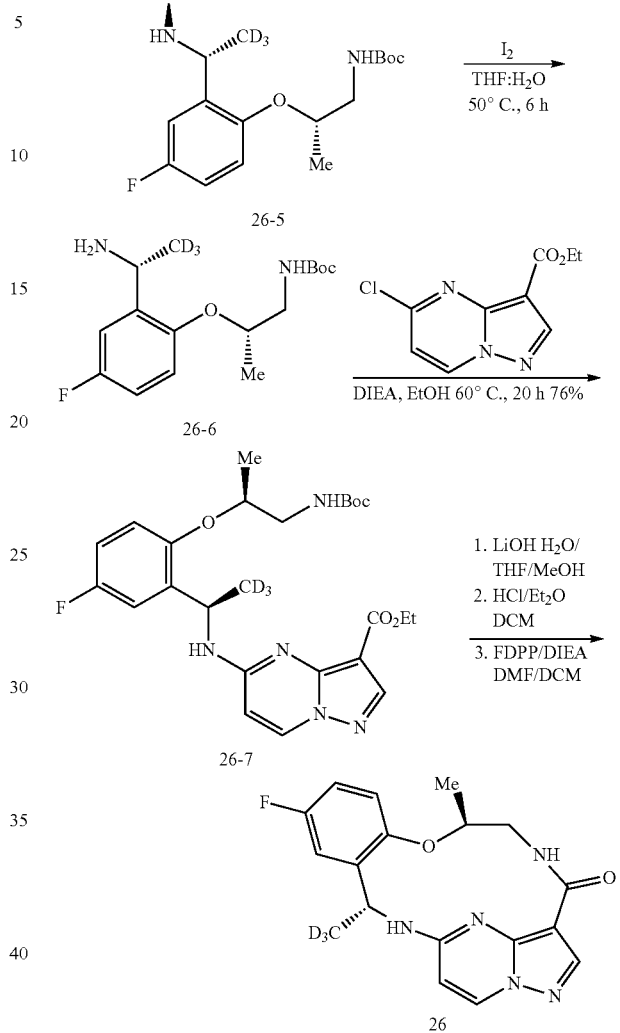

Step 1. To a mixture of 26-1 (10.00 g, 71.37 mmol, 1.00 eq.) and (R)-2-methylpropane-2-sulfinamide (8.65 g, 71.37 mmol, 1.00 eq.) in DCM (500.00 mL) was added cesium carbonate (69.76 g, 214.11 mmol, 3.00 eq.) in one portion at 20° C. under N$_2$ and then stirred at 50° C. for 12 hr. The mixture was cooled to 20° C. and concentrated in reduced pressure at 45° C. The residue was poured into water (300 mL). The aqueous phase was extracted with ethyl acetate (500 mL×3), combined organic phase and washed with saturated brine (500 mL), dried over anhydrous sodium sulfate, filtered and concentrated in vacuum to give a residue which triturated by petroleum ether to give 26-2 (15.00 g, 61.65 mmol, 86.38% yield) as a white solid. $^1$HNMR (400 MHz, CDCl$_3$) δ 10.85 (s, 1H), 8.64 (s, 1H), 7.21-7.14 (m, 2H), 6.99 (dd, J=4.4, 10.0 Hz, 1H), 1.27 (s, 9H).

Step 2. To a mixture of tert-butyl (R)-(2-hydroxypropyl) carbamate (5.00 g, 28.54 mmol, 1.20 eq.) and 26-2 (5.79 g, 23.78 mmol, 1.00 eq.) in toluene/THF (15 mL, v/v=1:1) was added PPh$_3$ (7.49 g, 28.54 mmol, 1.20 eq.). The reaction mixture was cooled to about 0° C., and DIAD (5.77 g, 28.54 mmol, 5.55 mL, 1.20 eq.) was added drop-wise for 10 min. The mixture was allowed warm to 25° C., and after stirring for about ten minutes, an additional 15 ml of toluene and 15 ml of THF were added to the thick orange solution. The mixture was stirred at 25° C. for an additional 24 hours, The reaction mixture was concentrated in vacuum and the residue was purified by column chromatography (Petroleum ether:Ethyl acetate=20/1 to 5/1) to give 26-3 (11.00 g, 19.23 mmol, 80.84% yield, 70% purity) as a white solid. $^1$HNMR (400 MHz, CDCl$_3$) δ 8.95 (s, 1H), 7.65 (dd, J=2.8, 8.8 Hz, 1H), 7.21-7.10 (m, 1H), 7.00 (br dd, J=4.0, 8.8 Hz, 1H), 5.08 (br s, 1H), 4.57 (br s, 1H), 3.45 (br s, 1H), 3.36-3.22 (m, 1H), 1.43 (s, 9H), 1.30 (br d, J=6.4 Hz, 3H), 1.25 (br s, 9H)

Step 3. CD$_3$MgI (1 M, 22.5 mL) was added to a solution of 26-3 (3.00 g, 7.49 mmol) and MgBr$_2$.Et$_2$O (12.7 g, 45 mmol) in MeTHF (37.5 mL) at −10° C. Reaction was slowly warmed to 0° C. over 3 hours then quenched by addition to saturated NH$_4$Cl solution (50 mL).

The mixture was extracted with DCM (3×50 mL), dried with Na$_2$SO$_4$ and concentrated under reduced pressure. Flash chromatography (ISCO system, silica (40 g), 0-50% ethyl acetate in hexane) provide 26-4 (1.72 g, 4.10 mmol, 54% yield) and 26-5 (970 mg, 2.31 mmol, 30% yield).

Step 2. I$_2$ (117 mg, 46 μmol) was added to 26-5 (970 mg, 2.31 mmol) in THF (9.96 mL) and water (2.04 mL). The reaction was heated to 50° C. for 6 hours, concentrated under reduced pressure, and dried under high vacuum to obtain crude 26-6.

Step 3. To a solution of crude 26-6 and ethyl 5-chloropyrazolo[1,5-a]pyrimidine-3-carboxylate (521 mg, 2.31 mmol) in EtOH (12 mL) was added Hunig's base (750 mg, 5.8 mmol). The mixture was heated to 60° C. with stirring for 20 hours. The reaction was cooled to ambient temperature, quenched by addition to saturate NaHCO$_3$ solution (25 mL) and water (75 mL) and extracted with DCM (3×50 mL). The combined extracts were dried with Na$_2$SO$_4$ and concentrated under reduced pressure. Flash chromatography (ISCO system, silica (40 g), 0-40% ethyl acetate in hexane) provided 26-7 (894 mg, 1.77 mmol, 76% yield over 2 steps). LC-MS m/z 505.3 (M+H)$^+$.

Step 4. To a solution of 26-7 (894 mg, 1.77 mmol) in MeOH (40 mL) and THF (10 mL) at ambient temperature was added aqueous LiOH solution (2.0 M, 15 mL). The mixture was heated at 70° C. for 22 hours, cooled to −20° C. then quenched with aqueous HCl solution (2.0 M, 15.1 mL) to acidic. The mixture was extracted with DCM (3×50 mL), dried with Na$_2$SO$_4$, concentrated under reduced pressure, and dried under high vacuum overnight. To the residue was added DCM (30 mL) followed by addition of HCl in ether (2 M, 10 mL). The mixture was stirred at ambient temperature for 20 hours, concentrated under reduced pressure, and dried under high vacuum. To a solution of DMF (20 mL), DCM (100 mL) and Hünig's base (3.71 g, 28.70 mmol) was added 1/3 of this crude material then 1/3 of FDPP (603.21 mg, 1.57 mmol) and them mixture stirred for 1 hour. The additions were preformed 2 more times and the final mixture was stirred at ambient temperature for 18 hours, quenched with aqueous Na$_2$CO$_3$ solution (2M, 100 mL), and stirred for 5 min. The mixture was extracted with DCM (3×50 mL), and the combined extracts were dried with Na$_2$SO$_4$ and concentrated under reduced pressure. Flash chromatography (ISCO system, silica (40 g), 0-8.75% methanol in dichloromethane) provided 26 (446 mg, 79% yield).

General Method I.

Preparation of 7-methyl-6,7,14,15-tetrahydro-2H-3,5-(azenometheno)pyrrolo[3,4-f][1,4,8,10]benzoxatriazacyclotridecin-16(13H)-one (33)

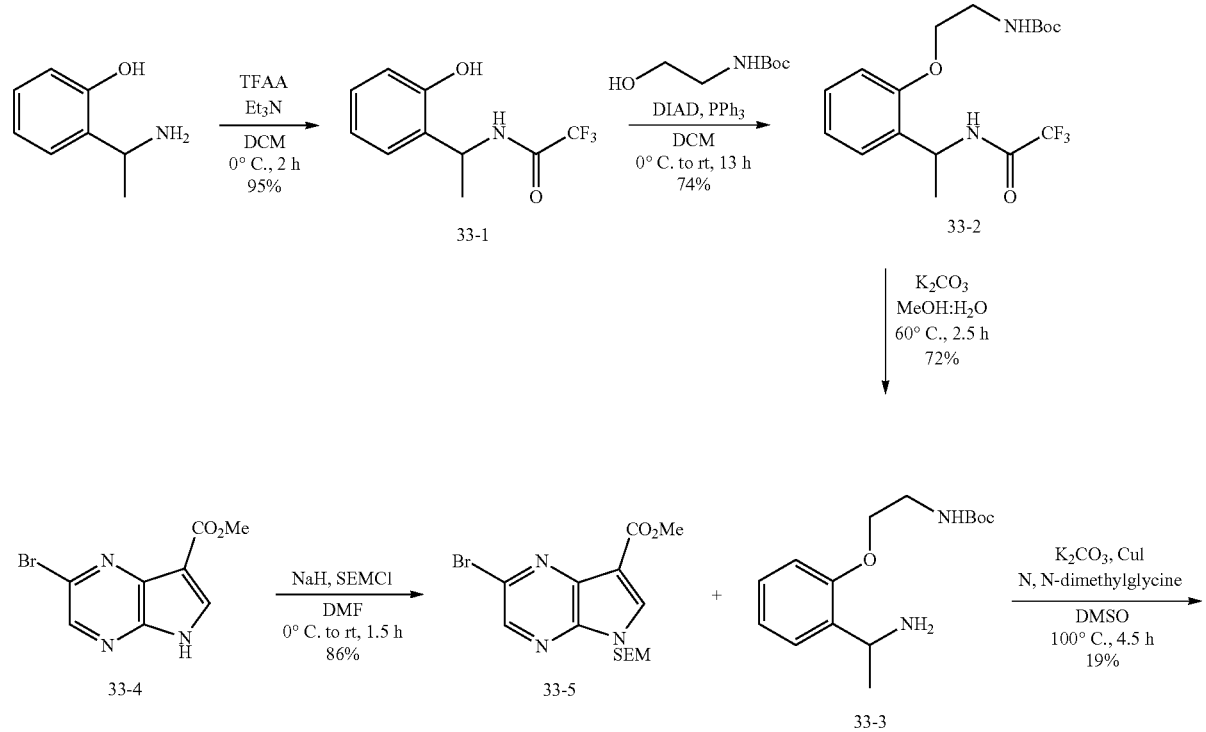

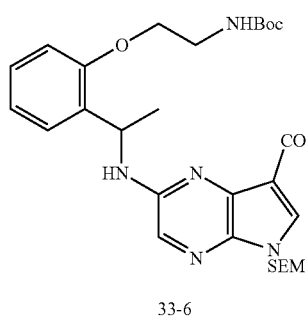 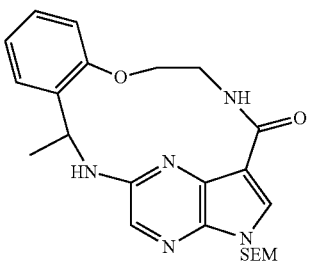 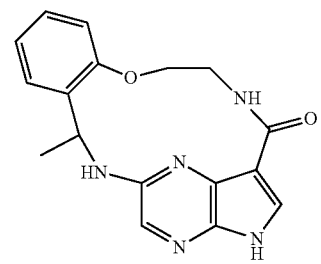

Step 1. Triethylamine (1.10 g, 10.9 mmol) was added to a solution of 2-(1-aminoethyl)phenol (499 mg, 3.64 mmol) and trifluoroacetic anhydride (841 mg, 4.0 mmol) in DCM (18.2 mL) at 0° C. Reaction was stirred for 2 hours at 0° C. then quenched by adding to 0.5 M HCl (100 mL). The mixture was extracted with DCM (150 mL). The extracts was washed with 0.5 M HCl (3×100 mL), dried with Na$_2$SO$_4$, and concentrated under reduced pressure. The residue was dried under high vacuum to obtain 33-1 (809.3 mg, 3.47 mmol, 95% yield).

Step 2. 33-1 (550 mg, 2.36 mmol) and tert-butyl (2-hydroxyethyl)carbamate (760 mg, 4.72 mmol) were mixed together and azeotrope dried from DCM:Toluene. The dried mixture was re-dissolved in DCM (1.50 mL) and PPh3 (1.27 g, 4.84 mmol) was added to the solution. The mixture was stirred till everything was completely dissolved. The solution was cooled to 0° C. and DIAD (1.03 g, 5.07 mmol) was added very slowly under stirring. The reaction was warmed to room temperature and stirred for 13 hours. The reaction was quenched by pouring to water (100 mL), and extracted with DCM (3×75 mL). The combined extracts were dried with Na$_2$SO$_4$ and concentrated under reduced pressure. Flash chromatography (ISCO system, silica (24 g), 5-20% ethyl acetate in hexane) provided 33-2 (655 mg, 1.74 mmol, 74% yield).

Step 3. To a solution of 33-2 (421 mg, 1.12 mmol) in MeOH (4.80 mL) and H2O (1.20 mL) was added K$_2$CO$_3$ (309 mg, 2.24 mmol) at room temperature. The reaction was heated to 60° C. for 2.5 hours, then cooled and poured into 0.4 M NaOH solution (50 mL), and extracted with DCM (3×50 mL). The combined extracts were dried with Na$_2$SO$_4$, and concentrated under reduced pressure. The residue was dried under high vacuum to obtain 33-3 (227.8 mg, 812 μmol, 72% yield).

Step 4. To a mixture of NaH (28 mg, 1.18 mmol) in DMF (4.06 mL) was added 33-4 (200 mg, 812 μmol) at 0° C. The mixture was stirred for 30 min followed by addition of SEMCl (176 mg, 1.06 mmol). The reaction was warmed to room temp and stirred for 2.5 hours, then quenched by addition to water (25 mL). The mixture was extracted with DCM (3×15 mL), and the combined extracts were dried with Na$_2$SO$_4$ and concentrated under reduced pressure. Flash chromatography (ISCO system, silica (12 g), 0-50% ethyl acetate in hexane) provide 33-5 (261.9 mg, 696 μmol, 86% yield).

Step 5. To a degassed solution of 33-3 (75 mg, 267 μmol), 33-5 (103 mg, 267 μmol), N,N-dimethylglycine (8.3 mg, 80 μmol) and K$_2$CO$_3$ (92 mg, 668 μmol) in DMSO (1.34 mL) was added CuI (7.6 mg, 40 μmol). The reaction was heated to 100° C. for 4.5 hours, poured into water (25 mL), and extracted with DCM (3×15 mL). The combined extracts were dried with Na$_2$SO$_4$ and concentrated under reduced pressure. Flash chromatography (ISCO system, silica (12 g), 0-40% ethyl acetate in hexane) provided 33-6 (30.2 mg, 51.5 μmol, 19% yield).

Step 6. To a solution of 33-6 (30.2 mg, 51.5 μmol) in MeOH (3 mL) and THF (1 mL) at ambient temperature was added aqueous LiOH solution (2.0 M, 1 mL). The mixture was heated at 70° C. for 45 minutes, cooled to −20° C. then quenched with aqueous HCl solution (2.0 M, 1.1 mL) to acidic. The mixture was extracted with DCM (3×5 mL), dried with Na$_2$SO$_4$, concentrated under reduced pressure, and dried under high vacuum. The crude material was dissolved in DCM (4 mL) followed by addition of HCl in ether (2 M, 2 mL). The mixture was stirred ambient temperature for 2 hours, concentrated under reduced pressure, and dried under high vacuum. The crude material was dissolved in in DMF (1.0 mL) and DCM (4.0 mL) and Hünig's base (33 mg, 256 μmol) then FDPP (20.7 mg, 54 μmol) was added in one portion. The reaction was stirred for 4 hours then quenched with 2 M Na$_2$CO$_3$ solution (5 mL). Mixture was stirred for 5 min then extracted with DCM (4×10 mL). Combined extracts were dried with Na$_2$SO$_4$ and concentrated under reduced pressure. Flash chromatography (ISCO system, silica (12 g), 0-100% ethyl acetate in hexane) provided 33-7 (13.9 mg, 30.6 μmol, 59% yield).

Step 7. 33-7 (13.9 mg, 30.6 μmol) was dissolved in DCM (1.00 mL) and TFA (1.00 mL). The mixture was stirred for 30 min until all starting material was consumed. The reaction solution was concentrated to dryness under reduced pressure and azeotrope dried with toluene (1 mL). The residue was re-dissolved in DCM (1.00 mL) and MeOH (0.5 mL) and NH₄OH (18 M, 150 μL) was added. The solution was stirred for 15 minutes, and concentrated under reduced pressure. Flash chromatography (ISCO system, silica (12 g), 0-15% methanol in dichloromethane) provided 33 (4.9 mg, 15 μmol, 49% yield).

General Method J.

Preparation of [(7S,13R)-11-fluoro-7-methyl-4-oxo-4,5,6,7,13,14-hexahydro-1,15-ethenopyrazolo[4,3-f][1,4,8,10]benzoxatriazacyclotridecin-13-yl]acetonitrile (38)

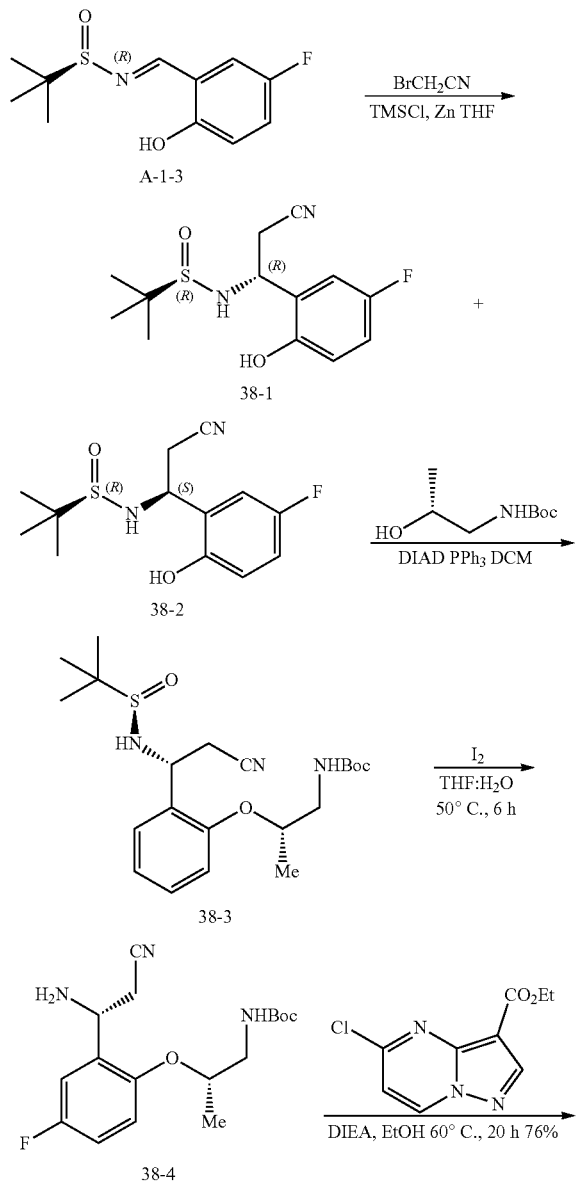

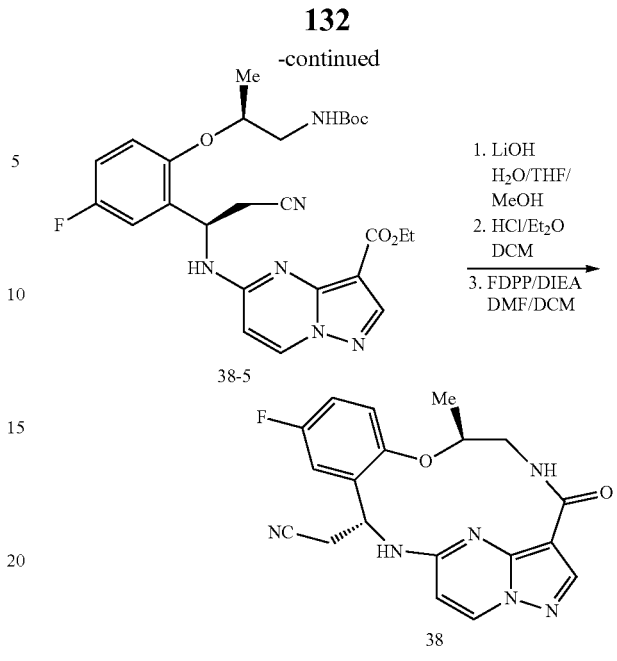

Step 1. To a solution of Zn (3.02 g, 46.24 mmol, 3.75 eq.) and 2-bromoacetonitrile (3.70 g, 30.83 mmol, 2.50 eq.) in THF (20.00 mL) was added TMSCl (254.52 mg, 2.34 mmol, 0.19 eq.) dropwised under N₂. The mixture was stirred at 0° C. to 20° C. for 2 hr. Then A-1-3 (3.00 g, 12.33 mmol, 1.00 eq.) was added to the mixture and the mixture was stirred at 50° C. for 12 hr. The TLC (PE:EtOAc=1:2) showed the reaction worked well. Then the mixture was quenched by water (20 mL) and extracted with EtOAc (50 mL*5), the organic layer washed by brine (50 mL), dried over Na₂SO₄. The residue was purified by column chromatography (SiO₂, Petroleum ether/Ethyl acetate=10/1 to 1:5) to give 38-1 (260 mg, PE:EtOAc=1:2, Rf=0.5) and 38-2 (441 mg, PE:EtOAc=1:2, Rf=0.4) as white solid. ¹H NMR (400 MHz, CDCl₃, 38-1) δ 9.60 (s, 1H), 6.78 (dd, J=3.0, 8.3 Hz, 1H), 6.49 (dt, J=3.1, 8.5 Hz, 1H), 6.17 (dd, J=4.6, 8.9 Hz, 1H), 5.62 (d, J=10.2 Hz, 1H), 4.45 (dt, J=4.6, 10.3 Hz, 1H), 3.12 (dd, J=10.5, 17.0 Hz, 1H), 2.65 (dd, J=4.7, 17.0 Hz, 1H), 1.38 (s, 9H); ¹H NMR (400 MHz, CDCl₃, 38-2) δ 9.10 (br. s., 1H), 6.92 (dq, J=3.0, 8.7 Hz, 2H), 6.81 (dd, J=4.6, 8.7 Hz, 1H), 4.83-4.71 (m, 2H), 3.11-3.02 (m, 2H), 1.31 (s, 9H).

Step 2. 38-1 (100.00 mg, 351.68 μmol) and tert-butyl (R)-(2-hydroxypropyl)carbamate (123.25 mg, 703.36 μmol) were mixed together and azetrope dried from DCM:Toluene. The mixture was redissolved in DCM (200.00 μL) and PPh₃ (189.10 mg, 720.94 μmol) was added to the solution. The mixture was stirred till everything completely dissolved and then cooled to 0° C. To the solution was added DIAD (145.78 mg, 720.94 μmol, 141.53 μL) very slowly with mixing. The reaction was warmed to room temperature, stirred for 19 hour, quenched by addition to water (4 solvent volume), and extracted with DCM (3×3 mL). The combined extracts were dried with Na₂SO₄ and concentrated under reduced pressure. Flash chromatography (ISCO system, silica (12 g), 0-100% ethyl acetate in hexane) to provide 38-3 (58.8 mg, 37% yield).

38-3 was converted to 38 following the reaction steps 2-4 in General Method H.

General Method K

Preparation of tert-butyl ((S)-2-(2-((R)-1-amino-ethyl)-4-fluorophenoxy)-propyl)carbamate (40-5)

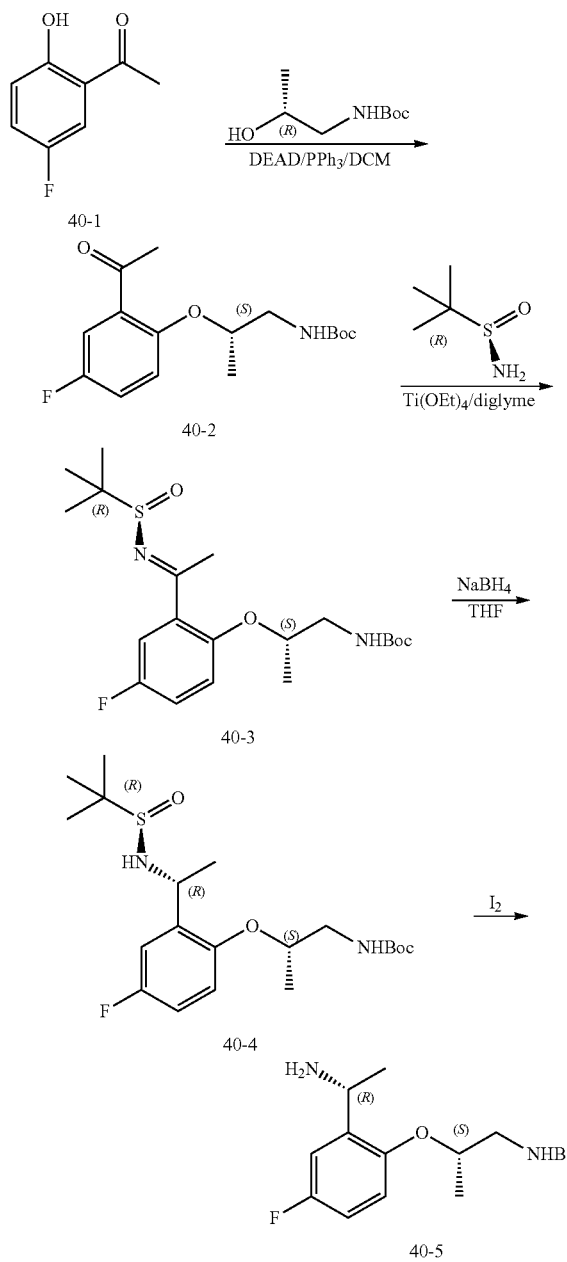

Step 1. To a solution of 40-1 (500.00 g, 3.24 mol, 1.00 eq.), tert-butyl (R)-(2-hydroxypropyl)carbamate (851.57 g, 4.86 mol, 1.50 eq.) and PPh$_3$ (1.27 kg, 4.86 mol, 1.50 eq.) in dichloromethane (1.5 L) was added DEAD (902.79 g, 5.18 mol, 940.41 mL, 1.60 eq.) drop-wise at 0° C. The solution was stirred at 25° C. for 4 hours. TLC indicated one major new spot with larger polarity was detected, and the starting material was consumed completely. Petroleum ether (1.5 L) was added to the mixture, then filtrated the solid, the solvent of the filtrate was removed and the residue was purified by column chromatography (SiO$_2$, Petroleum ether/Ethyl acetate=20/1 to 10:1) to give 40-2 (680.00 g, 2.18 mol, 67.28% yield) as a red oil. $^1$H NMR (400 MHz, CHLOROFORM-d) δ 7.38 (dd, J=3.2, 8.8 Hz, 1H), 7.13 (ddd, J=3.2, 7.2, 8.8 Hz, 1H), 6.97 (dd, J=4.0, 8.8 Hz, 1H), 5.06 (br. s., 1H), 4.63-4.52 (m, 1H), 3.52-3.39 (m, 1H), 3.38-3.27 (m, 1H), 2.59 (s, 3H), 1.42 (s, 9H), 1.32 (d, J=6.4 Hz, 3H).

Step 2. To a mixture of (R)-2-methylpropane-2-sulfinamide (219.98 g, 1.82 mol, 1.50 eq.), diglyme (162.35 g, 1.21 mol, 172.71 mL, 1.00 eq.) and 40-2 (376.00 g, 1.21 mol, 1.00 eq.) in THF (1.88 L) and 2-methyltetrahydrofuran (1.88 L) was added tetraethoxytitanium (552.03 g, 2.42 mol, 501.85 mL, 2.00 eq.) in one portion at 20° C. under N$_2$. The mixture was stirred at 60° C. for 12 hr. TLC showed about 15% starting material remaining. The mixture was cooled to 20° C. Water (2 L) was added. The aqueous phase was extracted with ethyl acetate (2000 mL×3). The combined organic phase was washed with saturated brine (1 L), dried over anhydrous Na$_2$SO$_4$, filtered and concentrated in vacuum to give a 40-3 (520.00 g, crude) as a red oil which used for the next step without further purification.

Step 3. To a solution of 40-3 (520.00 g, 1.25 mol, 1.00 eq.) in THF/H$_2$O (3.82 L/78 mL) was added NaBH$_4$ (142.37 g, 3.76 mol, 3.00 eq.) at −50° C., the reaction was warmed to 25° C., and then stirred at 25° C. for 12 hr. TLC showed starting material was completely consumed. Water (1 L) was added to the mixture and extracted with EtOAc (2 L×2). The organic layer was washed with saturated NaCl (1 L) and dried over Na$_2$SO$_4$. Removed the solvent and the residue was purified by column chromatography (SiO$_2$, Petroleum ether/Ethyl acetate=20/1 to 10:1) to give 40-4 (270.00 g, 570.40 mmol, 45.47% yield). $^1$H NMR (400 MHz, CHLOROFORM-d) δ 7.06 (dd, J=3.2, 9.2 Hz, 1H), 6.95 (dt, J=3.2, 8.4 Hz, 1H), 6.80 (dd, J=4.4, 9.2 Hz, 1H), 6.70 (br. s., 1H), 4.93 (d, J=6.0 Hz, 1H), 4.57-4.46 (m, 1H), 3.68-3.65 (m, 1H), 3.59-3.57 (m, 1H), 3.22-3.10 (m, 1H), 1.47 (d, J=6.8 Hz, 3H), 1.40 (s, 9H), 1.27-1.25 (m, 3H), 1.22 (s, 9H).

Step 4. To a solution of 40-4 (270.00 g, 570.40 mmol, 1.00 eq.) and molecular iodine (28.95 g, 114.08 mmol, 22.98 mL, 0.20 eq.) in THF (2.16 L) was added H$_2$O (540.00 mL) at 25° C. under N$_2$. The mixture was stirred at 50° C. for 3 hours. TLC showed the starting material was consumed completely. The mixture was concentrated to give 40-5 (330.00 g, crude) as a white solid. LCMS: m/z 313.2 (M+H+). $^1$H NMR (400 MHz, CHLOROFORM-d) δ 7.08 (dd, J=2.8, 9.4 Hz, 1H), 6.91-6.79 (m, 2H), 5.72 (br. s., 1H), 4.55-4.32 (m, 2H), 3.52-3.41 (m, 1H), 3.31-3.19 (m, 1H), 1.42 (s, 9H), 1.38 (d, J=6.8 Hz, 3H), 1.29 (d, J=6.0 Hz, 3H).

General Method L.

Preparation of (3aR,9R,17aS)-7-fluoro-9-methyl-1,2,3,3a,9,10,17,17a-octahydro-16H-11,13-ethenocyclopenta[b]pyrazolo[4,3-f][1,4,8,10]benzoxatriazacyclotridecin-16-one (41)

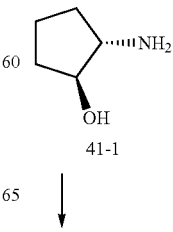

41-1

↓

135

-continued

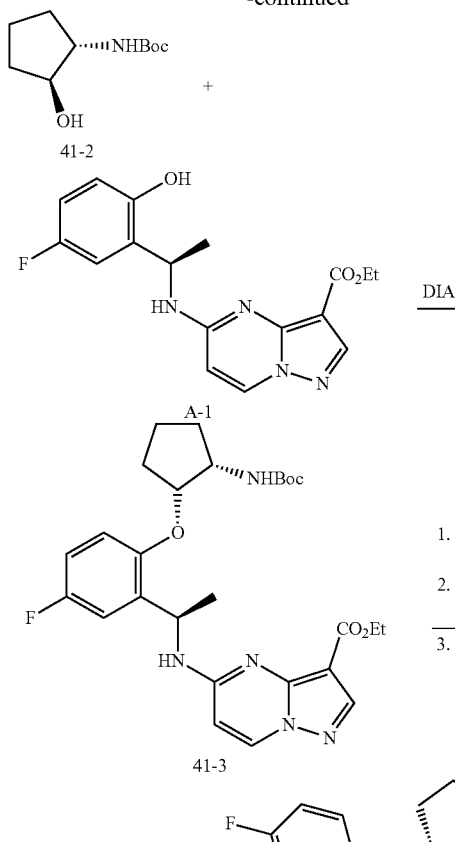

General Method M.

Preparation of (7R,13R)-7-ethyl-11-fluoro-13-methyl-6,7,13,14-tetrahydro-1,15-ethenopyrazolo[4,3-f]pyrido[3,2-l][1,4,8,10]oxatriazacyclotridecin-4(5H)-one (58)

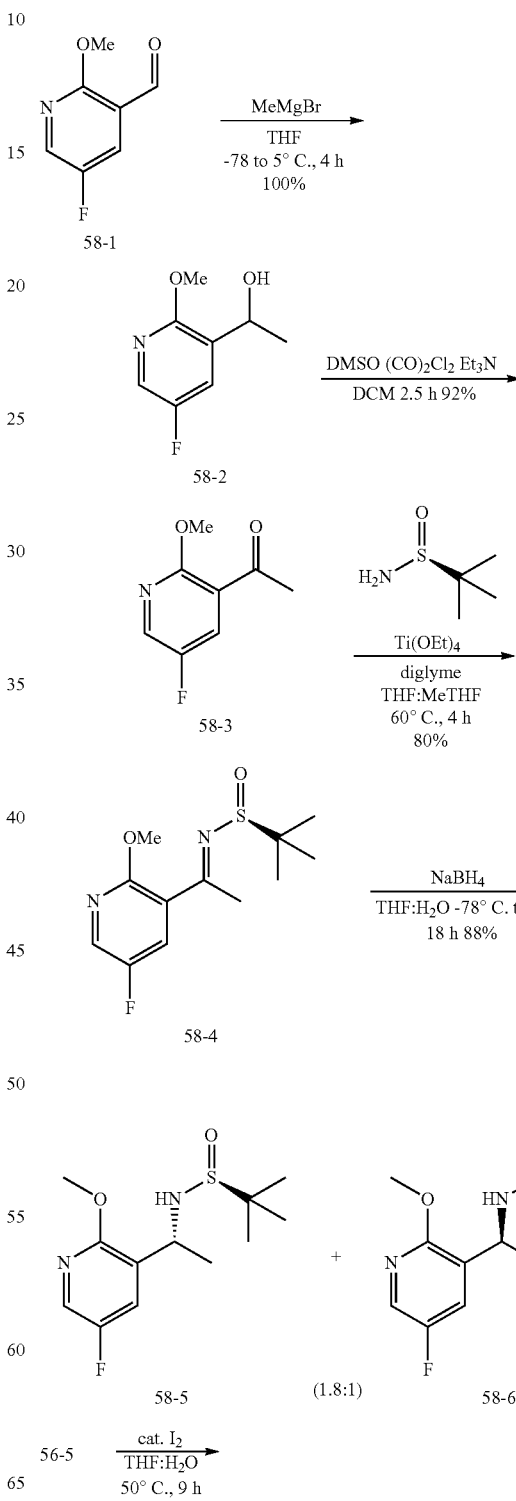

Step 1. To a solution of (1S,2S)-2-aminocyclopentan-1-ol (41-1) HCl salt (500.00 mg, 3.63 mmol) and triethylamine (1.10 g, 10.89 mmol, 1.51 mL) in MeOH (18.15 mL) was added Boc$_2$O (1.58 g, 7.26 mmol). The reaction was stirred for 22 hour, concentrated under reduced pressure. Flash chromatography (ISCO system, silica (24 g), 0-50% ethyl acetate in hexane) provide 41-2 (714.2 mg, 3.55 mmol, 97.76% yield).

Step 2. 41-2 (100.00 mg, 496.87 µmol) and A-1 (171.09 mg, 496.87 µmol) were mixed together and azetrope dried from DCM:Toluene. The mixture was redissolved in DCM (248.43 µL) and PPh$_3$ (136.84 mg, 521.71 µmol) was added to the solution. The mixture was stirred till everything completely dissolved. DIAD (105.50 mg, 521.71 µmol, 102.43 µL) was added very slowly with mixing. The reaction was stirred for 16 hour, then quenched by addition to water (4 mL), and extracted with DCM (3×3 mL). The combined extracts were dried with Na$_2$SO$_4$ and concentrated under reduced pressure. Flash chromatography (ISCO system, silica (12 g), 0-50% ethyl acetate in hexane) to provide 41-3 (17.6 mg, 6.7% yield).

Step 3. 41-3 was converted to 41 following the step 4 in General method H.

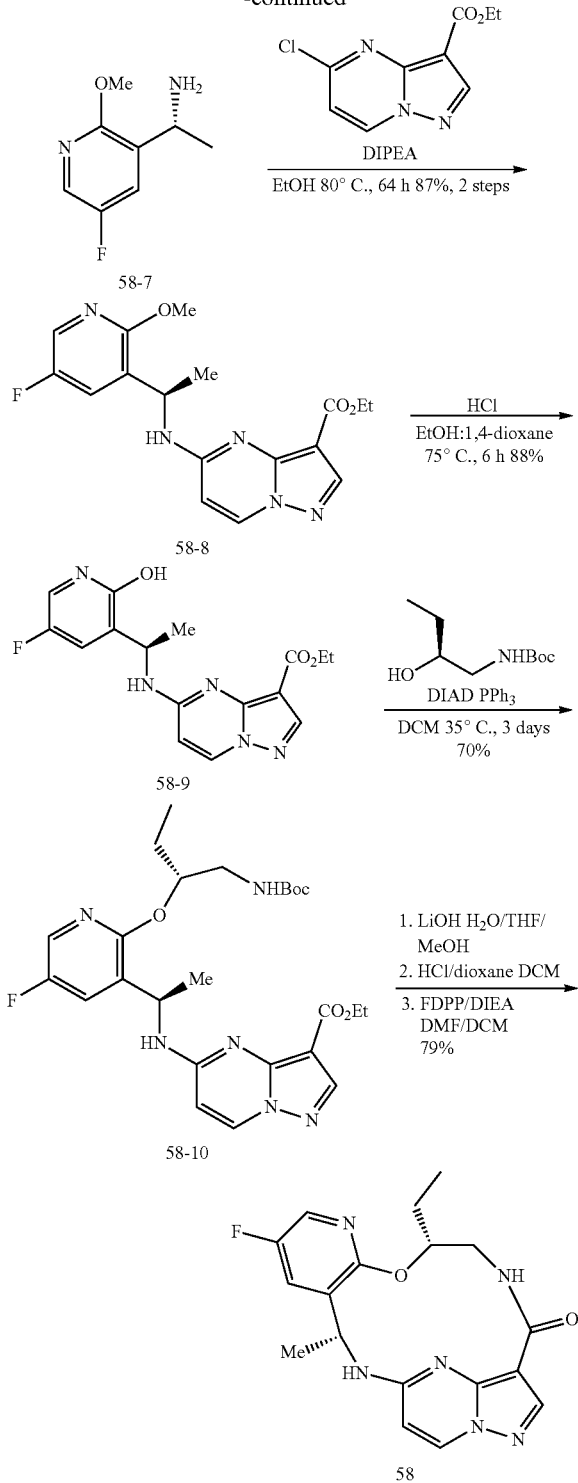

Flash chromatography (ISCO system, silica (24 g), 0-50% ethyl acetate in hexane) provided 58-2 (1.10 g, 6.43 mmol, 100% yield).

Step 2: DMSO (753 mg, 9.65 mmol, 685 µL) in DCM (5 mL) was added dropwise to oxalyl chloride (1.22 g, 9.65 mmol, 827 µL) in DCM (15 mL) at −78° C. The solution was stir for 20 min, and then 58-2 (1.10 g, 6.43 mmol) in DCM (8 mL) was added dropwise. The reaction was stirred for 20 min and then TEA (3.25 g, 32 mmol, 4.46 mL) was added dropwise. The reaction was slowly warmed to room temperature, stirred for 2.5 hours, and quenched by addition to water (100 mL). The mixture was extracted with DCM (3×25 mL), and the combined extracts were dried with $Na_2SO_4$ and concentrated under reduced pressure. Flash chromatography (ISCO system, silica (24 g), 0-40% ethyl acetate in hexane) provided 58-3 (1.01 g, 5.97 mmol, 92% yield).

Step 3: To a solution of 58-3 (1.01 g, 5.97 mmol), (S)-2-methylpropane-2-sulfinamide (1.00 g, 8.25 mmol) and diglyme (801 mg, 5.97 mmol, 852 µL) in THF (6.0 mL) and MeTHF (6.0 mL) was added Ti(OEt)$_4$ (2.59 g, 11.34 mmol, 2.37 mL). The mixture was heated at 60° C. for 4 hours, cooled to room temperature, and quenched by addition to water (100 mL). The mixture was extracted with DCM (3×50 mL), and the extracts were dried with $Na_2SO_4$ and concentrated under reduced pressure. Flash chromatography (ISCO system, silica (24 g), 5-30% ethyl acetate in hexane) provided 58-4 (1.31 g, 4.81 mmol, 80% yield).

Step 4: Added NaBH$_4$ (546 mg, 14.4 mmol) to 58-4 (1.31 g, 4.81 mmol) and H$_2$O (260 mg, 14.43 mmol, 260 µL) in THF (24 mL) at −78° C. Allowed reaction to slowly warm to room temperature, and stirred for 18 hours. Cooled reaction back down to −78° C. and quenched reaction with MeOH (3 mL) then water (5 mL) then adjusted pH till neutral with 2 M HCl further dilute with water (75 mL) and extracted with DCM (3×75 mL). Combined extracts were dried with $Na_2SO_4$ and concentrated under reduced pressure. Flash chromatography (ISCO system, silica (40 g), 30-60% ethyl acetate in hexane) provided 56-5 (758.1 mg, 2.76 mmol, 57% yield) and 58-6 (414.9 mg, 1.51 mmol, 31% yield).

Step 5: To a solution of 58-5 (757 mg, 2.76 mmol) in THF (11.5 mL) and H$_2$O (2.30 mL) was added I$_2$ (140 mg, 552 µmol). The mixture was heated at 50° C. for 9 hours, and then concentrated under reduced pressure to give 58-7. Compound was dried on high vacuum and used as is.

Step 6: To a solution of 58-7 (469.7 mg, 2.76 mmol) and 5-chloropyrazolo[1,5-a]pyrimidine-3-carboxylate (778 mg, 3.45 mmol) in EtOH (14.0 mL) was added Hünig's base (2.96 g, 22.9 mmol, 4.0 mL). The solution was heated at 80° C. for 64 hours. The mixture was concentrated under reduced pressure. Flash chromatography (ISCO system, silica (40 g), 50-100% ethyl acetate in hexane) provided 58-8 (871.4 mg, 2.42 mmol, 87% yield).

Step 7: To 58-8 (869.65 mg, 2.42 mmol) in EtOH (15.0 mL) was added HCl in 1,4-dioxane (4 M, 15.0 mL). The mixture was heated to 75° C., stirred for 6 hours and concentrated under reduced pressure. Flash chromatography [loaded with DCM containing Et$_3$N (200 µL)] (ISCO system, silica (24 g), 0-10% methanol in dichloromethane) provide 58-9 (736.1 mg, 2.13 mmol, 88% yield).

Step 8: 58-9 (100 mg, 289 µmol) and (S)-tert-butyl (2-hydroxybutyl)carbamate (68.5 mg, 362 µmol) were mixed together and azeotrope dried from DCM:Toluene. The residue was re-dissolved in DCM (150 µL) and PPh$_3$ (99 mg, 376 µmol) was added to the solution. The mixture was stirred till everything completely dissolved, and DIAD (76

Step 1: MeMgBr (3 M, 6.45 mL) in Et$_2$O was added to a solution of 58-1 (1.00 g, 6.45 mmol) in THF (32 mL) at −78° C. The reaction was slowly warmed to 5° C. over 4 hours, and then cooled back down to −78° C., and quenched by addition of saturated aqueous NH$_4$Cl solution (20 mL). The mixture was warmed to room temperature and extracted with DCM (3×10 mL). The combined extracts were dried with Na$_2$SO$_4$ and concentrated under reduced pressure.

mg, 376 μmol, 73.9 μL) was added very slowly with mixing. The mixture was heated at 35° C. for 2 hours, cooled to room temperature, and stirred for 3 days. The reaction was quenched by addition to water (4 mL) and extracted with DCM (3×4 mL). The combined extracts were dried with Na₂SO₄ and concentrated under reduced pressure. Flash chromatography (ISCO system, silica (12 g), 0-60% ethyl acetate in hexane) provided 58-10 (105.8 mg, 204 μmol, 70% yield).

Step 9. To a solution of 58-10 (105.8 mg, 204 μmol) in MeOH (4 mL) and THF (1.5 mL) at ambient temperature was added aqueous LiOH solution (2.0 M, 1.5 mL). The mixture was heated at 70° C. for 3 hours, cooled to −20° C. then quenched with aqueous HCl solution (2.0 M, 1.6 mL) to acidic. The mixture was extracted with DCM (3×5 mL), dried with Na₂SO₄, concentrated under reduced pressure, and dried under high vacuum. The crude material was dissolved in DCM (4 mL) followed by addition of HCl in 1,4-dioxane (4 M, 3 mL). The mixture was stirred ambient temperature for 15 hours, concentrated under reduced pressure, and dried under high vacuum. The crude material was dissolved in in DMF (2.0 mL) and DCM (8.0 mL) and Hünig's base (264 mg, 2.05 mmol, 357 μL) then FDPP (98 mg, 255 μmol) was added in one portion. The reaction was stirred for 3 hours then quenched with 2 M Na₂CO₃ solution (5 mL). Mixture was stirred for 5 min then extracted with DCM (3×10 mL). Combined extracts were dried with Na₂SO₄ and concentrated under reduced pressure. Flash chromatography (ISCO system, silica (12 g), 0-10% methanol in dichloromethane) provided 58 (49.3 mg, 133 μmol, 65% yield).

General Method N.

Preparation of (7S)-11-fluoro-N,7-dimethyl-4-oxo-4,5,6,7,13,14-hexahydro-1,15-ethenopyrazolo[4,3-f][1,4,8,10]benzoxatriazacyclotridecine-13-carboxamide (61)

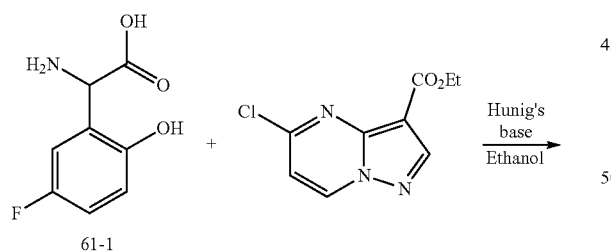

61-1

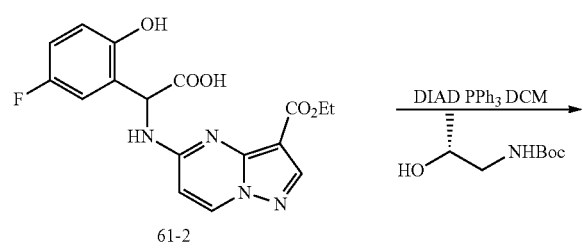

61-2

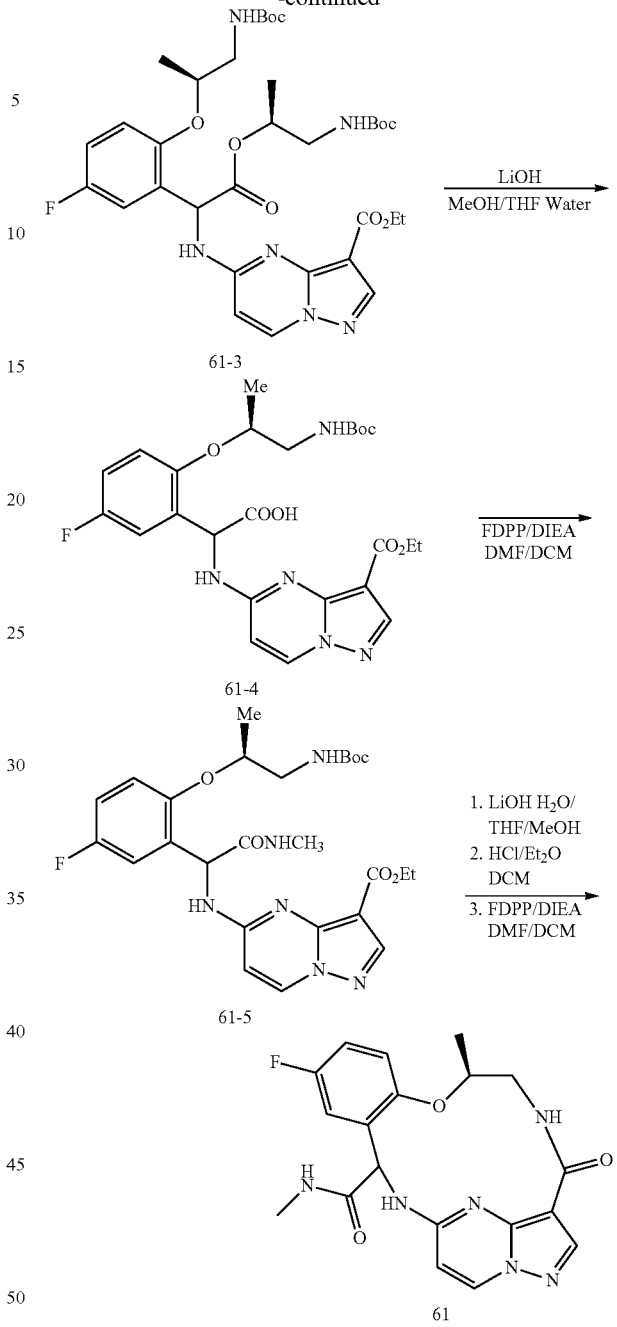

Step 1. The HCl salt of 61-1 (250.42 mg, 1.13 mmol) and ethyl 5-chloropyrazolo[1,5-a]pyrimidine-3-carboxylate (254.96 mg, 1.13 mmol) were combined in ethanol (5.65 mL) and Hunig's base (1.46 g, 11.30 mmol, 1.97 mL) was added. The mixture was stirred and warmed to 80° C. The reaction was checked after 3 hours and was complete by LC-MS. The reaction was cooled and worked up with water and ethyl acetate. The aqueous layer was extracted twice more with ethyl acetate. The combined organic layer was washed with brine, dried over sodium sulfate, filtered. The crude was purified by column chromatography (DCM/methanol) to provide 61-2 (176 mg). Additional 61-2 (130 mg) was obtained from acidifying aqueous layer and extracting with ethyl acetate and purification to give a final 72% yield.

Step 2. 61-2 (130.00 mg, 347.30 μmol) and tert-butyl (R)-(2-hydroxypropyl)carbamate (182.56 mg, 1.04 mmol) were combined in toluene and was dried azeotropically under reduced pressure. The resulting dried compounds were dissolved in dichloromethane (231.53 μL) and triphenylphosphine (277.83 mg, 1.06 mmol) was added into the solution at room temperature. After ~10 minutes, the mixture was cooled in an ice bath and DIAD (214.19 mg, 1.06 mmol, 207.95 μL) was added. The reaction was stirred gradually to room temperature and stirred for 19 hour, quenched by addition to water (4 solvent volume), and extracted with DCM (3×3 mL). The combined extracts were dried with Na$_2$SO$_4$ and concentrated under reduced pressure. Flash chromatography (ISCO system, silica (12 g), 0-100% ethyl acetate in hexane) to provide 61-3 (138.5 mg, 57% yield).

Step 3. To a solution of 61-3 (138.50 mg, 201.09 μmol) in methanol (0.5 mL), THF (2.00 mL) and water (1.80 mL) was added LiOH (2.0 M, 0.15 mL). The mixture was stirred at room temperature until the hydrolysis was complete. The reaction was neutralized to pH ~5 with HCl, and extracted with DCM. The combined extracts were dried with Na$_2$SO$_4$, filtered, concentrated, and dried in high vacuum to provide 61-4 (100 mg).

Step 4. To a solution of 61-4 (53.5 mg, 0.10 mmol) in DCM (4.5 mL) and DMF (0.5 mL) was added FDPP (50.3 mg, 0.13 mmol). Hünig's base (130.1 mg, 1.01 mmol) and methylamine HCl salt (13.6 mg, 0.20 mmol). The mixture was stirred until LC-MS showed the completion, and then quenched with aqueous Na$_2$CO$_3$ solution. The mixture was extracted with DCM (3×50 mL), and the combined extracts were dried with Na$_2$SO$_4$ and concentrated under reduced pressure. Flash chromatography (ISCO system, silica (40 g), 0-8.75% methanol in dichloromethane) provided 61-5 (24.4 mg, 44% yield)

61-5 was converted to 61 following the reaction step 4 in General method H.

Compounds 27-31 were prepared according to General Method F using A-5 and (S)-1-((tert-butoxycarbonyl)amino)butan-2-yl methanesulfonate for 27, (S)-1-((tert-butoxycarbonyl)amino)propan-2-yl methanesulfonate for 28, (R)-1-((tert-butoxycarbonyl)amino)propan-2-yl methanesulfonate for 29, (R)-2-((tert-butoxycarbonyl)amino)propyl methanesulfonate for 30, and (S)-2-((tert-butoxycarbonyl)amino)propyl methanesulfonate for 31 in step 1.

Compound 32 was prepared according to General Method F using A-6 and (R)-1-((tert-butoxycarbonyl)amino)propan-2-yl methanesulfonate in step 1.

Compounds 34 and 35 were prepared according to General Methods A and F using ethyl 3-ethoxy-2-methylacrylate in General Method A to get ethyl 5-chloro-6-methylpyrazolo[1,5-a]pyrimidine-3-carboxylate in replacement of ethyl 5-chloropyrazolo[1,5-a]pyrimidine-3-carboxylate (A-1-8), and using tert-butyl (2-chloroethyl)carbamate for 34 and (R)-1-((tert-butoxycarbonyl)amino)propan-2-yl methanesulfonate for 35 in General Method F.

Compounds 36 and 37 were prepared according to General Methods A and F using A-1-8 for 36 and ethyl 5-chloro-6-methylpyrazolo[1,5-a]pyrimidine-3-carboxylate for 37, and 2-hydroxybenzaldehyde in place of 5-fluoro-2-hydroxybenzaldehyde in General Method A, and using tert-butyl (2-chloroethyl)carbamate for both 36 and 37 in General Method F.

Compound 39 was prepared according to General Methods A and F using ethyl 5-amino-3-ethyl-1H-pyrazole-4-carboxylate in place of ethyl 5-amino-1H-pyrazole-4-carboxylate (A-1-6) in General Method A, and using (R)-1-((tert-butoxycarbonyl)amino)propan-2-yl methanesulfonate in General Method F.

Compound 40 was prepared according to General Method I using 40-5 in place of 33-3.

Compounds 42-54 were prepared according to General Method L using the following starting material in place of (1S,2S)-2-aminocyclopentan-1-ol in General Method L.

| Compound # | Starting material in place of 41-1 in General Method L |
|---|---|
| 41 | (1S,2S)-2-aminocyclopentan-1-ol |
| 42 | (1R,2R)-2-aminocyclopentan-1-ol |
| 43 | (1S,2R)-2-aminocyclopentan-1-ol |
| 44 | (1R,2S)-2-aminocyclohexan-1-ol |
| 45 | (1S,2R)-2-aminocyclohexan-1-ol |
| 46 | (1R,2S)-2-aminocyclopentan-1-ol |
| 47 | (1R,2R)-2-aminocyclohexan-1-ol |
| 48 | (3S,4S)-4-aminopyrrolidin-3-ol |
| 49 | (3R,4S)-4-aminopyrrolidin-3-ol |
| 50 | (R)-pyrrolidin-3-ol |
| 51 | (S)-pyrrolidin-3-ol |
| 52 | (R)-piperidin-3-ol |
| 53 | (S)-piperidin-3-ol |
| 54 | piperidin-4-ol |

Compounds 55-57 were prepared according to General Method E using compound 7 in place of compound 6, and dimethylamine for 55, methylamine for 56, and pyrrolidine for 57.

Compounds 59 and 60 were prepared according to General Method M using tert-butyl (R)-(2-hydroxypropyl)carbamate in place of tert-butyl (S)-(2-hydroxypropyl)carbamate in place of tert-butyl (S)-(2-hydroxybutyl)carbamate.

Compound 62 was prepared according to General Method N using dimethyl amine in place of methylamine.

| Compd # | Structure | MS m/z | $^1$H NMR (500 MHz, DMSO-d$_6$) δ ppm |
|---|---|---|---|
| 1 | 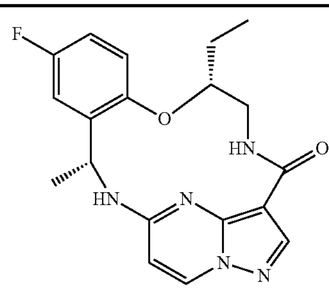 | 370.2 | 9.35 (br t, J = 4.58 Hz, 1 H), 8.73 (d, J = 5.73 Hz, 1 H), 8.58 (d, J = 7.45 Hz, 1 H), 8.04 (s, 1 H), 7.05-7.12 (m, 2 H), 6.91 (td, J = 8.59, 3.44 Hz, 1 H), 6.38 (d, J = 7.45 Hz, 1 H), 5.48-5.61 (m, 1 H), 4.46-4.58 (m, 1 H), 3.59-3.77 (m, 2 H), 1.92-2.05 (m, 2 H), 1.50-1.63 (m, 1 H), 1.43 (d, J = 6.87 Hz, 3 H), 0.94 (t, J = 7.45 Hz, 3 H) |

| Compd # | Structure | MS m/z | ¹H NMR (500 MHz, DMSO-d$_6$) δ ppm |
|---|---|---|---|
| 2 | 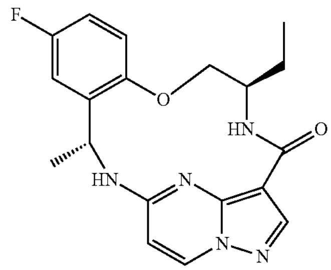 [SMILES: CC[C@@H]1COc2ccc(F)cc2[C@@H](C)Nc2ccn3ncc(c3n2)C(=O)N1] | 370.2 | 9.94 (d, J = 9.17 Hz, 1 H), 8.78 (d, J = 7.45 Hz, 1 H), 8.58 (d, J = 7.45 Hz, 1 H), 8.04 (s, 1 H), 7.16 (dd, J = 9.74, 3.44 Hz, 1 H), 6.98-7.05 (m, 1 H), 6.91-6.97 (m, 1 H), 6.33 (d, J = 7.45 Hz, 1 H), 5.66 (m, 1 H), 4.48 (d, J = 9.74 Hz, 1 H), 3.99-4.09 (m, 1 H), 3.84 (dd, J = 9.74, 3.44 Hz, 1 H), 1.68-1.82 (m, 2 H), 1.46 (d, J = 7.45 Hz, 3 H), 0.99 (t, J = 7.45 Hz, 3 H) |
| 3 | 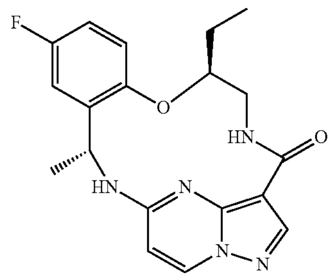 [SMILES: CC[C@H]1CNC(=O)c2cnn3ccc(nc23)N[C@H](C)c2cc(F)ccc2O1] | 370.2 | 9.69 (dd, J = 6.30, 3.44 Hz, 1 H), 8.80 (d, J = 6.87 Hz, 1 H), 8.58 (d, J = 7.45 Hz, 1 H), 8.03 (s, 1 H), 7.09-7.14 (m, 1 H), 7.03 (dd, J = 9.17, 4.58 Hz, 1 H), 6.92-6.98 (m, 1 H), 6.37 (d, J = 7.45 Hz, 1 H), 5.46-5.57 (m, 1 H), 4.41-4.49 (m, 1 H), 3.88 (ddd, J = 13.60, 6.73, 4.30 Hz, 1 H), 3.22 (ddd, J = 13.75, 7.45, 3.44 Hz, 1 H), 1.85-1.97 (m, 1 H), 1.74-1.82 (m, 1 H), 1.44 (d, J = 6.87 Hz, 3 H), 1.02 (t, J = 7.45 Hz, 3 H) |
| 4 | 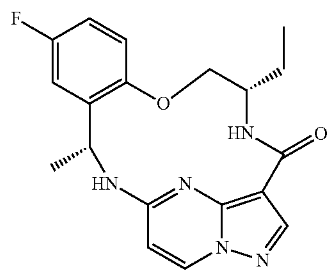 [SMILES: CC[C@H]1COc2ccc(F)cc2[C@@H](C)Nc2ccn3ncc(c3n2)C(=O)N1] | 370.2 | 9.28 (d, J = 2.29 Hz, 1 H), 8.71 (d, J = 6.87 Hz, 1 H), 8.56 (d, J = 8.02 Hz, 1 H), 8.01 (s, 1 H), 7.16 (dd, J = 9.17, 2.86 Hz, 1 H), 7.07-7.11 (m, 1 H), 6.98-7.06 (m, 1 H), 6.34 (d, J = 7.45 Hz, 1 H), 5.63-5.72 (m, 1 H), 4.40 (dd, J = 10.31, 4.01 Hz, 1 H), 4.05 (dd, J = 10.31, 8.59 Hz, 1 H), 3.81-3.92 (m, 1 H), 2.10-2.30 (m, 1 H), 1.87 (dt, J = 14.46, 7.37 Hz, 1 H), 1.42 (d, J = 6.87 Hz, 3 H), 0.97 (t, J = 7.45 Hz, 3 H) |
| 5 | 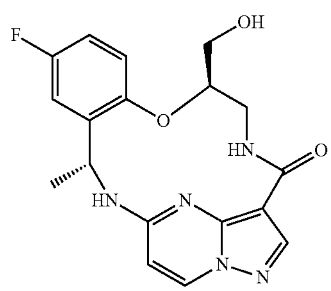 [SMILES: C[C@H]1Nc2ccn3ncc(c3n2)C(=O)NC[C@H](CO)Oc2ccc(F)cc21] | 372.2 | 9.73 (dd, J = 7.73, 2.58 Hz, 1 H), 8.82 (d, J = 6.30 Hz, 1 H), 8.51-8.63 (m, 1 H), 8.03 (s, 1 H), 7.15 (dd, J = 9.16, 4.58 Hz, 1 H), 7.11 (dd, J = 9.45, 3.15 Hz, 1 H), 6.94-7.00 (m, 1 H), 6.37 (d, J = 8.02 Hz, 1 H), 5.47-5.55 (m, 1 H), 5.14 (t, J = 5.73 Hz, 1 H), 4.40-4.46 (m, 1 H), 3.93 (ddd, J = 13.75, 7.73, 4.30 Hz, 1 H), 3.77 (dt, J = 11.17, 5.30 Hz, 1 H), 3.69 (dt, J = 11.74, 6.16 Hz, 1 H), 3.26 (ddd, J = 13.60, 7.88, 3.15 Hz, 1 H), 1.44 (d, J = 6.87 Hz, 3 H) |
| 6 | 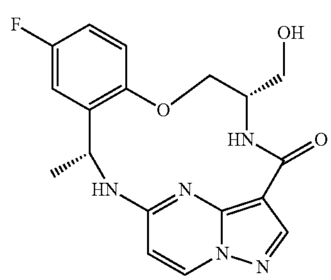 [SMILES: C[C@H]1Nc2ccn3ncc(c3n2)C(=O)N[C@@H](CO)COc2ccc(F)cc21] | 372.2 | 9.62 (d, J = 3.44 Hz, 1 H), 8.79 (d, J = 6.87 Hz, 1 H), 8.59 (d, J = 7.45 Hz, 1 H), 8.06 (s, 1 H), 7.14 (dd, J = 9.45, 3.15 Hz, 1 H), 7.10 (dd, J = 9.17, 4.58 Hz, 1 H), 6.99-7.04 (m, 1 H), 6.37 (d, J = 7.45 Hz, 1 H), 5.60-5.67 (m, 1 H), 5.54 (dd, J = 7.73, 4.30 Hz, 1 H), 4.42 (dd, J = 10.88, 4.58 Hz, 1 H), 4.28 (dd, J = 10.88, 7.45 Hz, 1 H), 3.91-3.99 (m, 1 H), 3.83 (ddd, J = 11.03, 6.16, 4.58 Hz, 1 H), 3.44-3.54 (m, 1 H), 1.43 (d, J = 6.87 Hz, 3 H) |

| Compd # | Structure | MS m/z | ¹H NMR (500 MHz, DMSO-d$_6$) δ ppm |
|---|---|---|---|
| 7 | 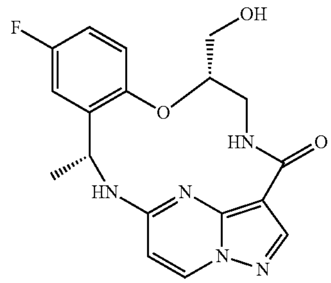 [SMILES: C[C@H]1Nc2ccn3ncc(c3n2)C(=O)NC[C@@H](CO)Oc2ccc(F)cc21] | 372.2 | 9.27 (dd, J = 6.87, 1.72 Hz, 1 H), 8.74 (d, J = 5.16 Hz, 1 H), 8.59 (d, J = 7.45 Hz, 1 H), 8.02 (s, 1 H), 7.29 (dd, J = 9.16, 4.58 Hz, 1 H), 7.05 (dd, J = 9.45, 3.15 Hz, 1 H), 6.85-6.94 (m, 1 H), 6.40 (d, J = 7.45 Hz, 1 H), 5.36-5.48 (m, 1 H), 5.19 (t, J = 5.44 Hz, 1 H), 4.56 (dq, J = 9.88, 5.11 Hz, 1 H), 3.90 (dt, J = 11.74, 5.01 Hz, 1 H), 3.71-3.79 (m, 2 H), 3.59-3.70 (m, 1 H), 1.43 (d, J = 6.87 Hz, 3 H) |
| 8 | 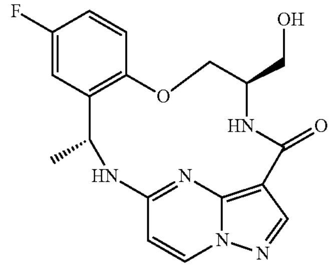 [SMILES: C[C@H]1Nc2ccn3ncc(c3n2)C(=O)N[C@H](CO)COc2ccc(F)cc21] | 372.2 | 9.93 (d, J = 8.59 Hz, 1 H), 8.80 (d, J = 6.87 Hz, 1 H), 8.58 (d, J = 7.45 Hz, 1 H), 8.05 (s, 1 H), 7.16 (dt, J = 9.17, 1.72 Hz, 1 H), 7.02 (dd, J = 6.01, 1.43 Hz, 2 H), 6.34 (d, J = 7.45 Hz, 1 H), 5.59-5.71 (m, 1 H), 5.11 (dd, J = 6.59, 4.87 Hz, 1 H), 4.66 (d, J = 9.17 Hz, 1H), 4.01-4.13 (m, 1 H), 3.86 (dd, J = 9.74, 3.44 Hz, 1 H), 3.55-3.64 (m, 1 H), 3.50-3.55 (m, 1 H), 1.45 (d, J = 7.45 Hz, 3 H) |
| 9 | 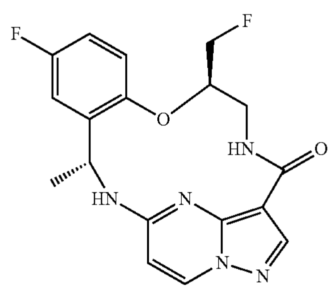 [SMILES: C[C@H]1Nc2ccn3ncc(c3n2)C(=O)NC[C@H](CF)Oc2ccc(F)cc21] | 374.2 | 9.70 (dd, J = 7.16, 3.15 Hz, 1 H), 8.84 (d, J = 6.30 Hz, 1 H), 8.59 (d, J = 8.02 Hz, 1 H), 8.04 (s, 1 H), 7.08-7.18 (m, 2 H), 6.92-7.02 (m, 1 H), 6.38 (d, J = 7.45 Hz, 1 H), 5.51 (quind, J = 6.80, 6.80, 6.80, 6.80, 1.43 Hz, 1 H), 4.66-4.91 (m, 3 H), 3.92 (ddd, J = 14.03, 7.16, 4.01 Hz, 1 H), 3.33-3.38 (m, 1 H), 1.45 (d, J = 7.45 Hz, 3 H) |
| 10 | 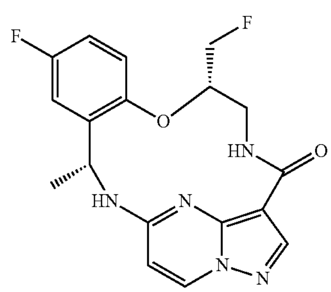 [SMILES: C[C@H]1Nc2ccn3ncc(c3n2)C(=O)NC[C@@H](CF)Oc2ccc(F)cc21] | 374.2 | 9.22-9.32 (m, 1 H), 8.78 (d, J = 5.16 Hz, 1 H), 8.60 (d, J = 7.45 Hz, 1 H), 8.04 (s, 1 H), 7.16-7.25 (m, 1 H), 7.07 (dd, J = 9.16, 3.44 Hz, 1 H), 6.86-6.96 (m, 1 H), 6.42 (d, J = 7.45 Hz, 1 H), 5.33-5.45 (m, 1 H), 4.71-5.07 (m, 3 H), 3.78-3.90 (m, 1 H), 3.68 (ddd, J = 14.03, 10.60, 1.72 Hz, 1 H), 1.44 (d, J = 6.87 Hz, 3 H) |
| 11 | 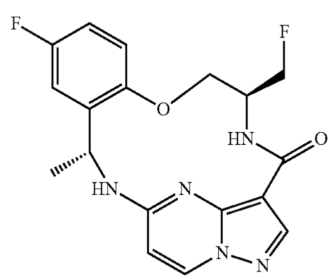 [SMILES: C[C@H]1Nc2ccn3ncc(c3n2)C(=O)N[C@H](CF)COc2ccc(F)cc21] | 374.2 | 10.04 (d, J = 8.59 Hz, 1 H), 8.83 (d, J = 7.45 Hz, 1 H), 8.59 (d, J = 8.02 Hz, 1 H), 8.07 (s, 1 H), 7.17 (dd, J = 9.17, 2.86 Hz, 1 H), 6.96-7.06 (m, 2 H), 6.35 (d, J = 8.02 Hz, 1 H), 5.60-5.72 (m, 1 H), 4.48-4.74 (m, 3 H), 4.37-4.47 (m, 1 H), 3.98 (dt, J = 10.31, 3.44 Hz, 1 H), 1.46 (d, J = 6.87 Hz, 3 H) |

| Compd # | Structure | MS m/z | ¹H NMR (500 MHz, DMSO-d₆) δ ppm |
|---|---|---|---|
| 12 | 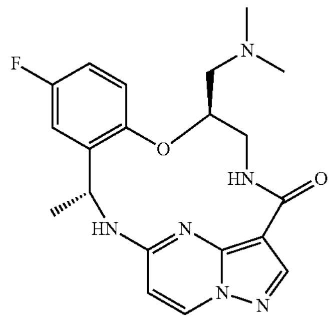 [SMILES: C[C@H]1Nc2ccn3ncc(c3n2)C(=O)NC[C@H](CN(C)C)Oc2ccc(F)cc21] | 399.2 | 9.64 (dd, J = 6.59, 3.72 Hz, 1 H), 8.83 (d, J = 6.30 Hz, 1 H), 8.55-8.62 (m, 1 H), 8.02 (s, 1 H), 7.08-7.17 (m, 2H), 6.93-7.02 (m, 1 H), 6.38 (d, J = 8.02 Hz, 1 H), 5.44-5.55 (m, 1 H), 4.57-4.66 (m, 1 H), 3.87 (ddd, J = 13.60, 6.73, 4.30 Hz, 1 H), 3.35 (dd, J = 7.16, 3.72 Hz, 1 H), 2.59-2.71 (m, 2 H), 2.27 (s, 6 H), 1.43 (d, J = 6.87 Hz, 3 H) |
| 13 | 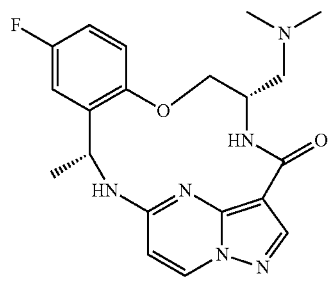 [SMILES: C[C@H]1Nc2ccn3ncc(c3n2)C(=O)N[C@@H](CN(C)C)COc2ccc(F)cc21] | 399.2 | 10.31 (br dd, J = 4.87, 2.58 Hz, 1 H), 9.96 (s, 1 H), 8.95 (d, J = 7.45 Hz, 1 H), 8.60 (d, J = 8.02 Hz, 1 H), 8.12 (s, 1 H), 7.16-7.25 (m, 1 H), 7.03-7.11 (m, 1 H), 6.98 (dd, J = 9.17, 4.01 Hz, 1 H), 6.38 (d, J = 7.45 Hz, 1 H), 5.61-5.72 (m, 1 H), 4.49 (td, J = 10.17, 2.58 Hz, 1 H), 4.42 (dd, J = 9.45, 3.72 Hz, 1 H), 3.88 (t, J = 10.02 Hz, 1 H), 3.59 (br s, 1 H), 3.59-3.59 (m, 1 H), 3.25 (br dd, J = 12.89, 8.88 Hz, 1 H), 2.94 (d, J = 4.58 Hz, 3 H), 2.93 (d, J = 5.16 Hz, 3 H), 1.42 (d, J = 6.87 Hz, 3 H) |
| 14 | 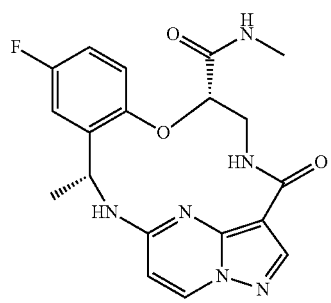 [SMILES: CNC(=O)[C@@H]1CNC(=O)c2cnn3ccc(nc23)N[C@H](C)c2cc(F)ccc2O1] | 399.2 | 9.18 (br d, J = 7.14 Hz, 1 H), 8.77 (d, J = 4.94 Hz, 1 H), 8.59 (d, J = 7.68 Hz, 1 H), 8.14 (q, J = 4.40 Hz, 1 H), 8.02 (s, 1 H), 7.08 (dd, J = 9.33, 3.29 Hz, 1 H), 6.92 (td, J = 8.51, 3.29 Hz, 1 H), 6.74 (dd, J = 8.78, 4.39 Hz, 1 H), 6.43 (d, J = 7.68 Hz, 1 H), 5.42 (dt, J = 6.60 Hz, 1 H), 5.12 (dd, J = 10.43, 4.94 Hz, 1 H), 4.01 (ddd, J = 14.00, 7.96, 5.49 Hz, 1 H), 3.62-3.69 (m, 1 H), 2.62 (d, J = 4.39 Hz, 3 H), 1.52 (d, J = 7.14 Hz, 3 H) |
| 15 | 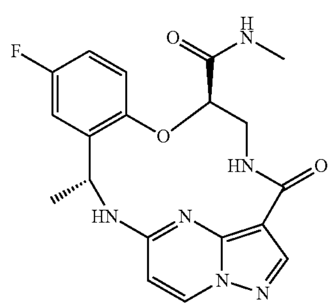 [SMILES: CNC(=O)[C@H]1CNC(=O)c2cnn3ccc(nc23)N[C@H](C)c2cc(F)ccc2O1] | 399.2 | 9.84 (br d, J = 8.23 Hz, 1 H), 8.84 (d, J = 7.14 Hz, 1 H), 8.58 (d, J = 7.68 Hz, 1 H), 8.21 (dt, J = 4.40 Hz, 1 H), 8.05 (s, 1 H) 7.18 (dd, J = 9.33, 3.29 Hz, 1 H), 6.96-7.03 (m, 1 H), 6.72 (dd, J = 9.33, 4.39 Hz, 1 H), 6.37 (d, J = 7.68 Hz, 1 H), 5.59-5.69 (m, 1 H), 4.53 (dd, J = 9.88, 3.84 Hz, 1 H), 4.18 (ddd, J = 13.31, 9.19, 3.84 Hz, 1 H), 3.25-3.29 (m, 1 H), 2.70 (d, J = 4.39 Hz, 3 H), 1.53 (d, J = 7.14 Hz, 3 H) |
| 16 | 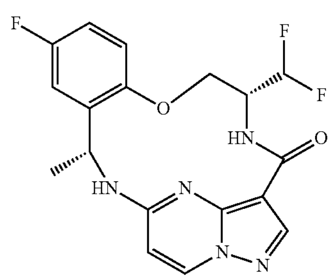 [SMILES: C[C@H]1Nc2ccn3ncc(c3n2)C(=O)N[C@@H](C(F)F)COc2ccc(F)cc21] | 392.2 | 9.54 (s, 1 H), 8.82 (d, J = 6.87 Hz, 1 H), 8.60 (d, J = 7.45 Hz, 1 H), 8.08 (s, 1 H), 7.17 (dd, J = 9.45, 3.15 Hz, 1 H), 7.08-7.12 (m, 1 H), 7.02-7.07 (m, 1 H), 6.65-6.96 (m, 1 H), 6.65-6.96 (m, 1 H), 6.39 (d, J = 7.45 Hz, 1 H), 5.61 (quind, J = 7.02, 7.02, 7.02, 7.02, 1.72 Hz, 1 H), 4.58-4.71 (m, 1 H), 4.37-4.51 (m, 2 H), 1.42 (d, J = 6.87 Hz, 3 H) |

| Compd # | Structure | MS m/z | ¹H NMR (500 MHz, DMSO-d₆) δ ppm |
|---|---|---|---|
| 17 | 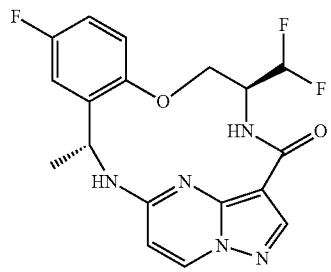 [SMILES: C[C@H]1Nc2ccn3ncc(c3n2)C(=O)N[C@H](C(F)F)COc2ccc(F)cc21] | 392.2 | 10.23 (d, J = 8.59 Hz, 1 H), 8.86 (d, J = 7.45 Hz, 1 H), 8.60 (d, J = 7.45 Hz, 1 H), 8.10 (s, 1 H), 7.18 (dd, J = 9.45, 3.15 Hz, 1 H), 7.00-7.09 (m, 1 H), 6.91-7.00 (m, 1 H), 6.36 (d, J = 7.45 Hz, 1 H), 6.21-6.48 (m, 1 H), 5.61-5.73 (m, 1 H), 4.67 (d, J = 10.31 Hz, 1 H), 4.40-4.56 (m, 1 H), 3.96-4.09 (m, 1 H), 1.45 (d, J = 6.87 Hz, 3 H) |
| 18 | 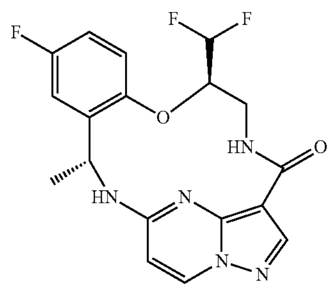 [SMILES: C[C@H]1Nc2ccn3ncc(c3n2)C(=O)NC[C@H](C(F)F)Oc2ccc(F)cc21] | 392.2 | 9.67 (dd, J = 6.30, 3.44 Hz, 1 H), 8.87 (d, J = 6.30 Hz, 1 H), 8.60 (d, J = 7.45 Hz, 1 H), 8.05 (s, 1 H), 7.17 (dd, J = 9.17, 4.58 Hz, 1 H), 7.14 (dd, J = 9.45, 3.15 Hz, 1 H), 7.01 (ddd, J = 9.02, 7.88, 3.15 Hz, 1 H), 6.32-6.61 (m, 2 H), 5.40-5.54 (m, 1 H), 4.94-5.09 (m, 1 H), 3.90-4.00 (m, 1 H), 3.46 (ddd, J = 14.03, 6.87, 3.72 Hz, 1 H), 1.45 (d, J = 7.45 Hz, 3 H) |
| 19 | 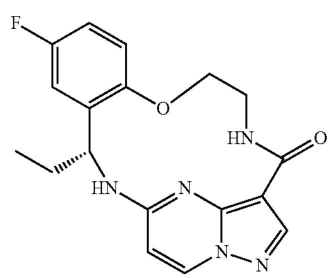 [SMILES: CC[C@H]1Nc2ccn3ncc(c3n2)C(=O)NCCOc2ccc(F)cc21] | 356.2 | 9.74 (dd, J = 7.45, 2.29 Hz, 1 H), 8.75 (d, J = 6.87 Hz, 1 H), 8.53-8.63 (m, 1 H), 8.04 (s, 1 H), 7.05-7.17 (m, 1H), 6.96-7.04 (m, 2 H), 6.37 (d, J = 7.45 Hz, 1 H), 5.39 (qd, J = 7.64, 1.72 Hz, 1 H), 4.51 (dt, J = 10.02, 3.58 Hz, 1 H), 3.98 (td, J = 9.74, 3.44 Hz, 1 H), 3.86 (ddt, J = 13.82, 7.52, 3.94, 3.94 Hz, 1 H), 3.35-3.46 (m, 1 H), 1.83-2.03 (m, 1 H), 1.63-1.74 (m, 1 H), 0.87 (t, J = 7.45 Hz, 3 H) |
| 20 | 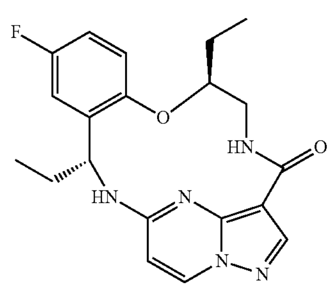 [SMILES: CC[C@H]1CNC(=O)c2cnn3ccc(nc23)N[C@H](CC)c2cc(F)ccc2O1] | 384.2 | 9.64 (dd, J = 6.59, 3.72 Hz, 1 H), 8.78 (d, J = 6.30 Hz, 1 H), 8.53-8.61 (m, 1 H), 8.02 (s, 1 H), 6.99-7.09 (m, 2 H), 6.90-6.98 (m, 1 H), 6.38 (d, J = 7.45 Hz, 1 H), 5.23-5.33 (m, 1 H), 4.43-4.53 (m, 1 H), 3.84 (ddd, J = 13.60, 6.44, 4.58 Hz, 1 H), 3.23 (ddd, J = 13.60, 6.73, 3.72 Hz, 1 H), 1.91-1.98 (m, 1 H), 1.85-1.91 (m, 1 H), 1.75-1.83 (m, 1 H), 1.65-1.72 (m, 1 H), 1.02 (t, J = 7.45 Hz, 3 H), 0.86 (t, J = 7.45 Hz, 3 H) |
| 21 | 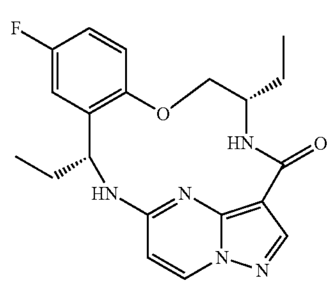 [SMILES: CC[C@H]1COc2ccc(F)cc2[C@@H](CC)Nc2ccn3ncc(c3n2)C(=O)N1] | 384.2 | 9.28 (d, J = 2.29 Hz, 1 H), 8.68 (d, J = 7.45 Hz, 1 H), 8.51-8.60 (m, 1 H), 8.01 (s, 1 H), 7.06-7.16 (m, 2 H), 6.98-7.06 (m, 1 H), 6.36 (d, J = 7.45 Hz, 1 H), 5.43 (qd, J = 7.64, 1.72 Hz, 1 H), 4.41 (dd, J = 10.31, 4.01 Hz, 1 H), 4.02 (dd, J = 10.31, 8.59 Hz, 1 H), 3.79-3.92 (m, 1 H), 2.13-2.30 (m, 1 H), 1.80-1.96 (m, 2 H), 1.65 (dt, J = 13.75, 7.45 Hz, 1 H), 0.97 (t, J = 7.45 Hz, 3 H), 0.82 (t, J = 7.45 Hz, 3 H) |

-continued

| Compd # | Structure | MS m/z | $^1$H NMR (500 MHz, DMSO-d$_6$) δ ppm |
|---|---|---|---|
| 22 | 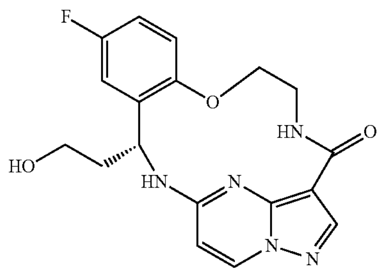 [SMILES: O=C1NCCOc2ccc(F)cc2[C@@H](CCO)Nc2ccn3ncc1c3n2] | 372.2 | 9.75 (dd, J = 7.73, 2.00 Hz, 1 H), 8.72 (d, J = 7.45 Hz, 1 H), 8.57 (d, J = 7.45 Hz, 1 H), 8.05 (s, 1 H), 7.11 (dt, J = 9.17, 1.72 Hz, 1 H), 6.97-7.04 (m, 2 H), 6.37 (d, J = 8.02 Hz, 1 H), 5.61-5.71 (m, 1 H), 4.58 (t, J = 4.87 Hz, 1 H) 4.50 (dt, J = 10.17, 3.79 Hz, 1 H), 3.98 (td, J = 9.74, 4.01 Hz, 1 H), 3.82-3.91 (m, 1 H), 3.35-3.56 (m, 3 H), 2.05 (ddt, J = 13.89, 8.74, 5.58, 5.58 Hz, 1 H), 1.78 (dq, J = 13.68, 6.71 Hz, 1 H) |
| 23 | 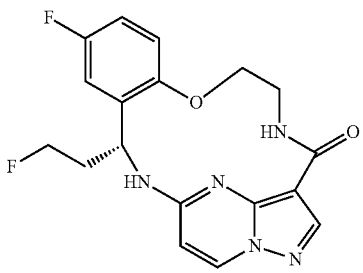 [SMILES: O=C1NCCOc2ccc(F)cc2[C@@H](CCF)Nc2ccn3ncc1c3n2] | 374.2 | 9.71 (dd, J = 7.73, 2.00 Hz, 1 H), 8.82 (d, J = 7.45 Hz, 1 H), 8.60 (d, J = 7.45 Hz, 1 H), 8.06 (s, 1 H), 7.12-7.22 (m, 1 H), 6.97-7.06 (m, 2 H), 6.38 (d, J = 8.02 Hz, 1 H), 5.64-5.77 (m, 1 H), 4.34-4.62 (m, 3 H), 3.97 (td, J = 9.74, 4.01 Hz, 1 H), 3.84-3.91 (m, 1 H), 3.35-3.42 (m, 1 H), 2.22-2.35 (m, 1 H), 1.98-2.12 (m, 1 H) |
| 24 | 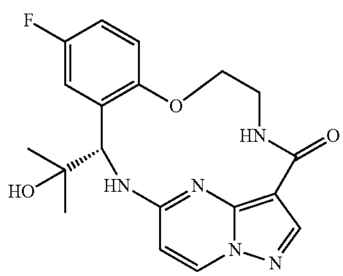 [SMILES: CC(C)(O)[C@H]1Nc2ccn3ncc(c3n2)C(=O)NCCOc2ccc(F)cc21] | 386.2 | 9.70 (dd, J = 7.45, 2.86 Hz, 1 H), 8.75 (d, J = 7.45 Hz, 1 H), 8.53-8.61 (m, 1 H), 8.02 (s, 1 H), 7.17-7.25 (m, 1H), 6.97-7.02 (m, 2 H), 6.67 (d, J = 8.02 Hz, 1 H), 5.42 (dd, J = 7.73, 1.43 Hz, 1 H), 5.01 (s, 1 H), 4.52 (dt, J = 10.31, 4.01 Hz, 1 H), 4.02 (ddd, J = 10.31, 9.17, 4.01 Hz, 1 H), 3.79-3.88 (m, 1 H), 3.35-3.44 (m, 1 H), 1.32 (s, 3 H), 0.97 (s, 3 H) |
| 25 | 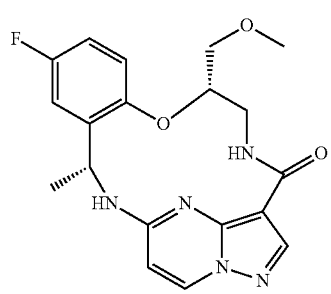 [SMILES: COC[C@@H]1CNC(=O)c2cnn3ccc(nc23)N[C@H](C)c2cc(F)ccc2O1] | 386.2 | 9.28 (dd, J = 6.01, 2.58 Hz, 1 H), 8.75 (d, J = 5.73 Hz, 1 H), 8.59 (d, J = 7.45 Hz, 1 H), 8.03 (s, 1 H), 7.24 (dd, J = 8.88, 4.87 Hz, 1 H), 7.06 (dd, J = 9.17, 3.44 Hz, 1 H), 6.87-6.95 (m, 1 H), 6.40 (d, J = 8.02 Hz, 1 H), 5.37-5.47 (m, 1 H), 4.72 (dq, J = 9.31, 4.92 Hz, 1 H), 3.84 (dd, J = 10.88, 5.16 Hz, 1 H), 3.62-3.77 (m, 3 H) 3.31 (s, 3 H), 1.43 (d, J = 6.87 Hz, 3 H) |
| 26 | 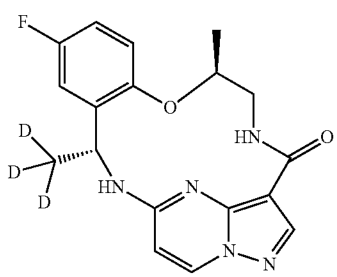 [SMILES: [2H]C([2H])([2H])[C@H]1Nc2ccn3ncc(c3n2)C(=O)NC[C@H](C)Oc2ccc(F)cc21] | 359.2 | 9.41 (dd, J = 6.01, 3.72 Hz, 1 H), 8.69 (d, J = 6.87 Hz, 1 H), 8.58 (d, J = 7.45 Hz, 1 H), 8.06 (s, 1 H), 7.14 (dd, J = 9.45, 3.15 Hz, 1 H), 7.07 (dd, J = 9.17, 4.58 Hz, 1 H), 6.90-7.01 (m, 1 H), 6.35 (d, J = 7.45 Hz, 1 H), 5.68 (br d, J = 6.30 Hz, 1 H), 4.78-4.88 (m, 1 H), 3.79 (dt, J = 13.46, 5.87 Hz, 1 H), 3.55 (dt, J = 13.75, 3.44 Hz, 1 H), 1.19 (br d, J = 5.73 Hz, 3 H) |

-continued

| Compd # | Structure | MS m/z | $^1$H NMR (500 MHz, DMSO-d$_6$) δ ppm |
|---|---|---|---|
| 27 | 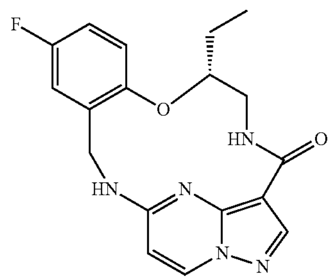 [SMILES: CC[C@@H]1CNC(=O)c2cnn3ccc(nc23)NCc2cc(F)ccc2O1] | 356.2 | 9.76 (dd, J = 6.87, 2.86 Hz, 1 H), 8.94 (t, J = 6.01 Hz, 1 H), 8.58 (d, J = 7.45 Hz, 1 H), 8.04 (s, 1 H), 7.10 (dd, J = 9.16, 2.86 Hz, 1 H), 7.00-7.05 (m, 1 H), 6.95-7.00 (m, 1 H), 6.41 (d, J = 8.02 Hz, 1 H), 5.06 (ddd, J = 14.61, 6.01, 1.15 Hz, 1 H), 4.40-4.46 (m, 1 H), 3.96 (dd, J = 14.32, 5.73 Hz, 1 H), 3.91 (ddd, J = 13.60, 7.30, 4.30 Hz, 1 H), 3.21 (ddd, J = 13.60, 7.59, 2.86 Hz, 1 H), 1.86-1.96 (m, 1 H), 1.73-1.82 (m, 1 H), 1.02 (t, J = 7.45 Hz, 3 H) |
| 28 | 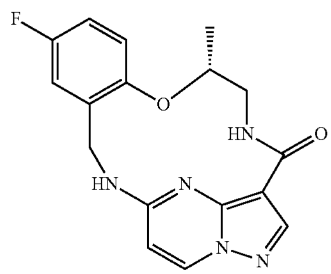 [SMILES: C[C@@H]1CNC(=O)c2cnn3ccc(nc23)NCc2cc(F)ccc2O1] | 342.2 | 9.83-9.92 (m, 1 H), 8.94 (t, J = 6.01 Hz, 1 H), 8.58 (d, J = 7.45 Hz, 1 H), 8.04 (s, 1 H), 7.12 (dd, J = 9.17, 2.86 Hz, 1 H), 6.94-7.06 (m, 2 H), 6.40 (d, J = 7.45 Hz, 1 H), 5.08 (ddd, J = 14.61, 6.59, 1.72 Hz, 1 H), 4.42-4.52 (m, 1 H), 3.85-4.02 (m, 2 H), 3.13 (ddd, J = 13.60, 8.74, 2.29 Hz, 1 H), 1.45 (d, J = 5.73 Hz, 3 H) |
| 29 | 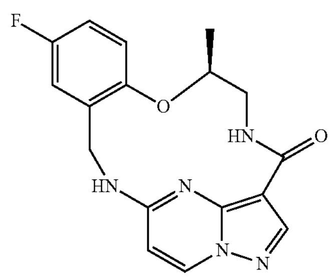 [SMILES: C[C@H]1CNC(=O)c2cnn3ccc(nc23)NCc2cc(F)ccc2O1] | 342.2 | 9.83-9.90 (m, 1 H), 8.94 (t, J = 6.01 Hz, 1 H), 8.55-8.61 (m, 1 H), 8.04 (s, 1 H), 7.12 (dd, J = 9.45, 3.15 Hz, 1 H), 6.94-7.06 (m, 2 H), 6.40 (d, J = 8.02 Hz, 1 H), 5.08 (ddd, J = 14.46, 6.73, 1.72 Hz, 1 H), 4.43-4.51 (m, 1 H), 3.87-4.00 (m, 2 H), 3.13 (ddd, J = 13.46, 8.88, 2.29 Hz, 1 H), 1.45 (d, J = 5.73 Hz, 3 H) |
| 30 | 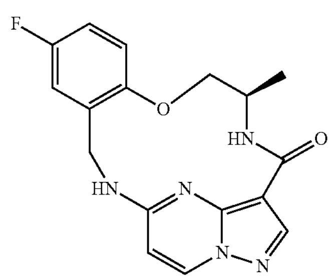 [SMILES: C[C@@H]1COc2ccc(F)cc2CNc2ccn3ncc(c3n2)C(=O)N1] | 342.2 | 10.02 (d, J = 8.59 Hz, 1 H), 8.90 (t, J = 6.30 Hz, 1 H), 8.58 (d, J = 7.45 Hz, 1 H), 8.04 (s, 1 H), 7.15 (dd, J = 9.17, 3.44 Hz, 1 H), 7.00-7.08 (m, 1 H), 6.93-6.99 (m, 1 H), 6.38 (d, J = 8.02 Hz, 1 H), 5.20 (ddd, J = 14.46, 7.30, 1.72 Hz, 1 H), 4.34 (dd, J = 9.16, 1.15 Hz, 1 H), 4.23-4.31 (m, 1 H), 3.98 (dd, J = 14.32, 5.73 Hz, 1 H), 3.88 (dd, J = 9.45, 3.72 Hz, 1 H), 1.37 (d, J = 6.87 Hz, 3 H) |
| 31 | 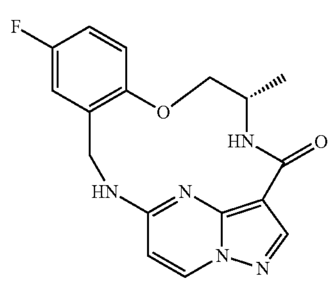 [SMILES: C[C@H]1COc2ccc(F)cc2CNc2ccn3ncc(c3n2)C(=O)N1] | 342.2 | 9.96-10.07 (m, 1 H), 8.84-8.93 (m, 1 H), 8.58 (dd, J = 7.73, 4.87 Hz, 1 H), 8.04 (d, J = 4.58 Hz, 1 H), 7.11-7.21 (m, 1 H), 7.00-7.09 (m, 1 H), 6.91-6.98 (m, 1 H), 6.38 (dd, J = 7.45, 4.58 Hz, 1 H), 5.15-5.25 (m, 1 H), 4.34 (dd, J = 9.45, 3.15 Hz, 1 H), 4.21-4.32 (m, 1 H), 3.93-4.03 (m, 1 H), 3.84-3.91 (m, 1 H), 1.37 (dd, J = 6.30, 4.58 Hz, 3 H) |

| Compd # | Structure | MS m/z | ¹H NMR (500 MHz, DMSO-d$_6$) δ ppm |
|---|---|---|---|
| 32 | 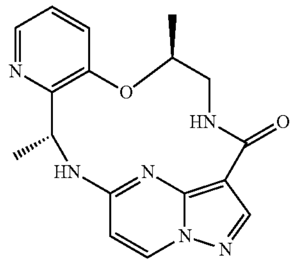 [SMILES: C[C@H]1CNC(=O)c2cnn3ccc(nc23)N[C@H](C)c2ncccc2O1] | 339.2 | 9.85 (br d, J = 7.45 Hz, 1 H), 8.83 (d, J = 6.87 Hz, 1 H), 8.53 (d, J = 7.45 Hz, 1 H), 8.12 (dd, J = 4.58, 1.15 Hz, 1 H), 8.02 (s, 1 H), 7.45 (d, J = 8.59 Hz, 1 H), 7.15-7.25 (m, 1 H), 6.40 (d, J = 8.02 Hz, 1 H), 5.64 (quin, J = 6.87 Hz, 1 H), 4.49 (ddd, J = 9.31, 5.87, 3.72 Hz, 1 H), 3.91-4.01 (m, 1 H), 3.14 (ddd, J = 13.32, 9.02, 1.72 Hz, 1 H), 1.44-1.52 (m, 6H) |
| 33 | 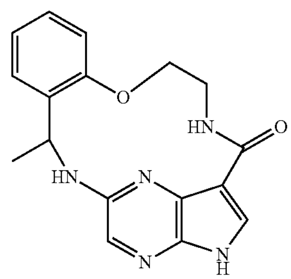 [SMILES: CC1Nc2cnc3[nH]cc(c3n2)C(=O)NCCOc2ccccc21] | 324.2 | 12.02 (br d, J = 2.29 Hz, 1 H), 10.32 (dd, J = 7.16, 2.58 Hz, 1 H), 7.79-7.86 (m, 2 H), 7.70 (s, 1 H), 7.42 (dd, J = 7.45, 1.72 Hz, 1 H), 7.09-7.16 (m, 1 H), 6.95 (d, J = 7.45 Hz, 1 H), 6.88-6.93 (m, 1 H), 5.55 (quin, J = 7.02 Hz, 1 H), 4.50 (dt, J = 10.17, 4.08 Hz, 1 H), 4.05-4.13 (m, 1 H), 3.89 (ddt, J = 13.75, 7.59, 3.94, 3.94 Hz, 1 H), 3.41-3.49 (m, 1 H), 1.43 (d, J = 7.45 Hz, 3 H) |
| 34 | 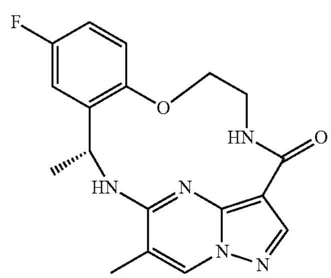 [SMILES: Cc1cn2ncc3c2nc1N[C@H](C)c1cc(F)ccc1OCCNC3=O] | 356.2 | 9.58-9.69 (m, 1 H), 8.58 (d, J = 1.15 Hz, 1 H), 7.97-8.05 (m, 2 H), 7.42 (dt, J = 9.74, 1.72 Hz, 1 H), 6.99 (dd, J = 6.30, 1.72 Hz, 2 H), 5.72-5.82 (m, 1 H), 4.52 (dt, J = 9.88, 3.65 Hz, 1 H), 3.97 (td, J = 9.88, 3.72 Hz, 1 H), 3.83-3.92 (m, 1 H), 3.37-3.44 (m, 1 H), 2.18 (d, J = 1.15 Hz, 3 H), 1.51 (d, J = 6.87 Hz, 3 H) |
| 35 | 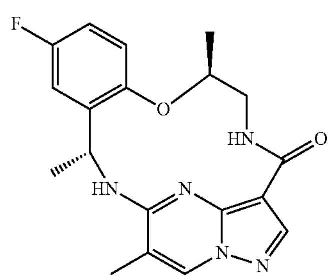 [SMILES: Cc1cn2ncc3c2nc1N[C@H](C)c1cc(F)ccc1O[C@@H](C)CNC3=O] | 370.2 | 9.70-9.77 (m, 1 H), 8.57 (d, J = 1.15 Hz, 1 H), 8.03 (d, J = 7.45 Hz, 1 H), 7.99 (s, 1 H), 7.37 (dd, J = 9.74, 2.86 Hz, 1 H), 6.99-7.04 (m, 1 H), 6.92-6.98 (m, 1 H), 5.63-5.72 (m, 1 H), 4.41-4.50 (m, 1 H), 3.87-3.96 (m, 1 H), 3.13 (ddd, J = 13.46, 8.88, 1.72 Hz, 1 H), 2.20 (d, J = 1.15 Hz, 3 H), 1.50 (d, J = 7.45 Hz, 3 H), 1.46 (d, J = 5.73 Hz, 3 H) |
| 36 | 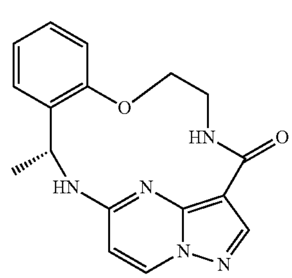 [SMILES: C[C@H]1Nc2ccn3ncc(c3n2)C(=O)NCCOc2ccccc21] | 324.2 | 9.79 (dd, J = 7.45, 2.29 Hz, 1 H), 8.83 (d, J = 6.87 Hz, 1 H), 8.53-8.59 (m, 1 H), 8.03 (s, 1 H), 7.36 (dd, J = 8.02, 1.72 Hz, 1 H), 7.14-7.20 (m, 1 H), 6.91-7.02 (m, 2 H), 6.34 (d, J = 8.02 Hz, 1 H), 5.66 (quin, J = 7.02 Hz, 1 H), 4.49 (dt, J = 10.17, 3.79 Hz, 1 H), 4.03 (td, J = 9.74, 4.01 Hz, 1 H), 3.87 (ddt, J = 13.75, 7.73, 3.58, 3.58 Hz, 1 H), 3.37-3.45 (m, 1 H), 1.45 (d, J = 6.87 Hz, 3 H) |

| Compd # | Structure | MS m/z | ¹H NMR (500 MHz, DMSO-d$_6$) δ ppm |
|---|---|---|---|
| 37 | 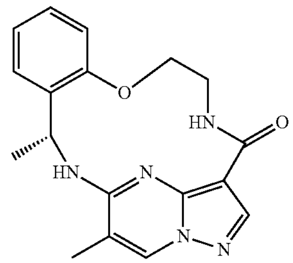 [SMILES: Cc1cn2ncc3c2nc1N[C@H](C)c1ccccc1OCCNC3=O] | 338.2 | 9.70 (dd, J = 7.73, 2.00 Hz, 1 H), 8.55 (d, J = 1.72 Hz, 1 H), 8.06 (d, J = 6.87 Hz, 1 H), 7.99 (s, 1 H), 7.56 (dd, J = 8.02, 1.72 Hz, 1 H), 7.12-7.20 (m, 1 H), 6.90-7.00 (m, 2 H), 5.81 (quin, J = 7.16 Hz, 1 H), 4.50 (dt, J = 10.02, 3.58 Hz, 1 H), 4.01 (td, J = 9.74, 4.01 Hz, 1 H), 3.89 (ddt, J = 13.68, 7.52, 3.72, 3.72 Hz, 1 H), 3.37-3.46 (m, 1 H), 2.18 (d, J = 1.15 Hz, 3 H), 1.51 (d, J = 7.45 Hz, 3 H) |
| 38 | 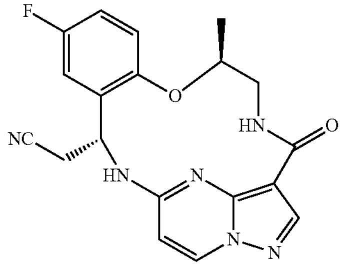 [SMILES: C[C@H]1CNC(=O)c2cnn3ccc(nc23)N[C@H](CC#N)c2cc(F)ccc2O1] | 381.2 | 9.69-9.77 (m, 1 H), 9.10 (d, J = 6.87 Hz, 1 H), 8.66 (d, J = 7.45 Hz, 1 H), 8.09 (s, 1 H), 7.20 (dd, J = 8.88, 2.58 Hz, 1 H), 7.03-7.10 (m, 2 H), 6.44 (d, J = 7.45 Hz, 1 H), 5.75-5.83 (m, 1 H), 4.45-4.54 (m, 1 H), 3.93 (ddd, J = 13.03, 8.74, 4.01 Hz, 1 H), 3.13-3.17 (m, 1 H), 1.46 (d, J = 6.30 Hz, 3 H) |
| 39 | 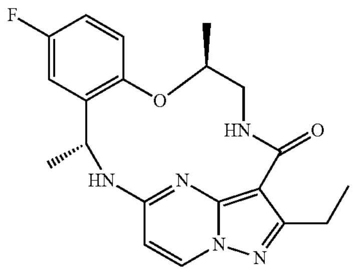 [SMILES: CCc1nn2ccc3nc2c1C(=O)NC[C@H](C)Oc1ccc(F)cc1[C@@H](C)N3] | 384.2 | 9.85 (dd, J = 8.02, 2.29 Hz, 1 H), 8.72 (d, J = 6.30 Hz, 1 H), 8.48 (d, J = 7.45 Hz, 1 H), 7.12 (dd, J = 9.45, 3.15 Hz, 1 H), 6.99-7.05 (m, 1 H), 6.91-6.99 (m, 1 H), 6.28 (d, J = 7.45 Hz, 1 H), 5.47-5.57 (m, 1 H), 4.43-4.52 (m, 1 H), 3.90 (ddd, J = 13.46, 8.31, 3.44 Hz, 1 H), 3.11 (ddd, J = 13.32, 8.45, 2.29 Hz, 1 H), 2.81-2.91 (m, 2 H), 1.45 (d, J = 6.30 Hz, 3 H), 1.43 (d, J = 6.87 Hz, 3 H), 1.17 (t, J = 7.45 Hz, 3 H) |
| 40 | 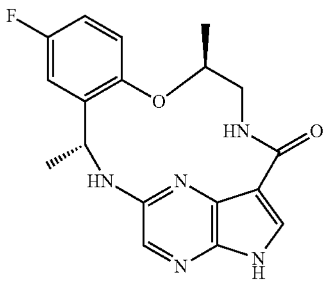 [SMILES: C[C@H]1CNC(=O)c2c[nH]c3ncc(nc23)N[C@H](C)c2cc(F)ccc2O1] | 356.2 | 12.05 (d, J = 2.29 Hz, 1 H), 10.36 (dd, J = 8.02, 2.29 Hz, 1 H), 7.79-7.87 (m, 2 H), 7.71 (s, 1 H), 7.21 (dd, J = 9.74, 2.86 Hz, 1 H), 6.95-7.01 (m, 1 H), 6.86-6.94 (m, 1 H), 5.40-5.49 (m, 1 H), 4.49 (ddd, J = 8.31, 6.01, 4.01 Hz, 1 H), 3.94 (ddd, J = 13.60, 8.16, 4.01 Hz, 1 H), 3.18 (ddd, J = 13.60, 8.45, 2.58 Hz, 1 H), 1.38-1.48 (m, 6 H) |
| 41 | 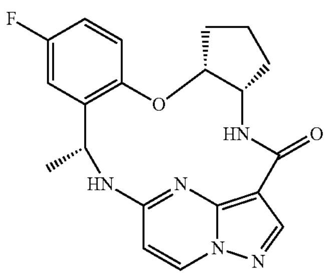 [SMILES: C[C@H]1Nc2ccn3ncc(c3n2)C(=O)N[C@H]2CCC[C@H]2Oc2ccc(F)cc21] | 382.2 | 9.76 (s, 1 H), 9.49 (d, J = 6.30 Hz, 1 H), 8.90 (d, J = 6.87 Hz, 1 H), 8.55-8.62 (m, 2 H), 8.52 (d, J = 7.45 Hz, 1 H), 8.03 (s, 1 H), 8.00 (s, 1 H), 7.20 (dd, J = 9.45, 3.15 Hz, 1 H), 6.91-7.09 (m, 5 H), 6.28-6.36 (m, 2 H), 5.87-5.98 (m, 1 H), 4.96 (td, J = 8.02, 4.58 Hz, 1 H), 4.86 (td, J = 5.87, 2.58 Hz, 1 H), 4.71 (quin, J = 7.16 Hz, 1 H), 4.27-4.35 (m, 1 H), 4.14 (br s, 1 H), 2.96-3.05 (m, 1 H), 2.27-2.40 (m, 1 H), 2.08-2.19 (m, 1 H), 1.98-2.07 (m, 1 H), 1.87-1.97 (m, 3 H), 1.75-1.87 (m, 3 H), 1.58-1.68 (m, 4 H), 1.41 (d, J = 6.87 Hz, 3 H), 1.25-1.33 (m, 1 H) |

| Compd # | Structure | MS m/z | $^1$H NMR (500 MHz, DMSO-d$_6$) δ ppm |
|---|---|---|---|
| 42 | 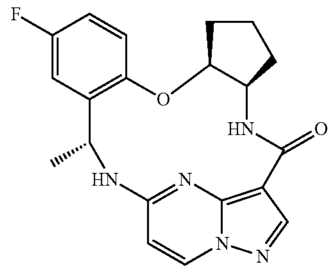 [SMILES: C[C@H]1Nc2ccn3ncc(c3n2)C(=O)N[C@@H]2CCC[C@@H]2Oc2ccc(F)cc21] | 382.2 | 9.60 (d, J = 6.87 Hz, 1 H), 8.76 (d, J = 6.30 Hz, 1 H), 8.52-8.62 (m, 1 H), 8.01 (s, 1 H), 7.10 (dd, J = 9.45, 3.15 Hz, 1 H), 6.99-7.05 (m, 1 H), 6.93-6.99 (m, 1 H), 6.35 (d, J = 7.45 Hz, 1 H), 5.50-5.60 (m, 1 H), 4.85 (td, J = 5.87, 2.58 Hz, 1 H), 4.25 (quin, J = 6.59 Hz, 1 H), 2.15-2.26 (m, 1 H), 1.98-2.07 (m, 1 H), 1.81-1.91 (m, 3 H), 1.59-1.69 (m, 1 H), 1.45 (d, J = 6.87 Hz, 3 H) |
| 43 | 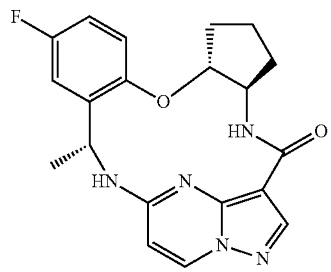 [SMILES: C[C@H]1Nc2ccn3ncc(c3n2)C(=O)N[C@@H]2CCC[C@H]2Oc2ccc(F)cc21] | 382.2 | 8.99 (s, 1 H), 8.78 (d, J = 4.58 Hz, 1 H), 8.55-8.63 (m, 1 H), 7.97 (s, 1 H), 7.14 (dd, J = 8.88, 4.87 Hz, 1 H), 6.95 (dd, J = 9.45, 3.15 Hz, 1 H), 6.86 (td, J = 8.45, 3.15 Hz, 1 H), 6.43 (d, J = 7.45 Hz, 1 H), 5.24-5.35 (m, 1 H), 4.54 (td, J = 10.88, 8.59 Hz, 1 H), 3.99 (td, J = 10.60, 7.45 Hz, 1 H), 2.52-2.61 (m, 1 H), 2.14-2.24 (m, 1 H), 2.03-2.14 (m, 1 H), 1.80-1.93 (m, 1 H), 1.69-1.79 (m, 1 H), 1.47-1.57 (m, 1H), 1.41 (d, J = 6.87 Hz, 3 H) |
| 44 | 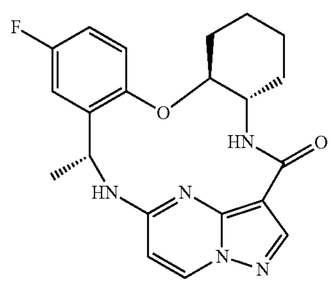 [SMILES: C[C@H]1Nc2ccn3ncc(c3n2)C(=O)N[C@H]2CCCC[C@@H]2Oc2ccc(F)cc21] | 396.2 | 9.29 (s, 1 H), 8.77 (d, J = 7.45 Hz, 1 H), 8.55 (d, J = 8.02 Hz, 1 H), 7.98 (s, 1 H), 7.16 (dd, J = 9.45, 3.15 Hz, 1 H), 6.97-7.05 (m, 2 H), 6.32 (d, J = 8.02 Hz, 1 H), 5.58 (td, J = 7.16, 1.72 Hz, 1 H), 4.01-4.07 (m, 1 H), 3.54-3.60 (m, 1 H), 3.25-3.31 (m, 1 H), 2.21-2.27 (m, 1 H), 1.69-1.78 (m, 2 H), 1.49-1.61 (m, 3 H), 1.42 (d, J = 7.45 Hz, 3 H), 1.35 (td, J = 12.89, 2.29 Hz, 1 H) |
| 45 | 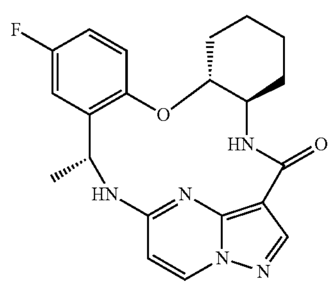 [SMILES: C[C@H]1Nc2ccn3ncc(c3n2)C(=O)N[C@@H]2CCCC[C@H]2Oc2ccc(F)cc21] | 396.2 | 8.73 (s, 1 H), 8.69 (d, J = 4.58 Hz, 1 H), 8.54 (d, J = 7.45 Hz, 1 H), 7.96 (s, 1 H), 7.22 (dd, J = 9.17, 4.58 Hz, 1 H), 6.95 (dd, J = 9.45, 3.15 Hz, 1 H), 6.81 (td, J = 8.59, 2.86 Hz, 1 H), 6.37 (d, J = 8.02 Hz, 1 H), 5.32 (s, 1 H), 4.25-4.32 (m, 1 H), 4.04 (td, J = 10.60, 4.01 Hz, 1 H), 3.17-3.22 (m, 1 H), 2.32-2.40 (m, 1 H), 2.08-2.13 (m, 1 H), 1.82 (br d, J = 12.60 Hz, 1 H), 1.64 (br d, J = 12.03 Hz, 1 H), 1.39-1.52 (m, 5 H), 1.19-1.27 (m, 1 H) |
| 46 | 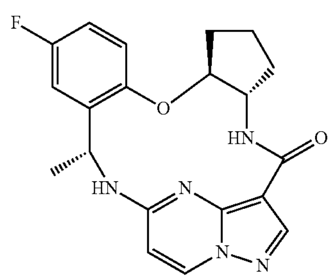 [SMILES: C[C@H]1Nc2ccn3ncc(c3n2)C(=O)N[C@H]2CCC[C@@H]2Oc2ccc(F)cc21] | 382.2 | 9.62 (s, 1 H), 8.82 (d, J = 7.45 Hz, 1 H), 8.58 (d, J = 7.45 Hz, 1 H), 8.00 (s, 1 H), 7.13-7.19 (m, 1 H), 7.00-7.05 (m, 2 H), 6.35 (d, J = 7.45 Hz, 1 H), 5.60-5.68 (m, 1 H), 4.01-4.09 (m, 1 H), 3.62-3.71 (m, 1 H), 2.43-2.49 (m, 1 H), 2.27-2.37 (m, 1 H), 1.79-1.90 (m, 2 H), 1.65-1.79 (m, 2 H), 1.42 (d, J = 6.87 Hz, 3 H) |

| Compd # | Structure | MS m/z | ¹H NMR (500 MHz, DMSO-d$_6$) δ ppm |
|---|---|---|---|
| 47 | 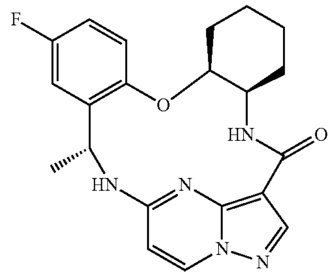 [SMILES: C[C@H]1Nc2ccn3ncc(c3n2)C(=O)N[C@@H]2CCCC[C@@H]2Oc2ccc(F)cc21] | 396.2 | 1.41-1.50 (m, 5 H), 1.50-1.57 (m, 1 H), 1.62-1.67 (m, 1 H), 1.71-1.83 (m, 3 H), 2.19-2.26 (m, 1 H), 3.88-3.97 (m, 1 H), 4.42 (br d, J = 2.86 Hz, 1 H), 5.58 (td, J = 7.16, 1.72 Hz, 1 H), 6.35 (d, J = 8.02 Hz, 1 H), 6.93-6.98 (m, 2 H), 7.14 (dd, J = 9.74, 2.29 Hz, 1 H), 8.03 (s, 1 H), 8.56-8.59 (m, 1 H), 8.85 (d, J = 6.87 Hz, 1 H), 10.05 (d, J = 9.74 Hz, 1 H) |
| 48 | 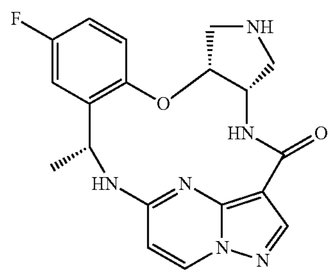 [SMILES: C[C@H]1Nc2ccn3ncc(c3n2)C(=O)N[C@H]2CNC[C@H]2Oc2ccc(F)cc21] | 383.2 | 1.40 (d, J = 7.45 Hz, 3 H), 3.14 (br dd, J = 12.32, 5.44 Hz, 1 H), 3.56 (dd, J = 12.03, 6.87 Hz, 1 H), 3.60-3.69 (m, 1 H), 3.90 (br d, J = 4.01 Hz, 1 H), 4.36-4.46 (m, 1 H), 5.24 (br s, 1 H), 5.86 (br t, J = 6.87 Hz, 1 H), 6.27 (d, J = 7.45 Hz, 1 H), 7.02 (ddd, J = 9.16, 8.02, 3.44 Hz, 1 H), 7.21-7.31 (m, 3 H), 7.60-7.67 (m, 1 H), 7.97 (s, 1 H), 8.50 (d, J = 7.45 Hz, 1 H), 8.54 (d, J = 8.59 Hz, 1 H) |
| 49 | 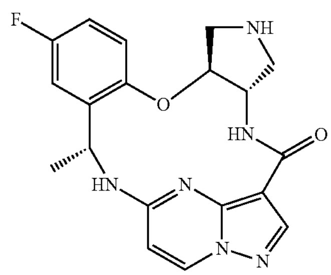 [SMILES: C[C@H]1Nc2ccn3ncc(c3n2)C(=O)N[C@H]2CNC[C@@H]2Oc2ccc(F)cc21] | 383.2 | 1.34 (br d, J = 7.45 Hz, 3 H), 1.41 (br d, J = 5.73 Hz, 1 H), 1.86-2.30 (m, 2 H), 2.63 (br d, J = 9.74 Hz, 1 H), 3.43-3.53 (m, 3 H), 3.62-3.70 (m, 1 H), 3.77-3.83 (m, 1 H), 3.83-3.92 (m, 1 H), 4.74 (br s, 1 H), 4.97-5.07 (m, 1 H), 5.33-5.42 (m, 1 H), 6.05-6.15 (m, 1 H), 6.20 (d, J = 7.45 Hz, 1 H), 6.38-6.44 (m, 1 H), 6.86-6.94 (m, 1 H), 6.99-7.07 (m, 1 H), 7.10 (br d, J = 9.17 Hz, 1 H), 7.14 (dd, J = 9.17, 4.58 Hz, 1 H), 7.20 (dd, J = 9.45, 3.15 Hz, 1 H), 7.90 (s, 1 H), 7.97 (br s, 1 H), 8.20 (br d, J = 8.02 Hz, 1 H), 8.47 (d, J = 7.45 Hz, 1 H), 8.51-8.58 (m, 1 H) |
| 50 | 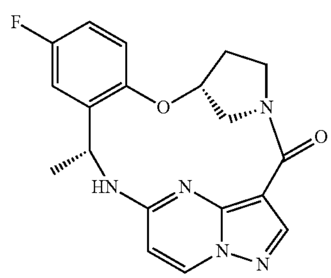 | 368.2 | 1.34 (br d, J = 7.45 Hz, 3 H), 1.82-1.94 (m, 1 H), 2.15 (br dd, J = 12.89, 4.87 Hz, 1 H), 2.95 (br t, J = 9.17 Hz, 1 H), 3.34-3.39 (m, 1 H), 3.60 (br d, J = 11.46 Hz, 1 H), 3.90 (br d, J = 12.60 Hz, 1 H), 5.18 (br s, 1 H), 6.07-6.17 (m, 1 H), 6.20 (d, J = 7.45 Hz, 1 H), 6.96-7.08 (m, 2 H), 7.16-7.25 (m, 1 H), 7.91 (s, 1 H), 8.22 (br d, J = 8.02 Hz, 1 H), 8.47 (br d, J = 7.45 Hz, 1 H) |
| 51 | 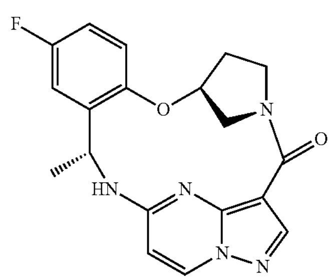 | 368.2 | 1.38 (d, J = 6.87 Hz, 3 H), 2.02-2.12 (m, 1 H), 2.52-2.59 (m, 1 H), 3.05 (dd, J = 12.03, 6.30 Hz, 1 H), 3.07-3.15 (m, 1 H), 3.95 (t, J = 10.31 Hz, 1 H), 4.39 (d, J = 12.03 Hz, 1 H), 5.49 (dt, J = 8.02, 5.44 Hz, 1 H), 5.71-5.79 (m, 2 H), 6.26 (d, J = 8.02 Hz, 1 H), 6.94-7.03 (m, 1 H), 7.22 (dd, J = 9.74, 3.44 Hz, 1 H), 7.27 (dd, J = 9.17, 4.58 Hz, 1 H), 7.97 (s, 1 H), 8.48 (d, J = 7.45 Hz, 1 H), 8.51 (d, J = 8.59 Hz, 1 H) |

| Compd # | Structure | MS m/z | ¹H NMR (500 MHz, DMSO-d$_6$) δ ppm |
|---|---|---|---|
| 52 | 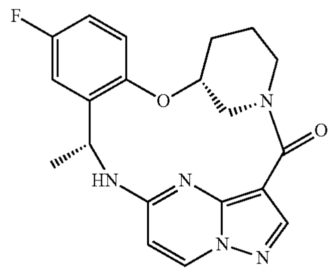 | 382.2 | 1.43 (d, J = 6.87 Hz, 3 H), 1.67-1.83 (m, 2 H), 2.32 (br d, J = 10.88 Hz, 1 H), 2.46-2.49 (m, 1 H), 2.78-2.87 (m, 1 H), 4.09-4.18 (m, 1 H), 4.49-4.58 (m, 1 H), 4.94-5.04 (m, 1 H), 5.29-5.38 (m, 1 H), 6.40 (d, J = 8.02 Hz, 1 H), 6.81-6.90 (m, 1 H), 6.94 (dd, J = 9.17, 5.16 Hz, 1 H), 7.06 (dd, J = 9.74, 2.86 Hz, 1 H), 8.03 (s, 1 H), 8.46 (d, J = 6.87 Hz, 1 H), 8.51 (d, J = 7.45 Hz, 1 H) |
| 53 | 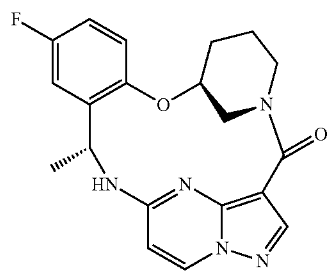 | 382.2 | 1.42 (d, J = 7.45 Hz, 3 H), 1.55-1.66 (m, 1 H), 1.82 (dtt, J = 13.25, 8.77, 8.77, 4.08, 4.08 Hz, 1 H), 1.92-2.03 (m, 1 H), 2.03-2.13 (m, 1 H), 3.26-3.31 (m, 1 H), 3.65 (ddd, J = 12.89, 6.59, 4.01 Hz, 1 H), 3.74 (dd, J = 13.46, 4.87 Hz, 1 H), 4.20 (dd, J = 13.46, 3.15 Hz, 1 H), 4.23-4.31 (m, 1 H), 5.94-6.04 (m, 1 H), 6.23 (d, J = 7.45 Hz, 1 H), 6.94-7.02 (m, 1 H), 7.07 (dd, J = 9.17, 4.58 Hz, 1 H), 7.19 (dd, J = 9.74, 3.44 Hz, 1 H), 8.04 (s, 1 H), 8.29 (d, J = 8.59 Hz, 1 H), 8.46 (d, J = 7.45 Hz, 1 H) |
| 54 | 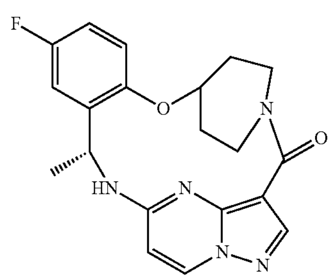 [SMILES: C[C@H]1Nc2ccn3ncc(c3n2)C(=O)N2CCC(CC2)Oc2ccc(F)cc21] | 382.2 | 1.35 (d, J = 6.87 Hz, 3 H), 1.78-1.89 (m, 1 H), 2.01 (td, J = 13.60, 7.16 Hz, 1 H), 2.15 (br d, J = 15.47 Hz, 1 H), 2.33-2.45 (m, 1 H), 2.84 (dd, J = 10.60, 4.87 Hz, 1 H), 3.02 (td, J = 13.17, 5.16 Hz, 1 H), 4.13 (ddd, J = 12.60, 11.17, 4.87 Hz, 1 H), 4.21 (dd, J = 13.17, 6.87 Hz, 1 H), 5.05 (br d, J = 9.17 Hz, 1 H), 6.12-6.19 (m, 1 H), 6.20 (d, J = 8.02 Hz, 1 H), 6.95-7.03 (m, 2 H), 7.24 (dd, J = 9.16, 2.29 Hz, 1 H), 7.89 (s, 1 H), 8.39 (d, J = 9.17 Hz, 1 H), 8.47 (d, J = 7.45 Hz, 1 H) |
| 55 | 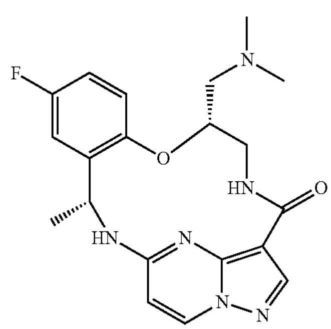 [SMILES: C[C@H]1Nc2ccn3ncc(c3n2)C(=O)NC[C@@H](CN(C)C)Oc2ccc(F)cc21] | 399.2 | 1.43 (d, J = 6.87 Hz, 3 H), 2.23 (s, 6 H), 2.65-2.84 (m, 2 H), 3.66-3.77 (m, 2 H), 4.64-4.71 (m, 1 H), 5.42-5.51 (m, 1 H), 6.39 (d, J = 7.45 Hz, 1 H), 6.91 (td, J = 8.45, 3.15 Hz, 1 H), 7.05-7.12 (m, 2 H), 8.04 (s, 1 H), 8.59 (d, J = 7.45 Hz, 1 H), 8.74 (d, J = 5.73 Hz, 1 H), 9.32 (br t, J = 4.01 Hz, 1 H) |
| 56 | 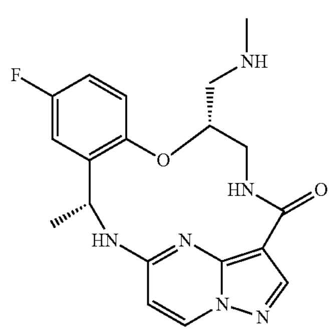 [SMILES: CNC[C@@H]1CNC(=O)c2cnn3ccc(nc23)N[C@H](C)c2cc(F)ccc2O1] | 385.2 | 1.43-1.48 (m, 3 H), 2.87-2.98 (m, 4 H), 3.56-3.66 (m, 1 H), 3.88-4.12 (m, 2 H), 5.03 (br s, 1 H), 5.24-5.35 (m, 1 H), 6.41-6.50 (m, 1 H), 6.94 (td, J = 8.31, 3.44 Hz, 1 H), 7.04-7.13 (m, 1 H), 7.17-7.25 (m, 1 H), 8.04 (s, 1 H), 8.59-8.65 (m, 1 H), 8.86 (d, J = 5.16 Hz, 1 H), 9.23 (d, J = 8.59 Hz, 1 H), 9.75 (br s, 1 H) |

-continued

| Compd # | Structure | MS m/z | ¹H NMR (500 MHz, DMSO-d₆) δ ppm |
|---|---|---|---|
| 57 | 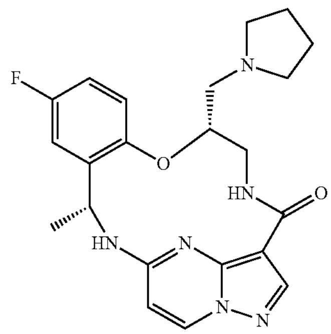 [SMILES: C[C@H]1Nc2ccn3ncc(c3n2)C(=O)NC[C@@H](CN2CCCC2)Oc2ccc(F)cc21] | 425.2 | 1.23 (s, 4 H), 1.43 (d, J = 6.87 Hz, 3 H), 1.69 (br s, 4 H), 2.79-3.07 (m, 2 H), 3.60-3.83 (m, 2 H), 4.69 (br s, 1 H), 5.37-5.50 (m, 1 H), 6.40 (d, J = 8.02 Hz, 1 H), 6.90 (td, J = 8.59, 3.44 Hz, 1 H), 7.06 (dd, J = 9.16, 3.44 Hz, 1 H), 7.12 (dd, J = 9.17, 4.58 Hz, 1 H), 8.03 (s, 1 H), 8.59 (d, J = 8.02 Hz, 1 H), 8.74 (d, J = 5.16 Hz, 1 H), 9.31 (br d, J = 5.16 Hz, 1 H) |
| 58 | 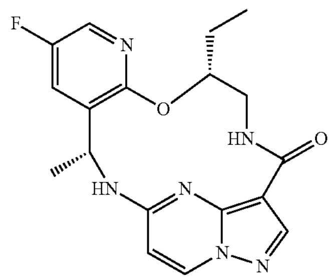 [SMILES: CC[C@@H]1CNC(=O)c2cnn3ccc(nc23)N[C@H](C)c2cc(F)cnc2O1] | 371.2 | 0.99 (t, J = 7.45 Hz, 3 H), 1.48 (d, J = 6.87 Hz, 3 H), 1.87-2.00 (m, 1 H), 2.42-2.49 (m, 1 H), 3.65-3.80 (m, 2 H), 4.45-4.54 (m, 1 H), 5.13-5.24 (m, 1 H), 6.42 (d, J = 7.45 Hz, 1 H), 7.59 (dd, J = 8.59, 2.86 Hz, 1 H), 7.92 (d, J = 2.86 Hz, 1 H), 8.03 (s, 1 H), 8.60 (d, J = 7.45 Hz, 1 H), 8.75 (d, J = 4.58 Hz, 1 H), 9.07 (br d, J = 6.30 Hz, 1 H) |
| 59 | 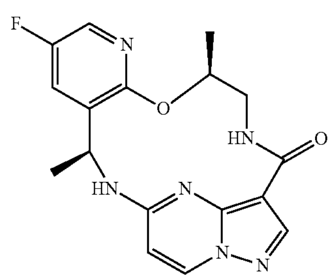 [SMILES: C[C@@H]1Nc2ccn3ncc(c3n2)C(=O)NC[C@H](C)Oc2ncc(F)cc21] | 371.2 | 9.11 (dd, J = 6.59, 2.58 Hz, 1 H), 8.73 (d, J = 5.16 Hz, 1 H), 8.60 (d, J = 8.02 Hz, 1 H), 8.04 (s, 1 H), 7.95-7.98 (m, 1 H), 7.62 (dd, J = 8.88, 3.15 Hz, 1 H), 6.41 (d, J = 8.02 Hz, 1 H), 5.22-5.29 (m, 1 H), 4.73-4.84 (m, 1 H), 3.74-3.79 (m, 2 H), 3.67 (ddd, J = 13.17, 6.87, 4.58 Hz, 2 H), 1.63 (d, J = 6.30 Hz, 3 H), 1.48 (d, J = 6.87 Hz, 3 H) |
| 60 | 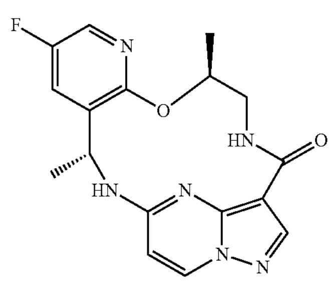 [SMILES: C[C@H]1CNC(=O)c2cnn3ccc(nc23)N[C@H](C)c2cc(F)cnc2O1] | 371.2 | 9.67 (d, J = 8.02 Hz, 1 H), 8.81 (d, J = 6.87 Hz, 1 H), 8.59 (d, J = 7.45 Hz, 1 H), 8.05 (s, 1 H), 8.02 (d, J = 2.86 Hz, 1 H), 7.68 (dd, J = 8.59, 2.86 Hz, 1 H), 6.37 (d, J = 7.45 Hz, 1 H), 5.34-5.42 (m, 1 H), 5.02-5.12 (m, 1 H), 3.97 (ddd, J = 13.32, 9.02, 4.01 Hz, 1 H), 3.13 (td, J = 11.74, 1.15 Hz, 1 H), 1.50 (d, J = 7.45 Hz, 3 H), 1.46 (d, J = 6.30 Hz, 3 H) |
| 61 | 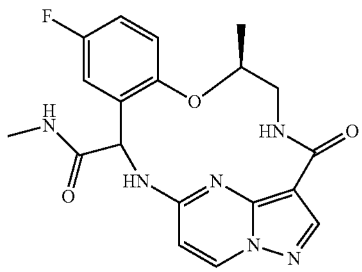 [SMILES: CNC(=O)C1Nc2ccn3ncc(c3n2)C(=O)NC[C@H](C)Oc2ccc(F)cc21] | 399.2 | 9.33-9.81 (m, 1 H), 8.98-9.17 (m, 1 H), 8.60-8.66 (m, 1 H), 8.03-8.18 (m, 2 H), 7.18-7.28 (m, 1 H), 7.01-7.12 (m, 2 H), 6.59-6.66 (m, 1 H), 6.28-6.34 (m, 1 H), 6.07 (dd, J = 7.16, 1.43 Hz, 1 H), 4.88 (dt, J = 5.87, 3.94 Hz, 1 H), 4.43-4.51 (m, 1 H), 3.83-3.98 (m, 1 H), 3.51-3.57 (m, 1 H), 3.13-3.20 (m, 1 H), 2.61 (dd, J = 11.46, 4.58 Hz, 3 H), 1.49 (d, J = 6.30 Hz, 2 H), 1.08 (d, J = 6.30 Hz, 1 H) |

| Compd # | Structure | MS m/z | $^1$H NMR (500 MHz, DMSO-$d_6$) δ ppm |
|---|---|---|---|
| 62 | 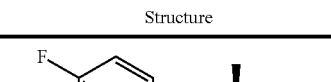 | 413.2 | 9.35-9.81 (m, 1 H), 8.92-9.03 (m, 1 H), 8.59-8.65 (m, 1 H), 8.04-8.12 (m, 1 H), 7.05-7.15 (m, 3 H), 6.70-6.79 (m, 1 H), 6.35-6.69 (m, 1 H), 4.53-4.99 (m, 1 H), 3.91-4.01 (m, 1 H), 3.45-3.50 (m, 1 H), 3.44-3.49 (m, 1 H), 3.11-3.19 (m, 1 H), 2.93-3.09 (m, 3 H), 2.83-2.88 (m, 3 H), 1.45 (d, J = 5.73 Hz, 2 H), 1.00 (d, J = 6.30 Hz, 1 H) |

Biologic Assays

Creation of CD74-ROS1 and EML4-ALK Ba/F3 Stable Cell Lines and Cell Proliferation Assays.

The CD74-ROS1 wild-type gene and EML4-ALK wild-type gene (variant 1) were synthesized at GenScript and cloned into pCDH-CMV-MCS-EF1-Puro plasmid (System Biosciences, Inc). Ba/F3-CD74-ROS1 and Ba/F3-EML4-ALK wild type cell lines were generated by infecting Ba/F3 cells with lentivirus containing CD74-ROS1 wide-type and EML4-ALK wild type. Stable cell lines were selected by puromycin treatment, followed by IL-3 withdrawal. 3000 cells were seeded in 384 well white plate overnight before compound treatment. Cell proliferation was measured using CellTiter-Glo luciferase-based ATP detection assay (Promega) following the manufactures's protocol after 72 hours of various concentration of compound incubation. $IC_{50}$ determinations were performed using GraphPad Prism software (GraphPad, Inc., San Diego, Calif.).

Cell Proliferation Assays.

Colorectal cell lines KM 12 (harboring endogenous TPM3-TRKA fusion gene) cells were cultured in DMEM medium, supplemented with 10% fetal bovine serum and 100 U/mL of penicillin/streptomycin. 5000 cells were seeded in 384 well white plate for 24 hours before compounds treatment. Cell proliferation was measured using CellTiter-Glo luciferase-based ATP detection assay (Promega) following the manufactures's protocol after 72 hours incubation. $IC_{50}$ determinations were performed using GraphPad Prism software (GraphPad, Inc., San Diego, Calif.). Alternatively, essential thrombocythemia cell line SET-2 cells (harboring endogenous JAK2 V618F point mutation) or T cell lymphoma Karpas-299 cell line (harboring endogenous NPM-ALK fusion gene) were cultured in RPMI medium, supplemented with 10% fetal bovine serum and 100 U/mL of penicillin/streptomycin. 5000 cells were seeded in 384 well white plate for 24 hours before compounds treatment. Cell proliferation was measured using CellTiter-Glo luciferase-based ATP detection assay (Promega) following the manufactures's protocol after 72 hours incubation. $IC_{50}$ determinations were performed using GraphPad Prism software (GraphPad, Inc., San Diego, Calif.).

| | Cell Proliferation $IC_{50}$ (μM) | | | | |
|---|---|---|---|---|---|
| Compound | CD74-ROS1 Ba/F3 | EML4-ALK Ba/F3 | Karpas 299 | KM12 | SET2 |
| 1 | 0.0002 | 0.0134 | 0.0167 | 0.0002 | 0.0676 |
| 2 | 0.0007 | 0.681 | 0.354 | 0.006 | 0.956 |
| 3 | 0.0002 | 0.138 | 0.083 | 0.0003 | 0.263 |
| 4 | 0.0002 | 0.892 | 1.368 | 0.0003 | 1.371 |
| 5 | 0.0279 | 2.032 | 0.794 | 0.0165 | 0.852 |
| 6 | 0.0028 | 0.1165 | 0.065 | 0.0005 | 0.164 |
| 7 | 0.0226 | 0.715 | 0.438 | 0.0168 | 0.190 |
| 8 | 0.0347 | 2.129 | 1.502 | 0.017 | 0.406 |
| 9 | 0.0002 | 0.0002 | 0.073 | 0.0004 | 0.093 |
| 10 | 0.0002 | 0.0963 | 0.080 | 0.0014 | 0.057 |
| 11 | 0.0189 | 2.429 | 0.59 | 0.002 | 0.187 |
| 12 | 0.130 | 5.095 | 2.27 | 0.042 | 1.96 |
| 13 | 0.112 | 1.482 | 3.215 | 0.069 | 4.033 |
| 14 | 0.300 | >10 | >10 | 0.180 | 3.777 |
| 15 | 1.00 | >10 | >10 | 0.160 | 4.789 |
| 16 | 0.112 | 1.908 | 0.470 | 0.0004 | 0.665 |
| 17 | 0.003 | 2.687 | 0.297 | 0.0002 | 0.005 |
| 18 | 0.0002 | 0.0284 | 0.0247 | 0.0002 | 0.0986 |
| 19 | 0.0005 | 0.406 | 0.193 | 0.0006 | 0.294 |
| 20 | 0.0002 | 0.151 | 0.144 | 0.003 | 0.404 |
| 21 | 0.0452 | 6.786 | 8.033 | 0.003 | 1.131 |
| 22 | 1.00 | >10 | 0.352 | 0.022 | 0.854 |
| 23 | 0.0051 | 0.459 | N/A | 0.0013 | 0.236 |
| 24 | 0.008 | 0.475 | 0.264 | 0.005 | 1.325 |
| 25 | NA | 0.0885 | 0.166 | 0.0061 | 0.134 |
| 26 | | | | 0.0002 | 0.162 |
| 27 | | | | 0.053 | 3.0 |
| 28 | | | | 0.229 | 4.5 |
| 29 | | | | 0.0055 | 0.492 |
| 30 | | | | 0.003 | 0.671 |
| 31 | | | | >10 | >10 |
| 32 | | | | 0.192 | 5.8 |
| 33 | | | | 8.0 | >10 |
| 34 | | | | 0.0059 | 0.899 |
| 35 | | | | 0.00027 | 1.07 |
| 36 | | | | 0.0078 | 1.24 |
| 37 | | | | 0.30 | 5.0 |
| 38 | | | | 0.0071 | |
| 39 | | 3.0 | | 0.315 | |
| 40 | | 3.0 | | 0.042 | |
| 41 | | 0.150 | | 0.003 | 0.0785 |
| 42 | | 0.080 | | 0.0002 | 0.030 |
| 43 | | 0.080 | | 0.001 | 0.044 |
| 44 | | 3.00 | | 0.056 | 1.80 |
| 45 | | >10 | | 0.0004 | 0.206 |
| 46 | | 2.00 | | 0.011 | 0.400 |
| 47 | | 0.504 | | 0.006 | 0.127 |
| 48 | | 5.0 | | >10 | >10 |
| 49 | | >10 | | 2.41 | |
| 50 | | 3.0 | | 0.178 | |
| 51 | | >10 | | 0.0518 | |
| 52 | | 1.482 | | 0.0087 | 0.768 |
| 53 | | 3.0 | | 0.0373 | 0.505 |
| 54 | | >10 | | 0.464 | >10 |

-continued

| | Cell Proliferation IC$_{50}$ (μM) | | | |
|---|---|---|---|---|
| Compound | CD74-ROS1 Ba/F3 | EML4-ALK Ba/F3 | Karpas 299 | KM12 | SET2 |
| 55 | | 0.709 | | 0.0235 | 0.300 |
| 56 | | >10 | | 0.527 | |
| 57 | | 0.665 | | 0.070 | 0.132 |
| 58 | | 0.031 | | 0.0002 | 0.174 |
| 59 | | 2.0 | | 0.0055 | 0.402 |
| 60 | | 0.218 | | 0.00035 | 0.0303 |
| 61 | | 8.0 | | 0.0737 | 1.07 |
| 62 | | 3.0 | | 0.112 | 3.569 |

What is claimed is:

1. A method for modulating anaplastic lymphoma kinase activity or tropomysin receptor kinase A activity in a subject, comprising administering to the subject an effective amount of a compound of formula I:

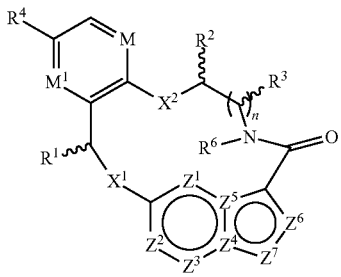

or a pharmaceutically acceptable salt thereof, wherein:
  n is 1 or 2;
  M is CR$^4$ or N;
  M$^1$ is CR$^5$ or N;
  X$^1$ is —NR$^9$—, —O—, —S—, —S(O)—, or —S(O)$_2$-;
  X$^2$ is —NR$^9$—, —O—, —S—, —S(O)—, or —S(O)$_2$-;
  Z$^1$ is C, CR$^{10}$, N, or NH;
  Z$^2$ is C, CR$^{10}$, N, or NH;
  Z$^3$ is C, CR$^{10}$, N, or NH;
  Z$^4$ is C, CR$^{10}$, N, or NH;
  Z$^5$ is C, CR$^{10}$, N, or NH;
  Z$^6$ is C, CR$^{10}$, N, or NH;
  Z$^7$ is C, CR$^{10}$, N, or NH;
  R$^1$ is H, deuterium, C$_1$-C$_6$ alkyl, C$_2$-C$_6$ alkenyl, C$_2$-C$_6$ alkynyl, C(O)NR$^7$R$^8$, C(O)OR$^7$, C$_3$-C$_6$ cycloalkyl, or C$_6$-C$_{10}$ aryl, wherein the C$_1$-C$_6$ alkyl, C$_2$-C$_6$ alkenyl, C$_2$-C$_6$ alkynyl, C$_3$-C$_6$ cycloalkyl, or C$_6$-C$_{10}$ aryl is optionally substituted by one or more substituents independently selected from the group consisting of deuterium, halogen, CN, C(O)NH$_2$, C(O)NHC$_1$-C$_6$ alkyl, C(O)N(C$_1$-C$_6$ alkyl)$_2$, C(O)OH, C(O)OC$_1$-C$_6$ alkyl, NH$_2$, NHC$_1$-C$_6$ alkyl, N(C$_1$-C$_6$ alkyl)$_2$, NHC(O)C$_1$-C$_6$ alkyl, N(C$_1$-C$_6$ alkyl)C(O)C$_1$-C$_6$ alkyl, NHC(O)NH$_2$, NHC(O)NHC$_1$-C$_6$ alkyl, N(C$_1$-C$_6$ alkyl)C(O)NH$_2$, N(C$_1$-C$_6$ alkyl)C(O)NHC$_1$-C$_6$ alkyl, NHC(O)N(C$_1$-C$_6$ alkyl)$_2$, N(C$_1$-C$_6$ alkyl)C(O)N(C$_1$-C$_6$ alkyl)$_2$, NHC(O)OC$_1$-C$_6$ alkyl, N(C$_1$-C$_6$ alkyl)C(O)OC$_1$-C$_6$ alkyl, NHS(O)C$_1$-C$_6$ alkyl, NHS(O)$_2$C$_1$-C$_6$ alkyl, N(C$_1$-C$_6$ alkyl)S(O)C$_1$-C$_6$ alkyl, N(C$_1$-C$_6$ alkyl)S(O)$_2$C$_1$-C$_6$ alkyl, NHS(O)NH$_2$, NHS(O)$_2$NH$_2$, N(C$_1$-C$_6$ alkyl)S(O)NH$_2$, N(C$_1$-C$_6$ alkyl)S(O)$_2$NH$_2$, NHS(O)NHC$_1$-C$_6$ alkyl, NHS(O)$_2$NHC$_1$-C$_6$ alkyl, NHS(O)N(C$_1$-C$_6$ alkyl)$_2$, NHS(O)$_2$N(C$_1$-C$_6$ alkyl)$_2$, N(C$_1$-C$_6$ alkyl)S(O)NHC$_1$-C$_6$ alkyl, N(C$_1$-C$_6$ alkyl)S(O)$_2$NHC$_1$-C$_6$ alkyl, N(C$_1$-C$_6$ alkyl)S(O)N(C$_1$-C$_6$ alkyl)$_2$, N(C$_1$-C$_6$ alkyl)S(O)$_2$N(C$_1$-C$_6$ alkyl)$_2$, OH, OC$_1$-C$_6$ alkyl, P(C$_1$-C$_6$ alkyl)$_2$, P(O)(C$_1$-C$_6$ alkyl)$_2$, SC$_1$-C$_6$ alkyl, S(O)C$_1$-C$_6$ alkyl, S(O)NHC$_1$-C$_6$ alkyl, S(O)N(C$_1$-C$_6$ alkyl)$_2$, S( )$_2$C$_1$-C$_6$ alkyl, S(O)$_2$NHC$_1$-C$_6$ alkyl, S(O)$_2$N(C$_1$-C$_6$ alkyl)$_2$, C$_3$-C$_6$ cycloalkyl, and 3- to 7-membered heterocycloalkyl;
  R$^2$ and R$^6$, taken together with the atoms to which they are attached, form a 5- to 7-membered heterocycloalkyl;
  each R$^3$ is independently H, deuterium, C$_1$-C$_6$ alkyl, C$_2$-C$_6$ alkenyl, C$_2$-C$_6$ alkynyl, C(O)NR$^7$R$^8$, C(O)OR$^7$, C$_3$-C$_6$ cycloalkyl, or C$_6$-C$_{10}$ aryl, wherein each C$_1$-C$_6$ alkyl, C$_2$-C$_6$ alkenyl, C$_2$-C$_6$ alkynyl, C$_3$-C$_6$ cycloalkyl, and C$_6$-C$_{10}$ aryl is optionally and independently substituted by one or more substituents independently selected from the group consisting of deuterium, halogen, CN, C(O)NH$_2$, C(O)NHC$_1$-C$_6$ alkyl, C(O)N(C$_1$-C$_6$ alkyl)$_2$, C(O)OH, C(O)OC$_1$-C$_6$ alkyl, NH$_2$, NHC$_1$-C$_6$ alkyl, N(C$_1$-C$_6$ alkyl)$_2$, NHC(O)C$_1$-C$_6$ alkyl, N(C$_1$-C$_6$ alkyl)C(O)C$_1$-C$_6$ alkyl, NHC(O)NH$_2$, NHC(O)NHC$_1$-C$_6$ alkyl, N(C$_1$-C$_6$ alkyl)C(O)NH$_2$, N(C$_1$-C$_6$ alkyl)C(O)NHC$_1$-C$_6$ alkyl, NHC(O)N(C$_1$-C$_6$ alkyl)$_2$, N(C$_1$-C$_6$ alkyl)C(O)N(C$_1$-C$_6$ alkyl)$_2$, NHC(O)OC$_1$-C$_6$ alkyl, N(C$_1$-C$_6$ alkyl)C(O)OC$_1$-C$_6$ alkyl, NHS(O)C$_1$-C$_6$ alkyl, NHS(O)$_2$C$_1$-C$_6$ alkyl, N(C$_1$-C$_6$ alkyl)S(O)C$_1$-C$_6$ alkyl, N(C$_1$-C$_6$ alkyl)S(O)$_2$C$_1$-C$_6$ alkyl, NHS(O)NH$_2$, NHS(O)$_2$NH$_2$, N(C$_1$-C$_6$ alkyl)S(O)NH$_2$, N(C$_1$-C$_6$ alkyl)S(O)$_2$NH$_2$, NHS(O)NHC$_1$-C$_6$ alkyl, NHS(O)$_2$NHC$_1$-C$_6$ alkyl, NHS(O)N(C$_1$-C$_6$ alkyl)$_2$, NHS(O)$_2$N(C$_1$-C$_6$ alkyl)$_2$, N(C$_1$-C$_6$ alkyl)S(O)NHC$_1$-C$_6$ alkyl, N(C$_1$-C$_6$ alkyl)S(O)$_2$NHC$_1$-C$_6$ alkyl, N(C$_1$-C$_6$ alkyl)S(O)N(C$_1$-C$_6$ alkyl)$_2$, N(C$_1$-C$_6$ alkyl)S(O)$_2$N(C$_1$-C$_6$ alkyl)$_2$, OH, OC$_1$-C$_6$ alkyl, P(C$_1$-C$_6$ alkyl)$_2$, P(O)(C$_1$-C$_6$ alkyl)$_2$, SC$_1$-C$_6$ alkyl, S(O)C$_1$-C$_6$ alkyl, S(O)NHC$_1$-C$_6$ alkyl, S(O)N(C$_1$-C$_6$ alkyl)$_2$, S(O)$_2$C$_1$-C$_6$ alkyl, S(O)$_2$NHC$_1$-C$_6$ alkyl, S(O)$_2$N(C$_1$-C$_6$ alkyl)$_2$, C$_3$-C$_6$ cycloalkyl, and 3- to 7-membered heterocycloalkyl;
  R$^4$ is H, F, Cl, Br, CN, C$_1$-C$_6$ alkyl, CF$_3$, NHC$_1$-C$_6$ alkyl, N(C$_1$-C$_6$ alkyl)$_2$, OH, or OC$_1$-C$_6$ alkyl;
  R$^4$, is H, F, Cl, Br, CN, C$_1$-C$_6$ alkyl, CF$_3$, NHC$_1$-C$_6$ alkyl, N(C$_1$-C$_6$ alkyl)$_2$, OH, or OC$_1$-C$_6$ alkyl;
  R$_5$ is H, F, Cl, Br, CN, C$_1$-C$_6$ alkyl, CF$_3$, NHC$_1$-C$_6$ alkyl, N(C$_1$-C$_6$ alkyl)$_2$, OH, or OC$_1$-C$_6$ alkyl;
  each R$^7$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_1$ aryl, or heteroaryl;
  each R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_1$ aryl, or heteroaryl;
  each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or monocyclic or bicyclic heteroaryl, wherein each C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, and monocyclic or bicyclic heteroaryl is optionally and independently substituted by one or more substituents independently selected from the group consisting of deuterium, halogen, C$_1$-C$_6$ alkyl, C$_1$-C$_6$ haloalkyl, and OR$^7$; and
  each R$^{10}$ is independently H, deuterium, halogen, CN, C$_1$-C$_6$ alkyl, CF$_3$, NH$_2$, NHC$_1$-C$_6$ alkyl, NH(phenyl), NH(heteroaryl), OH, or OC$_1$-C$_6$ alkyl;

with the provisos that:
(1) at least one of $Z^1$, $Z^2$, $Z^3$, $Z^4$, $Z^5$, $Z^6$, and $Z^7$ is N or NH; and
(2) at least one of $R^1$ and $R^3$ is not H.

2. The method of claim 1, wherein the subject has cancer, inflammation, pain, an autoimmune disease, or ta neurological disease.

3. The method of claim 1, wherein $X^2$ is —O—.

4. The method of claim 3, wherein $X^1$ is —$NR^9$-.

5. The method of claim 4, wherein $R^9$ is H.

6. The method of claim 1, wherein:
$Z^1$ is N;
$Z^2$ is CH;
$Z^3$ is CH;
$Z^4$ is N;
$Z^5$ is C;
$Z^6$ is CH; and
$Z^7$ is N.

7. The method of claim 1, wherein each $R^3$ is independently $C_1$-$C_6$ alkyl, wherein each $C_1$-$C_6$ alkyl is optionally and independently substituted.

8. The method of claim 1, wherein each $R^3$ is independently H.

9. The method of claim 8, wherein $R_5$ is H.

10. The method of claim 9, wherein $R^4$ is F.

11. The method of claim 1, wherein the compound has formula Ia:

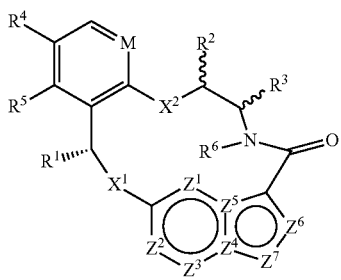

Ia or a pharmaceutically acceptable salt thereof,
wherein:
$R^1$ is $C_1$-$C_6$ alkyl, $C_2$-$C_6$ alkenyl, $C_2$-$C_6$ alkynyl, C(O)$NR^7R^8$, C(O)$OR^7$, $C_3$-$C_6$ cycloalkyl, or $C_6$-$C_{10}$ aryl, wherein the $C_1$-$C_6$ alkyl, $C_2$-$C_6$ alkenyl, $C_2$-$C_6$ alkynyl, $C_3$-$C_6$ cycloalkyl, or $C_6$-$C_{10}$ aryl is optionally substituted.

12. The method of claim 1, wherein the compound has formula II:

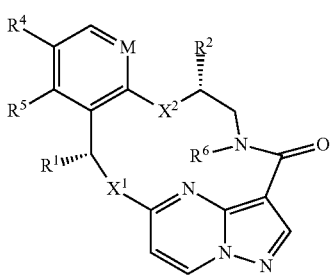

II or a pharmaceutically acceptable salt thereof,
wherein:
M is CH or N; and
$R^1$ is $C_1$-$C_6$ alkyl, $C_2$-$C_6$ alkenyl, $C_2$-$C_6$ alkynyl, C(O)$NR^7R^8$, C(O)$OR^7$, $C_3$-$C_6$ cycloalkyl, or $C_6$-$C_{10}$ aryl, wherein the $C_1$-$C_6$ alkyl, $C_2$-$C_6$ alkenyl, $C_2$-$C_6$ alkynyl, $C_3$-$C_6$ cycloalkyl, or $C_6$-$C_{10}$ aryl is optionally substituted.

13. The method of claim 1, wherein the compound has formula III:

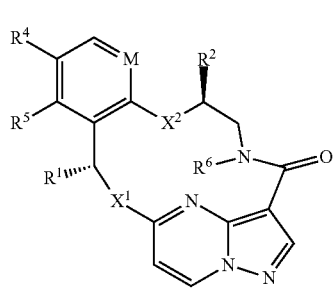

III or a pharmaceutically acceptable salt thereof,
wherein:
M is CH or N; and
$R^1$ is $C_1$-$C_6$ alkyl, $C_2$-$C_6$ alkenyl, $C_2$-$C_6$ alkynyl, C(O)$NR^7R^8$, C(O)$OR^7$, $C_3$-$C_6$ cycloalkyl, or $C_6$-$C_{10}$ aryl, wherein the $C_1$-$C_6$ alkyl, $C_2$-$C_6$ alkenyl, $C_2$-$C_6$ alkynyl, $C_3$-$C_6$ cycloalkyl, or $C_6$-$C_1$ aryl is optionally substituted.

14. The method of claim 1, wherein the compound has formula XI, formula XII, or formula XIII:

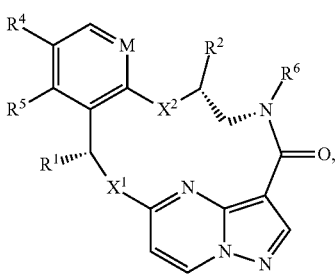

XI

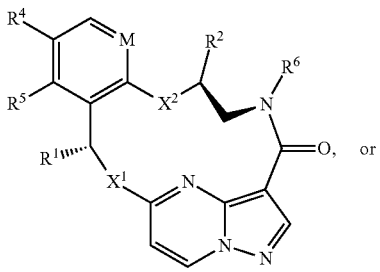

XII or,

173
-continued

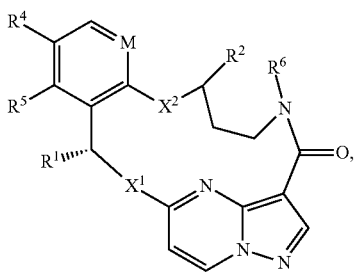

XIII or a pharmaceutically acceptable salt thereof,
wherein:
  M is CH or N; and
  $R^1$ is $C_1$-$C_6$ alkyl, $C_2$-$C_6$ alkenyl, $C_2$-$C_6$ alkynyl, C(O)$NR^7R^8$, C(O)$OR^7$, $C_3$-$C_6$ cycloalkyl, or $C_6$-$C_{10}$ aryl, wherein the $C_1$-$C_6$ alkyl, $C_2$-$C_6$ alkenyl, $C_2$-$C_6$ alkynyl, $C_3$-$C_6$ cycloalkyl, or $C_6$-$C_1$ aryl is optionally substituted.

15. The method of claim 14, wherein M is CH.

16. The method of claim 15, wherein $R_5$ is H.

17. The method of claim 16, wherein $X^1$ is —NH—.

18. The method of claim 17, wherein $X^2$ is —O—.

19. The method of claim 18, wherein $R^1$ is $C_1$-$C_6$ alkyl, wherein the $C_1$-$C_6$ alkyl is optionally substituted.

20. The method of claim 1, wherein the compound is selected from the group consisting of:

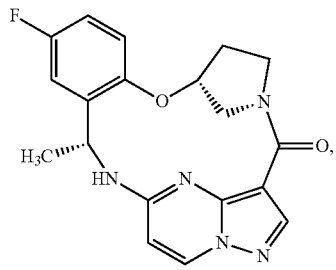

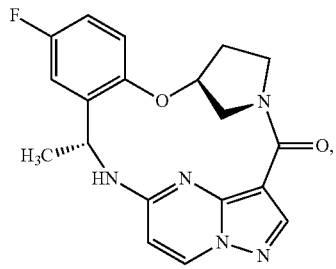

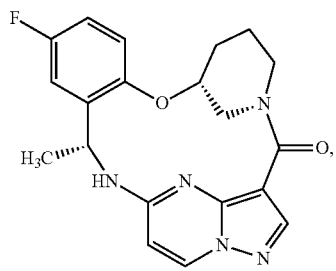

174
-continued

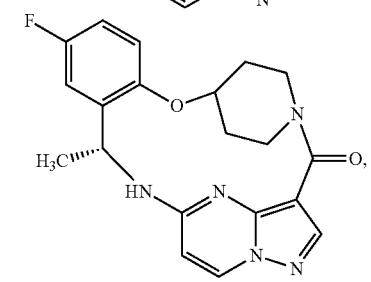

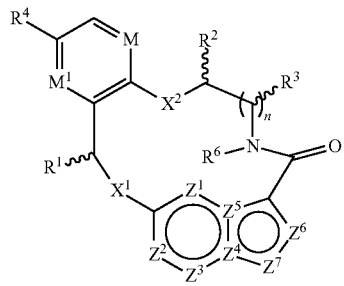

or a pharmaceutically acceptable salt thereof.

21. A method for modulating anaplastic lymphoma kinase activity or tropomysin receptor kinase A activity in a subject, comprising administering to the subject an effective amount of a pharmaceutical composition comprising at least one diluent, carrier, or excipient and a compound of formula I:

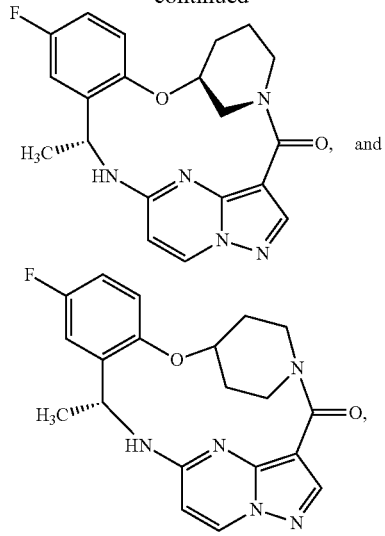

I or a pharmaceutically acceptable salt thereof,
wherein:
  n is 1 or 2;
  M is $CR^4$ or N;
  $M^1$ is $CR^5$ or N;
  $X^1$ is —$NR^9$—, —O—, —S—, —S(O)—, or —S(O)$_2$-;
  $X^2$ is —$NR^9$—, —O—, —S—, —S(O)—, or —S(O)$_2$-;
  $Z^1$ is C, $CR^{10}$, N, or NH;
  $Z^2$ is C, $CR^{10}$, N, or NH;
  $Z^3$ is C, $CR^{10}$, N, or NH;
  $Z^4$ is C, $CR^{10}$, N, or NH;
  $Z^5$ is C, $CR^{10}$, N, or NH;
  $Z^6$ is C, $CR^{10}$, N, or NH;
  $Z^7$ is C, $CR^{10}$, N, or NH;
  $R^1$ is H, deuterium, $C_1$-$C_6$ alkyl, $C_2$-$C_6$ alkynyl, C(O)$NR^7R^8$, C(O)$OR^7$, $C_3$-$C_6$ cycloalkyl, or $C_6$-$C_1$ aryl, wherein the $C_1$-$C_6$ alkyl, $C_2$-$C_6$ alkenyl, $C_2$-$C_6$ alkynyl, $C_3$-$C_6$ cycloalkyl, or $C_6$-$C_{10}$ aryl is optionally substituted by one or more substituents independently selected from the group consisting of deuterium, halogen, CN, C(O)$NH_2$, C(O)$NHC_1$-$C_6$ alkyl, C(O)N($C_1$-$C_6$ alkyl)$_2$, C(O)OH, C(O)O$C_1$-$C_6$ alkyl, $NH_2$, $NHC_1$-$C_6$ alkyl, N($C_1$-$C_6$ alkyl)$_2$, NHC(O)

C$_1$-C$_6$ alkyl, N(C$_1$-C$_6$ alkyl)C(O)C$_1$-C$_6$ alkyl, NHC(O)NH$_2$, NHC(O)NHC$_1$-C$_6$ alkyl, N(C$_1$-C$_6$ alkyl)C(O)NH$_2$, N(C$_1$-C$_6$ alkyl)C(O)NHC$_1$-C$_6$ alkyl, NHC(O)N(C$_1$-C$_6$ alkyl)$_2$, N(C$_1$-C$_6$ alkyl)C(O)N(C$_1$-C$_6$ alkyl)$_2$, NHC(O)OC$_1$-C$_6$ alkyl, N(C$_1$-C$_6$ alkyl)C(O)OC$_1$-C$_6$ alkyl, NHS(O)C$_1$-C$_6$ alkyl, NHS(O)$_2$C$_1$-C$_6$ alkyl, N(C$_1$-C$_6$ alkyl)S(O)C$_1$-C$_6$ alkyl, N(C$_1$-C$_6$ alkyl)S(O)$_2$C$_1$-C$_6$ alkyl, NHS(O)NH$_2$, NHS(O)$_2$NH$_2$, N(C$_1$-C$_6$ alkyl)S(O)NH$_2$, N(C$_1$-C$_6$ alkyl)S(O)$_2$NH$_2$, NHS(O)NHC$_1$-C$_6$ alkyl, NHS(O)$_2$NHC$_1$-C$_6$ alkyl, NHS(O)N(C$_1$-C$_6$ alkyl)$_2$, NHS(O)$_2$N(C$_1$-C$_6$ alkyl)$_2$, N(C$_1$-C$_6$ alkyl)S(O)NHC$_1$-C$_6$ alkyl, N(C$_1$-C$_6$ alkyl)S(O)$_2$NHC$_1$-C$_6$ alkyl, N(C$_1$-C$_6$ alkyl)S(O)N(C$_1$-C$_6$ alkyl)$_2$, N(C$_1$-C$_6$ alkyl)S(O)$_2$N(C$_1$-C$_6$ alkyl)$_2$, OH, OC$_1$-C$_6$ alkyl, P(C$_1$-C$_6$ alkyl)$_2$, P(O)(C$_1$-C$_6$ alkyl)$_2$, SC$_1$-C$_6$ alkyl, S(O)C$_1$-C$_6$ alkyl, S(O)NHC$_1$-C$_6$ alkyl, S(O)N(C$_1$-C$_6$ alkyl)$_2$, S(O)$_2$C$_1$-C$_6$ alkyl, S(O)$_2$NHC$_1$-C$_6$ alkyl, S(O)$_2$N(C$_1$-C$_6$ alkyl)$_2$, C$_3$-C$_6$ cycloalkyl, and 3- to 7-membered heterocycloalkyl;

R$^2$ and R$^6$, taken together with the atoms to which they are attached, form a 5- to 7-membered heterocycloalkyl;

each R$^3$ is independently H, deuterium, C$_1$-C$_6$ alkyl, C$_2$-C$_6$ alkenyl, C$_2$-C$_6$ alkynyl, C(O)NR$^7$R$^8$, C(O)OR$^7$, C$_3$-C$_6$ cycloalkyl, or C$_6$-C$_{10}$ aryl, wherein each C$_1$-C$_6$ alkyl, C$_2$-C$_6$ alkenyl, C$_2$-C$_6$ alkynyl, C$_3$-C$_6$ cycloalkyl, and C$_6$-C$_{10}$ aryl is optionally and independently substituted by one or more substituents independently selected from the group consisting of deuterium, halogen, CN, C(O)NH$_2$, C(O)NHC$_1$-C$_6$ alkyl, C(O)N(C$_1$-C$_6$ alkyl)$_2$, C(O)OH, C(O)OC$_1$-C$_6$ alkyl, NH$_2$, NHC$_1$-C$_6$ alkyl, N(C$_1$-C$_6$ alkyl)$_2$, NHC(O)C$_1$-C$_6$ alkyl, N(C$_1$-C$_6$ alkyl)C(O)C$_1$-C$_6$ alkyl, NHC(O)NH$_2$, NHC(O)NHC$_1$-C$_6$ alkyl, N(C$_1$-C$_6$ alkyl)C(O)NH$_2$, N(C$_1$-C$_6$ alkyl)C(O)NHC$_1$-C$_6$ alkyl, NHC(O)N(C$_1$-C$_6$ alkyl)$_2$, N(C$_1$-C$_6$ alkyl)C(O)N(C$_1$-C$_6$ alkyl)$_2$, NHC(O)OC$_1$-C$_6$ alkyl, N(C$_1$-C$_6$ alkyl)C(O)OC$_1$-C$_6$ alkyl, NHS(O)C$_1$-C$_6$ alkyl, NHS(O)$_2$C$_1$-C$_6$ alkyl, N(C$_1$-C$_6$ alkyl)S(O)C$_1$-C$_6$ alkyl, N(C$_1$-C$_6$ alkyl)S(O)$_2$C$_1$-C$_6$ alkyl, NHS(O)NH$_2$, NHS(O)$_2$NH$_2$, N(C$_1$-C$_6$ alkyl)S(O)NH$_2$, N(C$_1$-C$_6$ alkyl)S(O)$_2$NH$_2$, NHS(O)NHC$_1$-C$_6$ alkyl, NHS(O)$_2$NHC$_1$-C$_6$ alkyl, NHS(O)N(C$_1$-C$_6$ alkyl)$_2$, NHS(O)$_2$N(C$_1$-C$_6$ alkyl)$_2$, N(C$_1$-C$_6$ alkyl)S(O)NHC$_1$-C$_6$ alkyl, N(C$_1$-C$_6$ alkyl)S(O)$_2$NHC$_1$-C$_6$ alkyl, N(C$_1$-C$_6$ alkyl)S(O)N(C$_1$-C$_6$ alkyl)$_2$, N(C$_1$-C$_6$ alkyl)S(O)$_2$N(C$_1$-C$_6$ alkyl)$_2$, OH, OC$_1$-C$_6$ alkyl, P(C$_1$-C$_6$ alkyl)$_2$, P(O)(C$_1$-C$_6$ alkyl)$_2$, SC$_1$-C$_6$ alkyl, S(O)C$_1$-C$_6$ alkyl, S(O)NHC$_1$-C$_6$ alkyl, S(O)N(C$_1$-C$_6$ alkyl)$_2$, S(O)$_2$C$_1$-C$_6$ alkyl, S(O)$_2$NHC$_1$-C$_6$ alkyl, S(O)$_2$N(C$_1$-C$_6$ alkyl)$_2$, C$_3$-C$_6$ cycloalkyl, and 3- to 7-membered heterocycloalkyl;

R$^4$ is H, F, Cl, Br, CN, C$_1$-C$_6$ alkyl, CF$_3$, NHC$_1$-C$_6$ alkyl, N(C$_1$-C$_6$ alkyl)$_2$, OH, or OC$_1$-C$_6$ alkyl;

R$^{4a}$ is H, F, Cl, Br, CN, C$_1$-C$_6$ alkyl, CF$_3$, NHC$_1$-C$_6$ alkyl, N(C$_1$-C$_6$ alkyl)$_2$, OH, or OC$_1$-C$_6$ alkyl;

R$_5$ is H, F, Cl, Br, CN, C$_1$-C$_6$ alkyl, CF$_3$, NHC$_1$-C$_6$ alkyl, N(C$_1$-C$_6$ alkyl)$_2$, OH, or OC$_1$-C$_6$ alkyl;

each R$^7$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_1$ aryl, or heteroaryl;

each R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_1$ aryl, or heteroaryl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or monocyclic or bicyclic heteroaryl, wherein each C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, and monocyclic or bicyclic heteroaryl is optionally and independently substituted by one or more substituents independently selected from the group consisting of deuterium, halogen, C$_1$-C$_6$ alkyl, C$_1$-C$_6$ haloalkyl, and OR$^7$; and each R$^{10}$ is independently H, deuterium, halogen, CN, C$_1$-C$_6$ alkyl, CF$_3$, NH$_2$, NHC$_1$-C$_6$ alkyl, NH(phenyl), NH(heteroaryl), OH, or OC$_1$-C$_6$ alkyl;

with the provisos that:
(1) at least one of Z$^1$, Z$^2$, Z$^3$, Z$^4$, Z$^5$, Z$^6$, and Z$^7$ is N or NH; and
(2) at least one of R$^1$ and R$^3$ is not H.

22. The method of claim 21, wherein the subject has cancer, inflammation, pain, an autoimmune disease, or a neurological disease.

* * * * *